United States Patent [19]

Annus et al.

[11] Patent Number: 5,462,938
[45] Date of Patent: Oct. 31, 1995

[54] ARTHROPODICIDAL OXADIAZINYL, THIADIAZINYL AND TRIAZINYL CARBOXANILIDES

[76] Inventors: Gary D. Annus, 13 Franklin Rd., Landenberg, Pa. 19350; William E. Barnette, 107 Oxford Rd., West Chester, Pa. 19380; Stephen F. McCann, 11 Old Stable Farm, Newark, Del. 19711; Keith D. Wing, 1304 Hillside Blvd., Wilmington, Del. 19803

[21] Appl. No.: 75,534
[22] PCT Filed: Dec. 21, 1990
[86] PCT No.: PCT/US91/09164
§ 371 Date: Jun. 18, 1993
§ 102(e) Date: Jun, 18, 1993
[87] PCT Pub. No.: WO/92/11249
PCT Pub. Date: Sept. 7, 1992

Related U.S. Application Data

[63] Continuation of Ser. No. 714,401, Jun. 11, 1991, abandoned, which is a continuation of Ser. No. 632,438, Dec. 21, 1990, abandoned.

[51] Int. Cl.$^6$ .................. A61K 31/535; C07D 273/04
[52] U.S. Cl. .................. 514/229.8; 514/230.2; 544/66; 544/67; 544/68
[58] Field of Search ............ 514/229.8, 230.2; 544/66, 67, 68

[56] References Cited

U.S. PATENT DOCUMENTS

| | | | |
|---|---|---|---|
| 4,070,365 | 1/1978 | van Daalen | 548/379 |
| 4,863,947 | 9/1989 | Jacobson | 514/403 |
| 5,091,405 | 2/1992 | Stevenson | 514/403 |

FOREIGN PATENT DOCUMENTS

| | | | |
|---|---|---|---|
| 0286346 | 10/1988 | European Pat. Off. | C07D 231/54 |
| 0363051 | 4/1990 | European Pat. Off. | C07D 471/04 |
| 0365201 | 4/1990 | European Pat. Off. | C07D 231/54 |
| WO88/05046 | 7/1988 | WIPO | C07D 231/06 |
| WO88/07994 | 10/1988 | WIPO | C07D 231/54 |
| WO90/07495 | 7/1990 | WIPO | C07C 281/12 |
| WO92/11249 | 7/1992 | WIPO | C07D 273/04 |
| WO92/20682 | 11/1992 | WIPO | C07D 491/052 |

*Primary Examiner*—Yogendra N. Gupta

[57] ABSTRACT

Arthropodicidal carboxanilides of Formula I and II

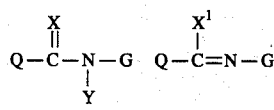

wherein Q is selected from the group

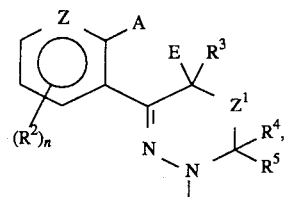

Q-1

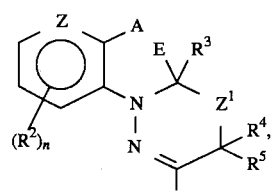

Q-2

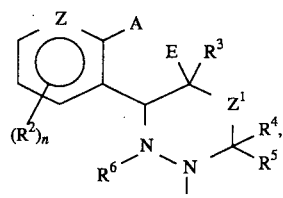

Q-3

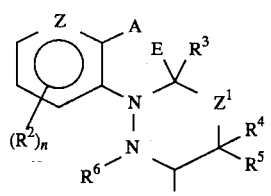

Q-4

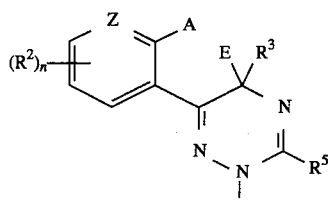

Q-5 and

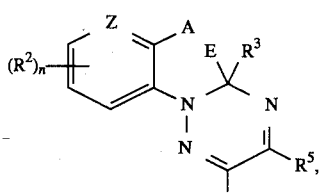

Q-6

A, E, G, X, $X^1$, Y, Z, $Z^1$, $R^2$, $R^3$, $R^4$, $R^5$, $R^6$ and n are as defined in the text, arthropodicidal compositions containing said compounds and a method for using the compounds to control arthropods.

16 Claims, No Drawings

ARTHROPODICIDAL OXADIAZINYL, THIADIAZINYL AND TRIAZINYL CARBOXANILIDES

This is the national stage of PCT/U.S. Ser. No. 91/09164, filed Dec. 17, 1991 which is a continuation of Ser. No. 07/714,401, filed Jun. 11, 1991, now abandoned, which is a continuation of Ser. No. 07/632,438, filed Dec. 21, 1990, now abandoned.

BACKGROUND OF THE INVENTION

Arthropodicidal carboxanilides, compositions containing them, and use of the carboxanilides to control arthropods. Relevant to this invention are WO 88/07,994 and EPA 330,678 which disclose insecticidal pyrazolines and WO 90/07495 which discloses insecticidal semicarbazone arthropodicides.

SUMMARY OF THE INVENTION

The invention pertains to compounds of Formula I and II, including all geometric and stereoisomers, agriculturally suitable salts thereof, agricultural compositions containing them and their use for the control of arthropods in both agronomic and non-agronomic uses. The term "compounds" will be understood to include all such isomers and salts thereof. The compounds are:

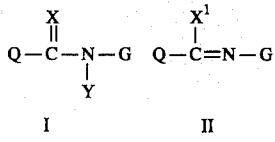

wherein:

Q is selected from the group

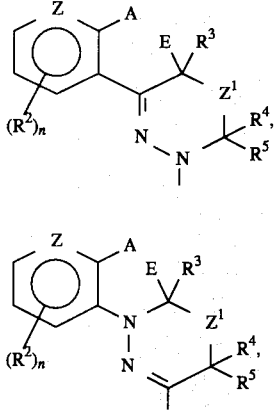

and

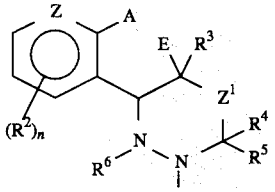

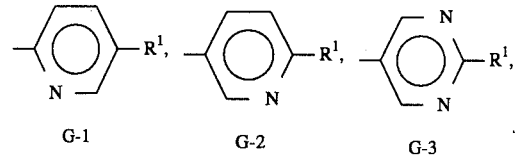

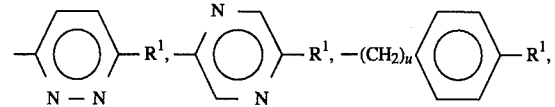

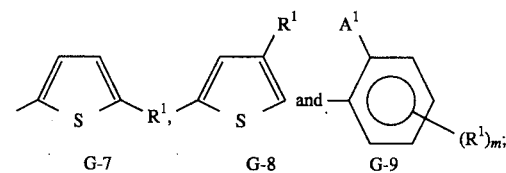

A is H;

E is selected from the group H and $C_1$–$C_3$ alkyl; or

A and E can be taken together to form —$CH_2$—, —$CH_2CH_2$—, —O—, —S—, —S(O)—, —S(O)$_2$—, —$NR^7$—, —$OCH_2$—, —$SCH_2$—, —N($R^7$)$CH_2$—, substituted —$CH_2$—, and substituted —$CH_2CH_2$— the substituents independently selected from 1–2 halogen and 1–2 methyl;

G is selected from the group

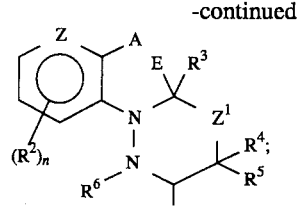

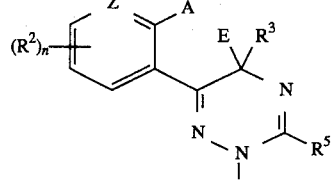

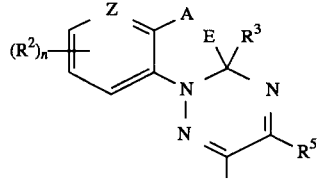

X is selected from the group O, S and N—$X^2$;

$X^1$ is selected from the group Cl, Br, $OR^8$, $SR^8$ and $NR^8R^9$;

$X^2$ is selected from the group $R^8$, OH, $OR^8$, CN, $SO_2R^8$, $SO_2Ph$, OC(O)$NR^9R^{10}$, OC(O)$OR^8$, $NR^9R^{10}$ and phenyl optionally substituted with $R^{11}$;

Y is selected from the group H; $C_1$–$C_6$ alkyl, benzyl; $C_2$–$C_6$ alkoxyalkyl; $C_2$–$C_6$ alkenyl; $C_2$–$C_6$ alkynyl; $C_1$–$C_6$ alkyl optionally substituted by halogen, $C_1$–$C_3$ alkoxy, $C_1$–$C_3$ haloalkoxy, CN, $NO_2$, S(O)$_rR^{32}$, $COR^{32}$, $CO_2R^{32}$, phenyl optionally substituted by halogen, CN, $C_1$–$C_2$ haloalkyl and $C_1$–$C_2$ haloalkoxy; $C_3$–$C_6$ cycloalkyl; $C_3$–$C_6$ cyclohaloalkyl; $C_3$–$C_6$ cycloalkylalkyl; CHO; $C_2$–$C_6$ alkylcarbonyl; $C_2$–$C_6$ alkoxycarbonyl; $C_2$–$C_6$ haloalkylcarbonyl; $COR^{36}$; $CO_2R^{36}$; $C_1$–$C_6$ alkylthio; $C_1$–$C_6$ haloalkylthio; phenylthio; $R^{12}OC(O)N(R^{13})S-$ and $R^{14}(R^{15})NS-$;

$A^1$ is H;

$A^1$ and Y can be taken together to form $-(CH_2)_t-$;

Z is C or N:

$Z^1$ is O, S or $NR^{31}$;

$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{17}$, $SR^{17}$, $S(O)R^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, $NR^{18}C(O)R^{17}$, $OC(O)NHR^{17}$, $NR^{18}C(O)NHR^{17}$, $NR^{18}SO_2R^{17}$, phenyl optionally substituted with 1 to 3 substituents independently selected from W, and benzyl optionally substituted with 1 to 3 substituents independently selected from W; or when m or n is 2, $(R^1)_2$ can be taken together, or $(R^2)_2$ can be taken together as $-OCH_2O-$, $-OCF_2O-$, $-OCH_2CH_2O-$, $-CH_2C(CH_3)_2O-$, $-CF_2CF_2O$ or $-OCF_2CF_2O-$ to form a cyclic bridge; provided that when $R^1$ or $R^2$ is $S(O)R^{17}$, $S(O)_2R^{17}$, $OC(O)R^{17}$ or $OS(O)_2R^{17}$ then $R^{17}$ is other than H;

$R^3$ is selected from the group H, J, $N_3$, $NO_2$, halogen, $N(R^{22})R^{23}$, $C(R^{34})=N-O-R^{35}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxyalkyl, $C_3$–$C_8$ alkoxycarbonylalkyl, $CO_2R^{17}$, $OR^{19}$, $C(O)R^{17}$, $C(O)NR^{17}R^{18}$, $C(S)NR^{17}R^{18}$, $C(S)R^{17}$, $C(S)SR^{17}$, CN, $Si(R^{28})(R^{29})R^{27}$, $SR^{27}$, $S(O)R^{27}$, $SO_2R^{27}$, $-P(O)(OR^{27})_2$, phenyl, phenyl substituted with $(R^{16})_p$, benzyl and benzyl substituted with 1 to 3 substituents independently selected from W; or $R^3$ is $C_2$–$C_6$ epoxyalkyl optionally substituted with a group selected from $C_1$–$C_3$ alkyl, CN, $C(O)R^{24}$, $CO_2R^{24}$ and phenyl optionally substituted with W; or $R^3$ is $C_1$–$C_6$ alkyl substituted with a group selected from $C(O)N(R^{25})R^{26}$, $C(O)R^{25}$, $SR^{27}$, $S(O)R^{27}$, $SO_2R^{27}$, SCN, CN, $C_1$–$C_2$ haloalkoxy, $Si(R^{28})(R^{29})R^{30}$, $N(R^{22})R^{23}$, $NO_2$, $OC(O)R^{25}$, $-P(O)(OR^{27})_2$ and J;

J is selected from the group saturated, partially unsaturated or aromatic 5- or 6-membered heterocyclic ring, bonded through carbon or nitrogen, containing 1–4 heteroatoms independently selected from the group consisting of 0–2 oxygen, 0–2 sulfur and 0–4 nitrogen, this substituent optionally containing one carbonyl and optionally substituted with one or more members selected from W;

$R^4$ and $R^5$ are independently selected from the group H, $C_1$–$C_4$ alkyl, $COR^{20}$ and $C_2$–$C_4$ alkoxycarbonyl; or $R^4$ and $R^5$ can be taken together to form $=O$ or $=S$;

$R^6$ is selected from the group H, $C_1$–$C_4$ alkyl, $C_1$–$C_4$ haloalkyl, $C_2$–$C_4$ alkylcarbonyl, $C_2$–$C_4$ haloalkoxycarbonyl, $C_2$–$C_4$ alkoxycarbonyl $C_2$–$C_4$ haloalkoxycarbonyl, $COR^{36}$, $CO_2R^{36}$, $C_2$–$C_5$ alkylaminocarbonyl, $C_3$–$C_6$ cycloalkyl, $C_3$–$C_6$ halocycloalkyl, $C_4$–$C_7$ alkylcycloalkyl, $C_4$–$C_7$ haloalkylcycloalkyl, $C_1$–$C_4$ alkylsulfonyl, $C_1$–$C_4$ haloalkylsulfonyl and $SO_2Ph$ optionally substituted with Cl, Br or $CH_3$;

$R^7$ is selected from the group H, $C_1$–$C_4$ alkyl, $C_1$–$C_4$ haloalkyl, $C_2$–$C_4$ alkenyl, $C_2$–$C_4$ haloalkenyl, $SR^{17}$, $S(O)R^{17}$, $S(O)_2R^{17}$, $C(O)R^{17}$, $CO_2R^{17}$, $C(O)NR^{17}R^{21}$, $C(S)NR^{17}R^{21}$, $C(S)R^{17}$, $C(S)OR^{17}$, $-P(O)(OR^{17})_2$, $-P(S)(OR^{17})_2$, $P(O)(R^{17})OR^{17}$, $P(O)(R^{17})SR^{21}$, and optionally substituted phenyl and benzyl wherein the substituent(s) are selected from F, Cl, Br, $CH_3$, $CF_3$ or $OCF_3$; provided that when $R^7$ is other than $C(O)R^{17}$, $C(O)NR^{17}R^{21}$ or $C(S)NR^{17}R^{21}$ then $R^{17}$ is other than H;

$R^8$ is selected from the group $C_1$–$C_3$ alkyl, $C_2$–$C_4$ alkenyl, $C_2$–$C_4$ alkynyl, $C_1$–$C_3$ haloalkyl, $C_2$–$C_4$ haloalkenyl, $C_3$–$C_6$ cycloalkyl; $C_1$–$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$ and benzyl optionally substituted with $R^{11}$;

$R^9$ is selected from the group H, $C_1$–$C_4$ alkyl $C_1$–$C_4$ haloalkyl, $C_2$–$C_4$ alkoxycarbonyl, and optionally substituted phenyl and pyridine wherein the substituent(s) are selected from $R^{15}$; or $R^8$ and $R^9$ can be taken together to form $-(CH_2)_4-$, $-(CH_2)_5-$ or $-CH_2CH_2OCH_2CH_2-$ each of which is optionally and independently substituted with 1 or 2 $CH_3$ groups;

$R^{10}$ is selected from the group H and $C_1$–$C_4$ alkyl; or $R^9$ and $R^{10}$ can be taken together to form $-(CH_2)_4-$, $-(CH_2)_5-$ or $-CH_2CH_2OCH_2CH_2-$ each of which is optionally and independently substituted with 1 or 2 $CH_3$ groups;

$R^{11}$ is selected from halogen, CN, $C_1$–$C_3$ haloalkyl and $C_1$–$C_3$ haloalkoxy;

$R^{12}$ is $C_1$–$C_6$ alkyl;

$R^{13}$ is $C_1$–$C_4$ alkyl;

$R^{14}$ and $R^{15}$ are independently $C_1$–$C_4$ alkyl; or $R^{14}$ and $R^{15}$ can be taken together as $-CH_2CH_2CH_2CH_2CH_2-$ or $-CH_2CH_2OCH_2CH_2-$;

$R^{16}$ is selected from the group $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{17}$, $SR^{17}$, $S(O)R^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, $NR^{18}C(O)R^{17}$, $OC(O)NHR^{17}$, $NR^{18}C(O)NHR^{17}$, $NR^{18}SO_2R^{17}$, phenyl optionally substituted with 1 to 3 substituents independently selected from W, and benzyl optionally substituted with 1 to 3 substituents independently selected from W; or when p is 2, $(R^{16})_2$ can be taken together as $-OCH_2O-$, $-OCF_2O-$, $-OCH_2CH_2O-$, $-CH_2C(CH_3)_2O-$, $-CF_2CF_2O$ or $-OCF_2CF_2O-$ to form a cyclic bridge; provided that when $R^{16}$ is $S(O)R^{17}$, $S(O)_2R^{17}$, $OC(O)R^{17}$ or $OS(O)_2R^{17}$ then $R^{17}$ is other than H;

$R^{17}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, and optionally substituted phenyl and benzyl wherein the substituents are 1 to 3 substituents independently selected from W;

$R^{18}$ is selected from the group H and $C_1$–$C_4$ alkyl; or $R^{17}$ and $R^{18}$ when attached to the same atom, can be taken together as —$(CH_2)_4$—, —$(CH_2)_5$—, or —$CH_2CH_2OCH_2CH_2$—;

$R^{19}$ is selected from the group H, $C_1$–$C_4$ alkyl, $C_2$–$C_4$ alkenyl, $C_2$–$C_4$ alkynyl, $C_2$–$C_4$ alkylcarbonyl, $C_2$–$C_4$ alkoxycarbonyl and $C_1$–$C_4$ alkylsulfonyl;

$R^{20}$ is $C_1$–$C_3$ alkyl;

$R^{21}$ is selected from the group H, $C_1$–$C_4$ alkyl, $C_2$–$C_4$ alkenyl and $C_2$–$C_4$ alkynyl;

$R^{22}$ is selected from the group H, $C_2$–$C_7$ alkylcarbonyl, $C_2$–$C_7$ alkoxycarbonyl, optionally substituted $C_1$–$C_4$ alkyl, optionally substituted $C_2$–$C_4$ alkenyl, and optionally substituted $C_2$–$C_4$ alkynyl, the substituents selected from $C_1$–$C_2$ alkoxy, CN, $C(O)R^{30}$ and $C(O)_2R^{27}$;

$R^{23}$ is selected from the group H, $C_1$–$C_3$ alkyl, phenyl, phenyl substituted with W, benzyl and benzyl substituted with W;

$R^{24}$ is selected from the group H, $C_1$–$C_4$ alkyl, $C_2$–$C_4$ alkenyl and $C_2$–$C_4$ alkynyl;

$R^{25}$ and $R^{26}$ are independently selected from the group H and $C_1$–$C_2$ alkyl;

$R^{27}$ is selected from the group $C_1$–$C_3$ alkyl, phenyl and phenyl substituted with W;

$R^{28}$ is $C_1$–$C_3$ alkyl;

$R^{29}$ is $C_1$–$C_3$ alkyl;

$R^{30}$ is selected from the group H, $C_1$–$C_3$ alkyl, phenyl and phenyl substituted by W;

$R^{31}$ is selected from the group H, $C_1$–$C_4$ alkyl, $C_2$–$C_4$ alkylcarbonyl or $C_2$–$C_4$ alkoxycarbonyl;

$R^{32}$ is selected from the group $C_1$–$C_3$ alkyl;

$R^{34}$ is selected from the group H, Cl, $C_1$–$C_4$ alkyl, $C_1$–$C_4$ alkoxy, $C_1$–$C_2$ thioalkyl and CN;

$R^{35}$ is selected from the group H, $C_1$–$C_4$ alkyl, $C_2$–$C_3$ alkylcarbonyl and $C_2$–$C_3$ alkoxycarbonyl;

$R^{36}$ is selected from the group phenyl and phenyl substituted with W;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl;

m is 1 to 3;

n is 1 to 3;

p is 1 to 3;

r is 0, 1 or 2;

t is 2 or 3; and u is 1 or 2.

Exemplary values of J include:

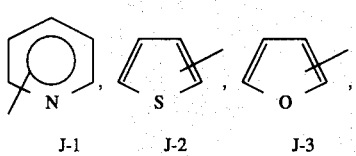

J-1   J-2   J-3

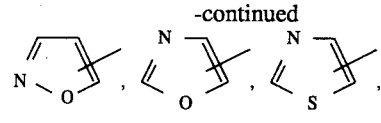

J-4   J-5   J-6

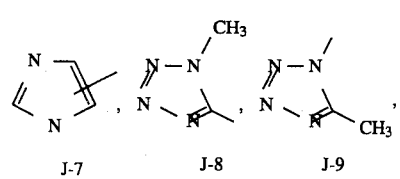

J-7   J-8   J-9

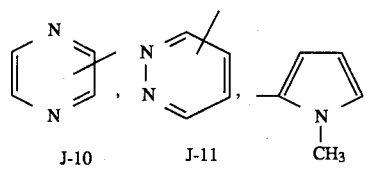

J-10   J-11   J-12

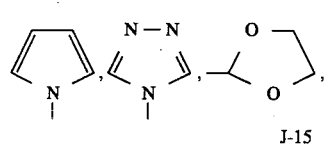

J-13   J-14   J-15

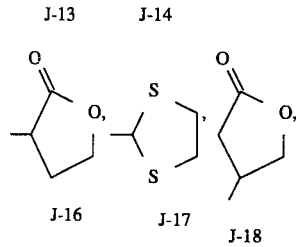

J-16   J-17   J-18

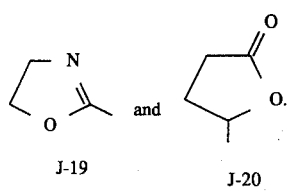

J-19   J-20

Preferred Compounds A are those of Formulae I and II wherein:

$R^1$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, SCN, $NO_2$, $OR^{17}$, $SR^{17}$, $SO_2R^{17}$, $CO_2R^{17}$, $C(O)R^{17}$, phenyl optionally substituted with 1 to 3 substituents independently selected from W, and benzyl optionally substituted with 1 to 3 substituents independently selected from W; with one $R^1$ substituent in the 4-position, or when m is 2 then $(R^1)_2$ can be taken together as —$CH_2C(CH_3)_2O$—, —$OCH_2CH_2O$—, —$OCF_2CF_2O$—, or —$CF_2CF_2O$— to form a 5- or 6-membered fused ring;

$R^2$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3-C_8$ alkoxycarbonylalkyl, $C_3-C_6$ cycloalkyl, $C_3-C_6$ halocycloalkyl, halogen, CN, SCN, $NO_2$, $OR^{17}$, $SR^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, phenyl optionally substituted with 1 to 3 substituents independently selected from W, and benzyl optionally substituted with 1 to 3 substituents independently selected from W;

$R^3$ is selected from the group H, $C_1-C_4$ alkyl, $C_3-C_4$ alkoxycarbonylalkyl $CO_2R^{17}$, $C(O)R^{17}$, phenyl and phenyl substituted by $(R^{16})_p$;

$R^{16}$ is selected from the group $C_1-C_6$ alkyl, $C_1-C_6$ haloalkyl, $C_2-C_6$ alkenyl, $C_2-C_6$ haloalkenyl, $C_2-C_6$ alkynyl, $C_3-C_6$ haloalkynyl, $C_2-C_6$ alkoxyalkyl, $C_2-C_6$ alkylthioalkyl, $C_1-C_6$ nitroalkyl, $C_2-C_6$ cyanoalkyl, $C_3-C_8$ alkoxycarbonylalkyl, $C_3-C_6$ cycloalkyl, $C_3-C_6$ halocycloalkyl, halogen, CN, SCN, $NO_2$, $OR^{17}$, $SR^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, phenyl optionally substituted with 1 to 3 substituents independently selected from W, and benzyl optionally substituted with 1 to 3 substituents independently selected from W;

$R^{17}$ is selected from the group $C_1-C_4$ alkyl, $C_1-C_2$ haloalkyl, $C_3-C_4$ alkenyl and propargyl;

$R^{18}$ is selected from the group H and $CH_3$;

$X^1$ is selected from the group $C_1$, $OR^8$, $SR^8$ and $N(CH_3)_2$;

$X^2$ is selected from the group $R^8$, $OR^8$ and $N(CH_3)_2$;

m is 1 or 2;

n is 1 or 2; and p is 1 or 2.

Preferred Compounds B are those of Preferred A wherein G is selected from the group G-2, G-3, G-7 and G-9. Preferred Compounds C are those of Preferred B wherein J is selected from the group J-1, J-2, J-8, J-9 and J-16. Preferred Compounds D are those of Preferred C wherein A and E are taken together to form —O—, —$CH_2$—, —$CH_2CH_2$—, —$OCH_2$—, —S—, —$SCH_2$— or $NR^7$; $R^7$ is selected from the group H, Me, $SO_2R^{17}$, $CO_2R^{17}$ and $CON(R^{17})R^{21}$. Preferred Compounds E are Compounds D of Formula I wherein $Z^1$ is O. Preferred Compounds F are Compounds D of Formula I wherein $Z^1$ is S. Preferred Compounds G are Compounds D of Formula I wherein $Z^1$ is $NR^{31}$. Preferred Compounds H are those of Preferred E wherein Q is Q-1. Preferred Compounds I are those of Preferred E wherein Q is Q-2. Preferred Compounds J are those of Preferred E wherein Y is $C_1-C_6$ alkyl. Preferred Compounds K are those of Preferred J wherein Y is $CH_3$.

Specifically preferred are compounds:

(L) methyl 7-chloro-2,3-dihydro-2-[[4-trifluoromethoxy)phenylamino] carbonyl]indeno[1,2-e]-[1,3,4]oxadiazine- 4a(5H) -carboxylate;

(M) methyl 7-chloro-2,5-dihydro-2-[N-methyl-N-[4-(trifluoromethoxy)phenyl] aminocarbonyl]indeno-[1,2-e][1,3,4]oxadiazine-4a(3H) -carboxylate;

(N) methyl 7-chloro-2,5-dihydro-2-[[N-methyl-N-[4-trifluoromethyl)phenyl]amino] carbonyl]indeno-[1,2-e][1,3,4]oxadiazine-4a(3H) -carboxylate;

(O) 7-fluoro-4a-(4-fluorophenyl)-4a,5-dihydro-N-[4-(trifluoromethoxy)phenyl]indeno[1,2-e] [1,3,4]-oxadiazine-2(3H)-carboxamide; and (P) 7-chloro-4a,5-dihydro-4a-methyl-N-[4-(trifluoromethoxy)phenyl] indeno [1,2-e][1,3,4]oxadiazine-2(3H)-carboxamide.

In the above definitions, the term "alkyl", used either alone or in compounds words such as "alkylthio" or "haloalkyl", denotes straight chain or branched alkyl, such as methyl, ethyl, n-propyl, isopropyl or the different butyl, pentyl, hexyl isomers. Alkoxy denotes methoxy, ethoxy, n-propyloxy, isopropyloxy and the different butoxy or pentoxy isomers. Alkenyl denotes straight chain or branched alkenes, such as vinyl, 1-propenyl, 2-propenyl, 3-propenyl and the different butenyl, pentenyl and hexenyl isomers. Alkynyl denotes straight chain or branched alkynes, such as ethynyl, 1-propynyl, 3-propynyl and the different butynyl, pentynyl and hexynyl isomers. Alkylthio denotes methylthio, ethylthio and the different propylthio, butylthio, pentylthio and hexylthio isomers. Alkylsulfinyl, alkylsulfonyl, alkylamino, and the like are defined analogously to the above examples. Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_2$ and $CH_2CHFCl$. The terms "halocycloalkyl", "haloalkenyl" and "haloalkynyl" are defined analogously to the term "haloalkyl".

The total number of carbon atoms in a substituent group is indicated by the "$C_i-C_j$" prefix where i and j are numbers from 1 to 8. For example, $C_1-C_3$ alkylsulfonyl designates methylsulfonyl through propylsulfonyl; $C_2$ alkoxyalkoxy designates $OCH_2OCH_3$; $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl designates $CH_2CN$ and $C_3$ cyanoalkyl designates $CH_2CH_2CN$ and $CH(C-N)CH_3$; $C_2$ alkylcarbonyl designates $C(O)CH_3$ and $C_4$ alkylcarbonyl includes $C(O)CH_2CH_2CH_3$ and $C(O)CH(CH_3)_2$; $C_2$ alkoxycarbonyl designates $C(O)OCH_3$ and $C_4$ alkoxycarbonyl designates $C(O)OCH_2CH_2CH_3$ and $C(O)OCH(CH_3)_2$; and as a final example, $C_3$ alkoxycarbonylalkyl designates $CH_2CO_2CH_3$ and $C_4$ alkoxycarbonylalkyl includes $CH_2CH_2CO_2CH_3$, $CH_2CO_2CH_2CH_3$ and $CH(CH_3)CO_2CH_3$.

DETAILS OF THE INVENTION

Compounds of Formulae I and II are prepared as described in Schemes 1 through 30 with substituents as previously defined, unless otherwise noted. The substituents $R^4$ and $R^5$ have been depicted as hydrogen for the purposes of clarity but also included are the values of these substituents as previously defined.

Compounds of Formula II (Q-1) can be prepared by the reaction of imidoylhalides of Formula II (Q-1) with sulfur, oxygen and nitrogen nucleophiles of Formula III as illustrated in Scheme 1. Typical reactions involve the combination of equimolar amounts of II (Q-1) and III in the presence of a base such as an alkali metal, tertiary amine, metal hydride and the like in conventional organic solvents, including ether, tetrahydrofuran, 1,2-dimethoxyethane, methylene chloride, chloroform, N,N-dimethylformamide and dimethylsulfoxide. The reaction can be conducted at temperatures ranging from –20° C. to 100° C. with temperatures in the range of –10° C. to 30° C. generally being preferred. One skilled in the art will recognize that reactions of this general type can be extended to other nucleophilic reagents.

SCHEME 1

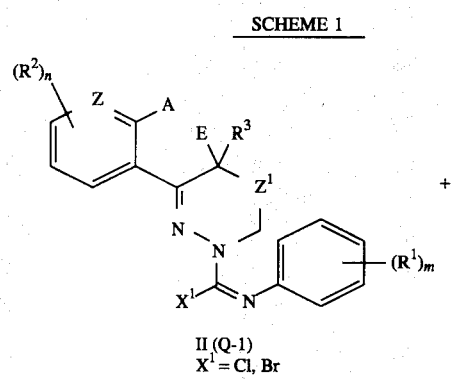

II (Q-1)
$X^1 = Cl, Br$ $$\begin{array}{c} R^8M-H \\ III \\ M=O, S, NR^7 \end{array} \xrightarrow{\text{base}} \begin{array}{c} II\,(Q\text{-}1) \\ X^1 = OR^8, SR^8, \\ NR^7R^8 \end{array}$$

The imidoylhalides of Formula II (Q-1) can be prepared by the reaction of Formula I (Q-1) compounds with an appropriate halogenating agent such as phosphorous trichloride, phosphorous pentachloride, phosphorous tribromide, phosphorous pentabromide, thionyl chloride, sulfuryl chloride, triphenyl phosphine and carbon tetrachloride (Wolkoff, Can. J. Chem., 1975, 53, 1333) and the like (see Fieser and Fieser, Reagents for Organic Synthesis, Vol. I, 1967) as illustrated in Scheme 2. Typical reactions involve the combination of Formula I (Q-1) compounds with an excess of the halogenating agent ranging from 1.1 to 10 equivalents, with 2 to 4 equivalents being preferred. The reaction can be conducted in the absence of a solvent or in the presence of a conventional organic solvent such as benzene, toluene, xylene, chloroform, methylene chloride, hexane and the like. The reaction temperature can range from −10° C. to 200° C. with 35° C. to 100° C. being preferred. The reaction is generally complete after 24 hours.

is equal to $R^8$-S can be prepared by the reaction of compounds of the Formula I (Q-1) where X is equal to S with an electrophile of the Formula IV in the presence of a suitable base, as illustrated in Scheme 3. Typical reactions involve the combination of equimolar amounts of Formula I (Q-1) compounds and the appropriate electrophile of Formula IV. A base such as an alkali metal, tertiary amine or metal hydride can be used.

SCHEME 2

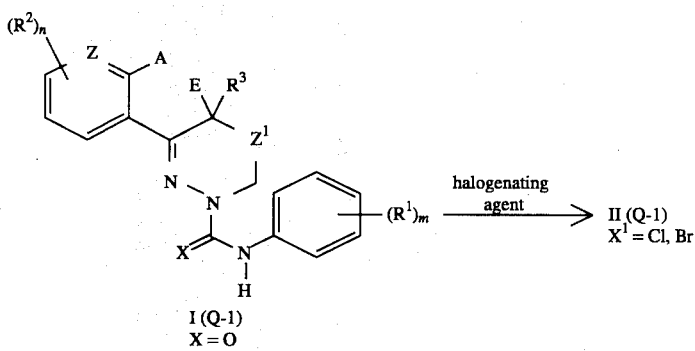

Alternatively, compounds of Formula II (Q-1), when $X^1$

SCHEME 3

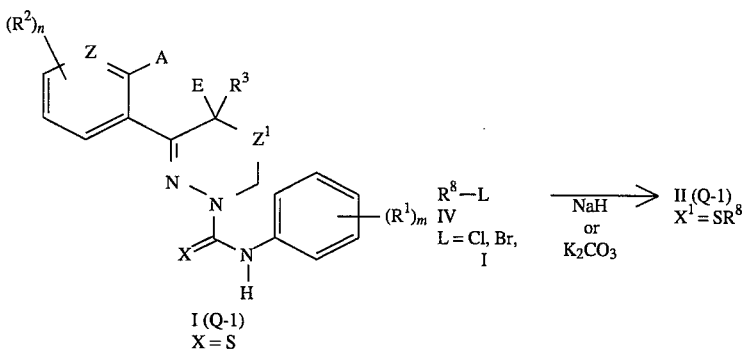

Compounds of Formula I (Q-1) where X is S or O can be prepared by the reaction of Formula V compounds with isocyanates of Formula VI. Typical reactions involve the combination of equimolar amounts of V and VI in a conventional organic solvent such as but not limited to ethyl acetate, methylene chloride, chloroform, benzene or toluene. A base such as an alkali metal, tertiary amine, alkali metal alkoxide or metal hydride can be used. Scheme 4 illustrates this transformation.

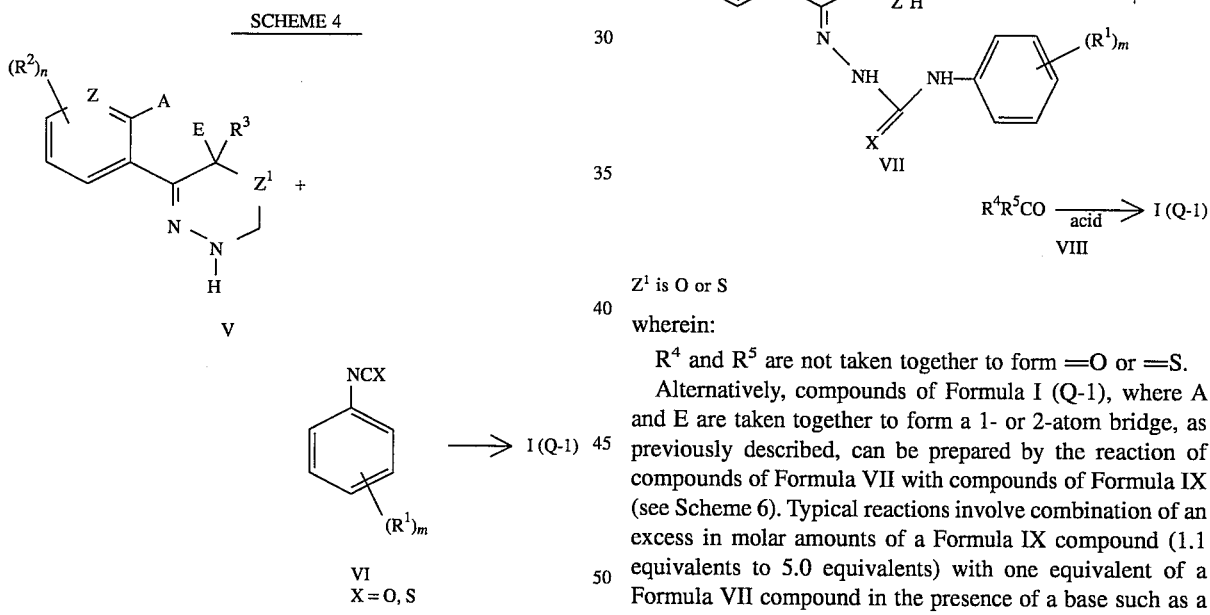

Alternatively, compounds of Formula I (Q-1), where A and E are taken together to form a 1- or 2-atom bridge, as previously described, can be prepared by the reaction of semicarbazones of Formula VII with compounds of Formula VIII. Typical reactions involve the combination of an excess in molar amounts of a Formula VIII compound (1.1 equivalents to 40 equivalents) with 1 equivalent of a Formula VII compound in the presence of less than one molar equivalent of an acid catalyst (0 equivalents to 0.9 equivalents). Typical acid catalysts include alkyl or aryl sulfonic acids (such as methyl, camphor or p-toluene sulfonic) and mineral acids (such as hydrochloric or sulfuric). Conventional, polar organic solvents such as acetonitrile, dimethylformamide, tetrahydrofuran, methanol or ethanol can be used. The reaction temperature can vary from 0° C. to the reflux temperature of the particular solvent being used and the reaction is usually complete in less than 24 hours. Scheme 5 illustrates this transformation.

$Z^1$ is O or S wherein:

$R^4$ and $R^5$ are not taken together to form =O or =S.

Alternatively, compounds of Formula I (Q-1), where A and E are taken together to form a 1- or 2-atom bridge, as previously described, can be prepared by the reaction of compounds of Formula VII with compounds of Formula IX (see Scheme 6). Typical reactions involve combination of an excess in molar amounts of a Formula IX compound (1.1 equivalents to 5.0 equivalents) with one equivalent of a Formula VII compound in the presence of a base such as a tertiary amine (such as triethylamine, pyridine or DBU), an alkali metal, an alkali metal hydride or an alkali metal alkoxide or hydroxide (such as sodium methoxide, potassium-t-butoxide, sodium hydroxide or potassium hydroxide). Conventional, polar organic solvents such as methanol, ethanol, propanol, dimethylformamide, THF, dichloromethane or acetonitrile can be used. The reaction temperatures can vary from 0° C. to the reflux temperature of the particular solvent being used and the reaction is usually complete in less than 24 hours.

Alternatively, when $Z^1=NR^{31}$, $R^4$ and $R^5$=H and $L^1$ and $L^2$ are taken together as =NMe$_2^{\oplus}$I$^{\ominus}$ the reaction can be performed in the absence of base in aprotic solvents such as THF, dioxane and the like. Equimolar amounts of VII and IX are used and the reaction is usually complete in 72 hours.

SCHEME 6

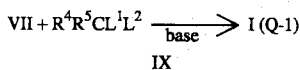

wherein:

$L^1$, $L^2$ are Cl, Br, I, imidazole, or $L^1$ and $L^2$ may be taken together to equal =O, =S or =$N(CH_3)_2^{\oplus}I^{\ominus}$ (where $Z^1$ is $NR^{31}$) provided that $R^4$ and $R^5$ are not taken together to form =O.

Compounds of Formula V, where A and E are taken together to form a 1- or 2-atom bridge, as previously described, can be prepared by the reaction of Formula X compounds with either compounds of Formula VIII or compounds of Formula IX using methods analogous to those shown for the preparation of Formula I (Q-1) compounds in Schemes 5 and 6. The preparation of Formula V compounds is shown in Scheme 7.

SCHEME 7

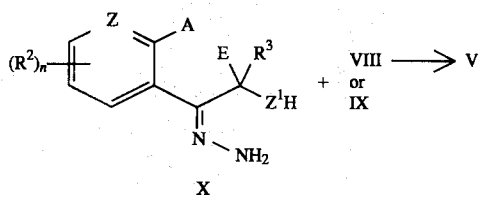

$Z^1$ is O or S

Compounds of Formula VII where X is O or S can be prepared by the reaction of Formula X compounds with isocyanates of Formula VI as shown in Scheme 8. Typical reactions involve the combination of equimolar amounts of X and VI in the presence of 1 molar equivalent of water in a polar organic solvent such as tetrahydrofuran or dimethylformamide. The reaction is usually complete in less than 24 hours.

SCHEME 8

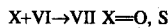

X+VI→VII X=O, S

Alternatively, Formula VII compounds where X is O or S can be prepared by the reaction of compounds of Formula XI with semicarbazides of Formula XII. Conditions for this reaction optionally include an acid catalyst such as hydrochloric, sulfuric or p-toluene sulfonic acid. Reaction temperatures can range from 0° to 150° C. with the reflux temperature of the solvent used generally preferred. Suitable solvents include, but are not limited to, methanol, ethanol, isopropanol, tetrahydrofuran and dioxane. Scheme 9 illustrates this transformation.

SCHEME 9

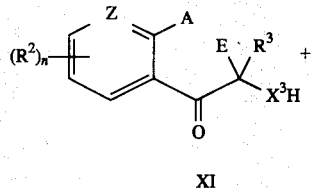

-continued
SCHEME 9

$X^3$ is O, S, $NR^{31}$, $NHR^{31\oplus}Cl^{\ominus}$

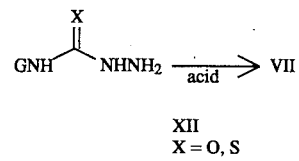

The preparation of Formula X compounds can be accomplished by the reaction of Formula XI compounds with an excess of equivalents (1.1 to 10.0 equivalents) of hydrazine, hydrazine monohydrate, hydrazine acetate, hydrazine hydrochloride and the like. The reaction is conducted in an alcohol solvent such as methanol, ethanol, n-propanol, isopropanol, n-butanol and the like or acetic acid and the temperature is governed by the reflux temperature of the particular solvent. The reaction is generally complete in 24 hours. Scheme 10 illustrates this transformation.

SCHEME 10

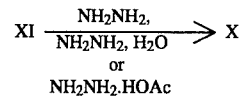

Compounds of Formula XI where $X^3$ is O can be prepared by the α-hydroxylation of ketones of Formula XIII using procedures that are well-known to one skilled in the art (e.g., J. Am. Chem. Soc., 1974, 96, 5944; Tetrahedron Lett., 1988, 29, 2835; J. Org. Chem., 1986, 51, 2402). Scheme 11 illustrates this transformation.

SCHEME 11

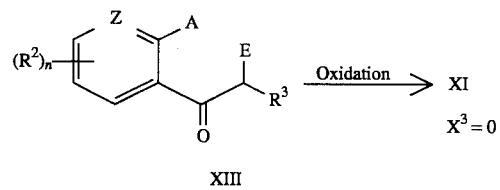

Numerous alternative procedures exist for the preparation of α-hydroxyketones of Formula XI (where $X^3$ is O). Such procedures are well-known to one skilled in the art (March, Advanced Organic Chemistry, 3rd Edition, 1985, p. 1164). Compounds of Formula XI where $X^3$ is O, $R^3$ is aryl and E is H are benzoins whose preparations are well-known to one skilled in the art.

α-Keto sulfides of Formula XI where $X^3$ is S can be prepared from ketones of Formula XIII using procedures known to the art (J. Am. Chem. Soc., 1985, 107, 4175; J. Org. Chem., 1988, 53, 3125).

α-Amino ketones of Formula XI where $X^3$ is $NR^{31}$ can be prepared from ketones of Formula XIII using procedures known in the art (J. Chem. Soc., 1959, 1479; Synthesis, 1972, 191).

Compounds XI where $X^3$ is $NHR^{31\oplus}Cl^{\ominus}$, can be prepared by the reaction of Formula XIII compounds with compounds of the type XIIIa using a procedure similar to those described in the art (Synthesis, 1991, 327). The conditions for this reaction are the combination of equimolar amounts of Formulae XIII and XIIIa derivatives in the presence of a base as a catalyst, such as, but not limited to, DABCO, DBU, sodium hydroxide and the like. Suitable solvents include, but are not limited to, toluene, dioxane and water. Scheme 11a illustrates this transformation.

SCHEME 11a

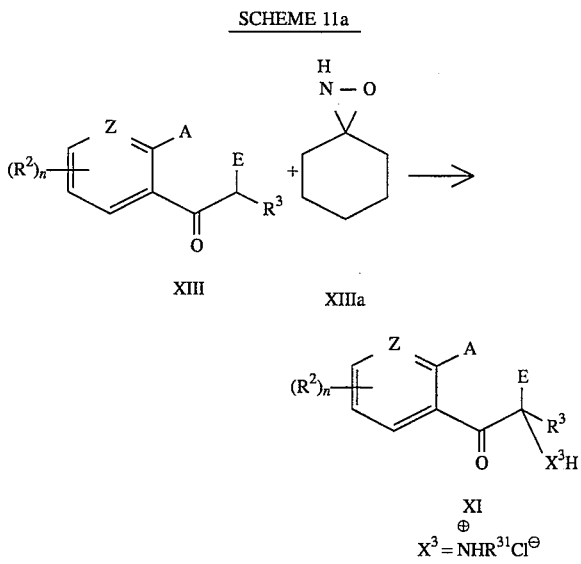

$X^3 = NHR^{31}Cl^{\ominus}$

The starting ketones of Formula XIII are known in the art or can be obtained by methods analogous to known procedures. Those skilled in the art will recognize the Formula XIII compounds to include indanones, tetralones, chromanones, thiochromanones, benzofuran-3-ones, isochromanones and others.

One skilled in the art will recognize that the transformation of Formula XIII compounds into Formula XI compounds may require the use of protecting groups to prevent unwanted side reactions of functionalities that may be sensitive to the reaction conditions (for example, an indoxyl nitrogen atom may require a protecting group to render it unreactive in an α-hydroxylation of the carbonyl group). Since numerous alternative synthetic methods for the preparations of Formula XI compounds exist, a further discussion of protecting-group chemistry will be omitted.

Semicarbazides of Formula XII where X is O or S and G is G-9 can be prepared using procedures well-known to those skilled in the art. Formula XII compounds where X is O or S and G is G-1 to G-8 can be prepared by using the procedure shown in Scheme 12.

SCHEME 12

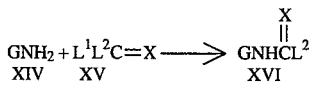

-continued
SCHEME 12

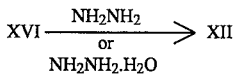

wherein:

G is G-1 through G-8 and $L^1$ and $L^2$ are as already defined.

Typical reaction conditions involve the reaction of equimolar amounts of an amine of Formula XIV with a compound of Formula XV (usually, 1,1'-carbonyldiimidazole or thiophosgene are preferred) in a suitable solvent at a temperature between −20° C. and 50° C. Suitable solvents include, but are not limited to, methylene chloride, chloroform, tetrahydrofuran or dioxane. The reaction product, XVI, is used without purification and is treated with an excess of a molar amount of hydrazine or hydrazine hydrate in an alcohol solvent such as methanol, ethanol or isopropanol at a temperature from 0° to 110° C. with the preferred temperature being the boiling point of the solvent used. The formation of semicarbazide XII is usually complete within 72 hours.

Compounds of Formula I, where Q is Q-1 and G is equal to G-1 through G-8 can be prepared by treating intermediates of Formula V with triphosgene ($O=C(OCCl_3)_2$) or phosgene and $NH_2$-G in the presence of a base such as pyridine as outlined in Scheme 13.

SCHEME 13

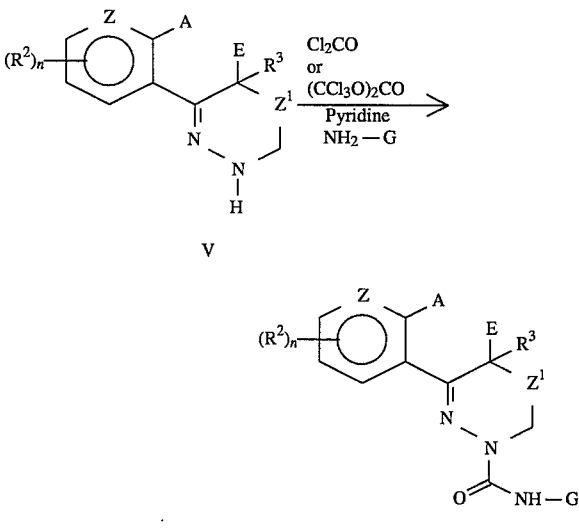

Compounds of Formula II (Q-2) can be prepared from Formula II (Q-2) imidoylhalide derivatives in an analogous fashion such as that described for the preparation of Formula II (Q-1) imidoylhalide compounds; see Scheme 14.

SCHEME 14

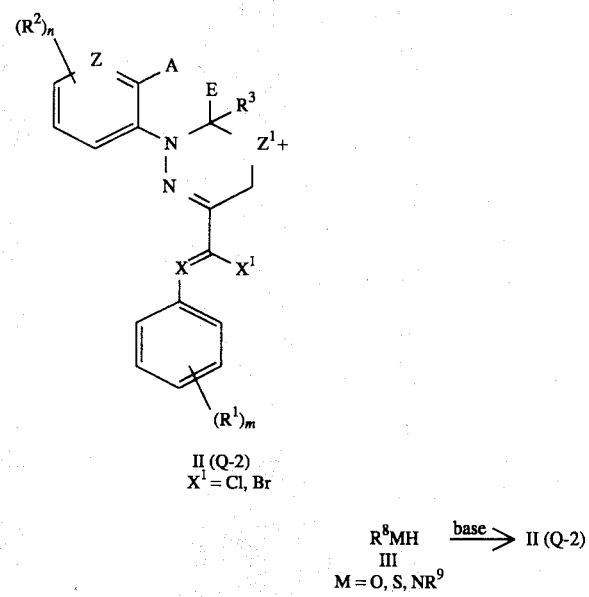

II (Q-2)
$X^1$ = Cl, Br $$\underset{\underset{M = O, S, NR^9}{III}}{R^8MH} \xrightarrow{base} II (Q-2)$$

Formula II (Q-2) imidoylhalide compounds can be prepared from Formula I (Q-2) compounds in an analogous fashion as that described for Formula II (Q-1) compounds; see Scheme 15.

SCHEME 14

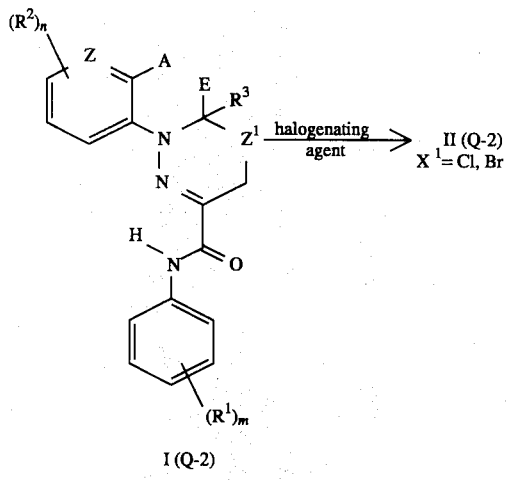

I (Q-2)

Compounds of Formula I (Q-2) can be prepared by the reaction of the acid chloride XVI with a substituted aniline of Formula XVII in equimolar proportions in the presence of an excess of an acid scavenger, such as tertiary alkylamines or pyridines, but not limited to these, in an aprotic organic solvent such as ether, tetrahydrofuran, chloroform, methylene chloride, benzene and/or toluene. Scheme 16 illustrates this transformation.

SCHEME 16

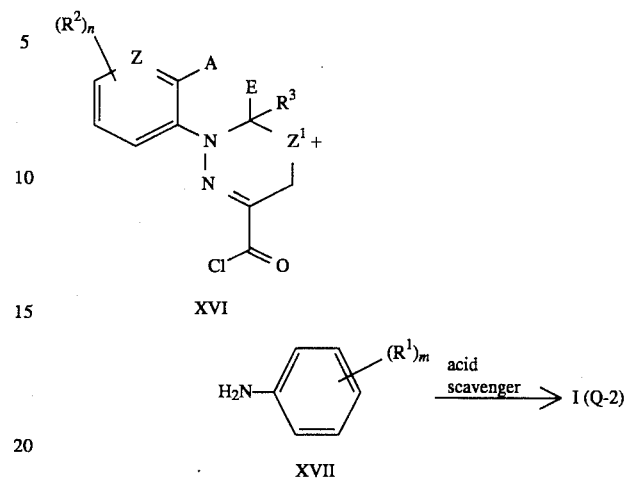

Compounds of the Formula XVI can be prepared from compounds of the Formula XVIII through conventional methodology generally used for the conversion of esters to their corresponding acid chlorides as illustrated in Scheme 17.

SCHEME 17

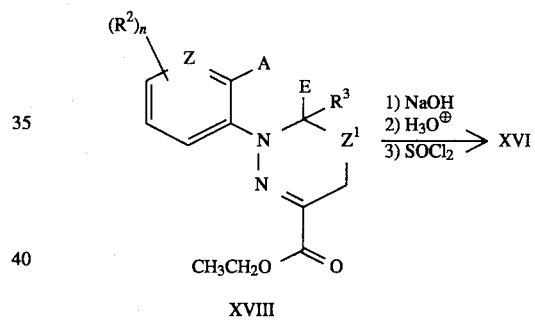

XVIII

Formula XVIII derivatives (where A is equal to H) can be prepared by the reaction of Formula XIX compounds with an equimolar or greater amount of a Formula XX compound in the presence of an acid catalyst (with 0.05 to 0.2 molar equivalents preferred). The reaction can be carried out in a variety of polar organic solvents, including, but not limited to, tetrahydrofuran, acetonitrile, methanol or ethanol at a temperature of between 0° and 80° C. with the preferred temperature being the reflux temperature of the solvent. This reaction is illustrated by Scheme 18.

SCHEME 18

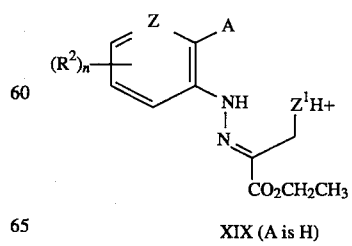

XIX (A is H)

-continued
SCHEME 18

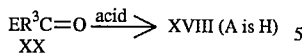

Compounds of Formula XIX where $Z^1$ is O can be prepared by treatment of Formula XXI compounds with a carboxylic acid such as formic, acetic or benzoic acid in the presence of 0 to 2.0 equivalents of a base including, but not limited to, potassium carbonate, sodium carbonate or sodium hydroxyde. Suitable solvents for the reaction include, but are not limited to, ethanol, tetrahydrofuran or dimethylformamide. The ester XXII formed in the initial reaction is subsequently hydrolyzed to the alcohol XIX ($Z^1$ is O) using a base such as sodium ethoxide in a solvent such as ethanol. Thiols of the Formula XIX (where $Z^1$ is S) can be prepared using analogous procedures starting with a thiocarboxylic acid (such as thiolacetic acid). The preparations of Formula XIX compounds ($Z^1$ is O or S) are illustrated by Scheme 19.

SCHEME 19

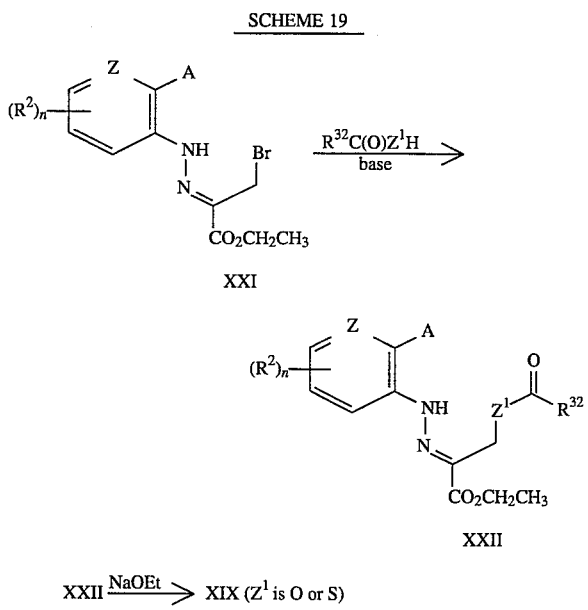

wherein:
$Z^1$ is O or S;
$R^{32}$ is H, alkyl or aryl.

Compounds of Formula XIX where $Z^1$ is $NR^{31}$ can be prepared using procedures analogous to those shown in Scheme 19 using either ammonia or a primary amine ($R^{31}NH_2$) in place of the carboxylic or thiocarboxylic acid.

Compounds of Formula XXI can be prepared from compounds of the Formula XXIII by the reaction with an equimolar amount of XXIV in conventional organic solvents such as, but not limited to, ether, tetrahydrofuran, methanol, ethanol, methylene chloride, benzene and toluene. Typical reaction temperatures can range from room temperature to the reflux temperature of the particular solvent utilized and the reaction is usually complete in 24 hours. Scheme 20 illustrates this reaction.

SCHEME 20

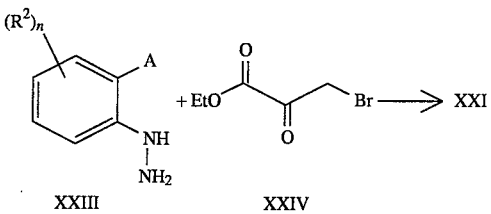

Formula XXIII compounds can be prepared from Formula XXV derivatives by a diazotization/reduction reaction well documented in the literature (see Organic Functional Group Preparation, 1983, pp. 452–453 and references cited therein). Scheme 21 illustrates this transformation.

SCHEME 21

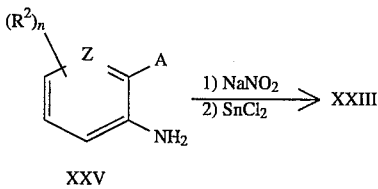

Formula XXV compounds are known in the art or can be obtained by methods analogous to known procedures. Those skilled in the art will recognize Formula XXV compounds to be substituted anilines or aminopyridines.

Compounds of Formula I (Q-3) can be prepared by the reaction of tri- and tetravalent metal species such as titanium, silicon, tin and the like in combination with reducing agents such as sodium, lithium, or zinc borohydride, lithium aluminum hydride and the like with compounds of Formula I (Q-1) as illustrated in Scheme 22. Literature precedent for analogous reactions can be found in *J.Org. Chem.*, 1987, 54, 3750, and *Synthesis*, 1980, 695. Typical reactions involve the addition of 1 equivalent of a compound of Formula I (Q-1) to a solution of 1.1 to 4.0 equivalents of titanium tetrachloride, with 1.5 to 2.5 equivalents being preferred, and 2.1 to 6.0 equivalents of sodium borohydride with 3.5 to 4.5 equivalents being preferred.

Conventional organic solvents such as ether, tetrahydrofuran, dimethoxyethane, methylene chloride and chloroform can be used with 1,2-dimethoxyethane being preferred. The reaction can be conducted at temperatures ranging from −70° C. to 50° C. with −10° C. to 30° C. being preferred. The reaction time can be 0.1 hour to 48 hours with 2 to 4 hours being preferred.

SCHEME 22

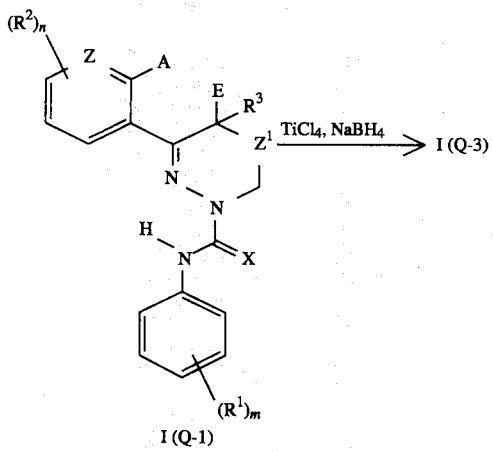

I (Q-1)

Formula I (Q-3) derivatives can be converted into Formula II (Q-3) compounds in an analogous fashion as described for the conversion of Formula I (Q-1) compounds into Formula II (Q-1) derivatives.

Formulae I (Q-4) and II (Q-4) compounds can be prepared in an analogous fashion as described for the preparation of Formulae I (Q-3) and II (Q-3) derivatives.

Additionally, compounds of Formula I, where Q is Q-1, A is H, Z is CH, E is H and $R^3$ is H, alkyl or aryl, can be prepared as outlined in Scheme 23. This is generally accomplished by the reaction of equimolar amounts of a heterocycle such as XXVI with an aryl isocyanate or isothiocyanate of Formula VI in conventional organic solvents such as ether or tetrahydrofuran. The Formula I compounds of Scheme 23, where E is H, can be converted to the analogs where E is $C_1$–$C_3$ alkyl by alkylation of the dianion with a $C_1$–$C_3$ alkyl halide as shown. This is typically done by treatment of the compound where E is H with at least two equivalents of a strong base such as lithium diisopropylamide at low temperatures in the range of 0° to −78° C. in a solvent such as tetrahydrofuran. An alkyl halide (typically the iodide) is then added to the preformed dianion affording, after workup, compounds of Formula I where Q is Q-1, A is H and E is $C_1$–$C_3$ alkyl.

SCHEME 23

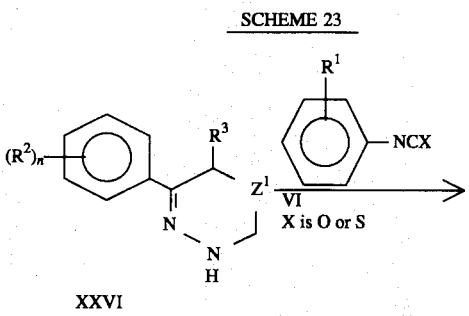

XXVI

-continued
SCHEME 23

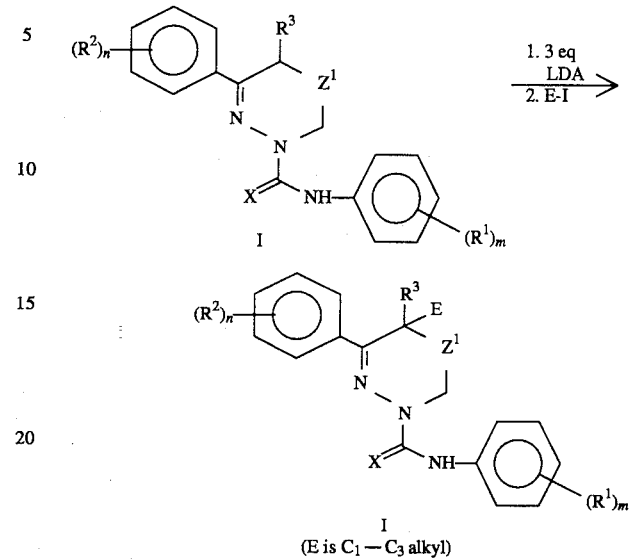

I
(E is $C_1$–$C_3$ alkyl)

Alkylation of the dianion of compounds such as XXVII is another useful method for the introduction of a variety of $R^3$ groups, this method is outlined in Scheme 24. The $R^3$ groups generally prepared by this method are derived from alkylating reagents $R^3$-L (where L is Cl, Br or I) and include, e.g., alkyl halides, substituted alkyl halides, acyl halides, alkylchloroformates, sulfenyl and sulfonyl halides, dialkylcarbamoyl halides and the like. Typical procedures are analogous to that described in Scheme 23 and include the use of strong base at low temperature. A second substituent E (where E is $C_1$–$C_3$ alkyl) can also be introduced in a similar fashion.

SCHEME 24

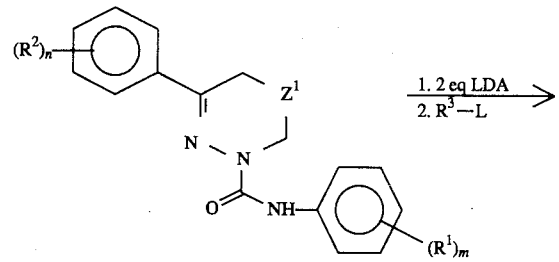

XXXVII

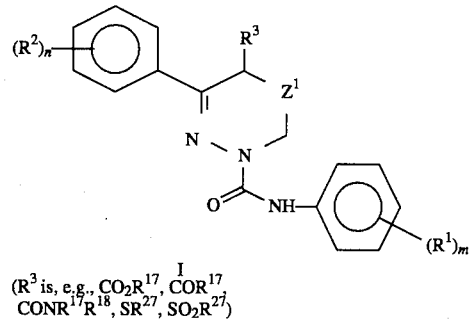

I
($R^3$ is, e.g., $CO_2R^{17}$, $COR^{17}$, $CONR^{17}R^{18}$, $SR^{27}$, $SO_2R^{27}$)

Compounds of Formula I, where Q is Q-1 and $R^4$ and $R^5$ are taken together to form a carbonyl group (such as compound XXVIII) can be prepared by the reaction of an amide such as V, where $R^4$ and $R^5$ are taken together to form =O, with an aryl isocyanate or isothiocyanate. This method is outlined in Scheme 25. This reaction can be run in a variety of conventional organic solvents such as ether, tetrahydrofuran or ethyl acetate and is preferably conducted at the reflux temperature of the solvent. It is also preferable, and in some cases necessary, to add a catalytic amount of an amine base such as triethylamine, pyridine or preferably N,N-dimethylaminopyridine.

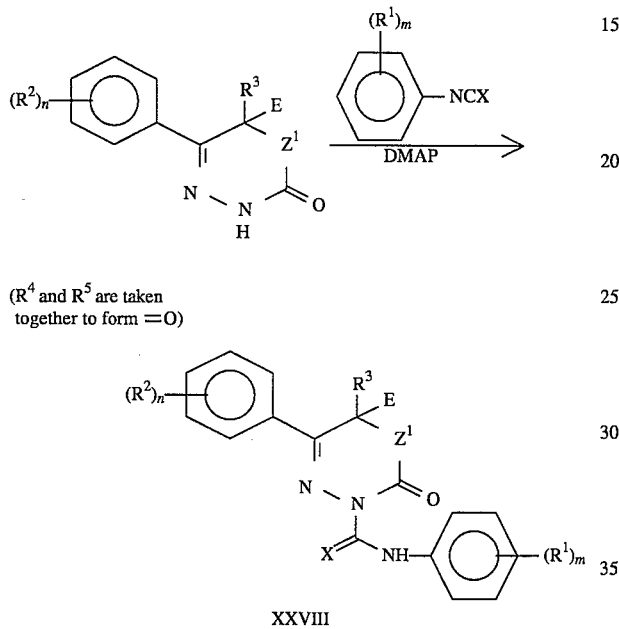

Compounds of Formulae I (Q-5) and II (Q-5) can be prepared by the reaction of Formulae I (Q-1) and II (Q-1) derivatives where $Z^1$ is NH and $R^4$ is H with an oxidizing agent, such as dichlorodicyanobenzoquinone (DDQ) (see Fieser and Fieser, Reagents for Organic Synthesis, 1967, Vol. I, pp. 215–219). The reaction involves the combination of an excess of molar equivalents of DDQ with one molar equivalent of Formula I (Q-1) or Formula II (Q-1) compounds where $Z^1$ is NH and $R^4$ is H in a suitable solvent such as, but not limited to, methanol, ethanol, acetone and benzene. The reaction is conducted at room temperature to reflux temperature of the particular solvent utilized. The reaction is usually complete in 24 hours. Scheme 25a illustrates this reaction.

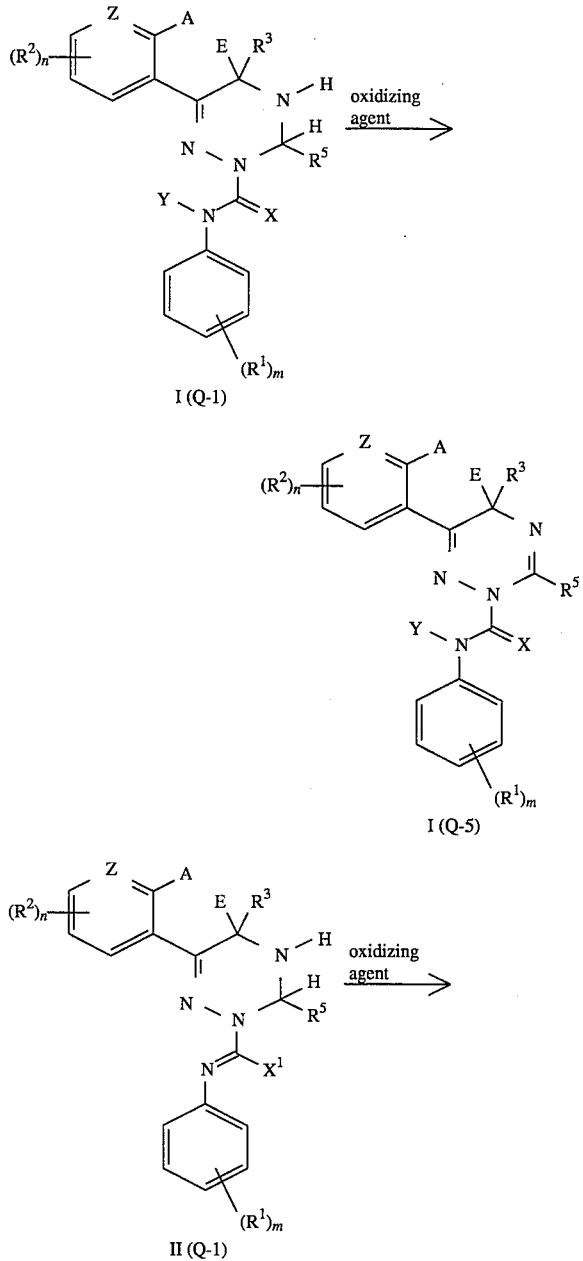

-continued
SCHEME 25a

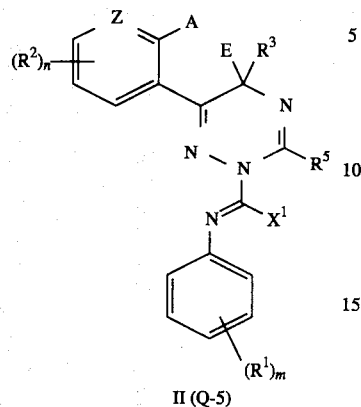

II (Q-5)

Compounds of Formulae I (Q-6) and II (Q-6) can be prepared in an analogous fashion as described in Scheme 25a for Formulae I (Q-5) and II (Q-5) derivatives.

Formulae I compounds where Y is other than H, can be prepared by standard alkylation, acylation or sulfenylation methods well documented in the literature.

Formula I compounds where Y and $A^1$ are taken together to form —$(CH_2)_t$— can be prepared by coupling of a Formula V compound with an indoline (t is 2) or tetrahydroquinoline (t is 3) of Formula XXIX in the presence of phosgene or a phosgene equivalent. Typical reaction conditions involve combination of di- or triphosgene with the Formula V compound in a solvent such as tetrahydrofuran or chloroform followed by addition of the indoline or tetrahydroquinoline of Formula XXIX. This chemistry is depicted in Scheme 26.

Formula XXIX are well known in the art as well as procedures for their preparation.

Alternatively, compounds of Formula I where Y and $A^1$ are taken together to form —$(CH_2)_t$— can be prepared by the reactions semicarbazones of Formula XXX with compounds of Formula VIII, as depicted in Scheme 27. Procedures for this transformation are analogous to those described for Scheme 5.

SCHEME 27

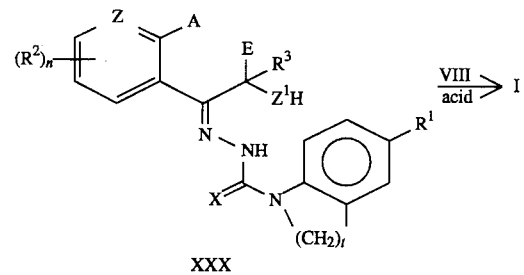

Compounds of Formula XXX can be prepared by the reaction of Formula XI compounds with semicarbazides of Formula XXXI using procedures analogous to those described for Scheme 9. The formation of Formula XXX compounds is depicted in Scheme 28.

SCHEME 26

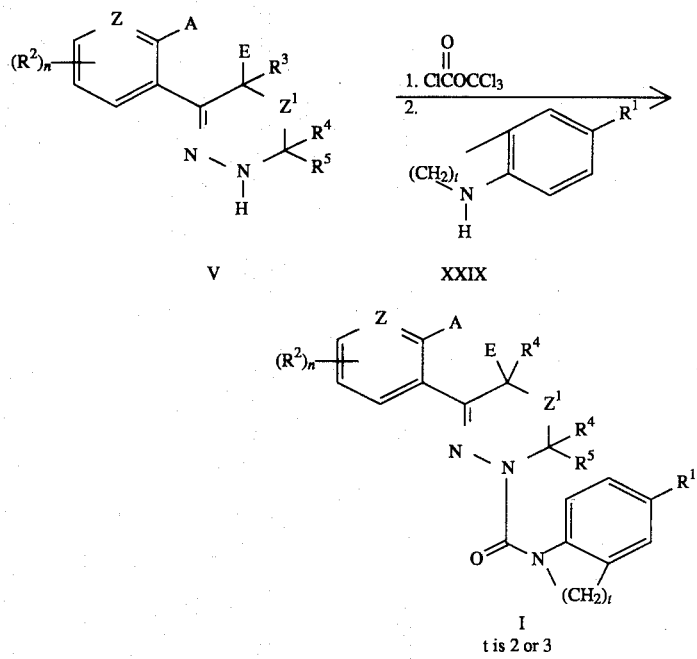

t is 2 or 3

The indoline (t is 2) and tetrahydroquinoline (t is 3) of

SCHEME 28

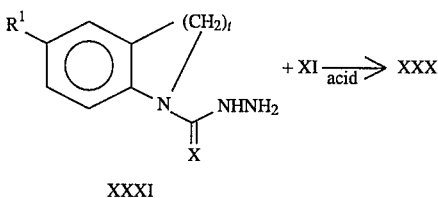

XXXI

The formation of Formula XXXI semicarbazides can be achieved using procedures analogous to those described in Scheme 12 for Formula XII compounds.

Alternatively, compounds of Formula I can be prepared by the reaction of Formula XXXII compounds with anilines of Formula XVII as depicted in Scheme 29.

SCHEME 29

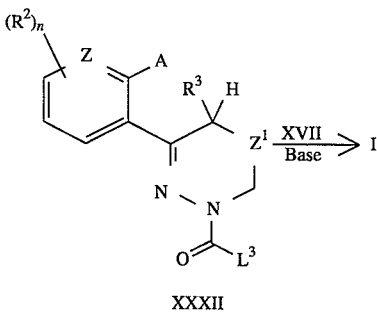

XXXII wherein:

$L^3$ is an alkoxy or aryloxy leaving group and $Z^1$ is O or S.

Typical reaction conditions involve the reaction of XXXII with between 1 to 5 molar equivalents of XVII in a suitable solvent in the presence of 0 to 10 molar equivalents of a base such as pyridine, potassium carbonate or triethylamine. Suitable solvents include THF, DMF and acetonitrile.

Formula XXXII compounds can be prepared by the reaction of a Formula XXXIII compound with an alkyl or aryl chloroformate of Formula XXXIV, as depicted in Scheme 30. The reaction is generally carried out using an excess of one molar equivalent of XXXIV in a non-nucleophilic solvent such as benzene or xylenes. Alternatively, the reaction can be carried out in the absence of solvent. Reactions are generally run at temperatures between 20°–100° C.

SCHEME 30

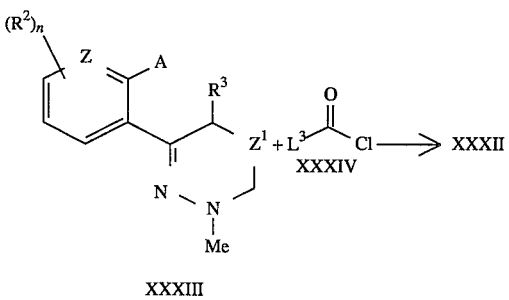

XXXIII wherein:

$L^3$ is an alkoxy or aryloxy group and $Z^1$ is O or S.

Formula XXXIII compounds are oxadiazines and thiadiazines whose preparations are known to the literature (see, e.g., Synthesis, 1988, 208; Synthesis, 1990, 491).

The following Examples further illustrate the invention.

EXAMPLE 1

Step A:
3-Chloro-α-(4-chlorophenyl)benzenepropanoic acid

To a solution of 6.8 g (0.17 mol) of 60% sodium hydride in 150 ml of dimethylformamide under nitrogen was added 30.0 g (0.162 mol) of methyl 4-chlorophenylacetate dropwise such that hydrogen evolution was moderate and the temperature of the reaction was maintained at less than 50° C. Once hydrogen evolution had ceased, a solution of 33.2 g (0.162 m) of 3-chlorobenzylbromide in 30 ml of dimethylformamide was added very cautiously such that the reaction temperature was maintained at less than 60° C. The reaction was maintained at 50° to 60° C. with stirring overnight after which time it was partitioned between 5% aqueous $NaHCO_3$ and diethyl ether, the aqueous extracts were washed twice with ether and the combined organic extracts were then washed with water. The ether extracts were dried over $MgSO_4$, filtered and concentrated to afford 48.0 g of a brown oil.

The crude product was combined with 300 ml of methanol, 40 ml of water and 20 ml of 50% aqueous sodium hydroxide and refluxed overnight. After this time the reaction was concentrated and the crude residue partitioned between water and ether. The aqueous extracts were acidified with conc. hydrochloric acid and extracted several times with ether. The ether extracts were dried over $MgSO_4$, filtered and concentrated to 48.8 g of a yellow, oily solid.

$^1$H NMR (CDCl$_3$) δ3.0 (dd, 1H), 3.3 (m, 1H), 3.84 (t, 1H), 6.77 (d, 1H), 6.9–7.4 (m).

Step B:
5-Chloro-2-(4-chlorophenyl)-2,3-dihydro-1H-inden-1-one

The crude product from Step A was combined with 50 ml of thionyl chloride and then heated at reflux for 2 hours. Thionyl chloride was removed by concentration at reduced pressure and then the mixture was concentrated several times from carbon tetrachloride. The residue was combined with 200 ml of dichloroethane, cooled under nitrogen to 0° C., and 24.5 g of aluminum trichloride was then added. After stirring overnight the reaction was poured onto a mixture of ice in 1N hydrochloric acid, extracted three times with ether and chromatographed on silica gel (10% ethyl acetate/hexane) to afford 18.6 g of a yellow oily solid.

$^1$H NMR (CDCl$_3$) δ3.20 (dd, 1H), 3.68 (dd, 1H), 3.90 (dd, 1H), 6.9–7.6 (m, 6H), 7.75 (d, 1H).

Step C:
5-Chloro-2-(4-chlorophenyl)-2,3-dihydro-2-hydroxy-1H-inden-1-one

A solution of 2.4 g (0.009 moles) of the product obtained from Step B and 20 mL of toluene was added with stirring to a mixture of 1.8 g (0.010 moles) of triethylphosphite, 0.1 g (0.0004 moles) of benzyltriethyl ammonium chloride, 100 mL of toluene and 50 mL of 50% aqueous sodium hydroxide solution. A steady stream of air was introduced into the vigorously stirred reaction mixture at room temperature for 1 hour. The resulting mixture was partitioned between 100 mL of Et$_2$O and 200 mL of water and the aqueous layer was extracted with two 100 mL portions of Et$_2$O. The combined organic layers were washed twice with 100 mL of water, twice with saturated aqueous sodium bisulfite solution, dried over MgSO$_4$ and concentrated. The resulting crude product was chromatographed on silica gel using 2:1 hexanes-ethyl acetate to give 1.2 g of an oil that solidified on standing.

$^1$H NMR (CDCl$_3$) δ3.23 (broadened s, 1H), 3.54 (apparent s, 2H), 7.25 (abq, 4H), 7.44 (d, 1H), 7.53 (broadened s, 1H), 7.78 (d, 1H).

Step D: 2-[5-Chloro-2-(4-chlorophenyl)-2,3-dihydro-2-hydroxy-1H-inden-1-ylidene]-N-[4-(trifluoromethyl)phenyl]hydrazine-carboxamide A solution of 1.0 g (0.003 moles) of the product obtained in Step C, 0.66 mL (0.014 moles) of hydrazine monohydrate and 17 mL of ethanol was heated at reflux for 3 hours. The resulting solution was partitioned between water and CH$_2$Cl$_2$ and the aqueous layer was extracted with CH$_2$Cl$_2$. The combined organic layers were washed twice with water, dried over MgSO$_4$ and concentrated. The residue was chromatographed on silica gel using 1:1 hexanes-ethyl acetate to give 0.53 g of a yellow solid.

A solution of 0.5 g of the above product, 0.24 mL (0.0016 moles) of α,α,α-trifluoro-p-tolyl isocyanate, 25 mL of tetrahydrofuran and 1 mL of water was stirred at room temperature for one hour and then concentrated. The residue was suspended in acetonitrile and concentrated to give 0.60 g of a white solid, melting point, 225° C. (decomposes).

$^1$H NMR (d$_6$-DMSO) δ 3.3 (d, 1H, partially obscured by H$_2$O peak), 3.55 (d, 1H), 7.3–7.5 (m, 7H), 7.64 (d, 2H), 7.82 (d, 2H), 8.00 (d, 1H), 9.52 (broadened s, 1H).

Step E: 7-Chloro-4a-(4-chlorophenyl)-4a,5-dihydro-N-[4-trifluoromethyl)phenyl]-indeno[1,2-e]-[1,3,4]oxadiazine-2(3H)-carboxamide A mixture of 0.30 g (0.0006 moles) of the product obtained in Step D, 0.36 g (0.012 moles) of paraformaldehyde, 50 mg of p-toluene sulfonic acid monohydrate and 30 mL of acetonitrile was refluxed for 1 hour. The resulting mixture was partitioned between CH$_2$Cl$_2$ and saturated aqueous sodium bicarbonate and the aqueous layer was extracted twice with CH$_2$Cl$_2$. The combined organic layers were dried over MgSO$_4$ and concentrated to give an oil that was chromatographed on silica gel using 4:1 hexanes-ethyl acetate to give 0.23 g of an oil that solidified on standing, melting point, 213°–214° C.

$^1$H NMR (CDCl$_3$) δ3.39 (d, 1H), 3.58 (d, 1H), 4.54 (d, 1H), 5.78 (d, 1H), 7.20–7.42 (m, 6H), 7.61 (abq, 4H), 7.72 (d, 1H), 8.58 (broadened s, 1H).

EXAMPLE 2

Step A: Methyl 5-chloro-2,3-dihydro-2-hydroxy-1-oxo-1H-indene-2-carboxylate

Sodium hydride (24 g of 60% solution in oil, 0.6 moles) was washed with hexanes to remove the oil. The resulting washed NaH was suspended in 200 mL of DMF and then treated with a solution of 50 g (0.3 moles) of 5-chloro-1-indanone and 150 mL of DMF at such a rate that reaction temperature remained below 35° C. The resulting mixture was stirred for 30 min and then treated with 38 mL (0.45 moles) of dimethyl carbonate added over 15 min. The resulting mixture was stirred at room temperature for 1.5 h and then allowed to stand overnight. The reaction mixture was poured carefully into a mixture of 100 mL of concentrated HCl and about 1000 mL of ice. Then, 500 mL of ether was added and the aqueous layer was extracted twice with ether. The combined organic layers were washed with three portions of H$_2$O, dried (MgSO$_4$) and concentrated to give 64.6 g of a brown oil.

A solution of 5.0 g (0.022 moles) of the above product and 70 mL of methylene chloride was treated with 10 g (ca. 0.032 moles) of 50–60% m-chloroperbenzoic acid (Aldrich) at room temperature. After 1 h, the reaction was cooled to 0° C. and quenched by careful addition of saturated aqueous sodium carbonate. The layer was washed twice with saturated aqeuous sodium carbonate, once with saturated sodium bisulfite, dried (MgSO$_4$) and concentrated to give 4.0 g of a yellow solid.

IR (CCl$_4$ solution) 3560, 1770, 1745 cm$^{-1}$.

$^1$H NMR (CDCl$_3$, 200 mHz) δ7.73 (d, 1H), 7.50 (br s, 1H), 7.42 (d, 1H), 4.04 (s, 1H, exchangeable with D$_2$O), 3.75 (s, 3H), 3.69 (d, 1H), 3.24 (d, 1H).

Step B: Methyl 5-chloro-2,3-dihydro-2-hydroxy-[[[[4-(trifluoromethoxy)phenyl]amino]carbonyl]hydrozono]-1H-indene-2-carboxylate A solution of 1 g (0.004 moles) of the product from Step A and 10 mL of methanol was added to a solution of 0.61 mL (0.012 moles) of hydrazine monohydrate, 0.72 mL (0.012 moles) of glacial acetic acid and 20 mL of methanol at 0° C. The resulting mixture was refluxed for 2 h, cooled to room temperature and partitioned between 200 mL of methylene chloride and 200 mL of water. The aqueous layer was extracted with methylene chloride and the combined organic layers were washed twice with water, dried (K$_2$CO$_3$) and concentrated to give 0.6 g of a yellow solid.

A solution of 0.5 g (0.002 moles) of the above product and 20 mL of THF was treated with a solution of 0.4 g (0.002 moles) 4-(trifluoromethoxy)phenyl isocyanate and 5 mL of THF. Two drops of water were added and the resulting solution was stirred at room temperature for 30 min. The reaction was then concentrated to give 0.90 g of slightly impure product that was used in the next step without further purification. An analytical sample was prepared by recrystallization from THF-hexanes, mp 233°–235° C.

$^1$H NMR (200 MHz, d$_6$-DMSO) δ9.43 (s, 1H), 9.40 (s, 1H), 7.93 (d, 1H), 7.78 (d, 2H), 7.45 (apparent d, 3H), 7.33 (d, 2H), ca. 3.67 (d, 1H), 3.66 (s, 3H), 3.22 (d, 1H).

Step C: Methyl 7-chloro-2,5-dihydro-2-[[[4-trifluoromethoxy)phenyl]amino]carbonyl] indeno[1,2-e]-[1,3,4]oxadiazine-4a(3H)-carboxylate A mixture of 0.85 g (0.002 moles) of the product from Step B, 0.9 g of paraformaldehyde, 0.05 g of p-toluene sulfonic acid monohydrate and 50 mL of acetonitrile was heated at reflux for 1 h. The resulting mixture was cooled to room temperature and partitioned between CH$_2$Cl$_2$ and saturated aqueous sodium bicarbonate. The aqueous layer was extracted with CH$_2$Cl$_2$ and the combined organics were washed with saturated aqueous NaHCO$_3$, dried (MgSO$_4$) and concentrated. The residue was purified by flash chromatography on silica gel using 4:1 hexanes-EtOAc to give 0.50 g of a pale yellow solid, mp 99°–101° C. Trituration with hot hexanes gave a white solid melting at 126.5°–128.0° C.

$^1$H NMR (200 MHz, CDCl$_3$) δ 8.37 (br s, 1H), 7.66–7.50 (m, 3H), 7.35 (d, 1H), 7.32 (s, 1H), 7.18 (d, 2H), 5.92 (d, 1H), 5.05 (d, 1H), 3.73 (s, 3H), 3.52 (d, 1H), 3.27 (d, 1H).

Step D: Methyl 7-chloro-2,5-dihydro-2-[[N-methyl-N-[4-(trifluoromethoxy)phenyl]amino] carbonyl]-indeno[1,2-e][1,3,4]oxadiazine-4a(3H)-carboxylate A solution of 1.0 g (0.002 moles) of the product from Step C and 10.5 mL of DMF was treated with 0.2 g (0.005 moles) of 60% NaH (in oil) at 0° C. After stirring for 10 min, 1.2 mL (0.02 moles) of iodomethane was added. The resulting mixture was stirred at room temperature for 2 h and then poured into ice-cold 1N HCl and extracted with three portions of ether. The combined organics were washed with water, dried (MgSO$_4$) and concentrated to give a crude yellow solid which was triturated with methanol to give 0.70 g of a yellow solid, mp 130°–131° C.

$^1$H NMR (200 MHz, CDCl$_3$) δ 7.20 (apparent s, 1H), 7.16 (apparent s, 5H), 6.84 (d, 1H), 5.29 (abq, 2H), 3.67 (s, 3H), 3.38 (overlapping d, 1H and s, 3H), 3.13 (d, 1H).

EXAMPLE 3

Step A: Methyl 2-amino-5-chloro-2,3-dihydro-1-oxo-1H-indene-2-carboxylate hydrochloride An ice cold solution of 11.4 g (100.8 mmol) of hydroxylamine-O-sulfonic acid in 102 mL of water and 50 mL of sodium hydroxide solution (2N) was added in one portion to 10 g (102 mmol) of cyclohexanone in 180 mL of toluene and 50 mL of sodium hydroxide solution (2N) at 0° C. The mixture was stirred for 10 minutes. The organic layer was removed and dried over magnesium sulphate. Then, 7 g (31.3 mmol) of methyl 5-chloro-2,3-dihydro-1-oxo-2-1H-indene-2-carboxylate was added to a 155 mL portion of the solution; and 0.1 g (0.89 mmol) DABCO was then added in one portion to the mixture which was stirred for 1 h at 5° C. The mixture was washed twice with 50 mL portions of hydrochloric acid (1N). The acid layer was evaporated under reduced pressure to give 4.37 g of a solid, m.p. 145° to 148° C. (dec).

$^1$H NMR (free base)(200 MHz, CDCl$_3$) δ 7.73 (d, 1H), 7.48 (s, 1H), 7.41 (d, 1H), 3.69 (s, 3H), 3.68 (½ ABq, 1H), and 3.05 (½ ABq, 1H).

Step B: Methyl 2-amino-5-chloro-2,3-dihydro-1-[[[[-4-(trifluoromethoxy)phenyl]amino] carbonyl]-hydrazono]-1H-indene-2-carboxylate A mixture of 2 g (7.24 mmol) of the product from Step A and 1.83 g (7.78 mmol) of 4-(4-trifluoromethoxy)phenylsemicarbazide in 18 mL of ethanol was boiled for 2 h. The mixture was allowed to cool and was stirred at room temperature overnight. The mixture was poured into 200 mL of saturated sodium bicarbonate solution and then extracted with 3×100 mL of ethyl acetate. The combined extracts were dried and evaporated and the material washed with ether to give 1.0 g of an off-white solid, of which a small portion was further purified by chromatography on silica gel (ethyl acetate/ethanol 5:1), m.p. 156.5° to 158° C. (dec).

$^1$H NMR (200 MHz, CDCl$_3$) δ 8.4 (s, 1H), 8.20 (s, 1H), 7.83 (d, 1H), 7.56 (d, 2H), 7.42–7.18 (m, 4H), 3.73–3.65 (m, 4H), 3.05 (½ ABq, 1H).

Step C: 7-chloro-2,3,4,5-tetrahydro-2-[[(4-trifluoromethoxy)phenylamino] carbonyl]-4aH-indeno[2,1-e]-1,2,4-triazine-4a-carboxylic acid, methyl ester A slurry of 0.12 g (6.48 mmol) of Eschenmoser's salt in 3 mL of tetrahydrofuran was added to 0.3 g (6.57 mmol) of the product from Step B in 2 mL of tetrahydrofuran at room temperature. The mixture was stirred at room temperature for 65 h. The mixture was poured into 100 mL of saturated sodium bicarbonate solution and extracted with 3×50 mL of ethyl acetate. The combined extracts were dried and evaporated. Chromatography on silica gel (eluted with ethyl acetate/hexanes 1:1) gave 0.14 g of a white solid, m.p. 135° to 140° C. (dec).

IR (mineral oil): 3372, 3298, 1751, 1658, 1631, 1603, 1535, 1415, 1315, 1266, 1199, 1109, 1009, 967, 919, 889, and 826 cm$^{-1}$.

$^1$H NMR (200 MHz, CDCl$_3$) δ 8.43 (s, 1H), 7.64–7.14 (m, 7H), 5.38 (½ ABq, 1H), 4.39 (½ ABq, 1H), 3.71 (s, H), 3.53 (½ ABq, 1H), 3.08 (½ ABq, 1H), 2.40 (bs, 1H).

By the general procedures described herein, or obvious modifications thereof, the compounds of Tables 1 through 72 can be prepared.

In Tables 1 through 72, the following notations have been used.

Me = CH$_3$ Et = CH$_2$CH$_3$
n-Pr = CH$_2$CH$_2$CH$_3$ i-Pr = CH(CH$_3$)$_2$
n-Bu = CH$_2$CH$_2$CH$_2$CH$_3$ i-Bu = CH$_2$CH(CH$_3$)$_2$
s-Bu = CH(CH$_3$)CH$_2$CH$_3$ t-Bu = C(CH$_3$)$_3$

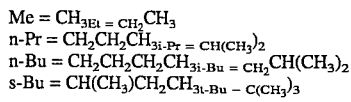

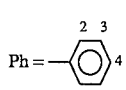 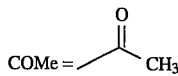

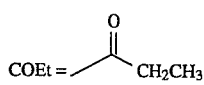 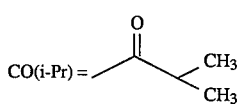

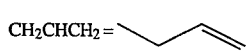 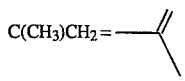

-continued

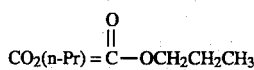
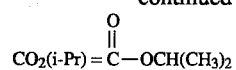

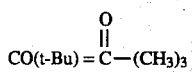
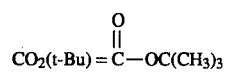

CH₂CCH = CH₂C≡CH

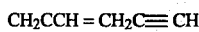
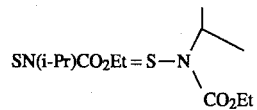

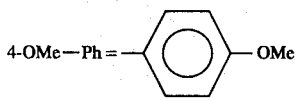
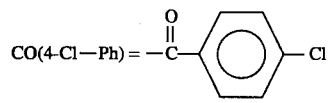

TABLE 1

| R¹ | R³ | Y | R¹ | R³ | Y |
|---|---|---|---|---|---|
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |

TABLE 1-continued

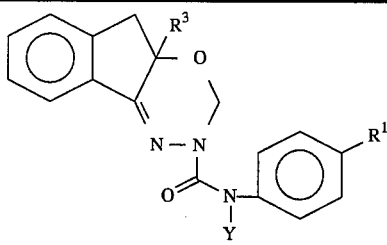

| R¹ | R³ | Y | R¹ | R³ | Y |
|---|---|---|---|---|---|
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |

TABLE 1-continued

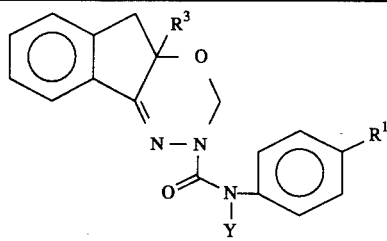

| R¹ | R³ | Y | R¹ | R³ | Y |
|---|---|---|---|---|---|
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |

TABLE 1-continued

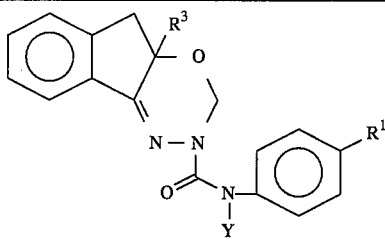

| $R^1$ | $R^3$ | Y | $R^1$ | $R^3$ | Y |
|---|---|---|---|---|---|
| Br | $CO_2Et$ | Me | Cl | $CO_2Et$ | $CO_2Et$ |
| $CF_3$ | $CO_2Et$ | Me | Br | $CO_2Et$ | $CO_2Et$ |
| $OCF_3$ | $CO_2Et$ | Me | $CF_3$ | $CO_2Et$ | $CO_2Et$ |
| Cl | $CO_2Et$ | Et | $OCF_3$ | $CO_2Et$ | $CO_2Et$ |
| Br | $CO_2Et$ | Et | Cl | $CO_2Et$ | $CH_2OMe$ |
| $CF_3$ | $CO_2Et$ | Et | Br | $CO_2Et$ | $CH_2OMe$ |
| $OCF_3$ | $CO_2Et$ | Et | $CF_3$ | $CO_2Et$ | $CH_2OMe$ |
| Cl | $CO_2Et$ | n-Pr | $OCF_3$ | $CO_2Et$ | $CH_2OMe$ |
| Br | $CO_2Et$ | n-Pr | Cl | $CO_2Et$ | $CH_2CHCH_2$ |
| $CF_3$ | $CO_2Et$ | n-Pr | Br | $CO_2Et$ | $CH_2CHCH_2$ |
| $OCF_3$ | $CO_2Et$ | n-Pr | $CF_3$ | $CO_2Et$ | $CH_2CHCH_2$ |
| Cl | $CO_2Et$ | COMe | $OCF_3$ | $CO_2Et$ | $CH_2CHCH_2$ |
| Br | $CO_2Et$ | COMe | Cl | $CO_2Et$ | $CH_2SCH_3$ |
| $CF_3$ | $CO_2Et$ | COMe | Br | $CO_2Et$ | $CH_2SCH_3$ |
| $OCF_3$ | $CO_2Et$ | COMe | $CF_3$ | $CO_2Et$ | $CH_2SCH_3$ |
| Cl | $CO_2Et$ | COEt | $OCF_3$ | $CO_2Et$ | $CH_2SCH_3$ |
| Br | $CO_2Et$ | COEt | $OCF_2H$ | $CO_2Et$ | COEt |
| $CF_3$ | $CO_2Et$ | COEt | $OCF_2H$ | $CO_2Et$ | $CO_2Me$ |
| $OCF_2H$ | $CO_2Et$ | H | $OCF_2H$ | $CO_2Et$ | $CO_2Et$ |
| $OCF_2H$ | $CO_2Et$ | Me | $OCF_2H$ | $CO_2Et$ | $CH_2OMe$ |
| $OCF_2H$ | $CO_2Et$ | Et | $OCF_2H$ | $CO_2Et$ | $CH_2CHCH_2$ |
| $OCF_2H$ | $CO_2Et$ | n-Pr | $OCF_2H$ | $CO_2Et$ | $CH_2SCH_3$ |
| $OCF_2H$ | $CO_2Et$ | COMe | | | |
| Cl | Ph | H | $OCF_3$ | Ph | COEt |
| Br | Ph | H | Cl | Ph | $CO_2Me$ |
| $CF_3$ | Ph | H | Br | Ph | $CO_2Me$ |
| $OCF_3$ | Ph | H | $CF_3$ | Ph | $CO_2Me$ |
| Cl | Ph | Me | $OCF_3$ | Ph | $CO_2Me$ |
| Br | Ph | Me | Cl | Ph | $CO_2Et$ |
| $CF_3$ | Ph | Me | Br | Ph | $CO_2Et$ |
| $OCF_3$ | Ph | Me | $CF_3$ | Ph | $CO_2Et$ |
| Cl | Ph | Et | $OCF_3$ | Ph | $CO_2Et$ |
| Br | Ph | Et | Cl | Ph | $CH_2OMe$ |
| $CF_3$ | Ph | Et | Br | Ph | $CH_2OMe$ |
| $OCF_3$ | Ph | Et | $CF_3$ | Ph | $CH_2OMe$ |
| Cl | Ph | n-Pr | $OCF_3$ | Ph | $CH_2OMe$ |
| Br | Ph | n-Pr | Cl | Ph | $CH_2CHCH_2$ |
| $CF_3$ | Ph | n-Pr | Br | Ph | $CH_2CHCH_2$ |
| $OCF_3$ | Ph | n-Pr | $CF_3$ | Ph | $CH_2CHCH_2$ |
| Cl | Ph | COMe | $OCF_3$ | Ph | $CH_2CHCH_2$ |
| Br | Ph | COMe | Cl | Ph | $CH_2SCH_3$ |
| $CF_3$ | Ph | COMe | Br | Ph | $CH_2SCH_3$ |
| $OCF_3$ | Ph | COMe | $CF_3$ | Ph | $CH_2SCH_3$ |
| Cl | Ph | COEt | $OCF_3$ | Ph | $CH_2SCH_3$ |
| Br | Ph | COEt | $OCF_2H$ | Ph | COEt |
| $CF_3$ | Ph | COEt | $OCF_2H$ | Ph | $CO_2Me$ |
| $OCF_2H$ | Ph | H | $OCF_2H$ | Ph | $CO_2Et$ |
| $OCF_2H$ | Ph | Me | $OCF_2H$ | Ph | $CH_2OMe$ |
| $OCF_2H$ | Ph | Et | $OCF_2H$ | Ph | $CH_2CHCH_2$ |
| $OCF_2H$ | Ph | n-Pr | $OCF_2H$ | Ph | $CH_2SCH_3$ |
| $OCF_2H$ | Ph | COMe | | | |
| Cl | 4-Cl—Ph | H | $OCF_3$ | 4-Cl—Ph | COEt |
| Br | 4-Cl—Ph | H | Cl | 4-Cl—Ph | $CO_2Me$ |
| $CF_3$ | 4-Cl—Ph | H | Br | 4-Cl—Ph | $CO_2Me$ |
| $OCF_3$ | 4-Cl—Ph | H | $CF_3$ | 4-Cl—Ph | $CO_2Me$ |
| Cl | 4-Cl—Ph | Me | $OCF_3$ | 4-Cl—Ph | $CO_2Me$ |
| Br | 4-Cl—Ph | Me | Cl | 4-Cl—Ph | $CO_2Et$ |
| $CF_3$ | 4-Cl—Ph | Me | Br | 4-Cl—Ph | $CO_2Et$ |
| $OCF_3$ | 4-Cl—Ph | Me | $CF_3$ | 4-Cl—Ph | $CO_2Et$ |
| Cl | 4-Cl—Ph | Et | $OCF_3$ | 4-Cl—Ph | $CO_2Et$ |
| Br | 4-Cl—Ph | Et | Cl | 4-Cl—Ph | $CH_2OMe$ |
| $CF_3$ | 4-Cl—Ph | Et | Br | 4-Cl—Ph | $CH_2OMe$ |
| $OCF_3$ | 4-Cl—Ph | Et | $CF_3$ | 4-Cl—Ph | $CH_2OMe$ |
| Cl | 4-Cl—Ph | n-Pr | $OCF_3$ | 4-Cl—Ph | $CH_2OMe$ |
| Br | 4-Cl—Ph | n-Pr | Cl | 4-Cl—Ph | $CH_2CHCH_2$ |

TABLE 1-continued

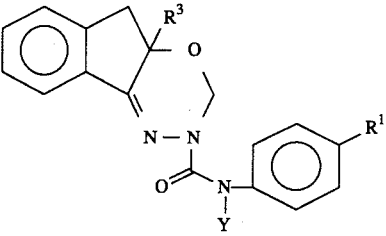

| R¹ | R³ | Y | R¹ | R³ | Y |
|---|---|---|---|---|---|
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |

TABLE 1-continued

| $R^1$ | $R^3$ | Y | $R^1$ | $R^3$ | Y |
|---|---|---|---|---|---|
| $OCF_2H$ | $CHCH_2$ | H | $OCF_2H$ | $CHCH_2$ | $CO_2Et$ |
| $OCF_2H$ | $CHCH_2$ | Me | $OCF_2H$ | $CHCH_2$ | $CH_2OMe$ |
| $OCF_2H$ | $CHCH_2$ | Et | $OCF_2H$ | $CHCH_2$ | $CH_2CHCH_2$ |
| $OCF_2H$ | $CHCH_2$ | n-Pr | $OCF_2H$ | $CHCH_2$ | $CH_2SCH_3$ |
| $OCF_2H$ | $CHCH_2$ | COMe | | | |
| Cl | $C(CH_3)CH_2$ | H | $OCF_3$ | $C(CH_3)CH_2$ | COEt |
| Br | $C(CH_3)CH_2$ | H | Cl | $C(CH_3)CH_2$ | $CO_2Me$ |
| $CF_3$ | $C(CH_3)CH_2$ | H | Br | $C(CH_3)CH_2$ | $CO_2Me$ |
| $OCF_3$ | $C(CH_3)CH_2$ | H | $CF_3$ | $C(CH_3)CH_2$ | $CO_2Me$ |
| Cl | $C(CH_3)CH_2$ | Me | $OCF_3$ | $C(CH_3)CH_2$ | $CO_2Me$ |
| Br | $C(CH_3)CH_2$ | Me | Cl | $C(CH_3)CH_2$ | $CO_2Et$ |
| $CF_3$ | $C(CH_3)CH_2$ | Me | Br | $C(CH_3)CH_2$ | $CO_2Et$ |
| $OCF_3$ | $C(CH_3)CH_2$ | Me | $CF_3$ | $C(CH_3)CH_2$ | $CO_2Et$ |
| Cl | $C(CH_3)CH_2$ | Et | $OCF_3$ | $C(CH_3)CH_2$ | $CO_2Et$ |
| Br | $C(CH_3)CH_2$ | Et | Cl | $C(CH_3)CH_2$ | $CH_2OMe$ |
| $CF_3$ | $C(CH_3)CH_2$ | Et | Br | $C(CH_3)CH_2$ | $CH_2OMe$ |
| $OCF_3$ | $C(CH_3)CH_2$ | Et | $CF_3$ | $C(CH_3)CH_2$ | $CH_2OMe$ |
| Cl | $C(CH_3)CH_2$ | n-Pr | $OCF_3$ | $C(CH_3)CH_2$ | $CH_2OMe$ |
| Br | $C(CH_3)CH_2$ | n-Pr | Cl | $C(CH_3)CH_2$ | $CH_2CHCH_2$ |
| $CF_3$ | $C(CH_3)CH_2$ | n-Pr | Br | $C(CH_3)CH_2$ | $CH_2CHCH_2$ |
| $OCF_3$ | $C(CH_3)CH_2$ | n-Pr | $CF_3$ | $C(CH_3)CH_2$ | $CH_2CHCH_2$ |
| Cl | $C(CH_3)CH_2$ | COMe | $OCF_3$ | $C(CH_3)CH_2$ | $CH_2CHCH_2$ |
| Br | $C(CH_3)CH_2$ | COMe | Cl | $C(CH_3)CH_2$ | $CH_2SCH_3$ |
| $CF_3$ | $C(CH_3)CH_2$ | COMe | Br | $C(CH_3)CH_2$ | $CH_2SCH_3$ |
| $OCF_3$ | $C(CH_3)CH_2$ | COMe | $CF_3$ | $C(CH_3)CH_2$ | $CH_2SCH_3$ |
| Cl | $C(CH_3)CH_2$ | COEt | $OCF_3$ | $C(CH_3)CH_2$ | $CH_2SCH_3$ |
| Br | $C(CH_3)CH_2$ | COEt | $OCF_2H$ | $C(CH_3)CH_2$ | COEt |
| $CF_3$ | $C(CH_3)CH_2$ | COEt | $OCF_2H$ | $C(CH_3)CH_2$ | $CO_2Me$ |
| $OCF_2H$ | $C(CH_3)CH_2$ | H | $OCF_2H$ | $C(CH_3)CH_2$ | $CO_2Et$ |
| $OCF_2H$ | $C(CH_3)CH_2$ | Me | $OCF_2H$ | $C(CH_3)CH_2$ | $CH_2OMe$ |
| $OCF_2H$ | $C(CH_3)CH_2$ | Et | $OCF_2H$ | $C(CH_3)CH_2$ | $CH_2CHCH_2$ |
| $OCF_2H$ | $C(CH_3)CH_2$ | n-Pr | $OCF_2H$ | $C(CH_3)CH_2$ | $CH_2SCH_3$ |
| $OCF_2H$ | $C(CH_3)CH_2$ | COMe | | | |
| $CF_3$ | Me | $CO_2$(n-Pr) | $CF_3$ | n-Pr | $CO_2$(n-Pr) |
| $CF_3$ | Me | $CO_2$(i-Pr) | $CF_3$ | n-Pr | $CO_2$(i-Pr) |
| $CF_3$ | Me | CO(n-Pr) | $CF_3$ | n-Pr | CO(n-Pr) |
| $CF_3$ | Me | CO(i-Pr) | $CF_3$ | n-Pr | CO(i-Pr) |
| $CF_3$ | Me | CO(t-Bu) | $CF_3$ | n-Pr | CO(t-Bu) |
| $CF_3$ | Me | $CO_2$(t-Bu) | $CF_3$ | n-Pr | $CO_2$(t-Bu) |
| $OCF_3$ | Me | $CO_2$(n-Pr) | $OCF_3$ | n-Pr | $CO_2$(n-Pr) |
| $OCF_3$ | Me | $CO_2$(i-Pr) | $OCF_3$ | n-Pr | $CO_2$(i-Pr) |
| $OCF_3$ | Me | CO(n-Pr) | $OCF_3$ | n-Pr | CO(n-Pr) |
| $OCF_3$ | Me | CO(i-Pr) | $OCF_3$ | n-Pr | CO(i-Pr) |
| $OCF_3$ | Me | CO(t-Bu) | $OCF_3$ | n-Pr | CO(t-Bu) |
| $OCF_3$ | Me | $CO_2$(t-Bu) | $OCF_3$ | n-Pr | $CO_2$(t-Bu) |
| $CF_3$ | Et | $CO_2$(n-Pr) | $CF_3$ | i-Pr | $CO_2$(n-Pr) |
| $CF_3$ | Et | $CO_2$(i-Pr) | $CF_3$ | i-Pr | $CO_2$(i-Pr) |
| $CF_3$ | Et | CO(n-Pr) | $CF_3$ | i-Pr | CO(n-Pr) |
| $CF_3$ | Et | CO(i-Pr) | $CF_3$ | i-Pr | CO(i-Pr) |
| $CF_3$ | Et | CO(t-Bu) | $CF_3$ | i-Pr | CO(t-Bu) |
| $CF_3$ | Et | $CO_2$(t-Bu) | $CF_3$ | i-Pr | $CO_2$(t-Bu) |
| $OCF_3$ | Et | $CO_2$(n-Pr) | $OCF_3$ | i-Pr | $CO_2$(n-Pr) |
| $OCF_3$ | Et | $CO_2$(i-Pr) | $OCF_3$ | i-Pr | $CO_2$(i-Pr) |
| $OCF_3$ | Et | CO(n-Pr) | $OCF_3$ | i-Pr | CO(n-Pr) |
| $OCF_3$ | Et | CO(i-Pr) | $OCF_3$ | i-Pr | CO(i-Pr) |
| $OCF_3$ | Et | CO(t-Bu) | $OCF_3$ | i-Pr | CO(t-Bu) |
| $OCF_3$ | Et | $CO_2$(t-Bu) | $OCF_3$ | i-Pr | $CO_2$(t-Bu) |
| $OCF_2H$ | Me | CO(n-Pr) | $OCF_2H$ | Et | CO(i-Pr) |
| $OCF_2H$ | Me | $CO_2$(n-Pr) | $OCF_2H$ | Et | $CO_2$(i-Pr) |
| $OCF_2H$ | Me | CO(i-Pr) | $OCF_2H$ | Et | CO(t-Bu) |
| $OCF_2H$ | Me | $CO_2$(i-Pr) | $OCF_2H$ | Et | $CO_2$(t-Bu) |
| $OCF_2H$ | Me | CO(t-Bu) | $OCF_2H$ | n-Pr | CO(n-Pr) |
| $OCF_2H$ | Me | $CO_2$(t-Bu) | $OCF_2H$ | n-Pr | $CO_2$(n-Pr) |
| $OCF_2H$ | Et | CO(n-Pr) | $OCF_2H$ | n-Pr | CO(i-Pr) |
| $OCF_2H$ | Et | $CO_2$(n-Pr) | $OCF_2H$ | n-Pr | $CO_2$(i-Pr) |

TABLE 1-continued

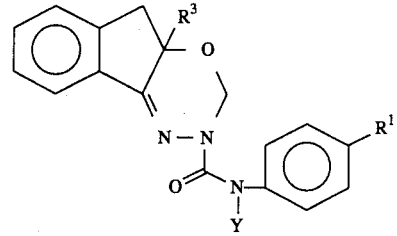

| R¹ | R³ | Y | R¹ | R³ | Y |
|---|---|---|---|---|---|
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂He | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(i-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(i-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(i-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂(i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 2

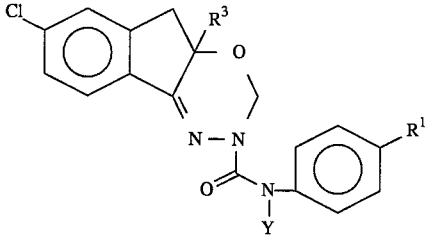

| R¹ | R³ | Y | R¹ | R³ | Y |
|---|---|---|---|---|---|
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |

TABLE 2-continued

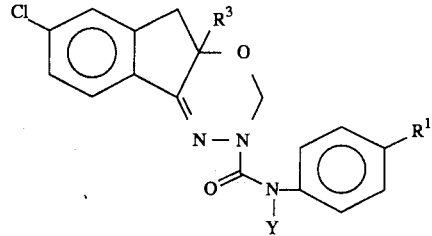

| R¹ | R³ | Y | R¹ | R³ | Y |
|---|---|---|---|---|---|
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |

TABLE 2-continued

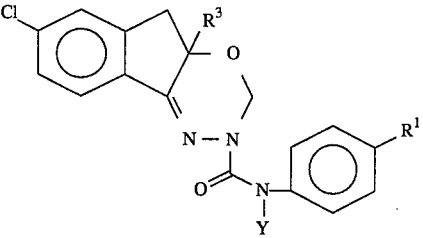

| R¹ | R³ | Y | R¹ | R³ | Y |
|---|---|---|---|---|---|
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |

TABLE 2-continued

| R¹ | R³ | Y | R¹ | R³ | Y |
|---|---|---|---|---|---|
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |

TABLE 2-continued

| R¹ | R³ | Y | R¹ | R³ | Y |
|---|---|---|---|---|---|
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |

TABLE 2-continued

[Structure: 5-chloro-indanone with R³ and O-ethyl substituents, connected via N-N-C(=O)-N(Y)-phenyl-R¹]

| R¹ | R³ | Y | R¹ | R³ | Y |
|---|---|---|---|---|---|
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |
| Br | C(CH₃)CH₂ | COEt | OCF₂H | C(CH₃)CH₂ | COEt |
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |

TABLE 2-continued

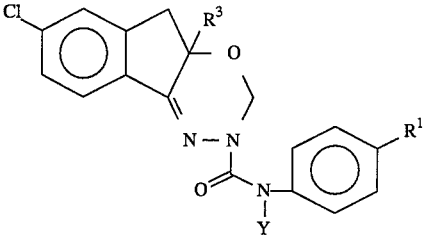

| R¹ | R³ | Y | R¹ | R³ | Y |
| --- | --- | --- | --- | --- | --- |
| OCF₃ | CO₂He | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(i-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(i-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(i-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂(i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 3

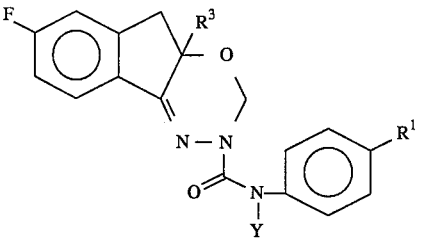

| R¹ | R³ | Y | R¹ | R³ | Y |
| --- | --- | --- | --- | --- | --- |
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |

TABLE 3-continued

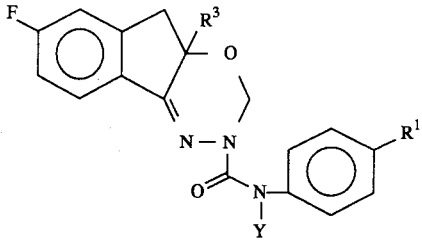

| R¹ | R³ | Y | R¹ | R³ | Y |
|---|---|---|---|---|---|
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |

TABLE 3-continued

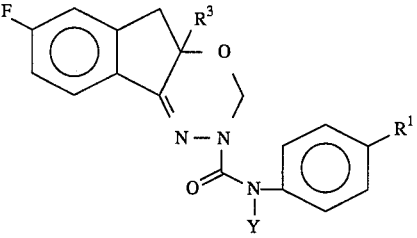

| R¹ | R³ | Y | R¹ | R³ | Y |
|---|---|---|---|---|---|
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |

TABLE 3-continued

| R¹ | R³ | Y | R¹ | R³ | Y |
|---|---|---|---|---|---|
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |

TABLE 3-continued

| R¹ | R³ | Y | R¹ | R³ | Y |
|---|---|---|---|---|---|
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |

TABLE 3-continued

| R¹ | R³ | Y | R¹ | R³ | Y |
|---|---|---|---|---|---|
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |

TABLE 3-continued

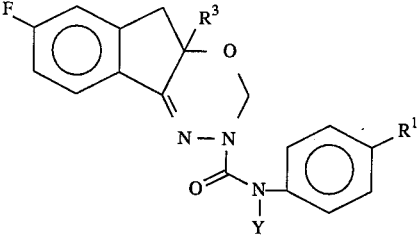

| R¹ | R³ | Y | R¹ | R³ | Y |
|---|---|---|---|---|---|
| Br | C(CH₃)CH₂ | COEt | OCF₂H | C(CH₃)CH₂ | COEt |
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂He | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |

TABLE 3-continued

[Structure: 5-fluoro indanone derivative with R³, OEt, N–N, C(=O)N(Y)–phenyl-R¹]

| R¹ | R³ | Y | R¹ | R³ | Y |
|---|---|---|---|---|---|
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(i-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(i-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(t-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂(i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 4

[Structure: 5-trifluoromethyl indanone derivative with R³, OEt, N–N, C(=O)N(Y)–phenyl-R¹]

| R¹ | R³ | Y | R¹ | R³ | Y |
|---|---|---|---|---|---|
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |

TABLE 4-continued

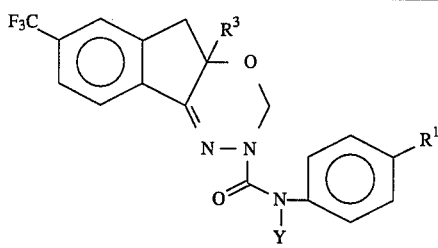

| R¹ | R³ | Y | R¹ | R³ | Y |
|---|---|---|---|---|---|
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |

TABLE 4-continued

| R¹ | R³ | Y | R¹ | R³ | Y |
|---|---|---|---|---|---|
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |

TABLE 4-continued

| R¹ | R³ | Y | R¹ | R³ | Y |
|---|---|---|---|---|---|
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |

TABLE 4-continued

| R¹ | R³ | Y | R¹ | R³ | Y |
|---|---|---|---|---|---|
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |

TABLE 4-continued

| R$^1$ | R$^3$ | Y | R$^1$ | R$^3$ | Y |
|---|---|---|---|---|---|
| Cl | 4-F—Ph | COMe | OCF$_3$ | 4-F—Ph | CH$_2$CHCH$_2$ |
| Br | 4-F—Ph | COMe | Cl | 4-F—Ph | CH$_2$SCH$_3$ |
| CF$_3$ | 4-F—Ph | COMe | Br | 4-F—Ph | CH$_2$SCH$_3$ |
| OCF$_3$ | 4-F—Ph | COMe | CF$_3$ | 4-F—Ph | CH$_2$SCH$_3$ |
| Cl | 4-F—Ph | COEt | OCF$_3$ | 4-F—Ph | CH$_2$SCH$_3$ |
| Br | 4-F—Ph | COEt | OCF$_2$H | 4-F—Ph | COEt |
| CF$_3$ | 4-F—Ph | COEt | OCF$_2$H | 4-F—Ph | CO$_2$Me |
| OCF$_2$H | 4-F—Ph | H | OCF$_2$H | 4-F—Ph | CO$_2$Et |
| OCF$_2$H | 4-F—Ph | Me | OCF$_2$H | 4-F—Ph | CH$_2$OMe |
| OCF$_2$H | 4-F—Ph | Et | OCF$_2$H | 4-F—Ph | CH$_2$CHCH$_2$ |
| OCF$_2$H | 4-F—Ph | n-Pr | OCF$_2$H | 4-F—Ph | CH$_2$SCH$_3$ |
| OCF$_2$H | 4-F—Ph | COMe | | | |
| Cl | CHCH$_2$ | H | OCF$_3$ | CHCH$_2$ | COEt |
| Br | CHCH$_2$ | H | Cl | CHCH$_2$ | CO$_2$Me |
| CF$_3$ | CHCH$_2$ | H | Br | CHCH$_2$ | CO$_2$Me |
| OCF$_3$ | CHCH$_2$ | H | CF$_3$ | CHCH$_2$ | CO$_2$Me |
| Cl | CHCH$_2$ | Me | OCF$_3$ | CHCH$_2$ | CO$_2$Me |
| Br | CHCH$_2$ | Me | Cl | CHCH$_2$ | CO$_2$Et |
| CF$_3$ | CHCH$_2$ | Me | Br | CHCH$_2$ | CO$_2$Et |
| OCF$_3$ | CHCH$_2$ | Me | CF$_3$ | CHCH$_2$ | CO$_2$Et |
| Cl | CHCH$_2$ | Et | OCF$_3$ | CHCH$_2$ | CO$_2$Et |
| Br | CHCH$_2$ | Et | Cl | CHCH$_2$ | CH$_2$OMe |
| CF$_3$ | CHCH$_2$ | Et | Br | CHCH$_2$ | CH$_2$OMe |
| OCF$_3$ | CHCH$_2$ | Et | CF$_3$ | CHCH$_2$ | CH$_2$OMe |
| Cl | CHCH$_2$ | n-Pr | OCF$_3$ | CHCH$_2$ | CH$_2$OMe |
| Br | CHCH$_2$ | n-Pr | Cl | CHCH$_2$ | CH$_2$CHCH$_2$ |
| CF$_3$ | CHCH$_2$ | n-Pr | Br | CHCH$_2$ | CH$_2$CHCH$_2$ |
| OCF$_3$ | CHCH$_2$ | n-Pr | CF$_3$ | CHCH$_2$ | CH$_2$CHCH$_2$ |
| Cl | CHCH$_2$ | COMe | OCF$_3$ | CHCH$_2$ | CH$_2$CHCH$_2$ |
| Br | CHCH$_2$ | COMe | Cl | CHCH$_2$ | CH$_2$SCH$_3$ |
| CF$_3$ | CHCH$_2$ | COMe | Br | CHCH$_2$ | CH$_2$SCH$_3$ |
| OCF$_3$ | CHCH$_2$ | COMe | CF$_3$ | CHCH$_2$ | CH$_2$SCH$_3$ |
| Cl | CHCH$_2$ | COEt | OCF$_3$ | CHCH$_2$ | CH$_2$SCH$_3$ |
| Br | CHCH$_2$ | COEt | OCF$_2$H | CHCH$_2$ | COEt |
| CF$_3$ | CHCH$_2$ | COEt | OCF$_2$H | CHCH$_2$ | CO$_2$Me |
| OCF$_2$H | CHCH$_2$ | H | OCF$_2$H | CHCH$_2$ | CO$_2$Et |
| OCF$_2$H | CHCH$_2$ | Me | OCF$_2$H | CHCH$_2$ | CH$_2$OMe |
| OCF$_2$H | CHCH$_2$ | Et | OCF$_2$H | CHCH$_2$ | CH$_2$CHCH$_2$ |
| OCF$_2$H | CHCH$_2$ | n-Pr | OCF$_2$H | CHCH$_2$ | CH$_2$SCH$_3$ |
| OCF$_2$H | CHCH$_2$ | COMe | | | |
| Cl | C(CH$_3$)CH$_2$ | H | OCF$_3$ | C(CH$_3$)CH$_2$ | COEt |
| Br | C(CH$_3$)CH$_2$ | H | Cl | C(CH$_3$)CH$_2$ | CO$_2$Me |
| CF$_3$ | C(CH$_3$)CH$_2$ | H | Br | C(CH$_3$)CH$_2$ | CO$_2$Me |
| OCF$_3$ | C(CH$_3$)CH$_2$ | H | CF$_3$ | C(CH$_3$)CH$_2$ | CO$_2$Me |
| Cl | C(CH$_3$)CH$_2$ | Me | OCF$_3$ | C(CH$_3$)CH$_2$ | CO$_2$Me |
| Br | C(CH$_3$)CH$_2$ | Me | Cl | C(CH$_3$)CH$_2$ | CO$_2$Et |
| CF$_3$ | C(CH$_3$)CH$_2$ | Me | Br | C(CH$_3$)CH$_2$ | CO$_2$Et |
| OCF$_3$ | C(CH$_3$)CH$_2$ | Me | CF$_3$ | C(CH$_3$)CH$_2$ | CO$_2$Et |
| Cl | C(CH$_3$)CH$_2$ | Et | OCF$_3$ | C(CH$_3$)CH$_2$ | CO$_2$Et |
| Br | C(CH$_3$)CH$_2$ | Et | Cl | C(CH$_3$)CH$_2$ | CH$_2$OMe |
| CF$_3$ | C(CH$_3$)CH$_2$ | Et | Br | C(CH$_3$)CH$_2$ | CH$_2$OMe |
| OCF$_3$ | C(CH$_3$)CH$_2$ | Et | CF$_3$ | C(CH$_3$)CH$_2$ | CH$_2$OMe |
| Cl | C(CH$_3$)CH$_2$ | n-Pr | OCF$_3$ | C(CH$_3$)CH$_2$ | CH$_2$OMe |
| Br | C(CH$_3$)CH$_2$ | n-Pr | Cl | C(CH$_3$)CH$_2$ | CH$_2$CHCH$_2$ |
| CF$_3$ | C(CH$_3$)CH$_2$ | n-Pr | Br | C(CH$_3$)CH$_2$ | CH$_2$CHCH$_2$ |
| OCF$_3$ | C(CH$_3$)CH$_2$ | n-Pr | CF$_3$ | C(CH$_3$)CH$_2$ | CH$_2$CHCH$_2$ |
| Cl | C(CH$_3$)CH$_2$ | COMe | OCF$_3$ | C(CH$_3$)CH$_2$ | CH$_2$CHCH$_2$ |
| Br | C(CH$_3$)CH$_2$ | COMe | Cl | C(CH$_3$)CH$_2$ | CH$_2$SCH$_3$ |
| CF$_3$ | C(CH$_3$)CH$_2$ | COMe | Br | C(CH$_3$)CH$_2$ | CH$_2$SCH$_3$ |
| OCF$_3$ | C(CH$_3$)CH$_2$ | COMe | CF$_3$ | C(CH$_3$)CH$_2$ | CH$_2$SCH$_3$ |
| Cl | C(CH$_3$)CH$_2$ | COEt | OCF$_3$ | C(CH$_3$)CH$_2$ | CH$_2$SCH$_3$ |
| Br | C(CH$_3$)CH$_2$ | COEt | OCF$_2$H | C(CH$_3$)CH$_2$ | COEt |
| CF$_3$ | C(CH$_3$)CH$_2$ | COEt | OCF$_2$H | C(CH$_3$)CH$_2$ | CO$_2$Me |
| OCF$_2$H | C(CH$_3$)CH$_2$ | H | OCF$_2$H | C(CH$_3$)CH$_2$ | CO$_2$Et |
| OCF$_2$H | C(CH$_3$)CH$_2$ | Me | OCF$_2$H | C(CH$_3$)CH$_2$ | CH$_2$OMe |

TABLE 4-continued

| R¹ | R³ | Y | R¹ | R³ | Y |
|---|---|---|---|---|---|
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |

TABLE 4-continued

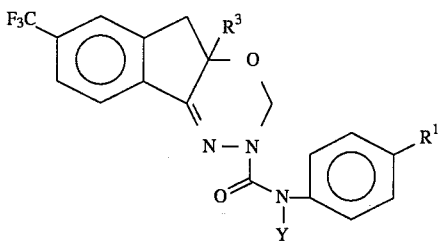

| $R^1$ | $R^3$ | Y | $R^1$ | $R^3$ | Y |
|---|---|---|---|---|---|
| $OCF_2H$ | i-Pr | CO(n-Pr) | $OCF_2H$ | $CO_2Et$ | CO(n-Pr) |
| $OCF_2H$ | i-Pr | $CO_2$(n-Pr) | $OCF_2H$ | $CO_2Et$ | $CO_2$(n-Pr) |
| $CF_3$ | 4-Cl—Ph | $CO_2$(n-Pr) | $CF_3$ | $CHCH_2$ | $CO_2$(n-Pr) |
| $CF_3$ | 4-Cl—Ph | $CO_2$(i-Pr) | $CF_3$ | $CHCH_2$ | $CO_2$(i-Pr) |
| $CF_3$ | 4-Cl—Ph | CO(n-Pr) | $CF_3$ | $CHCH_2$ | CO(n-Pr) |
| $CF_3$ | 4-Cl—Ph | CO(i-Pr) | $CF_3$ | $CHCH_2$ | CO(i-Pr) |
| $CF_3$ | 4-Cl—Ph | CO(t-Bu) | $CF_3$ | $CHCH_2$ | CO(t-Bu) |
| $CF_3$ | 4-Cl—Ph | $CO_2$(t-Bu) | $CF_3$ | $CHCH_2$ | $CO_2$(t-Bu) |
| $OCF_3$ | 4-Cl—Ph | $CO_2$(n-Pr) | $OCF_3$ | $CHCH_2$ | $CO_2$(n-Pr) |
| $OCF_3$ | 4-Cl—Ph | $CO_2$(i-Pr) | $OCF_3$ | $CHCH_2$ | $CO_2$(i-Pr) |
| $OCF_3$ | 4-Cl—Ph | CO(n-Pr) | $OCF_3$ | $CHCH_2$ | CO(n-Pr) |
| $OCF_3$ | 4-Cl—Ph | CO(i-Pr) | $OCF_3$ | $CHCH_2$ | CO(i-Pr) |
| $OCF_3$ | 4-Cl—Ph | CO(t-Bu) | $OCF_3$ | $CHCH_2$ | CO(t-Bu) |
| $OCF_3$ | 4-Cl—Ph | $CO_2$(t-Bu) | $OCF_3$ | $CHCH_2$ | $CO_2$(t-Bu) |
| $CF_3$ | 4-F—Ph | $CO_2$(n-Pr) | $CF_3$ | $C(CH_3)CH_2$ | $CO_2$(n-Pr) |
| $CF_3$ | 4-F—Ph | $CO_2$(i-Pr) | $CF_3$ | $C(CH_3)CH_2$ | $CO_2$(i-Pr) |
| $CF_3$ | 4-F—Ph | CO(n-Pr) | $CF_3$ | $C(CH_3)CH_2$ | CO(n-Pr) |
| $CF_3$ | 4-F—Ph | CO(i-Pr) | $CF_3$ | $C(CH_3)CH_2$ | CO(i-Pr) |
| $CF_3$ | 4-F—Ph | CO(t-Bu) | $CF_3$ | $C(CH_3)CH_2$ | CO(t-Bu) |
| $CF_3$ | 4-F—Ph | $CO_2$(t-Bu) | $CF_3$ | $C(CH_3)CH_2$ | $CO_2$(t-Bu) |
| $OCF_3$ | 4-F—Ph | $CO_2$(n-Pr) | $OCF_3$ | $C(CH_3)CH_2$ | $CO_2$(n-Pr) |
| $OCF_3$ | 4-F—Ph | $CO_2$(i-Pr) | $OCF_3$ | $C(CH_3)CH_2$ | $CO_2$(i-Pr) |
| $OCF_3$ | 4-F—Ph | CO(n-Pr) | $OCF_3$ | $C(CH_3)CH_2$ | CO(n-Pr) |
| $OCF_3$ | 4-F—Ph | CO(i-Pr) | $OCF_3$ | $C(CH_3)CH_2$ | CO(i-Pr) |
| $OCF_3$ | 4-F—Ph | CO(t-Bu) | $OCF_3$ | $C(CH_3)CH_2$ | CO(t-Bu) |
| $OCF_3$ | 4-F—Ph | $CO_2$(t-Bu) | $OCF_3$ | $C(CH_3)CH_2$ | $CO_2$(t-Bu) |
| $OCF_2H$ | $CO_2Et$ | CO(i-Pr) | $OCF_2H$ | 4-Cl—Ph | CO(t-Bu) |
| $OCF_2H$ | $CO_2Et$ | $CO_2$(i-Pr) | $OCF_2H$ | 4-Cl—Ph | $CO_2$(t-Bu) |
| $OCF_2H$ | $CO_2Et$ | CO(t-Bu) | $OCF_2H$ | 4-F—Ph | CO(n-Pr) |
| $OCF_2H$ | $CO_2Et$ | $CO_2$(t-Bu) | $OCF_2H$ | 4-F—Ph | $CO_2$(n-Pr) |
| $OCF_2H$ | 4-Cl—Ph | CO(n-Pr) | $OCF_2H$ | 4-F—Ph | CO(i-Pr) |
| $OCF_2H$ | 4-Cl—Ph | $CO_2$(n-Pr) | $OCF_2H$ | 4-F—Ph | $CO_2$(i-Pr) |
| $OCF_2H$ | 4-Cl—Ph | CO(i-Pr) | $OCF_2H$ | 4-F—Ph | CO(t-Bu) |
| $OCF_2H$ | 4-Cl—Ph | $CO_2$(i-Pr) | $OCF_2H$ | 4-F—Ph | $CO_2$(t-Bu) |

TABLE 5

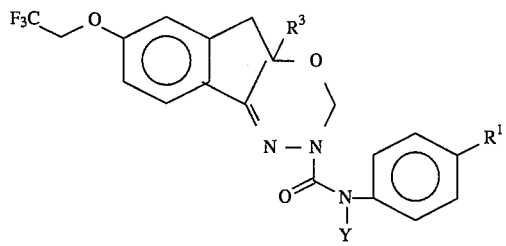

| $R^1$ | $R^3$ | Y | $R^1$ | $R^3$ | Y |
|---|---|---|---|---|---|
| Cl | Me | H | $OCF_3$ | Me | COEt |
| Br | Me | H | Cl | Me | $CO_2Me$ |
| $CF_3$ | Me | H | Br | Me | $CO_2Me$ |
| $OCF_3$ | Me | H | $CF_3$ | Me | $CO_2Me$ |
| Cl | Me | Me | $OCF_3$ | Me | $CO_2Me$ |
| Br | Me | Me | Cl | Me | $CO_2Et$ |
| $CF_3$ | Me | Me | Br | Me | $CO_2Et$ |
| $OCF_3$ | Me | Me | $CF_3$ | Me | $CO_2Et$ |
| Cl | Me | Et | $OCF_3$ | Me | $CO_2Et$ |
| Br | Me | Et | Cl | Me | $CH_2OMe$ |
| $CF_3$ | Me | Et | Br | Me | $CH_2OMe$ |
| $OCF_3$ | Me | Et | $CF_3$ | Me | $CH_2OMe$ |

TABLE 5-continued

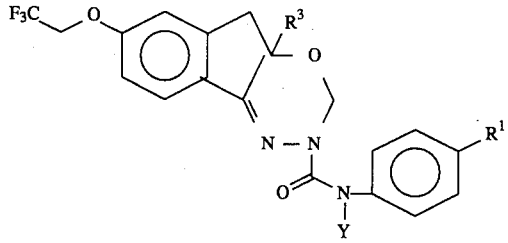

| R¹ | R³ | Y | R¹ | R³ | Y |
|---|---|---|---|---|---|
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | Me | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |

TABLE 5-continued

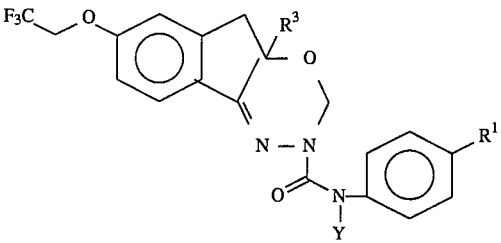

| R¹ | R³ | Y | R¹ | R³ | Y |
|---|---|---|---|---|---|
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |

TABLE 5-continued

| R¹ | R³ | Y | R¹ | R³ | Y |
|---|---|---|---|---|---|
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |

TABLE 5-continued

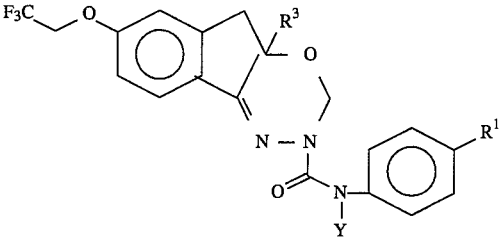

| R¹ | R³ | Y | R¹ | R³ | Y |
|---|---|---|---|---|---|
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |

TABLE 5-continued

[Structure: indanone derivative with F₃C-CH₂-O- substituent on aromatic ring, R³ and O-ethyl on sp3 carbon, =N-N(C(=O)-N(Y)-C₆H₄-R¹) group]

| R¹ | R³ | Y | R¹ | R³ | Y |
|---|---|---|---|---|---|
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | Me | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |
| Br | C(CH₃)CH₂ | COEt | OCF₂H | C(CH₃)CH₂ | COEt |
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |

TABLE 5-continued

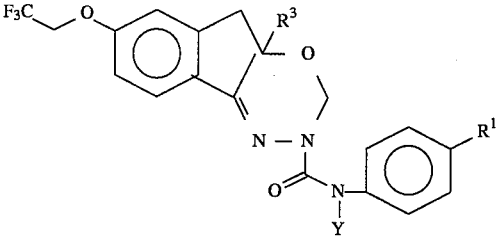

| R¹ | R³ | Y | R¹ | R³ | Y |
|---|---|---|---|---|---|
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |

TABLE 5-continued

| R¹ | R³ | Y | R¹ | R³ | Y |
|---|---|---|---|---|---|
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(i-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(i-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(i-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂(i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 6

| R¹ | R³ | Y | R¹ | R³ | Y |
|---|---|---|---|---|---|
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |

TABLE 6-continued

| R¹ | R³ | Y | R¹ | R³ | Y |
|---|---|---|---|---|---|
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | OCF₃ | n-Pr | COEt |
| OCF₂H | Et | CH₂CHCH₂ | Cl | n-Pr | CO₂Me |
| Cl | n-Pr | H | Br | n-Pr | CO₂Me |
| Br | n-Pr | H | CF₃ | n-Pr | CO₂Me |
| CF₃ | n-Pr | H | OCF₃ | n-Pr | CO₂Me |
| OCF₃ | n-Pr | H | Cl | n-Pr | CO₂Et |
| Cl | n-Pr | Me | Br | n-Pr | CO₂Et |
| Br | n-Pr | Me | CF₃ | n-Pr | CO₂Et |
| CF₃ | n-Pr | Me | OCF₃ | n-Pr | CO₂Et |
| OCF₃ | n-Pr | Me | Cl | n-Pr | CH₂OMe |
| Cl | n-Pr | Et | Br | n-Pr | CH₂OMe |
| Br | n-Pr | Et | CF₃ | n-Pr | CH₂OMe |
| CF₃ | n-Pr | Et | OCF₃ | n-Pr | CH₂OMe |
| OCF₃ | n-Pr | Et | Cl | n-Pr | CH₂CHCH₂ |
| Cl | n-Pr | n-Pr | Br | n-Pr | CH₂CHCH₂ |
| Br | n-Pr | n-Pr | CF₃ | n-Pr | CH₂CHCH₂ |
| CF₃ | n-Pr | n-Pr | OCF₃ | n-Pr | CH₂CHCH₂ |
| OCF₃ | n-Pr | n-Pr | Cl | n-Pr | CH₂SCH₃ |
| Cl | n-Pr | COMe | Br | n-Pr | CH₂SCH₃ |
| Br | n-Pr | COMe | CF₃ | n-Pr | CH₂SCH₃ |
| CF₃ | n-Pr | COMe | OCF₃ | n-Pr | CH₂SCH₃ |
| OCF₃ | n-Pr | COMe | OCF₂H | n-Pr | COEt |
| Cl | n-Pr | COEt | OCF₂H | n-Pr | CO₂Me |
| Br | n-Pr | COEt | OCF₂H | n-Pr | CO₂Et |

TABLE 6-continued

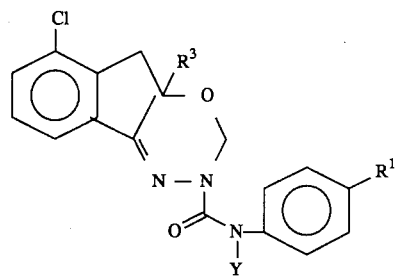

| R¹ | R³ | Y | R¹ | R³ | Y |
|---|---|---|---|---|---|
| CF₃ | n-Pr | COEt | OCF₂H | n-Pr | CH₂OMe |
| OCF₂H | n-Pr | H | OCF₂H | n-Pr | CH₂CHCH₂ |
| OCF₂H | n-Pr | Me | OCF₂H | n-Pr | CH₂SCH₃ |
| OCF₂H | n-Pr | Et | | | |
| OCF₂H | n-Pr | n-Pr | | | |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |

TABLE 6-continued

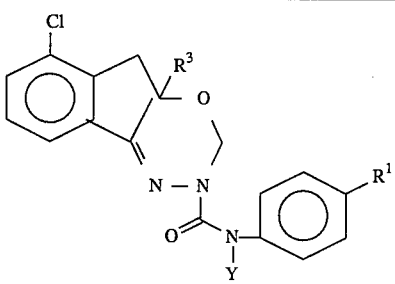

| R¹ | R³ | Y | R¹ | R³ | Y |
|---|---|---|---|---|---|
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |

TABLE 6-continued

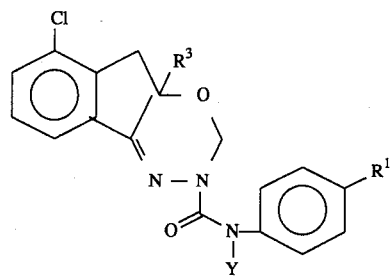

| R¹ | R³ | Y | R¹ | R³ | Y |
|---|---|---|---|---|---|
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |

TABLE 6-continued

[Chemical structure: 4-chloro-indane fused system with R³ substituent, connected via C=N-N(C(=O)N(Y)-phenyl-R¹) with OCH₂CH₂ ether bridge]

| R¹ | R³ | Y | R¹ | R³ | Y |
|---|---|---|---|---|---|
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |
| Br | C(CH₃)CH₂ | COEt | OCF₂H | C(CH₃)CH₂ | COEt |

TABLE 6-continued

| R¹ | R³ | Y | R¹ | R³ | Y |
|---|---|---|---|---|---|
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |

TABLE 6-continued

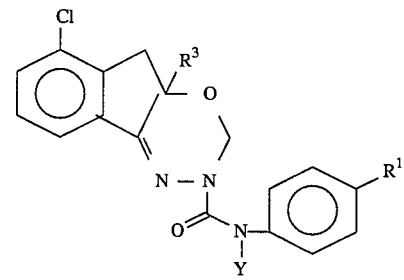

| R¹ | R³ | Y | R¹ | R³ | Y |
|---|---|---|---|---|---|
| $OCF_2H$ | n-Pr | $CO_2$(t-Bu) | $OCF_2H$ | $CO_2Me$ | $CO_2$(i-Pr) |
| $OCF_2H$ | i-Pr | CO(i-Pr) | $OCF_2H$ | $CO_2Me$ | CO(t-Bu) |
| $OCF_2H$ | i-Pr | $CO_2$(i-Pr) | $OCF_2H$ | $CO_2Me$ | $CO_2$(t-Bu) |
| $OCF_2H$ | i-Pr | CO(t-Bu) | $OCF_2H$ | $CO_2Me$ | CO(n-Pr) |
| $OCF_2H$ | i-Pr | $CO_2$(t-Bu) | $OCF_2H$ | $CO_2Me$ | $CO_2$(n-Pr) |
| $OCF_2H$ | i-Pr | CO(n-Pr) | $OCF_2H$ | $CO_2Et$ | CO(n-Pr) |
| $OCF_2H$ | i-Pr | $CO_2$(n-Pr) | $OCF_2H$ | $CO_2Et$ | $CO_2$(n-Pr) |
| $CF_3$ | 4-Cl—Ph | $CO_2$(n-Pr) | $CF_3$ | $CHCH_2$ | $CO_2$(n-Pr) |
| $CF_3$ | 4-Cl—Ph | $CO_2$(i-Pr) | $CF_3$ | $CHCH_2$ | $CO_2$(i-Pr) |
| $CF_3$ | 4-Cl—Ph | CO(n-Pr) | $CF_3$ | $CHCH_2$ | CO(n-Pr) |
| $CF_3$ | 4-Cl—Ph | CO(i-Pr) | $CF_3$ | $CHCH_2$ | CO(i-Pr) |
| $CF_3$ | 4-Cl—Ph | CO(t-Bu) | $CF_3$ | $CHCH_2$ | CO(t-Bu) |
| $CF_3$ | 4-Cl—Ph | $CO_2$(t-Bu) | $CF_3$ | $CHCH_2$ | $CO_2$(t-Bu) |
| $OCF_3$ | 4-Cl—Ph | $CO_2$(n-Pr) | $OCF_3$ | $CHCH_2$ | $CO_2$(n-Pr) |
| $OCF_3$ | 4-Cl—Ph | $CO_2$(i-Pr) | $OCF_3$ | $CHCH_2$ | $CO_2$(n-Pr) |
| $OCF_3$ | 4-Cl—Ph | CO(n-Pr) | $OCF_3$ | $CHCH_2$ | CO(n-Pr) |
| $OCF_3$ | 4-Cl—Ph | CO(i-Pr) | $OCF_3$ | $CHCH_2$ | CO(i-Pr) |
| $OCF_3$ | 4-Cl—Ph | CO(t-Bu) | $OCF_3$ | $CHCH_2$ | CO(t-Bu) |
| $OCF_3$ | 4-Cl—Ph | $CO_2$(t-Bu) | $OCF_3$ | $CHCH_2$ | $CO_2$(t-Bu) |
| $CF_3$ | 4-F—Ph | $CO_2$(n-Pr) | $CF_3$ | $C(CH_3)CH_2$ | $CO_2$(n-Pr) |
| $CF_3$ | 4-F—Ph | $CO_2$(i-Pr) | $CF_3$ | $C(CH_3)CH_2$ | $CO_2$(i-Pr) |
| $CF_3$ | 4-F—Ph | CO(n-Pr) | $CF_3$ | $C(CH_3)CH_2$ | CO(n-Pr) |
| $CF_3$ | 4-F—Ph | CO(i-Pr) | $CF_3$ | $C(CH_3)CH_2$ | CO(i-Pr) |
| $CF_3$ | 4-F—Ph | CO(t-Bu) | $CF_3$ | $C(CH_3)CH_2$ | CO(t-Bu) |
| $CF_3$ | 4-F—Ph | $CO_2$(t-Bu) | $CF_3$ | $C(CH_3)CH_2$ | $CO_2$(t-Bu) |
| $OCF_3$ | 4-F—Ph | $CO_2$(n-Pr) | $OCF_3$ | $C(CH_3)CH_2$ | $CO_2$(n-Pr) |
| $OCF_3$ | 4-F—Ph | $CO_2$(i-Pr) | $OCF_3$ | $C(CH_3)CH_2$ | $CO_2$(i-Pr) |
| $OCF_3$ | 4-F—Ph | CO(n-Pr) | $OCF_3$ | $C(CH_3)CH_2$ | CO(n-Pr) |
| $OCF_3$ | 4-F—Ph | CO(i-Pr) | $OCF_3$ | $C(CH_3)CH_2$ | CO(i-Pr) |
| $OCF_3$ | 4-F—Ph | CO(t-Bu) | $OCF_3$ | $C(CH_3)CH_2$ | CO(t-Bu) |
| $OCF_3$ | 4-F—Ph | $CO_2$(t-Bu) | $OCF_3$ | $C(CH_3)CH_2$ | $CO_2$(t-Bu) |
| $OCF_2H$ | $CO_2Et$ | CO(i-Pr) | $OCF_2H$ | 4-Cl—Ph | CO(t-Bu) |
| $OCF_2H$ | $CO_2Et$ | $CO_2$(i-Pr) | $OCF_2H$ | 4-Cl—Ph | $CO_2$(t-Bu) |
| $OCF_2H$ | $CO_2Et$ | CO(t-Bu) | $OCF_2H$ | 4-F—Ph | CO(n-Pr) |
| $OCF_2H$ | $CO_2Et$ | $CO_2$(t-Bu) | $OCF_2H$ | 4-F—Ph | $CO_2$(n-Pr) |
| $OCF_2H$ | 4-Cl—Ph | CO(n-Pr) | $OCF_2H$ | 4-F—Ph | CO(i-Pr) |
| $OCF_2H$ | 4-Cl—Ph | $CO_2$(n-Pr) | $OCF_2H$ | 4-F—Ph | $CO_2$(i-Pr) |
| $OCF_2H$ | 4-Cl—Ph | CO(i-Pr) | $OCF_2H$ | 4-F—Ph | CO(t-Bu) |
| $OCF_2H$ | 4-Cl—Ph | $CO_2$(i-Pr) | $OCF_2H$ | 4-F—Ph | $CO_2$(t-Bu) |

TABLE 7

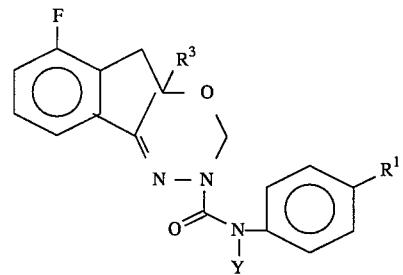

| R¹ | R³ | Y | R¹ | R³ | Y |
|---|---|---|---|---|---|
| Cl | Me | H | $OCF_3$ | Me | COEt |
| Br | Me | H | Cl | Me | $CO_2Me$ |
| $CF_3$ | Me | H | Br | Me | $CO_2Me$ |
| $OCF_3$ | Me | H | $CF_3$ | Me | $CO_2Me$ |

TABLE 7-continued

| R¹ | R³ | Y | R¹ | R³ | Y |
|---|---|---|---|---|---|
| Cl | Me | Me | OCF$_3$ | Me | CO$_2$Me |
| Br | Me | Me | Cl | Me | CO$_2$Et |
| CF$_3$ | Me | Me | Br | Me | CO$_2$Et |
| OCF$_3$ | Me | Me | CF$_3$ | Me | CO$_2$Et |
| Cl | Me | Et | OCF$_3$ | Me | CO$_2$Et |
| Br | Me | Et | Cl | Me | CH$_2$OMe |
| CF$_3$ | Me | Et | Br | Me | CH$_2$OMe |
| OCF$_3$ | Me | Et | CF$_3$ | Me | CH$_2$OMe |
| Cl | Me | n-Pr | OCF$_3$ | Me | CH$_2$OMe |
| Br | Me | n-Pr | Cl | Me | CH$_2$CHCH$_2$ |
| CF$_3$ | Me | n-Pr | Br | Me | CH$_2$CHCH$_2$ |
| OCF$_3$ | Me | n-Pr | CF$_3$ | Me | CH$_2$CHCH$_2$ |
| Cl | Me | COMe | OCF$_3$ | Me | CH$_2$CHCH$_2$ |
| Br | Me | COMe | Cl | Me | CH$_2$SCH$_3$ |
| CF$_3$ | Me | COMe | Br | Me | CH$_2$SCH$_3$ |
| OCF$_3$ | Me | COMe | CF$_3$ | Me | CH$_2$SCH$_3$ |
| Cl | Me | COEt | OCF$_3$ | Me | CH$_2$SCH$_3$ |
| Br | Me | COEt | OCF$_2$H | Me | H |
| CF$_3$ | Me | COEt | OCF$_2$H | Me | Me |
| Cl | Et | H | OCF$_3$ | Et | COEt |
| Br | Et | H | Cl | Et | CO$_2$Me |
| CF$_3$ | Et | H | Br | Et | CO$_2$Me |
| OCF$_3$ | Et | H | CF$_3$ | Et | CO$_2$Me |
| Cl | Et | Me | OCF$_3$ | Et | CO$_2$Me |
| Br | Et | Me | Cl | Et | CO$_2$Et |
| CF$_3$ | Et | Me | Br | Et | CO$_2$Et |
| OCF$_3$ | Et | Me | CF$_3$ | Et | CO$_2$Et |
| Cl | Et | Et | OCF$_3$ | Et | CO$_2$Et |
| Br | Et | Et | Cl | Et | CH$_2$OMe |
| CF$_3$ | Et | Et | Br | Et | CH$_2$OMe |
| OCF$_3$ | Et | Et | CF$_3$ | Et | CH$_2$OMe |
| Cl | Et | n-Pr | OCF$_3$ | Et | CH$_2$OMe |
| Br | Et | n-Pr | Cl | Et | CH$_2$CHCH$_2$ |
| CF$_3$ | Et | n-Pr | Br | Et | CH$_2$CHCH$_2$ |
| OCF$_3$ | Et | n-Pr | CF$_3$ | Et | CH$_2$CHCH$_2$ |
| Cl | Et | COMe | OCF$_3$ | Et | CH$_2$CHCH$_2$ |
| Br | Et | COMe | Cl | Et | CH$_2$SCH$_3$ |
| CF$_3$ | Et | COMe | Br | Et | CH$_2$SCH$_3$ |
| OCF$_3$ | Et | COMe | CF$_3$ | Et | CH$_2$SCH$_3$ |
| Cl | Et | COEt | OCF$_3$ | Et | CH$_2$SCH$_3$ |
| Br | Et | COEt | OCF$_2$H | Et | CH$_2$SCH$_3$ |
| CF$_3$ | Et | COEt | OCF$_2$H | Me | Et |
| OCF$_2$H | Et | H | OCF$_2$H | Me | n-Pr |
| OCF$_2$H | Et | Me | OCF$_2$H | Me | COMe |
| OCF$_2$H | Et | Et | OCF$_2$H | Me | COEt |
| OCF$_2$H | Et | n-Pr | OCF$_2$H | Me | CO$_2$Me |
| OCF$_2$H | Et | COMe | OCF$_2$H | Me | CO$_2$Et |
| OCF$_2$H | Et | COEt | OCF$_2$H | Me | CH$_2$OMe |
| OCF$_2$H | Et | CO$_2$Me | OCF$_2$H | Me | CH$_2$CHCH$_2$ |
| OCF$_2$H | Et | CO$_2$Et | OCF$_2$H | Me | CH$_2$SCH$_3$ |
| OCF$_2$H | Et | CH$_2$OMe | OCF$_3$ | n-Pr | COEt |
| OCF$_2$H | Et | CH$_2$CHCH$_2$ | Cl | n-Pr | CO$_2$Me |
| Cl | n-Pr | H | Br | n-Pr | CO$_2$Me |
| Br | n-Pr | H | CF$_3$ | n-Pr | CO$_2$Me |
| CF$_3$ | n-Pr | H | OCF$_3$ | n-Pr | CO$_2$Me |
| OCF$_3$ | n-Pr | H | Cl | n-Pr | CO$_2$Et |
| Cl | n-Pr | Me | Br | n-Pr | CO$_2$Et |
| Br | n-Pr | Me | CF$_3$ | n-Pr | CO$_2$Et |
| CF$_3$ | n-Pr | Me | OCF$_3$ | n-Pr | CO$_2$Et |
| OCF$_3$ | n-Pr | Me | Cl | n-Pr | CH$_2$OMe |
| Cl | n-Pr | Et | Br | n-Pr | CH$_2$OMe |
| Br | n-Pr | Et | CF$_3$ | n-Pr | CH$_2$OMe |
| CF$_3$ | n-Pr | Et | OCF$_3$ | n-Pr | CH$_2$OMe |

TABLE 7-continued

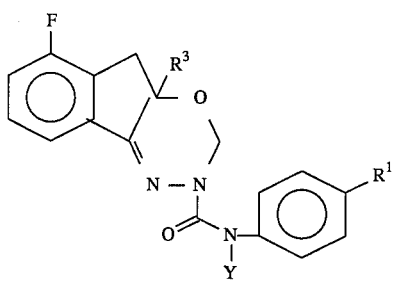

| R¹ | R³ | Y | R¹ | R³ | Y |
|---|---|---|---|---|---|
| OCF₃ | n-Pr | Et | Cl | n-Pr | CH₂CHCH₂ |
| Cl | n-Pr | n-Pr | Br | n-Pr | CH₂CHCH₂ |
| Br | n-Pr | n-Pr | CF₃ | n-Pr | CH₂CHCH₂ |
| CF₃ | n-Pr | n-Pr | OCF₃ | n-Pr | CH₂CHCH₂ |
| OCF₃ | n-Pr | n-Pr | Cl | n-Pr | CH₂SCH₃ |
| Cl | n-Pr | COMe | Br | n-Pr | CH₂SCH₃ |
| Br | n-Pr | COMe | CF₃ | n-Pr | CH₂SCH₃ |
| CF₃ | n-Pr | COMe | OCF₃ | n-Pr | CH₂SCH₃ |
| OCF₃ | n-Pr | COMe | OCF₂H | n-Pr | COEt |
| Cl | n-Pr | COEt | OCF₂H | n-Pr | CO₂Me |
| Br | n-Pr | COEt | OCF₂H | n-Pr | CO₂Et |
| CF₃ | n-Pr | COEt | OCF₂H | n-Pr | CH₂OMe |
| OCF₂H | n-Pr | H | OCF₂H | n-Pr | CH₂CHCH₂ |
| OCF₂H | n-Pr | Me | OCF₂H | n-Pr | CH₂SCH₃ |
| OCF₂H | n-Pr | Et | | | |
| OCF₂H | n-Pr | n-Pr | | | |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |

TABLE 7-continued

| R¹ | R³ | Y | R¹ | R³ | Y |
|---|---|---|---|---|---|
| CF₃ | i-Bu | COMe | Br | i-Bu | CH₂SCH₃ |
| OCF₃ | i-Bu | COMe | CF₃ | i-Bu | CH₂SCH₃ |
| Cl | i-Bu | COEt | OCF₃ | i-Bu | CH₂SCH₃ |
| Br | i-Bu | COEt | OCF₂H | i-Bu | COEt |
| CF₃ | i-Bu | COEt | OCF₂H | i-Bu | CO₂Me |
| OCF₂H | i-Bu | H | OCF₂H | i-Bu | CO₂Et |
| OCF₂H | i-Bu | Me | OCF₂H | i-Bu | CH₂OMe |
| OCF₂H | i-Bu | Et | OCF₂H | i-Bu | CH₂CHCH₂ |
| OCF₂H | i-Bu | n-Pr | OCF₂H | i-Bu | CH₂SCH₃ |
| OCF₂H | i-Bu | COMe | | | |
| Cl | CO₂Me | H | OCF₃ | CO₂Me | COEt |
| Br | CO₂Me | H | Cl | CO₂Me | CO₂Me |
| CF₃ | CO₂Me | H | Br | CO₂Me | CO₂Me |
| OCF₃ | CO₂Me | H | CF₃ | CO₂Me | CO₂Me |
| Cl | CO₂Me | Me | OCF₃ | CO₂Me | CO₂Me |
| Br | CO₂Me | Me | Cl | CO₂Me | CO₂Et |
| CF₃ | CO₂Me | Me | Br | CO₂Me | CO₂Et |
| OCF₃ | CO₂Me | Me | CF₃ | CO₂Me | CO₂Et |
| Cl | CO₂Me | Et | OCF₃ | CO₂Me | CO₂Et |
| Br | CO₂Me | Et | Cl | CO₂Me | CH₂OMe |
| CF₃ | CO₂Me | Et | Br | CO₂Me | CH₂OMe |
| OCF₃ | CO₂Me | Et | CF₃ | CO₂Me | CH₂OMe |
| Cl | CO₂Me | n-Pr | OCF₃ | CO₂Me | CH₂OMe |
| Br | CO₂Me | n-Pr | Cl | CO₂Me | CH₂CHCH₂ |
| CF₃ | CO₂Me | n-Pr | Br | CO₂Me | CH₂CHCH₂ |
| OCF₃ | CO₂Me | n-Pr | CF₃ | CO₂Me | CH₂CHCH₂ |
| Cl | CO₂Me | COMe | OCF₃ | CO₂Me | CH₂CHCH₂ |
| Br | CO₂Me | COMe | Cl | CO₂Me | CH₂SCH₃ |
| CF₃ | CO₂Me | COMe | Br | CO₂Me | CH₂SCH₃ |
| OCF₃ | CO₂Me | COMe | CF₃ | CO₂Me | CH₂SCH₃ |
| Cl | CO₂Me | COEt | OCF₃ | CO₂Me | CH₂SCH₃ |
| Br | CO₂Me | COEt | OCF₂H | CO₂Me | COEt |
| CF₃ | CO₂Me | COEt | OCF₂H | CO₂Me | CO₂Me |
| OCF₂H | CO₂Me | H | OCF₂H | CO₂Me | CO₂Et |
| OCF₂H | CO₂Me | Me | OCF₂H | CO₂Me | CH₂OMe |
| OCF₂H | CO₂Me | Et | OCF₂H | CO₂Me | CH₂CHCH₂ |
| OCF₂H | CO₂Me | n-Pr | OCF₂H | CO₂Me | CH₂SCH₃ |
| OCF₂H | CO₂Me | COMe | | | |
| Cl | CO₂Et | H | OCF₃ | CO₂Et | COEt |
| Br | CO₂Et | H | Cl | CO₂Et | CO₂Me |
| CF₃ | CO₂Et | H | Br | CO₂Et | CO₂Me |
| OCF₃ | CO₂Et | H | CF₃ | CO₂Et | CO₂Me |
| Cl | CO₂Et | Me | OCF₃ | CO₂Et | CO₂Me |
| Br | CO₂Et | Me | Cl | CO₂Et | CO₂Et |
| CF₃ | CO₂Et | Me | Br | CO₂Et | CO₂Et |
| OCF₃ | CO₂Et | Me | CF₃ | CO₂Et | CO₂Et |
| Cl | CO₂Et | Et | OCF₃ | CO₂Et | CO₂Et |
| Br | CO₂Et | Et | Cl | CO₂Et | CH₂OMe |
| CF₃ | CO₂Et | Et | Br | CO₂Et | CH₂OMe |
| OCF₃ | CO₂Et | Et | CF₃ | CO₂Et | CH₂OMe |
| Cl | CO₂Et | n-Pr | OCF₃ | CO₂Et | CH₂OMe |
| Br | CO₂Et | n-Pr | Cl | CO₂Et | CH₂CHCH₂ |
| CF₃ | CO₂Et | n-Pr | Br | CO₂Et | CH₂CHCH₂ |
| OCF₃ | CO₂Et | n-Pr | CF₃ | CO₂Et | CH₂CHCH₂ |
| Cl | CO₂Et | COMe | OCF₃ | CO₂Et | CH₂CHCH₂ |
| Br | CO₂Et | COMe | Cl | CO₂Et | CH₂SCH₃ |
| CF₃ | CO₂Et | COMe | Br | CO₂Et | CH₂SCH₃ |
| OCF₃ | CO₂Et | COMe | CF₃ | CO₂Et | CH₂SCH₃ |
| Cl | CO₂Et | COEt | OCF₃ | CO₂Et | CH₂SCH₃ |
| Br | CO₂Et | COEt | OCF₂H | CO₂Et | COEt |
| CF₃ | CO₂Et | COEt | OCF₂H | CO₂Et | CO₂Me |
| OCF₂H | CO₂Et | H | OCF₂H | CO₂Et | CO₂Et |
| OCF₂H | CO₂Et | Me | OCF₂H | CO₂Et | CH₂OMe |

TABLE 7-continued

| R¹ | R³ | Y | R¹ | R³ | Y |
|---|---|---|---|---|---|
| OCF₂H | CO₂Et | Et | OCF₂H | CO₂Et | CH₂CHCH₂ |
| OCF₂H | CO₂Et | n-Pr | OCF₂H | CO₂Et | CH₂SCH₃ |
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₂ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |

TABLE 7-continued

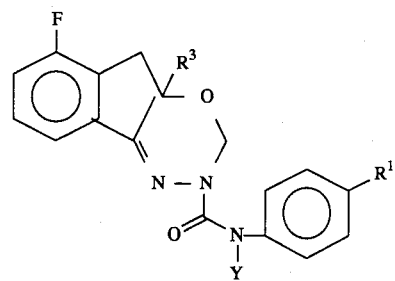

| R¹ | R³ | Y | R¹ | R³ | Y |
|---|---|---|---|---|---|
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CH₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |

TABLE 7-continued

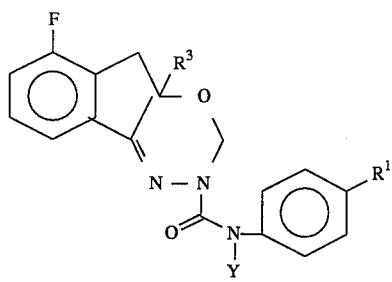

| R¹ | R³ | Y | R¹ | R³ | Y |
| --- | --- | --- | --- | --- | --- |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |
| Br | C(CH₃)CH₂ | COEt | OCF₂H | C(CH₃)CH₂ | COEt |
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-Pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |

TABLE 7-continued

| R¹ | R³ | Y | R¹ | R³ | Y |
|---|---|---|---|---|---|
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(n-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(i-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(i-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(i-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂(i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 8

| R¹ | R³ | Y | R¹ | R³ | Y |
|---|---|---|---|---|---|
| Cl | Me | H | OCF₃ | Me | COEt |
| Br | Me | H | Cl | Me | CO₂Me |
| CF₃ | Me | H | Br | Me | CO₂Me |
| OCF₃ | Me | H | CF₃ | Me | CO₂Me |
| Cl | Me | Me | OCF₃ | Me | CO₂Me |
| Br | Me | Me | Cl | Me | CO₂Et |
| CF₃ | Me | Me | Br | Me | CO₂Et |
| OCF₃ | Me | Me | CF₃ | Me | CO₂Et |
| Cl | Me | Et | OCF₃ | Me | CO₂Et |
| Br | Me | Et | Cl | Me | CH₂OMe |
| CF₃ | Me | Et | Br | Me | CH₂OMe |
| OCF₃ | Me | Et | CF₃ | Me | CH₂OMe |
| Cl | Me | n-Pr | OCF₃ | Me | CH₂OMe |
| Br | Me | n-Pr | Cl | Me | CH₂CHCH₂ |
| CF₃ | Me | n-Pr | Br | Me | CH₂CHCH₂ |
| OCF₃ | Me | n-Pr | CF₃ | Me | CH₂CHCH₂ |
| Cl | Me | COMe | OCF₃ | Me | CH₂CHCH₂ |
| Br | Me | COMe | Cl | Me | CH₂SCH₃ |
| CF₃ | Me | COMe | Br | Me | CH₂SCH₃ |
| OCF₃ | Me | COMe | CF₃ | Me | CH₂SCH₃ |
| Cl | Me | COEt | OCF₃ | Me | CH₂SCH₃ |
| Br | Me | COEt | OCF₂H | Me | H |
| CF₃ | Me | COEt | OCF₂H | Me | Me |
| Cl | Et | H | OCF₃ | Et | COEt |
| Br | Et | H | Cl | Et | CO₂Me |
| CF₃ | Et | H | Br | Et | CO₂Me |
| OCF₃ | Et | H | CF₃ | Et | CO₂Me |
| Cl | Et | Me | OCF₃ | Et | CO₂Me |
| Br | Et | Me | Cl | Et | CO₂Et |
| CF₃ | Et | Me | Br | Et | CO₂Et |
| OCF₃ | Et | Me | CF₃ | Et | CO₂Et |
| Cl | Et | Et | OCF₃ | Et | CO₂Et |
| Br | Et | Et | Cl | Et | CH₂OMe |
| CF₃ | Et | Et | Br | Et | CH₂OMe |
| OCF₃ | Et | Et | CF₃ | Et | CH₂OMe |
| Cl | Et | n-Pr | OCF₃ | Et | CH₂OMe |
| Br | Et | n-Pr | Cl | Et | CH₂CHCH₂ |
| CF₃ | Et | n-Pr | Br | Et | CH₂CHCH₂ |
| OCF₃ | Et | n-Pr | CF₃ | Et | CH₂CHCH₂ |
| Cl | Et | COMe | OCF₃ | Et | CH₂CHCH₂ |
| Br | Et | COMe | Cl | Et | CH₂SCH₃ |
| CF₃ | Et | COMe | Br | Et | CH₂SCH₃ |
| OCF₃ | Et | COMe | CF₃ | Et | CH₂SCH₃ |
| Cl | Et | COEt | OCF₃ | Et | CH₂SCH₃ |
| Br | Et | COEt | OCF₂H | Et | CH₂SCH₃ |
| CF₃ | Et | COEt | OCF₂H | Me | Et |
| OCF₂H | Et | H | OCF₂H | Me | n-Pr |
| OCF₂H | Et | Me | OCF₂H | Me | COMe |
| OCF₂H | Et | Et | OCF₂H | Me | COEt |
| OCF₂H | Et | n-Pr | OCF₂H | Me | CO₂Me |
| OCF₂H | Et | COMe | OCF₂H | Me | CO₂Et |
| OCF₂H | Et | COEt | OCF₂H | Me | CH₂OMe |
| OCF₂H | Et | CO₂Me | OCF₂H | Me | CH₂CHCH₂ |
| OCF₂H | Et | CO₂Et | OCF₂H | Me | CH₂SCH₃ |
| OCF₂H | Et | CH₂OMe | | | |
| OCF₂H | Et | CH₂CHCH₂ | | | |
| Cl | n-Pr | H | OCF₃ | n-Pr | COEt |
| Br | n-Pr | H | Cl | n-Pr | CO₂Me |
| CF₃ | n-Pr | H | Br | n-Pr | CO₂Me |
| OCF₃ | n-Pr | H | CF₃ | n-Pr | CO₂Me |
| Cl | n-Pr | Me | OCF₃ | n-Pr | CO₂Me |
| Br | n-Pr | Me | Cl | n-Pr | CO₂Et |
| CF₃ | n-Pr | Me | Br | n-Pr | CO₂Et |
| OCF₃ | n-Pr | Me | CF₃ | n-Pr | CO₂Et |
| Cl | n-Pr | Et | OCF₃ | n-Pr | CO₂Et |

TABLE 8-continued

| R¹ | R³ | Y | R¹ | R³ | Y |
|---|---|---|---|---|---|
| Br | n-Pr | Et | Cl | n-Pr | CH₂OMe |
| CF₃ | n-Pr | Et | Br | n-Pr | CH₂OMe |
| OCF₃ | n-Pr | Et | CF₃ | n-Pr | CH₂OMe |
| Cl | n-Pr | n-Pr | OCF₃ | n-Pr | CH₂OMe |
| Br | n-Pr | n-Pr | Cl | n-Pr | CH₂CHCH₂ |
| CF₃ | n-Pr | n-Pr | Br | n-Pr | CH₂CHCH₂ |
| OCF₃ | n-Pr | n-Pr | CF₃ | n-Pr | CH₂CHCH₂ |
| Cl | n-Pr | COMe | OCF₃ | n-Pr | CH₂CHCH₂ |
| Br | n-Pr | COMe | Cl | n-Pr | CH₂SCH₃ |
| CF₃ | n-Pr | COMe | Br | n-Pr | CH₂SCH₃ |
| OCF₃ | n-Pr | COMe | CF₃ | n-Pr | CH₂SCH₃ |
| Cl | n-Pr | COEt | OCF₃ | n-Pr | CH₂SCH₃ |
| Br | n-Pr | COEt | OCF₂H | n-Pr | COEt |
| CF₃ | n-Pr | COEt | OCF₂H | n-Pr | CO₂Me |
| OCF₂H | n-Pr | H | OCF₂H | n-Pr | CO₂Et |
| OCF₂H | n-Pr | Me | OCF₂H | n-Pr | CH₂OMe |
| OCF₂H | n-Pr | Et | OCF₂H | n-Pr | CH₂CHCH₂ |
| OCF₂H | n-Pr | n-Pr | OCF₂H | n-Pr | CH₂SCH₃ |
| OCF₂H | n-Pr | COMe | | | |
| Cl | i-Pr | H | OCF₃ | i-Pr | COEt |
| Br | i-Pr | H | Cl | i-Pr | CO₂Me |
| CF₃ | i-Pr | H | Br | i-Pr | CO₂Me |
| OCF₃ | i-Pr | H | CF₃ | i-Pr | CO₂Me |
| Cl | i-Pr | Me | OCF₃ | i-Pr | CO₂Me |
| Br | i-Pr | Me | Cl | i-Pr | CO₂Et |
| CF₃ | i-Pr | Me | Br | i-Pr | CO₂Et |
| OCF₃ | i-Pr | Me | CF₃ | i-Pr | CO₂Et |
| Cl | i-Pr | Et | OCF₃ | i-Pr | CO₂Et |
| Br | i-Pr | Et | Cl | i-Pr | CH₂OMe |
| CF₃ | i-Pr | Et | Br | i-Pr | CH₂OMe |
| OCF₃ | i-Pr | Et | CF₃ | i-Pr | CH₂OMe |
| Cl | i-Pr | n-Pr | OCF₃ | i-Pr | CH₂OMe |
| Br | i-Pr | n-Pr | Cl | i-Pr | CH₂CHCH₂ |
| CF₃ | i-Pr | n-Pr | Br | i-Pr | CH₂CHCH₂ |
| OCF₃ | i-Pr | n-Pr | CF₃ | i-Pr | CH₂CHCH₂ |
| Cl | i-Pr | COMe | OCF₃ | i-Pr | CH₂CHCH₂ |
| Br | i-Pr | COMe | Cl | i-Pr | CH₂SCH₃ |
| CF₃ | i-Pr | COMe | Br | i-Pr | CH₂SCH₃ |
| OCF₃ | i-Pr | COMe | CF₃ | i-Pr | CH₂SCH₃ |
| Cl | i-Pr | COEt | OCF₃ | i-Pr | CH₂SCH₃ |
| Br | i-Pr | COEt | OCF₂H | i-Pr | COEt |
| CF₃ | i-Pr | COEt | OCF₂H | i-Pr | CO₂Me |
| OCF₂H | i-Pr | H | OCF₂H | i-Pr | CO₂Et |
| OCF₂H | i-Pr | Me | OCF₂H | i-Pr | CH₂OMe |
| OCF₂H | i-Pr | Et | OCF₂H | i-Pr | CH₂CHCH₂ |
| OCF₂H | i-Pr | n-Pr | OCF₂H | i-Pr | CH₂SCH₃ |
| OCF₂H | i-Pr | COMe | | | |
| Cl | i-Bu | H | OCF₃ | i-Bu | COEt |
| Br | i-Bu | H | Cl | i-Bu | CO₂Me |
| CF₃ | i-Bu | H | Br | i-Bu | CO₂Me |
| OCF₃ | i-Bu | H | CF₃ | i-Bu | CO₂Me |
| Cl | i-Bu | Me | OCF₃ | i-Bu | CO₂Me |
| Br | i-Bu | Me | Cl | i-Bu | CO₂Et |
| CF₃ | i-Bu | Me | Br | i-Bu | CO₂Et |
| OCF₃ | i-Bu | Me | CF₃ | i-Bu | CO₂Et |
| Cl | i-Bu | Et | OCF₃ | i-Bu | CO₂Et |
| Br | i-Bu | Et | Cl | i-Bu | CH₂OMe |
| CF₃ | i-Bu | Et | Br | i-Bu | CH₂OMe |
| OCF₃ | i-Bu | Et | CF₃ | i-Bu | CH₂OMe |
| Cl | i-Bu | n-Pr | OCF₃ | i-Bu | CH₂OMe |
| Br | i-Bu | n-Pr | Cl | i-Bu | CH₂CHCH₂ |
| CF₃ | i-Bu | n-Pr | Br | i-Bu | CH₂CHCH₂ |
| OCF₃ | i-Bu | n-Pr | CF₃ | i-Bu | CH₂CHCH₂ |
| Cl | i-Bu | COMe | OCF₃ | i-Bu | CH₂CHCH₂ |
| Br | i-Bu | COMe | Cl | i-Bu | CH₂SCH₃ |

TABLE 8-continued

| R¹ | R³ | Y | R¹ | R³ | Y |
|---|---|---|---|---|---|
| $CF_3$ | i-Bu | COMe | Br | i-Bu | $CH_2SCH_3$ |
| $OCF_3$ | i-Bu | COMe | $CF_3$ | i-Bu | $CH_2SCH_3$ |
| Cl | i-Bu | COEt | $OCF_3$ | i-Bu | $CH_2SCH_3$ |
| Br | i-Bu | COEt | $OCF_2H$ | i-Bu | COEt |
| $CF_3$ | i-Bu | COEt | $OCF_2H$ | i-Bu | $CO_2Me$ |
| $OCF_2H$ | i-Bu | H | $OCF_2H$ | i-Bu | $CO_2Et$ |
| $OCF_2H$ | i-Bu | Me | $OCF_2H$ | i-Bu | $CH_2OMe$ |
| $OCF_2H$ | i-Bu | Et | $OCF_2H$ | i-Bu | $CH_2CHCH_2$ |
| $OCF_2H$ | i-Bu | n-Pr | $OCF_2H$ | i-Bu | $CH_2SCH_3$ |
| $OCF_2H$ | i-Bu | COMe | | | |
| Cl | $CO_2Me$ | H | $OCF_3$ | $CO_2Me$ | COEt |
| Br | $CO_2Me$ | H | Cl | $CO_2Me$ | $CO_2Me$ |
| $CF_3$ | $CO_2Me$ | H | Br | $CO_2Me$ | $CO_2Me$ |
| $OCF_3$ | $CO_2Me$ | H | $CF_3$ | $CO_2Me$ | $CO_2Me$ |
| Cl | $CO_2Me$ | Me | $OCF_3$ | $CO_2Me$ | $CO_2Me$ |
| Br | $CO_2Me$ | Me | Cl | $CO_2Me$ | $CO_2Et$ |
| $CF_3$ | $CO_2Me$ | Me | Br | $CO_2Me$ | $CO_2Et$ |
| $OCF_3$ | $CO_2Me$ | Me | $CF_3$ | $CO_2Me$ | $CO_2Et$ |
| Cl | $CO_2Me$ | Et | $OCF_3$ | $CO_2Me$ | $CO_2Et$ |
| Br | $CO_2Me$ | Et | Cl | $CO_2Me$ | $CH_2OMe$ |
| $CF_3$ | $CO_2Me$ | Et | Br | $CO_2Me$ | $CH_2OMe$ |
| $OCF_3$ | $CO_2Me$ | Et | $CF_3$ | $CO_2Me$ | $CH_2OMe$ |
| Cl | $CO_2Me$ | n-Pr | $OCF_3$ | $CO_2Me$ | $CH_2OMe$ |
| Br | $CO_2Me$ | n-Pr | Cl | $CO_2Me$ | $CH_2CHCH_2$ |
| $CF_3$ | $CO_2Me$ | n-Pr | Br | $CO_2Me$ | $CH_2CHCH_2$ |
| $OCF_3$ | $CO_2Me$ | n-Pr | $CF_3$ | $CO_2Me$ | $CH_2CHCH_2$ |
| Cl | $CO_2Me$ | COMe | $OCF_3$ | $CO_2Me$ | $CH_2CHCH_2$ |
| Br | $CO_2Me$ | COMe | Cl | $CO_2Me$ | $CH_2SCH_3$ |
| $CF_3$ | $CO_2Me$ | COMe | Br | $CO_2Me$ | $CH_2SCH_3$ |
| $OCF_3$ | $CO_2Me$ | COMe | $CF_3$ | $CO_2Me$ | $CH_2SCH_3$ |
| Cl | $CO_2Me$ | COEt | $OCF_3$ | $CO_2Me$ | $CH_2SCH_3$ |
| Br | $CO_2Me$ | COEt | $OCF_2H$ | $CO_2Me$ | COEt |
| $CF_3$ | $CO_2Me$ | COEt | $OCF_2H$ | $CO_2Me$ | $CO_2Me$ |
| $OCF_2H$ | $CO_2Me$ | H | $OCF_2H$ | $CO_2Me$ | $CO_2Et$ |
| $OCF_2H$ | $CO_2Me$ | Me | $OCF_2H$ | $CO_2Me$ | $CH_2OMe$ |
| $OCF_2H$ | $CO_2Me$ | Et | $OCF_2H$ | $CO_2Me$ | $CH_2CHCH_2$ |
| $OCF_2H$ | $CO_2Me$ | n-Pr | $OCF_2H$ | $CO_2Me$ | $CH_2SCH_3$ |
| $OCF_2H$ | $CO_2Me$ | COMe | | | |
| Cl | $CO_2Et$ | H | $OCF_3$ | $CO_2Et$ | COEt |
| Br | $CO_2Et$ | H | Cl | $CO_2Et$ | $CO_2Me$ |
| $CF_3$ | $CO_2Et$ | H | Br | $CO_2Et$ | $CO_2Me$ |
| $OCF_3$ | $CO_2Et$ | H | $CF_3$ | $CO_2Et$ | $CO_2Me$ |
| Cl | $CO_2Et$ | Me | $OCF_3$ | $CO_2Et$ | $CO_2Me$ |
| Br | $CO_2Et$ | Me | Cl | $CO_2Et$ | $CO_2Et$ |
| $CF_3$ | $CO_2Et$ | Me | Br | $CO_2Et$ | $CO_2Et$ |
| $OCF_3$ | $CO_2Et$ | Me | $CF_3$ | $CO_2Et$ | $CO_2Et$ |
| Cl | $CO_2Et$ | Et | $OCF_3$ | $CO_2Et$ | $CO_2Et$ |
| Br | $CO_2Et$ | Et | Cl | $CO_2Et$ | $CH_2OMe$ |
| $CF_3$ | $CO_2Et$ | Et | Br | $CO_2Et$ | $CH_2OMe$ |
| $OCF_3$ | $CO_2Et$ | Et | $CF_3$ | $CO_2Et$ | $CH_2OMe$ |
| Cl | $CO_2Et$ | n-Pr | $OCF_3$ | $CO_2Et$ | $CH_2OMe$ |
| Br | $CO_2Et$ | n-Pr | Cl | $CO_2Et$ | $CH_2CHCH_2$ |
| $CF_3$ | $CO_2Et$ | n-Pr | Br | $CO_2Et$ | $CH_2CHCH_2$ |
| $OCF_3$ | $CO_2Et$ | n-Pr | $CF_3$ | $CO_2Et$ | $CH_2CHCH_2$ |
| Cl | $CO_2Et$ | COMe | $OCF_3$ | $CO_2Et$ | $CH_2CHCH_2$ |
| Br | $CO_2Et$ | COMe | Cl | $CO_2Et$ | $CH_2SCH_3$ |
| $CF_3$ | $CO_2Et$ | COMe | Br | $CO_2Et$ | $CH_2SCH_3$ |
| $OCF_3$ | $CO_2Et$ | COMe | $CF_3$ | $CO_2Et$ | $CH_2SCH_3$ |
| Cl | $CO_2Et$ | COEt | $OCF_3$ | $CO_2Et$ | $CH_2SCH_3$ |
| Br | $CO_2Et$ | COEt | $OCF_2H$ | $CO_2Et$ | COEt |
| $CF_3$ | $CO_2Et$ | COEt | $OCF_2H$ | $CO_2Et$ | $CO_2Me$ |
| $OCF_2H$ | $CO_2Et$ | H | $OCF_2H$ | $CO_2Et$ | $CO_2Et$ |
| $OCF_2H$ | $CO_2Et$ | Me | $OCF_2H$ | $CO_2Et$ | $CH_2OMe$ |
| $OCF_2H$ | $CO_2Et$ | Et | $OCF_2H$ | $CO_2Et$ | $CH_2CHCH_2$ |
| $OCF_2H$ | $CO_2Et$ | n-Pr | $OCF_2H$ | $CO_2Et$ | $CH_2SCH_3$ |

TABLE 8-continued

| R¹ | R³ | Y | R¹ | R³ | Y |
|---|---|---|---|---|---|
| OCF₂H | CO₂Et | COMe | | | |
| Cl | Ph | H | OCF₃ | Ph | COEt |
| Br | Ph | H | Cl | Ph | CO₂Me |
| CF₃ | Ph | H | Br | Ph | CO₂Me |
| OCF₃ | Ph | H | CF₃ | Ph | CO₂Me |
| Cl | Ph | Me | OCF₃ | Ph | CO₂Me |
| Br | Ph | Me | Cl | Ph | CO₂Et |
| CF₃ | Ph | Me | Br | Ph | CO₂Et |
| OCF₃ | Ph | Me | CF₃ | Ph | CO₂Et |
| Cl | Ph | Et | OCF₃ | Ph | CO₂Et |
| Br | Ph | Et | Cl | Ph | CH₂OMe |
| CF₃ | Ph | Et | Br | Ph | CH₂OMe |
| OCF₃ | Ph | Et | CF₃ | Ph | CH₂OMe |
| Cl | Ph | n-Pr | OCF₃ | Ph | CH₂OMe |
| Br | Ph | n-Pr | Cl | Ph | CH₂CHCH₂ |
| CF₃ | Ph | n-Pr | Br | Ph | CH₂CHCH₂ |
| OCF₃ | Ph | n-Pr | CF₃ | Ph | CH₂CHCH₂ |
| Cl | Ph | COMe | OCF₃ | Ph | CH₂CHCH₂ |
| Br | Ph | COMe | Cl | Ph | CH₂SCH₃ |
| CF₃ | Ph | COMe | Br | Ph | CH₂SCH₃ |
| OCF₃ | Ph | COMe | CF₃ | Ph | CH₂SCH₃ |
| Cl | Ph | COEt | OCF₃ | Ph | CH₂SCH₃ |
| Br | Ph | COEt | OCF₂H | Ph | COEt |
| CF₃ | Ph | COEt | OCF₂H | Ph | CO₂Me |
| OCF₂H | Ph | H | OCF₂H | Ph | CO₂Et |
| OCF₂H | Ph | Me | OCF₂H | Ph | CH₂OMe |
| OCF₂H | Ph | Et | OCF₂H | Ph | CH₂CHCH₂ |
| OCF₂H | Ph | n-Pr | OCF₂H | Ph | CH₂SCH₃ |
| OCF₂H | Ph | COMe | | | |
| Cl | 4-Cl—Ph | H | OCF₃ | 4-Cl—Ph | COEt |
| Br | 4-Cl—Ph | H | Cl | 4-Cl—Ph | CO₂Me |
| CF₃ | 4-Cl—Ph | H | Br | 4-Cl—Ph | CO₂Me |
| OCF₃ | 4-Cl—Ph | H | CF₃ | 4-Cl—Ph | CO₂Me |
| Cl | 4-Cl—Ph | Me | OCF₃ | 4-Cl—Ph | CO₂Me |
| Br | 4-Cl—Ph | Me | Cl | 4-Cl—Ph | CO₂Et |
| CF₃ | 4-Cl—Ph | Me | Br | 4-Cl—Ph | CO₂Et |
| OCF₃ | 4-Cl—Ph | Me | CF₃ | 4-Cl—Ph | CO₂Et |
| Cl | 4-Cl—Ph | Et | OCF₃ | 4-Cl—Ph | CO₂Et |
| Br | 4-Cl—Ph | Et | Cl | 4-Cl—Ph | CH₂OMe |
| CF₃ | 4-Cl—Ph | Et | Br | 4-Cl—Ph | CH₂OMe |
| OCF₃ | 4-Cl—Ph | Et | CF₃ | 4-Cl—Ph | CH₂OMe |
| Cl | 4-Cl—Ph | n-Pr | OCF₃ | 4-Cl—Ph | CH₂OMe |
| Br | 4-Cl—Ph | n-Pr | Cl | 4-Cl—Ph | CH₂CHCH₂ |
| CF₃ | 4-Cl—Ph | n-Pr | Br | 4-Cl—Ph | CH₂CHCH₂ |
| OCF₃ | 4-Cl—Ph | n-Pr | CF₃ | 4-Cl—Ph | CH₂CHCH₂ |
| Cl | 4-Cl—Ph | COMe | OCF₃ | 4-Cl—Ph | CH₂CHCH₂ |
| Br | 4-Cl—Ph | COMe | Cl | 4-Cl—Ph | CH₂SCH₃ |
| CF₃ | 4-Cl—Ph | COMe | Br | 4-Cl—Ph | CH₂SCH₃ |
| OCF₃ | 4-Cl—Ph | COMe | CF₃ | 4-Cl—Ph | CH₂SCH₃ |
| Cl | 4-Cl—Ph | COEt | OCF₃ | 4-Cl—Ph | CH₂SCH₃ |
| Br | 4-Cl—Ph | COEt | OCF₂H | 4-Cl—Ph | COEt |
| CF₃ | 4-Cl—Ph | COEt | OCF₂H | 4-Cl—Ph | CO₂Me |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CH₂OMe |
| OCF₂H | 4-Cl—Ph | Et | OCF₂H | 4-Cl—Ph | CH₂CHCH₂ |
| OCF₂H | 4-Cl—Ph | n-Pr | OCF₂H | 4-Cl—Ph | CH₂SCH₃ |
| OCF₂H | 4-Cl—Ph | COMe | | | |
| Cl | 4-F—Ph | H | OCF₃ | 4-F—Ph | COEt |
| Br | 4-F—Ph | H | Cl | 4-F—Ph | CO₂Me |
| CF₃ | 4-F—Ph | H | Br | 4-F—Ph | CO₂Me |
| OCF₃ | 4-F—Ph | H | CF₃ | 4-F—Ph | CO₂Me |
| Cl | 4-F—Ph | Me | OCF₃ | 4-F—Ph | CO₂Me |
| Br | 4-F—Ph | Me | Cl | 4-F—Ph | CO₂Et |
| CF₃ | 4-F—Ph | Me | Br | 4-F—Ph | CO₂Et |
| OCF₃ | 4-F—Ph | Me | CF₃ | 4-F—Ph | CO₂Et |

TABLE 8-continued

| R¹ | R³ | Y | R¹ | R³ | Y |
|---|---|---|---|---|---|
| Cl | 4-F—Ph | Et | OCF₃ | 4-F—Ph | CO₂Et |
| Br | 4-F—Ph | Et | Cl | 4-F—Ph | CH₂OMe |
| CF₃ | 4-F—Ph | Et | Br | 4-F—Ph | CH₂OMe |
| OCF₃ | 4-F—Ph | Et | CF₃ | 4-F—Ph | CH₂OMe |
| Cl | 4-F—Ph | n-Pr | OCF₃ | 4-F—Ph | CH₂OMe |
| Br | 4-F—Ph | n-Pr | Cl | 4-F—Ph | CH₂CHCH₂ |
| CF₃ | 4-F—Ph | n-Pr | Br | 4-F—Ph | CH₂CHCH₂ |
| OCF₃ | 4-F—Ph | n-Pr | CF₃ | 4-F—Ph | CH₂CHCH₂ |
| Cl | 4-F—Ph | COMe | OCF₃ | 4-F—Ph | CH₂CHCH₂ |
| Br | 4-F—Ph | COMe | Cl | 4-F—Ph | CH₂SCH₃ |
| CF₃ | 4-F—Ph | COMe | Br | 4-F—Ph | CH₂SCH₃ |
| OCF₃ | 4-F—Ph | COMe | CF₃ | 4-F—Ph | CH₂SCH₃ |
| Cl | 4-F—Ph | COEt | OCF₃ | 4-F—Ph | CH₂SCH₃ |
| Br | 4-F—Ph | COEt | OCF₂H | 4-F—Ph | COEt |
| CF₃ | 4-F—Ph | COEt | OCF₂H | 4-F—Ph | CO₂Me |
| OCF₂H | 4-F—Ph | H | OCF₂H | 4-F—Ph | CO₂Et |
| OCF₂H | 4-F—Ph | Me | OCF₂H | 4-F—Ph | CO₂OMe |
| OCF₂H | 4-F—Ph | Et | OCF₂H | 4-F—Ph | CH₂CHCH₂ |
| OCF₂H | 4-F—Ph | n-Pr | OCF₂H | 4-F—Ph | CH₂SCH₃ |
| OCF₂H | 4-F—Ph | COMe | | | |
| Cl | CHCH₂ | H | OCF₃ | CHCH₂ | COEt |
| Br | CHCH₂ | H | Cl | CHCH₂ | CO₂Me |
| CF₃ | CHCH₂ | H | Br | CHCH₂ | CO₂Me |
| OCF₃ | CHCH₂ | H | CF₃ | CHCH₂ | CO₂Me |
| Cl | CHCH₂ | Me | OCF₃ | CHCH₂ | CO₂Me |
| Br | CHCH₂ | Me | Cl | CHCH₂ | CO₂Et |
| CF₃ | CHCH₂ | Me | Br | CHCH₂ | CO₂Et |
| OCF₃ | CHCH₂ | Me | CF₃ | CHCH₂ | CO₂Et |
| Cl | CHCH₂ | Et | OCF₃ | CHCH₂ | CO₂Et |
| Br | CHCH₂ | Et | Cl | CHCH₂ | CH₂OMe |
| CF₃ | CHCH₂ | Et | Br | CHCH₂ | CH₂OMe |
| OCF₃ | CHCH₂ | Et | CF₃ | CHCH₂ | CH₂OMe |
| Cl | CHCH₂ | n-Pr | OCF₃ | CHCH₂ | CH₂OMe |
| Br | CHCH₂ | n-Pr | Cl | CHCH₂ | CH₂CHCH₂ |
| CF₃ | CHCH₂ | n-Pr | Br | CHCH₂ | CH₂CHCH₂ |
| OCF₃ | CHCH₂ | n-Pr | CF₃ | CHCH₂ | CH₂CHCH₂ |
| Cl | CHCH₂ | COMe | OCF₃ | CHCH₂ | CH₂CHCH₂ |
| Br | CHCH₂ | COMe | Cl | CHCH₂ | CH₂SCH₃ |
| CF₃ | CHCH₂ | COMe | Br | CHCH₂ | CH₂SCH₃ |
| OCF₃ | CHCH₂ | COMe | CF₃ | CHCH₂ | CH₂SCH₃ |
| Cl | CHCH₂ | COEt | OCF₃ | CHCH₂ | CH₂SCH₃ |
| Br | CHCH₂ | COEt | OCF₂H | CHCH₂ | COEt |
| CF₃ | CHCH₂ | COEt | OCF₂H | CHCH₂ | CO₂Me |
| OCF₂H | CHCH₂ | H | OCF₂H | CHCH₂ | CO₂Et |
| OCF₂H | CHCH₂ | Me | OCF₂H | CHCH₂ | CH₂OMe |
| OCF₂H | CHCH₂ | Et | OCF₂H | CHCH₂ | CH₂CHCH₂ |
| OCF₂H | CHCH₂ | n-Pr | OCF₂H | CHCH₂ | CH₂SCH₃ |
| OCF₂H | CHCH₂ | COMe | | | |
| Cl | C(CH₃)CH₂ | H | OCF₃ | C(CH₃)CH₂ | COEt |
| Br | C(CH₃)CH₂ | H | Cl | C(CH₃)CH₂ | CO₂Me |
| CF₃ | C(CH₃)CH₂ | H | Br | C(CH₃)CH₂ | CO₂Me |
| OCF₃ | C(CH₃)CH₂ | H | CF₃ | C(CH₃)CH₂ | CO₂Me |
| Cl | C(CH₃)CH₂ | Me | OCF₃ | C(CH₃)CH₂ | CO₂Me |
| Br | C(CH₃)CH₂ | Me | Cl | C(CH₃)CH₂ | CO₂Et |
| CF₃ | C(CH₃)CH₂ | Me | Br | C(CH₃)CH₂ | CO₂Et |
| OCF₃ | C(CH₃)CH₂ | Me | CF₃ | C(CH₃)CH₂ | CO₂Et |
| Cl | C(CH₃)CH₂ | Et | OCF₃ | C(CH₃)CH₂ | CO₂Et |
| Br | C(CH₃)CH₂ | Et | Cl | C(CH₃)CH₂ | CH₂OMe |
| CF₃ | C(CH₃)CH₂ | Et | Br | C(CH₃)CH₂ | CH₂OMe |
| OCF₃ | C(CH₃)CH₂ | Et | CF₃ | C(CH₃)CH₂ | CH₂OMe |
| Cl | C(CH₃)CH₂ | n-Pr | OCF₃ | C(CH₃)CH₂ | CH₂OMe |
| Br | C(CH₃)CH₂ | n-Pr | Cl | C(CH₃)CH₂ | CH₂CHCH₂ |
| CF₃ | C(CH₃)CH₂ | n-Pr | Br | C(CH₃)CH₂ | CH₂CHCH₂ |
| OCF₃ | C(CH₃)CH₂ | n-Pr | CF₃ | C(CH₃)CH₂ | CH₂CHCH₂ |
| Cl | C(CH₃)CH₂ | COMe | OCF₃ | C(CH₃)CH₂ | CH₂CHCH₂ |

TABLE 8-continued

| R¹ | R³ | Y | R¹ | R³ | Y |
|---|---|---|---|---|---|
| Br | C(CH₃)CH₂ | COMe | Cl | C(CH₃)CH₂ | CH₂SCH₃ |
| CF₃ | C(CH₃)CH₂ | COMe | Br | C(CH₃)CH₂ | CH₂SCH₃ |
| OCF₃ | C(CH₃)CH₂ | COMe | CF₃ | C(CH₃)CH₂ | CH₂SCH₃ |
| Cl | C(CH₃)CH₂ | COEt | OCF₃ | C(CH₃)CH₂ | CH₂SCH₃ |
| Br | C(CH₃)CH₂ | COEt | OCF₂H | C(CH₃)CH₂ | COEt |
| CF₃ | C(CH₃)CH₂ | COEt | OCF₂H | C(CH₃)CH₂ | CO₂Me |
| OCF₂H | C(CH₃)CH₂ | H | OCF₂H | C(CH₃)CH₂ | CO₂Et |
| OCF₂H | C(CH₃)CH₂ | Me | OCF₂H | C(CH₃)CH₂ | CH₂OMe |
| OCF₂H | C(CH₃)CH₂ | Et | OCF₂H | C(CH₃)CH₂ | CH₂CHCH₂ |
| OCF₂H | C(CH₃)CH₂ | n-Pr | OCF₂H | C(CH₃)CH₂ | CH₂SCH₃ |
| OCF₂H | C(CH₃)CH₂ | COMe | | | |
| CF₃ | Me | CO₂(n-Pr) | CF₃ | n-Pr | CO₂(n-Pr) |
| CF₃ | Me | CO₂(i-Pr) | CF₃ | n-Pr | CO₂(i-Pr) |
| CF₃ | Me | CO(n-Pr) | CF₃ | n-Pr | CO(n-Pr) |
| CF₃ | Me | CO(i-Pr) | CF₃ | n-Pr | CO(i-Pr) |
| CF₃ | Me | CO(t-Bu) | CF₃ | n-Pr | CO(t-Bu) |
| CF₃ | Me | CO₂(t-Bu) | CF₃ | n-Pr | CO₂(t-Bu) |
| OCF₃ | Me | CO₂(n-Pr) | OCF₃ | n-Pr | CO₂(n-Pr) |
| OCF₃ | Me | CO₂(i-Pr) | OCF₃ | n-Pr | CO₂(i-Pr) |
| OCF₃ | Me | CO(n-Pr) | OCF₃ | n-Pr | CO(n-Pr) |
| OCF₃ | Me | CO(i-Pr) | OCF₃ | n-Pr | CO(i-Pr) |
| OCF₃ | Me | CO(t-Bu) | OCF₃ | n-Pr | CO(t-Bu) |
| OCF₃ | Me | CO₂(t-Bu) | OCF₃ | n-Pr | CO₂(t-Bu) |
| CF₃ | Et | CO₂(n-Pr) | CF₃ | i-Pr | CO₂(n-Pr) |
| CF₃ | Et | CO₂(i-Pr) | CF₃ | i-Pr | CO₂(i-Pr) |
| CF₃ | Et | CO(n-Pr) | CF₃ | i-Pr | CO(n-Pr) |
| CF₃ | Et | CO(i-Pr) | CF₃ | i-Pr | CO(i-Pr) |
| CF₃ | Et | CO(t-Bu) | CF₃ | i-Pr | CO(t-Bu) |
| CF₃ | Et | CO₂(t-Bu) | CF₃ | i-Pr | CO₂(t-Bu) |
| OCF₃ | Et | CO₂(n-Pr) | OCF₃ | i-pr | CO₂(n-Pr) |
| OCF₃ | Et | CO₂(i-Pr) | OCF₃ | i-Pr | CO₂(i-Pr) |
| OCF₃ | Et | CO(n-Pr) | OCF₃ | i-Pr | CO(n-Pr) |
| OCF₃ | Et | CO(i-Pr) | OCF₃ | i-Pr | CO(i-Pr) |
| OCF₃ | Et | CO(t-Bu) | OCF₃ | i-Pr | CO(t-Bu) |
| OCF₃ | Et | CO₂(t-Bu) | OCF₃ | i-Pr | CO₂(t-Bu) |
| OCF₂H | Me | CO(n-Pr) | OCF₂H | Et | CO(i-Pr) |
| OCF₂H | Me | CO₂(n-Pr) | OCF₂H | Et | CO₂(i-Pr) |
| OCF₂H | Me | CO(i-Pr) | OCF₂H | Et | CO(t-Bu) |
| OCF₂H | Me | CO₂(i-Pr) | OCF₂H | Et | CO₂(t-Bu) |
| OCF₂H | Me | CO(t-Bu) | OCF₂H | n-Pr | CO(n-Pr) |
| OCF₂H | Me | CO₂(t-Bu) | OCF₂H | n-Pr | CO₂(n-Pr) |
| OCF₂H | Et | CO(n-Pr) | OCF₂H | n-Pr | CO(i-Pr) |
| OCF₂H | Et | CO₂(n-Pr) | OCF₂H | n-Pr | CO₂(i-Pr) |
| CF₃ | i-Bu | CO₂(n-Pr) | CF₃ | CO₂Et | CO₂(n-Pr) |
| CF₃ | i-Bu | CO₂(i-Pr) | CF₃ | CO₂Et | CO₂(i-Pr) |
| CF₃ | i-Bu | CO(n-Pr) | CF₃ | CO₂Et | CO(n-Pr) |
| CF₃ | i-Bu | CO(i-Pr) | CF₃ | CO₂Et | CO(i-Pr) |
| CF₃ | i-Bu | CO(t-Bu) | CF₃ | CO₂Et | CO(t-Bu) |
| CF₃ | i-Bu | CO₂(t-Bu) | CF₃ | CO₂Et | CO₂(t-Bu) |
| OCF₃ | i-Bu | CO₂(n-Pr) | OCF₃ | CO₂Et | CO₂(n-Pr) |
| OCF₃ | i-Bu | CO₂(i-Pr) | OCF₃ | CO₂Et | CO₂(i-Pr) |
| OCF₃ | i-Bu | CO(n-Pr) | OCF₃ | CO₂Et | CO(n-Pr) |
| OCF₃ | i-Bu | CO(i-Pr) | OCF₃ | CO₂Et | CO(i-Pr) |
| OCF₃ | i-Bu | CO(t-Bu) | OCF₃ | CO₂Et | CO(t-Bu) |
| OCF₃ | i-Bu | CO₂(t-Bu) | OCF₃ | CO₂Et | CO₂(t-Bu) |
| CF₃ | CO₂Me | CO₂(n-Pr) | CF₃ | Ph | CO₂(n-Pr) |
| CF₃ | CO₂Me | CO₂(i-Pr) | CF₃ | Ph | CO₂(i-Pr) |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | CO₂(t-Bu) | CF₃ | Ph | CO₂(t-Bu) |
| OCF₃ | CO₂Me | CO₂(n-Pr) | OCF₃ | Ph | CO₂(n-Pr) |
| OCF₃ | CO₂Me | CO₂(i-Pr) | OCF₃ | Ph | CO₂(i-Pr) |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |

TABLE 8-continued

| R¹ | R³ | Y | R¹ | R³ | Y |
|---|---|---|---|---|---|
| OCF₃ | CO₂Me | CO(t-Bu) | OCF₃ | Ph | CO(t-Bu) |
| OCF₃ | CO₂Me | CO₂(t-Bu) | OCF₃ | Ph | CO₂(t-Bu) |
| OCF₂H | n-Pr | CO(t-Bu) | OCF₂H | CO₂Me | CO(i-Pr) |
| OCF₂H | n-Pr | CO₂(t-Bu) | OCF₂H | CO₂Me | CO₂(i-Pr) |
| OCF₂H | i-Pr | CO(i-Pr) | OCF₂H | CO₂Me | CO(t-Bu) |
| OCF₂H | i-Pr | CO₂(i-Pr) | OCF₂H | CO₂Me | CO₂(t-Bu) |
| OCF₂H | i-Pr | CO(t-Bu) | OCF₂H | CO₂Me | CO(n-Pr) |
| OCF₂H | i-Pr | CO₂(t-Bu) | OCF₂H | CO₂Me | CO₂(n-Pr) |
| OCF₂H | i-Pr | CO(n-Pr) | OCF₂H | CO₂Et | CO(n-Pr) |
| OCF₂H | i-Pr | CO₂(n-Pr) | OCF₂H | CO₂Et | CO₂(n-Pr) |
| CF₃ | 4-Cl—Ph | CO₂(n-Pr) | CF₃ | CHCH₂ | CO₂(n-Pr) |
| CF₃ | 4-Cl—Ph | CO₂(i-Pr) | CF₃ | CHCH₂ | CO₂(i-Pr) |
| CF₃ | 4-Cl—Ph | CO(n-Pr) | CF₃ | CHCH₂ | CO(n-Pr) |
| CF₃ | 4-Cl—Ph | CO(i-Pr) | CF₃ | CHCH₂ | CO(i-Pr) |
| CF₃ | 4-Cl—Ph | CO(t-Bu) | CF₃ | CHCH₂ | CO(t-Bu) |
| CF₃ | 4-Cl—Ph | CO₂(t-Bu) | CF₃ | CHCH₂ | CO₂(t-Bu) |
| OCF₃ | 4-Cl—Ph | CO₂(n-Pr) | OCF₃ | CHCH₂ | CO₂(n-Pr) |
| OCF₃ | 4-Cl—Ph | CO₂(i-Pr) | OCF₃ | CHCH₂ | CO₂(n-Pr) |
| OCF₃ | 4-Cl—Ph | CO(n-Pr) | OCF₃ | CHCH₂ | CO(n-Pr) |
| OCF₃ | 4-Cl—Ph | CO(i-Pr) | OCF₃ | CHCH₂ | CO(i-Pr) |
| OCF₃ | 4-Cl—Ph | CO(t-Bu) | OCF₃ | CHCH₂ | CO(t-Bu) |
| OCF₃ | 4-Cl—Ph | CO₂(t-Bu) | OCF₃ | CHCH₂ | CO₂(t-Bu) |
| CF₃ | 4-F—Ph | CO₂(n-Pr) | CF₃ | C(CH₃)CH₂ | CO₂(n-Pr) |
| CF₃ | 4-F—Ph | CO₂(i-Pr) | CF₃ | C(CH₃)CH₂ | CO₂(i-Pr) |
| CF₃ | 4-F—Ph | CO(n-Pr) | CF₃ | C(CH₃)CH₂ | CO(n-Pr) |
| CF₃ | 4-F—Ph | CO(i-Pr) | CF₃ | C(CH₃)CH₂ | CO(n-Pr) |
| CF₃ | 4-F—Ph | CO(t-Bu) | CF₃ | C(CH₃)CH₂ | CO(t-Bu) |
| CF₃ | 4-F—Ph | CO₂(t-Bu) | CF₃ | C(CH₃)CH₂ | CO₂(t-Bu) |
| OCF₃ | 4-F—Ph | CO₂(n-Pr) | OCF₃ | C(CH₃)CH₂ | CO₂(n-Pr) |
| OCF₃ | 4-F—Ph | CO₂(i-Pr) | OCF₃ | C(CH₃)CH₂ | CO₂(i-Pr) |
| OCF₃ | 4-F—Ph | CO(n-Pr) | OCF₃ | C(CH₃)CH₂ | CO(n-Pr) |
| OCF₃ | 4-F—Ph | CO(i-Pr) | OCF₃ | C(CH₃)CH₂ | CO(i-Pr) |
| OCF₃ | 4-F—Ph | CO(t-Bu) | OCF₃ | C(CH₃)CH₂ | CO(t-Bu) |
| OCF₃ | 4-F—Ph | CO₂(t-Bu) | OCF₃ | C(CH₃)CH₂ | CO₂(t-Bu) |
| OCF₂H | CO₂Et | CO(i-Pr) | OCF₂H | 4-Cl—Ph | CO(t-Bu) |
| OCF₂H | CO₂Et | CO₂(i-Pr) | OCF₂H | 4-Cl—Ph | CO₂(t-Bu) |
| OCF₂H | CO₂Et | CO(t-Bu) | OCF₂H | 4-F—Ph | CO(n-Pr) |
| OCF₂H | CO₂Et | CO₂(t-Bu) | OCF₂H | 4-F—Ph | CO₂(n-Pr) |
| OCF₂H | 4-Cl—Ph | CO(n-Pr) | OCF₂H | 4-F—Ph | CO(i-Pr) |
| OCF₂H | 4-Cl—Ph | CO₂(n-Pr) | OCF₂H | 4-F—Ph | CO₂i-Pr) |
| OCF₂H | 4-Cl—Ph | CO(i-Pr) | OCF₂H | 4-F—Ph | CO(t-Bu) |
| OCF₂H | 4-Cl—Ph | CO₂(i-Pr) | OCF₂H | 4-F—Ph | CO₂(t-Bu) |

TABLE 9

| R¹ | R³ | Y | R¹ | R³ | Y |
|---|---|---|---|---|---|
| Cl | Ph | H | Cl | 4-Cl—Ph | H |
| Br | Ph | H | Br | 4-Cl—Ph | H |
| CF₃ | Ph | H | CF₃ | 4-Cl—Ph | H |

TABLE 9-continued

| $R^1$ | $R^3$ | Y | $R^1$ | $R^3$ | Y |
|---|---|---|---|---|---|
| $OCF_3$ | Ph | H | $OCF_3$ | 4-Cl—Ph | H |
| Cl | Ph | Me | Cl | 4-Cl—Ph | Me |
| Br | Ph | Me | Br | 4-Cl—Ph | Me |
| $CF_3$ | Ph | Me | $CF_3$ | 4-Cl—Ph | Me |
| $OCF_3$ | Ph | Me | $OCF_3$ | 4-Cl—Ph | Me |
| Cl | Ph | Et | Cl | 4-Cl—Ph | Et |
| Br | Ph | Et | Br | 4-Cl—Ph | Et |
| $CF_3$ | Ph | Et | $CF_3$ | 4-Cl—Ph | Et |
| $OCF_3$ | Ph | Et | $OCF_3$ | 4-Cl—Ph- | Et |
| Cl | Ph | COMe | Cl | 4-Cl—Ph | COMe |
| Br | Ph | COMe | Br | 4-Cl—Ph | COMe |
| $CF_3$ | Ph | COMe | $CF_3$ | 4-Cl—Ph | COMe |
| $OCF_3$ | Ph | COMe | $OCF_3$ | 4-Cl—Ph | COMe |
| Cl | Ph | $CO_2Me$ | Cl | 4-Cl—Ph | $CO_2Me$ |
| Br | Ph | $CO_2Me$ | Br | 4-Cl—Ph | $CO_2Me$ |
| $CF_3$ | Ph | $CO_2Me$ | $CF_3$ | 4-Cl—Ph | $CO_2Me$ |
| $OCF_3$ | Ph | $CO_2Me$ | $OCF_3$ | 4-Cl—Ph | $CO_2Me$ |
| $OCF_2H$ | Ph | H | $OCF_2H$ | Ph | COMe |
| $OCF_2H$ | Ph | Me | $OCF_2H$ | Ph | $CO_2Me$ |
| $OCF_2H$ | Ph | Et | $OCF_2H$ | Ph | COEt |
| $OCF_2H$ | Ph | n-Pr | $OCF_2H$ | Ph | $CO_2Et$ |
| Cl | 4-F—Ph | H | $OCF_3$ | $CO_2Me$ | Me |
| Br | 4-F—Ph | H | Cl | $CO_2Me$ | Et |
| $CF_3$ | 4-F—Ph | H | Br | $CO_2Me$ | Et |
| $OCF_3$ | 4-F—Ph | H | $CF_3$ | $CO_2Me$ | Et |
| Cl | 4-F—Ph | Me | $OCF_3$ | $CO_2Me$ | Et |
| Br | 4-F—Ph | Me | Cl | $CO_2Me$ | COMe |
| $CF_3$ | 4-F—Ph | Me | Br | $CO_2Me$ | COMe |
| $OCF_3$ | 4-F—Ph | Me | $CF_3$ | $CO_2Me$ | COMe |
| Cl | 4-F—Ph | Et | $OCF_3$ | $CO_2Me$ | COMe |
| Br | 4-F—Ph | Et | Cl | $CO_2Me$ | $CO_2Me$ |
| $CF_3$ | 4-F—Ph | Et | Br | $CO_2Me$ | $CO_2Me$ |
| $OCF_3$ | 4-F—Ph | Et | $CF_3$ | $CO_2Me$ | $CO_2Me$ |
| Cl | 4-F—Ph | COMe | $OCF_3$ | $CO_2Me$ | $CO_2Me$ |
| Br | 4-F—Ph | COMe | Cl | n-Pr | H |
| $CF_3$ | 4-F—Ph | COMe | Br | n-Pr | H |
| $OCF_3$ | 4-F—Ph | COMe | $CF_3$ | n-Pr | H |
| Cl | 4-F—Ph | $CO_2Me$ | $OCF_3$ | n-Pr | H |
| Br | 4-F—Ph | $CO_2Me$ | Cl | n-Pr | Me |
| $CF_3$ | 4-F—Ph | $CO_2Me$ | Br | n-Pr | Me |
| $OCF_3$ | 4-F—Ph | $CO_2Me$ | $CF_3$ | n-Pr | Me |
| Cl | $CO_2Me$ | H | $OCF_3$ | n-Pr | Me |
| Br | $CO_2Me$ | H | Cl | n-Pr | Et |
| $CF_3$ | $CO_2Me$ | H | Br | n-Pr | Et |
| $OCF_3$ | $CO_2Me$ | H | $CF_3$ | n-Pr | Et |
| Cl | $CO_2Me$ | Me | $OCF_3$ | n-Pr | Et |
| Br | $CO_2Me$ | Me | $OCF_2H$ | 4-Cl—Ph | Et |
| $CF_3$ | $CO_2Me$ | Me | $OCF_2H$ | 4-Cl—Ph | n-Pr |
| $OCF_2H$ | Ph | CO(n-Pr) | $OCF_2H$ | 4-Cl—Ph | COMe |
| $OCF_2H$ | Ph | CO(i-Pr) | $OCF_2H$ | 4-Cl—Ph | $CO_2Me$ |
| $OCF_2H$ | Ph | CO(t-Bu) | $OCF_2H$ | 4-Cl—Ph | COEt |
| $OCF_2H$ | 4-Cl—Ph | H | $OCF_2H$ | 4-Cl—Ph | $CO_2Et$ |
| $OCF_2H$ | 4-Cl—Ph | Me | $OCF_2H$ | 4-Cl—Ph | CO(n-Pr) |
| Cl | n-Pr | COMe | Cl | $CHCH_2$ | $CO_2Me$ |
| Br | n-Pr | COMe | Br | $CHCH_2$ | $CO_2Me$ |
| $CF_3$ | n-Pr | COMe | $CF_3$ | $CHCH_2$ | $CO_2Me$ |
| $OCF_3$ | n-Pr | COMe | $OCF_3$ | $CHCH_2$ | $CO_2Me$ |
| Cl | n-Pr | $CO_2Me$ | Cl | $C(CH_3)CH_2$ | H |
| Br | n-Pr | $CO_2Me$ | Br | $C(CH_3)CH_2$ | H |
| $CF_3$ | n-Pr | $CO_2Me$ | $CF_3$ | $C(CH_3)CH_2$ | H |
| $OCF_3$ | n-Pr | $CO_2Me$ | $OCF_3$ | $C(CH_3)CH_2$ | H |
| Cl | $CHCH_2$ | H | Cl | $C(CH_3)CH_2$ | Me |
| Br | $CHCH_2$ | H | Br | $C(CH_3)CH_2$ | Me |
| $CF_3$ | $CHCH_2$ | H | $CF_3$ | $C(CH_3)CH_2$ | Me |

TABLE 9-continued

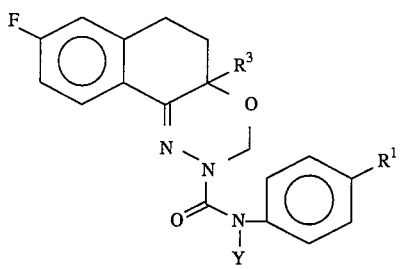

| R¹ | R³ | Y | R¹ | R³ | Y |
|---|---|---|---|---|---|
| OCF₃ | CHCH₂ | H | OCF₃ | C(CH₃)CH₂ | Me |
| Cl | CHCH₂ | Me | Cl | C(CH₃)CH₂ | Et |
| Br | CHCH₂ | Me | Br | C(CH₃)CH₂ | Et |
| CF₃ | CHCH₂ | Me | CF₃ | C(CH₃)CH₂ | Et |
| OCF₃ | CHCH₂ | Me | OCF₃ | C(CH₃)CH₂ | Et |
| Cl | CHCH₂ | Et | Cl | C(CH₃)CH₂ | COMe |
| Br | CHCH₂ | Et | Br | C(CH₃)CH₂ | COMe |
| CF₃ | CHCH₂ | Et | CF₃ | C(CH₃)CH₂ | COMe |
| OCF₃ | CHCH₂ | Et | OCF₃ | C(CH₃)CH₂ | COMe |
| Cl | CHCH₂ | COMe | Cl | C(CH₃)CH₂ | CO₂Me |
| Br | CHCH₂ | COMe | Br | C(CH₃)CH₂ | CO₂Me |
| CF₃ | CHCH₂ | COMe | CF₃ | C(CH₃)CH₂ | CO₂Me |
| OCF₃ | CHCH₂ | COMe | OCF₃ | C(CH₃)CH₂ | CO₂Me |
| OCF₂H | 4-Cl—Ph | CO(i-Pr) | OCF₂H | 4-F—Ph | COEt |
| OCF₂H | 4-Cl—Ph | CO(t-Bu) | OCF₂H | 4-F—Ph | CO₂Et |
| OCF₂H | 4-F—Ph | H | OCF₂H | 4-F—Ph | CO(n-Pr) |
| OCF₂H | 4-F—Ph | Me | OCF₂H | 4-F—Ph | CO(i-Pr) |
| OCF₂H | 4-F—Ph | Et | OCF₂H | 4-F—Ph | CO(t-Bu) |
| OCF₂H | 4-F—Ph | n-Pr | OCF₂H | CO₂Me | H |
| OCF₂H | 4-F—Ph | COMe | OCF₂H | CO₂Me | Me |
| OCF₂H | 4-F—Ph | CO₂Me | OCF₂H | CO₂Me | Et |
| CF₃ | Ph | COEt | CF₃ | 4-F—Ph | COEt |
| CF₃ | Ph | CO₂Et | CF₃ | 4-F—Ph | CO₂Et |
| CF₃ | Ph | CO(n-Pr) | CF₃ | 4-F—Ph | CO(n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | CO₂Me | COEt |
| CF₃ | 4-Cl—Ph | CO₂Et | CF₃ | CO₂Me | CO₂Et |
| CF₃ | 4-Cl—Ph | CO(n-Pr) | CF₃ | CO₂Me | CO(n-Pr) |
| CF₃ | 4-Cl—Ph | CO(i-Pr) | CF₃ | CO₂Me | CO(i-Pr) |
| CF₃ | 4-Cl—Ph | CO(t-Bu) | CF₃ | CO₂Me | CO(t-Bu) |
| CF₃ | 4-Cl—Ph | n-Pr | CF₃ | CO₂Me | n-Pr |
| OCF₃ | 4-Cl—Ph | COEt | OCF₃ | CO₂Me | COEt |
| OCF₃ | 4-Cl—Ph | CO₂Et | OCF₃ | CO₂Me | CO₂Et |
| OCF₃ | 4-Cl—Ph | CO(n-Pr) | OCF₃ | CO₂Me | CO(n-Pr) |
| OCF₃ | 4-Cl—Ph | CO(i-Pr) | OCF₃ | CO₂Me | CO(i-Pr) |
| OCF₃ | 4-Cl—Ph | CO(t-Bu) | OCF₃ | CO₂Me | CO(t-Bu) |
| OCF₃ | 4-Cl—Ph | n-Pr | OCF₃ | CO₂Me | n-Pr |
| OCF₂H | CO₂Me | n-Pr | OCF₂H | n-Pr | H |
| OCF₂H | CO₂Me | COMe | OCF₂H | n-Pr | Me |
| OCF₂H | CO₂Me | CO₂Me | OCF₂H | n-Pr | Et |
| OCF₂H | CO₂Me | COEt | OCF₂H | n-Pr | n-Pr |
| OCF₂H | CO₂Me | CO₂Et | OCF₂H | n-Pr | COMe |
| OCF₂H | CO₂Me | CO(n-Pr) | OCF₂H | n-Pr | CO₂Me |
| OCF₂H | CO₂Me | CO(i-Pr) | OCF₂H | n-Pr | COEt |
| OCF₂H | CO₂Me | CO(t-Bu) | OCF₂H | n-Pr | CO₂Et |
| CF₃ | n-Pr | COEt | CF₃ | C(CH₃)CH₂ | COEt |
| CF₃ | n-Pr | CO₂Et | CF₃ | C(CH₃)CH₂ | CO₂Et |
| CF₃ | n-Pr | CO(n-Pr) | CF₃ | C(CH₃)CH₂ | CO(n-Pr) |
| CF₃ | n-Pr | CO(i-Pr) | CF₃ | C(CH₃)CH₂ | CO(i-Pr) |
| CF₃ | n-Pr | CO(t-Bu) | CF₃ | C(CH₃)CH₂ | CO(t-Bu) |
| CF₃ | n-Pr | n-Pr | CF₃ | C(CH₃)CH₂ | n-Pr |
| OCF₃ | n-Pr | COEt | OCF₃ | C(CH₃)CH₂ | COEt |
| OCF₃ | n-Pr | CO₂Et | OCF₃ | C(CH₃)CH₂ | CO₂Et |
| OCF₃ | n-Pr | CO(n-Pr) | OCF₃ | C(CH₃)CH₂ | CO(n-Pr) |
| OCF₃ | n-Pr | CO(i-Pr) | OCF₃ | C(CH₃)CH₂ | CO(i-Pr) |
| OCF₃ | n-Pr | CO(t-Bu) | OCF₃ | C(CH₃)CH₂ | CO(t-Bu) |

TABLE 9-continued

| R¹ | R³ | Y | R¹ | R³ | Y |
|---|---|---|---|---|---|
| OCF₃ | n-Pr | n-Pr | OCF₃ | C(CH₃)CH₂ | n-Pr |
| CF₃ | CHCH₂ | COEt | OCF₂H | CHCH₂ | CO₂Me |
| CF₃ | CHCH₂ | CO₂Et | OCF₂H | CHCH₂ | COEt |
| CF₃ | CHCH₂ | CO(n-Pr) | OCF₂H | CHCH₂ | CO₂Et |
| CF₃ | CHCH₂ | CO(i-Pr) | OCF₂H | CHCH₂ | CO(n-Pr) |
| CF₃ | CHCH₂ | CO(t-Bu) | OCF₂H | CHCH₂ | CO(i-Pr) |
| CF₃ | CHCH₂ | n-Pr | OCF₂H | CHCH₂ | CO(t-Bu) |
| OCF₃ | CHCH₂ | COEt | OCF₂H | C(CH₃)CH₂ | H |
| OCF₃ | CHCH₂ | CO₂Et | OCF₂H | C(CH₃)CH₂ | Me |
| OCF₃ | CHCH₂ | CO(n-Pr) | OCF₂H | C(CH₃)CH₂ | Et |
| OCF₃ | CHCH₂ | CO(i-Pr) | OCF₂H | C(CH₃)CH₂ | n-Pr |
| OCF₃ | CHCH₂ | CO(t-Bu) | OCF₂H | C(CH₃)CH₂ | COMe |
| OCF₃ | CHCH₂ | n-Pr | OCF₂H | C(CH₃)CH₂ | CO₂Me |
| OCF₂H | n-Pr | CO(n-Pr) | OCF₂H | C(CH₃)CH₂ | COEt |
| OCF₂H | n-Pr | CO(i-Pr) | OCF₂H | C(CH₃)CH₂ | CO₂Et |
| OCF₂H | n-Pr | CO(t-Bu) | OCF₂H | C(CH₃)CH₂ | CO(n-Pr) |
| OCF₂H | CHCH₂ | H | OCF₂H | C(CH₃)CH₂ | CO(i-Pr) |
| OCF₂H | CHCH₂ | Me | OCF₂H | C(CH₃)CH₂ | CO(t-Bu) |
| OCF₂H | CHCH₂ | Et | | | |
| OCF₂H | CHCH₂ | n-Pr | | | |
| OCF₂H | CHCH₂ | COMe | | | |

TABLE 10

| R¹ | R³ | Y | R¹ | R³ | Y |
|---|---|---|---|---|---|
| Cl | Ph | H | Cl | 4-Cl—Ph | H |
| Br | Ph | H | Br | 4-Cl—Ph | H |
| CF₃ | Ph | H | CF₃ | 4-Cl—Ph | H |
| OCF₃ | Ph | H | OCF₃ | 4-Cl—Ph | H |
| Cl | Ph | Me | Cl | 4-Cl—Ph | Me |
| Br | Ph | Me | Br | 4-Cl—Ph | Me |
| CF₃ | Ph | Me | CF₃ | 4-Cl—Ph | Me |
| OCF₃ | Ph | Me | OCF₃ | 4-Cl—Ph | Me |
| Cl | Ph | Et | Cl | 4-Cl—Ph | Et |
| Br | Ph | Et | Br | 4-Cl—Ph | Et |
| CF₃ | Ph | Et | CF₃ | 4-Cl—Ph | Et |
| OCF₃ | Ph | Et | OCF₃ | 4-Cl—Ph | Et |
| Cl | Ph | COMe | Cl | 4-Cl—Ph | COMe |
| Br | Ph | COMe | Br | 4-Cl—Ph | COMe |
| CF₃ | Ph | COMe | CF₃ | 4-Cl—Ph | COMe |
| OCF₃ | Ph | COMe | OCF₃ | 4-Cl—Ph | COMe |
| Cl | Ph | CO₂Me | Cl | 4-Cl—Ph | CO₂Me |
| Br | Ph | CO₂Me | Br | 4-Cl—Ph | CO₂Me |
| CF₃ | Ph | CO₂Me | CF₃ | 4-Cl—Ph | CO₂Me |
| OCF₃ | Ph | CO₂Me | OCF₃ | 4-Cl—Ph | CO₂Me |
| OCF₂H | Ph | H | OCF₂H | Ph | COMe |
| OCF₂H | Ph | Me | OCF₂H | Ph | CO₂Me |

TABLE 10-continued

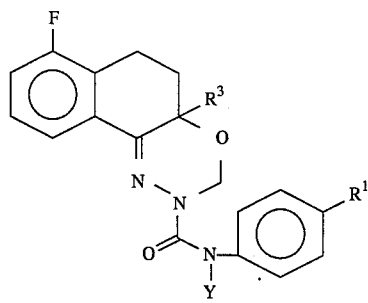

| R¹ | R³ | Y | R¹ | R³ | Y |
|---|---|---|---|---|---|
| OCF₂H | Ph | Et | OCF₂H | Ph | COEt |
| OCF₂H | Ph | n-Pr | OCF₂H | Ph | CO₂Et |
| Cl | 4-F—Ph | H | OCF₃ | CO₂Me | Me |
| Br | 4-F—Ph | H | Cl | CO₂Me | Et |
| CF₃ | 4-F—Ph | H | Br | CO₂Me | Et |
| OCF₃ | 4-F—Ph | H | CF₃ | CO₂Me | Et |
| Cl | 4-F—Ph | Me | OCF₃ | CO₂Me | Et |
| Br | 4-F—Ph | Me | Cl | CO₂Me | COMe |
| CF₃ | 4-F—Ph | Me | Br | CO₂Me | COMe |
| OCF₃ | 4-F—Ph | Me | CF₃ | CO₂Me | COMe |
| Cl | 4-F—Ph | Et | OCF₃ | CO₂Me | COMe |
| Br | 4-F—Ph | Et | Cl | CO₂Me | CO₂Me |
| CF₃ | 4-F—Ph | Et | Br | CO₂Me | CO₂Me |
| OCF₃ | 4-F—Ph | Et | CF₃ | CO₂Me | CO₂Me |
| Cl | 4-F—Ph | COMe | OCF₃ | CO₂Me | CO₂Me |
| Br | 4-F—Ph | COMe | Cl | n-Pr | H |
| CF₃ | 4-F—Ph | COMe | Br | n-Pr | H |
| OCF₃ | 4-F—Ph | COMe | CF₃ | n-Pr | H |
| Cl | 4-F—Ph | CO₂Me | OCF₃ | n-Pr | H |
| Br | 4-F—Ph | CO₂Me | Cl | n-Pr | Me |
| CF₃ | 4-F—Ph | CO₂Me | Br | n-Pr | Me |
| OCF₃ | 4-F—Ph | CO₂Me | CF₃ | n-Pr | Me |
| Cl | CO₂Me | H | OCF₃ | n-Pr | Me |
| Br | CO₂Me | H | Cl | n-Pr | Et |
| CF₃ | CO₂Me | H | Br | n-Pr | Et |
| OCF₃ | CO₂Me | H | CF₃ | n-Pr | Et |
| Cl | CO₂Me | Me | OCF₃ | n-Pr | Et |
| Br | CO₂Me | Me | OCF₂H | 4-Cl—Ph | Et |
| CF₃ | CO₂Me | Me | OCF₂H | 4-Cl—Ph | n-Pr |
| OCF₂H | Ph | CO(n-Pr) | OCF₂H | 4-Cl—Ph | COMe |
| OCF₂H | Ph | CO(i-Pr) | OCF₂H | 4-Cl—Ph | CO₂Me |
| OCF₂H | Ph | CO(t-Bu) | OCF₂H | 4-Cl—Ph | COEt |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CO(n-Pr) |
| Cl | n-Pr | COMe | Cl | CHCH₂ | CO₂Me |
| Br | n-Pr | COMe | Br | CHCH₂ | CO₂Me |
| CF₃ | n-Pr | COMe | CF₃ | CHCH₂ | CO₂Me |
| OCF₃ | n-Pr | COMe | OCF₃ | CHCH₂ | CO₂Me |
| Cl | n-Pr | CO₂Me | Cl | C(CH₃)CH₂ | H |
| Br | n-Pr | CO₂Me | Br | C(CH₃)CH₂ | H |
| CF₃ | n-Pr | CO₂Me | CF₃ | C(CH₃)CH₂ | H |
| OCF₃ | n-Pr | CO₂Me | OCF₃ | C(CH₃)CH₂ | H |
| Cl | CHCH₂ | H | Cl | C(CH₃)CH₂ | Me |
| Br | CHCH₂ | H | Br | C(CH₃)CH₂ | Me |
| CF₃ | CHCH₂ | H | CF₃ | C(CH₃)CH₂ | Me |
| OCF₃ | CHCH₂ | H | OCF₃ | C(CH₃)CH₂ | Me |
| Cl | CHCH₂ | Me | Cl | C(CH₃)CH₂ | Et |
| Br | CHCH₂ | Me | Br | C(CH₃)CH₂ | Et |
| CF₃ | CHCH₂ | Me | CF₃ | C(CH₃)CH₂ | Et |
| OCF₃ | CHCH₂ | Me | OCF₃ | C(CH₃)CH₂ | Et |
| Cl | CHCH₂ | Et | Cl | C(CH₃)CH₂ | COMe |
| Br | CHCH₂ | Et | Br | C(CH₃)CH₂ | COMe |
| CF₃ | CHCH₂ | Et | CF₃ | C(CH₃)CH₂ | COMe |
| OCF₃ | CHCH₂ | Et | OCF₃ | C(CH₃)CH₂ | COMe |
| Cl | CHCH₂ | COMe | Cl | C(CH₃)CH₂ | CO₂Me |
| Br | CHCH₂ | COMe | Br | C(CH₃)CH₂ | CO₂Me |
| CF₃ | CHCH₂ | COMe | CF₃ | C(CH₃)CH₂ | CO₂Me |
| OCF₃ | CHCH₂ | COMe | OCF₃ | C(CH₃)CH₂ | CO₂Me |
| OCF₂H | 4-Cl—Ph | CO(i-Pr) | OCF₂H | 4-F—Ph | COEt |
| OCF₂H | 4-Cl—Ph | CO(t-Bu) | OCF₂H | 4-F—Ph | CO₂Et |
| OCF₂H | 4-F—Ph | H | OCF₂H | 4-F—Ph | CO(n-Pr) |
| OCF₂H | 4-F—Ph | Me | OCF₂H | 4-F—Ph | CO(i-Pr) |

TABLE 10-continued

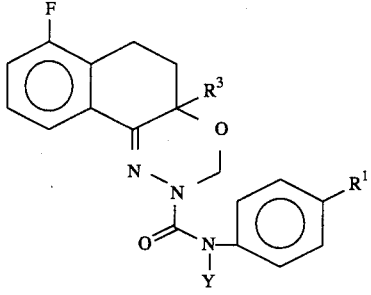

| R¹ | R³ | Y | R¹ | R³ | Y |
|---|---|---|---|---|---|
| OCF₂H | 4-F—Ph | Et | OCF₂H | 4-F—Ph | CO(t-Bu) |
| OCF₂H | 4-F—Ph | n-Pr | OCF₂H | CO₂Me | H |
| OCF₂H | 4-F—Ph | COMe | OCF₂H | CO₂Me | Me |
| OCF₂H | 4-F—Ph | CO₂Me | OCF₂H | CO₂Me | Et |
| CF₃ | Ph | COEt | CF₃ | 4-F—Ph | COEt |
| CF₃ | Ph | CO₂Et | CF₃ | 4-F—Ph | CO₂Et |
| CF₃ | Ph | CO(n-Pr) | CF₃ | 4-F—Ph | CO(n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | CO₂Me | COEt |
| CF₃ | 4-Cl—Ph | CO₂Et | CF₃ | CO₂Me | CO₂Et |
| CF₃ | 4-Cl—Ph | CO(n-Pr) | CF₃ | CO₂Me | CO(n-Pr) |
| CF₃ | 4-Cl—Ph | CO(i-Pr) | CF₃ | CO₂Me | CO(i-Pr) |
| CF₃ | 4-Cl—Ph | CO(t-Bu) | CF₃ | CO₂Me | CO(t-Bu) |
| CF₃ | 4-Cl—Ph | n-Pr | CF₃ | CO₂Me | n-Pr |
| OCF₃ | 4-Cl—Ph | COEt | OCF₃ | CO₂Me | COEt |
| OCF₃ | 4-Cl—Ph | CO₂Et | OCF₃ | CO₂Me | CO₂Et |
| OCF₃ | 4-Cl—Ph | CO(n-Pr) | OCF₃ | CO₂Me | CO(n-Pr) |
| OCF₃ | 4-Cl—Ph | CO(i-Pr) | OCF₃ | CO₂Me | CO(i-Pr) |
| OCF₃ | Me | CO₂Et | OCF₃ | CO₂Me | CO(t-Bu) |
| OCF₃ | Me | CO(n-Pr) | OCF₃ | CO₂Me | n-Pr |
| OCF₃ | Me | CO(i-Pr) | OCF₂H | n-Pr | H |
| OCF₃ | Me | CO(t-Bu) | OCF₂H | n-Pr | Me |
| OCF₃ | Me | n-Pr | OCF₂H | n-Pr | Et |
| OCF₂H | CO₂Me | Et | OCF₂H | n-Pr | n-Pr |
| OCF₂H | CO₂Me | n-Pr | OCF₂H | n-Pr | COMe |
| OCF₂H | CO₂Me | COMe | OCF₂H | n-Pr | CO₂Me |
| OCF₂H | CO₂Me | CO₂Me | OCF₂H | n-Pr | COEt |
| OCF₂H | CO₂Me | COEt | OCF₂H | n-Pr | CO₂Et |
| OCF₂H | CO₂Me | CO₂Et | | | |
| OCF₂H | CO₂Me | CO(n-Pr) | | | |
| OCF₂H | CO₂Me | CO(i-Pr) | | | |
| CF₃ | n-Pr | COEt | CF₃ | C(CH₃)CH₂ | COEt |
| CF₃ | n-Pr | CO₂Et | CF₃ | C(CH₃)CH₂ | CO₂Et |
| CF₃ | n-Pr | CO(n-Pr) | CF₃ | C(CH₃)CH₂ | CO(n-Pr) |
| CF₃ | n-Pr | CO(i-Pr) | CF₃ | C(CH₃)CH₂ | CO(n-Pr) |
| CF₃ | n-Pr | CO(t-Bu) | CF₃ | C(CH₃)CH₂ | CO(t-Bu) |
| CF₃ | n-Pr | n-Pr | CF₃ | C(CH₃)CH₂ | n-Pr |
| OCF₃ | n-Pr | COEt | OCF₃ | C(CH₃)CH₂ | COEt |
| OCF₃ | n-Pr | CO₂Et | OCF₃ | C(CH₃)CH₂ | CO₂Et |
| OCF₃ | n-Pr | CO(n-Pr) | OCF₃ | C(CH₃)CH₂ | CO(n-Pr) |
| OCF₃ | n-Pr | CO(i-Pr) | OCF₃ | C(CH₃)CH₂ | CO(i-Pr) |
| OCF₃ | n-Pr | CO(t-Bu) | OCF₃ | C(CH₃)CH₂ | CO(t-Bu) |
| OCF₃ | n-Pr | n-Pr | OCF₃ | C(CH₃)CH₂ | n-Pr |
| CF₃ | CHCH₂ | COEt | OCF₂H | CHCH₂ | CO₂Me |
| CF₃ | CHCH₂ | CO₂Et | OCF₂H | CHCH₂ | COEt |
| CF₃ | CHCH₂ | CO(n-Pr) | OCF₂H | CHCH₂ | CO₂Et |
| CF₃ | CHCH₂ | CO(i-Pr) | OCF₂H | CHCH₂ | CO(n-Pr) |
| CF₃ | CHCH₂ | CO(t-Bu) | OCF₂H | CHCH₂ | CO(i-Pr) |
| CF₃ | CHCH₂ | n-Pr | OCF₂H | CHCH₂ | CO(t-Bu) |
| OCF₃ | CHCH₂ | COEt | OCF₂H | C(CH₃)CH₂ | H |
| OCF₃ | CHCH₂ | CO₂Et | OCF₂H | C(CH₃)CH₂ | Me |
| OCF₃ | CHCH₂ | CO(n-Pr) | OCF₂H | C(CH₃)CH₂ | Et |
| OCF₃ | CHCH₂ | CO(i-Pr) | OCF₂H | C(CH₃)CH₂ | n-Pr |
| OCF₃ | CHCH₂ | CO(t-Bu) | OCF₂H | C(CH₃)CH₂ | COMe |

TABLE 10-continued

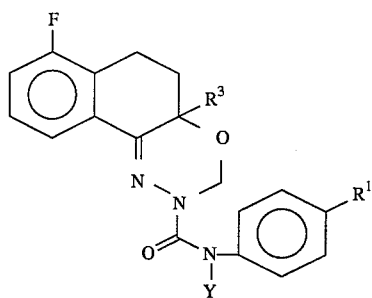

| R¹ | R³ | Y | R¹ | R³ | Y |
|---|---|---|---|---|---|
| OCF₃ | CHCH₂ | n-Pr | OCF₂H | C(CH₃)CH₂ | CO₂Me |
| OCF₂H | n-Pr | CO(n-Pr) | OCF₂H | C(CH₃)CH₂ | COEt |
| OCF₂H | n-Pr | CO(i-Pr) | OCF₂H | C(CH₃)CH₂ | CO₂Et |
| OCF₂H | n-Pr | CO(t-Bu) | OCF₂H | C(CH₃)CH₂ | CO(n-Pr) |
| OCF₂H | CHCH₂ | H | OCF₂H | C(CH₃)CH₂ | CO(i-Pr) |
| OCF₂H | CHCH₂ | Me | OCF₂H | C(CH₃)CH₂ | CO(t-Bu) |
| OCF₂H | CHCH₂ | Et | | | |
| OCF₂H | CHCH₂ | n-Pr | | | |
| OCF₂H | CHCH₂ | COMe | | | |

TABLE 11

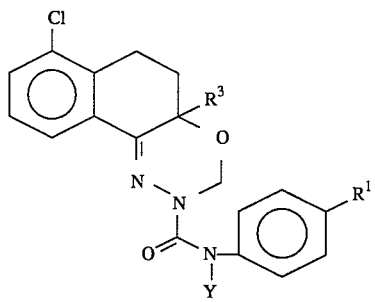

| R¹ | R³ | Y | R¹ | R³ | Y |
|---|---|---|---|---|---|
| Cl | Ph | H | Cl | 4-Cl—Ph | H |
| Br | Ph | H | Br | 4-Cl—Ph | H |
| CF₃ | Ph | H | CF₃ | 4-Cl—Ph | H |
| OCF₃ | Ph | H | OCF₃ | 4-Cl—Ph | H |
| Cl | Ph | Me | Cl | 4-Cl—Ph | Me |
| Br | Ph | Me | Br | 4-Cl—Ph | Me |
| CF₃ | Ph | Me | CF₃ | 4-Cl—Ph | Me |
| OCF₃ | Ph | Me | OCF₃ | 4-Cl—Ph | Me |
| Cl | Ph | Et | Cl | 4-Cl—Ph | Et |
| Br | Ph | Et | Br | 4-Cl—Ph | Et |
| CT3 | Ph | Et | CF₃ | 4-Cl—Ph | Et |
| OCF₃ | Ph | Et | OCF₃ | 4-Cl—Ph | Et |
| Cl | Ph | COMe | Cl | 4-Cl—Ph | COMe |
| Br | Ph | COMe | Br | 4-Cl—Ph | COMe |
| CF₃ | Ph | COMe | CF₃ | 4-Cl—Ph | COMe |
| OCF₃ | Ph | COMe | OCF₃ | 4-Cl—Ph | COMe |
| Cl | Ph | CO₂Me | Cl | 4-Cl—Ph | CO₂Me |
| Br | Ph | CO₂Me | Br | 4-Cl—Ph | CO₂Me |
| CF₃ | Ph | CO₂Me | CF₃ | 4-Cl—Ph | CO₂Me |
| OCF₃ | Ph | CO₂Me | OCF₃ | 4-Cl—Ph | CO₂Me |
| OCF₂H | Ph | H | OCF₂H | Ph | COMe |
| OCF₂H | Ph | Me | OCF₂H | Ph | CO₂Me |
| OCF₂H | Ph | Et | OCF₂H | Ph | COEt |
| OCF₂H | Ph | n-Pr | OCF₂H | Ph | CO₂Et |
| Cl | 4-F—Ph | H | OCF₃ | CO₂Me | Me |
| Br | 4-F—Ph | H | Cl | CO₂Me | Et |
| CF₃ | 4-F—Ph | H | Br | CO₂Me | Et |
| OCF₃ | 4-F—Ph | H | CF₃ | CO₂Me | Et |
| Cl | 4-F—Ph | Me | OCF₃ | CO₂Me | Et |
| Br | 4-F—Ph | Me | Cl | CO₂Me | COMe |
| CF₃ | 4-F—Ph | Me | Br | CO₂Me | COMe |
| OCF₃ | 4-F—Ph | Me | CF₃ | CO₂Me | COMe |

TABLE 11-continued

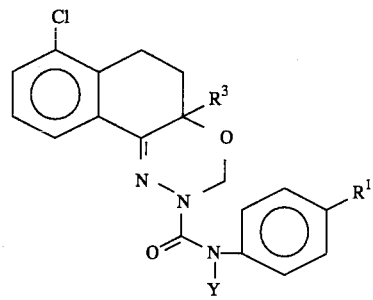

| R¹ | R³ | Y | R¹ | R³ | Y |
|---|---|---|---|---|---|
| Cl | 4-F—Ph | Et | OCF₃ | CO₂Me | COMe |
| Br | 4-F—Ph | Et | Cl | CO₂Me | CO₂Me |
| CF₃ | 4-F—Ph | Et | Br | CO₂Me | CO₂Me |
| OCF₃ | 4-F—Ph | Et | CF₃ | CO₂Me | CO₂Me |
| Cl | 4-F—Ph | COMe | OCF₃ | CO₂Me | CO₂Me |
| Br | 4-F—Ph | COMe | Cl | n-Pr | H |
| CF₃ | 4-F—Ph | COMe | Br | n-Pr | H |
| OCF₃ | 4-F—Ph | COMe | CF₃ | n-Pr | H |
| Cl | 4-F—Ph | CO₂Me | OCF₃ | n-Pr | H |
| Br | 4-F—Ph | CO₂Me | Cl | n-Pr | Me |
| CF₃ | 4-F—Ph | CO₂Me | Br | n-Pr | Me |
| OCF₃ | 4-F—Ph | CO₂Me | CF₃ | n-Pr | Me |
| Cl | CO₂Me | H | OCF₃ | n-Pr | Me |
| Br | CO₂Me | H | Cl | n-Pr | Et |
| CF₃ | CO₂Me | H | Br | n-Pr | Et |
| OCF₃ | CO₂Me | H | CF₃ | n-Pr | Et |
| Cl | CO₂Me | Me | OCF₃ | n-Pr | Et |
| Br | CO₂Me | Me | OCF₂H | 4-Cl—Ph | Et |
| CF₃ | CO₂Me | Me | OCF₂H | 4-Cl—Ph | n-Pr |
| OCF₂H | Ph | CO(n-Pr) | OCF₂H | 4-Cl—Ph | COMe |
| OCF₂H | Ph | CO(i-Pr) | OCF₂H | 4-Cl—Ph | CO₂Me |
| OCF₂H | Ph | CO(t-Bu) | OCF₂H | 4-Cl—Ph | COEt |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CO(n-Pr) |
| Cl | n-Pr | COMe | Cl | CHCH₂ | CO₂Me |
| Br | n-Pr | COMe | Br | CHCH₂ | CO₂Me |
| CF₃ | n-Pr | COMe | CF₃ | CHCH₂ | CO₂Me |
| OCF₃ | n-Pr | COMe | OCF₃ | CHCH₂ | CO₂Me |
| Cl | n-Pr | CO₂Me | Cl | C(CH₃)CH₂ | H |
| Br | n-Pr | CO₂Me | Br | C(CH₃)CH₂ | H |
| CF₃ | n-Pr | CO₂Me | CF₃ | C(CH₃)CH₂ | H |
| OCF₃ | n-Pr | CO₂Me | OCF₃ | C(CH₃)CH₂ | H |
| Cl | CHCH₂ | H | Cl | C(CH₃)CH₂ | Me |
| Br | CHCH₂ | H | Br | C(CH₃)CH₂ | Me |
| CF₃ | CHCH₂ | H | CF₃ | C(CH₃)CH₂ | Me |
| OCF₃ | CHCH₂ | H | OCF₃ | C(CH₃)CH₂ | Me |
| Cl | CHCH₂ | Me | Cl | C(CH₃)CH₂ | Et |
| Br | CHCH₂ | Me | Br | C(CH₃)CH₂ | Et |
| CF₃ | CHCH₂ | He | CF₃ | C(CH₃)CH₂ | Et |
| OCF₃ | CHCH₂ | Me | OCF₃ | C(CH₃)CH₂ | Et |
| Cl | CHCH₂ | Et | Cl | C(CH₃)CH₂ | COMe |
| Br | CHCH₂ | Et | Br | C(CH₃)CH₂ | COMe |
| CF₃ | CHCH₂ | Et | CF₃ | C(CH₃)CH₂ | COMe |
| OCF₃ | CHCH₂ | Et | OCF₃ | C(CH₃)CH₂ | COMe |
| Cl | CHCH₂ | COMe | Cl | C(CH₃)CH₂ | CO₂Me |
| Br | CHCH₂ | COMe | Br | C(CH₃)CH₂ | CO₂Me |
| CF₃ | CHCH₂ | COMe | CF₃ | C(CH₃)CH₂ | CO₂Me |
| OCF₃ | CHCH₂ | COMe | OCF₃ | C(CH₃)CH₂ | CO₂Me |
| OCF₂H | 4-Cl—Ph | CO(i-Pr) | OCF₂H | 4-F—Ph | COEt |
| OCF₂H | 4-Cl—Ph | CO(t-Bu) | OCF₂H | 4-F—Ph | CO₂Et |
| OCF₂H | 4-F—Ph | H | OCF₂H | 4-F—Ph | CO(n-Pr) |
| OCF₂H | 4-F—Ph | Me | OCF₂H | 4-F—Ph | CO(i-Pr) |
| OCF₂H | 4-F—Ph | Et | OCF₂H | 4-F—Ph | CO(t-Bu) |
| OCF₂H | 4-F—Ph | n-Pr | OCF₂H | CO₂Me | H |
| OCF₂H | 4-F—Ph | COMe | OCF₂H | CO₂Me | Me |
| OCF₂H | 4-F—Ph | CO₂Me | OCF₂H | CO₂Me | Et |
| CF₃ | Ph | COEt | CF₃ | 4-F—Ph | COEt |
| CF₃ | Ph | CO₂Et | CF₃ | 4-F—Ph | CO₂Et |
| CF₃ | Ph | CO(n-Pr) | CF₃ | 4-F—Ph | CO(n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |

TABLE 11-continued

| R¹ | R³ | Y | R¹ | R³ | Y |
|---|---|---|---|---|---|
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | CO₂Me | COEt |
| CF₃ | 4-Cl—Ph | CO₂Et | CF₃ | CO₂Me | CO₂Et |
| CF₃ | 4-Cl—Ph | CO(n-Pr) | CF₃ | CO₂Me | CO(n-Pr) |
| CF₃ | 4-Cl—Ph | CO(i-Pr) | CF₃ | CO₂Me | CO(i-Pr) |
| CF₃ | 4-Cl—Ph | CO(t-Bu) | CF₃ | CO₂Me | CO(t-Bu) |
| CF₃ | 4-Cl—Ph | n-Pr | CF₃ | CO₂Me | n-Pr |
| OCF₃ | 4-Cl—Ph | COEt | OCF₃ | CO₂Me | COEt |
| OCF₃ | 4-Cl—Ph | CO₂Et | OCF₃ | CO₂Me | CO₂Et |
| OCF₃ | 4-Cl—Ph | CO(n-Pr) | OCF₃ | CO₂Me | CO(n-Pr) |
| OCF₃ | 4-Cl—Ph | CO(i-Pr) | OCF₃ | CO₂Me | CO(i-Pr) |
| OCF₃ | 4-Cl—Ph | CO(t-BU) | OCF₃ | CO₂Me | CO(t-Bu) |
| OCF₃ | 4-Cl—Ph | n-Pr | OCF₃ | CO₂Me | n-Pr |
| OCF₂H | CO₂Me | n-Pr | OCF₂H | n-Pr | H |
| OCF₂H | CO₂Me | COMe | OCF₂H | n-Pr | Me |
| OCF₂H | CO₂Me | CO₂Me | OCF₂H | n-Pr | Et |
| OCF₂H | CO₂Me | COEt | H | n-Pr | n-Pr |
| OCF₂H | CO₂Me | CO₂Et | OCF₂H | n-Pr | COMe |
| OCF₂H | CO₂Me | CO(n-Pr) | OCF₂H | n-Pr | CO₂Me |
| OCF₂H | CO₂Me | CO(i-Pr) | OCF₂H | n-Pr | COEt |
| OCF₂H | CO₂Me | CO(t-Bu) | OCF₂H | n-Pr | CO₂Et |
| CF₃ | n-Pr | COEt | CF₃ | C(CH₃)CH₂ | COEt |
| CF₃ | n-Pr | CO₂Et | CF₃ | C(CH₃)CH₂ | CO₂Et |
| CF₃ | n-Pr | CO(n-Pr) | CF₃ | C(CH₃)CH₂ | CO(n-Pr) |
| CF₃ | n-Pr | CO(i-Pr) | CF₃ | C(CH₃)CH₂ | CO(i-Pr) |
| CF₃ | n-Pr | CO(t-Bu) | CF₃ | C(CH₃)CH₂ | CO(t-Bu) |
| CF₃ | n-Pr | n-Pr | CF₃ | C(CH₃)CH₂ | n-Pr |
| OCF₃ | n-Pr | COEt | OCF₃ | C(CH₃)CH₂ | COEt |
| OCF₃ | n-Pr | CO₂Et | OCF₃ | C(CH₃)CH₂ | CO₂Et |
| OCF₃ | n-Pr | CO(n-Pr) | OCF₃ | C(CH₃)CH₂ | CO(n-Pr) |
| OCF₃ | n-Pr | CO(i-Pr) | OCF₃ | C(CH₃)CH₂ | CO(i-Pr) |
| OCF₃ | n-Pr | CO(t-Bu) | OCF₃ | C(CH₃)CH₂ | CO(t-Bu) |
| OCF₃ | n-Pr | n-Pr | OCF₃ | C(CH₃)CH₂ | n-Pr |
| CF₃ | CHCH₂ | COEt | OCF₂H | CHCH₂ | CO₂Me |
| CF₃ | CHCH₂ | CO₂Et | OCF₂H | CHCH₂ | COEt |
| CF₃ | CHCH₂ | CO(n-Pr) | OCF₂H | CHCH₂ | CO₂Et |
| CF₃ | CHCH₂ | CO(i-Pr) | OCF₂H | CHCH₂ | CO(n-Pr) |
| CF₃ | CHCH₂ | CO(t-Bu) | OCF₂H | CHCH₂ | CO(i-Pr) |
| CF₃ | CHCH₂ | n-Pr | OCF₂H | CHCH₂ | CO(t-Bu) |
| OCF₃ | CHCH₂ | COEt | OCF₂H | C(CH₃)CH₂ | H |
| OCF₃ | CHCH₂ | CO₂Et | OCF₂H | C(CH₃)CH₂ | Me |
| OCF₃ | CHCH₂ | CO(n-Pr) | OCF₂H | C(CH₃)CH₂ | Et |
| OCF₃ | CHCH₂ | CO(i-Pr) | OCF₂H | C(CH₃)CH₂ | n-Pr |
| OCF₃ | CHCH₂ | CO(t-Bu) | OCF₂H | C(CH₃)CH₂ | COMe |
| OCF₃ | CHCH₂ | n-Pr | OCF₂H | C(CH₃)CH₂ | CO₂Me |
| OCF₂H | n-Pr | CO(n-Pr) | OCF₂H | C(CH₃)CH₂ | COEt |
| OCF₂H | n-Pr | CO(i-Pr) | OCF₂H | C(CH₃)CH₂ | CO₂Et |
| OCF₂H | n-Pr | CO(t-Bu) | OCF₂H | C(CH₃)CH₂ | CO(n-Pr) |
| OCF₂H | CHCH₂ | H | OCF₂H | C(CH₃)CH₂ | CO(i-Pr) |
| OCF₂H | CHCH₂ | Me | OCF₂H | C(CH₃)CH₂ | CO(t-Bu) |
| OCF₂H | CHCH₂ | Et | | | |
| OCF₂H | CHCH₂ | n-Pr | | | |
| OCF₂H | CHCH₂ | COMe | | | |

TABLE 12

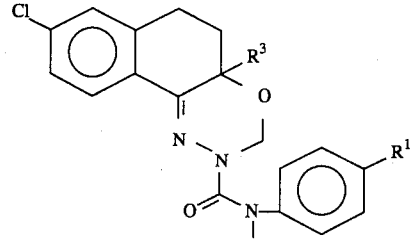

| R¹ | R³ | Y | R¹ | R³ | Y |
|---|---|---|---|---|---|
| Cl | Ph | H | Cl | 4-Cl—Ph | H |
| Br | Ph | H | Br | 4-Cl—Ph | H |
| CF$_3$ | Ph | H | CF$_3$ | 4-Cl—Ph | H |
| OCF$_3$ | Ph | H | OCF$_3$ | 4-Cl—Ph | H |
| Cl | Ph | Me | Cl | 4-Cl—Ph | Me |
| Br | Ph | Me | Br | 4-Cl—Ph | Me |
| CF$_3$ | Ph | Me | CF$_3$ | 4-Cl—Ph | Me |
| OCF$_3$ | Ph | Me | OCF$_3$ | 4-Cl—Ph | Me |
| Cl | Ph | Et | Cl | 4-Cl—Ph | Et |
| Br | Ph | Et | Br | 4-Cl—Ph | Et |
| CF$_3$ | Ph | Et | CF$_3$ | 4-Cl—Ph | Et |
| OCF$_3$ | Ph | Et | OCF$_3$ | 4-Cl—Ph | Et |
| Cl | Ph | COMe | Cl | 4-Cl—Ph | COMe |
| Br | Ph | COMe | Br | 4-Cl—Ph | COMe |
| CF$_3$ | Ph | COMe | CF$_3$ | 4-Cl—Ph | COMe |
| OCF$_3$ | Ph | COMe | OCF$_3$ | 4-Cl—Ph | COMe |
| Cl | Ph | CO$_2$Me | Cl | 4-Cl—Ph | CO$_2$Me |
| Br | Ph | CO$_2$Me | Br | 4-Cl—Ph | CO$_2$Me |
| CF$_3$ | Ph | CO$_2$Me | CF$_3$ | 4-Cl—Ph | CO$_2$Me |
| OCF$_3$ | Ph | CO$_2$Me | OCF$_3$ | 4-Cl—Ph | CO$_2$Me |
| OCF$_2$H | Ph | H | OCF$_2$H | Ph | COMe |
| OCF$_2$H | Ph | Me | OCF$_2$H | Ph | CO$_2$Me |
| OCF$_2$H | Ph | Et | OCF$_2$H | Ph | COEt |
| OCF$_2$H | Ph | n-Pr | OCF$_2$H | Ph | CO$_2$Et |
| Cl | 4-F—Ph | H | OCF$_3$ | CO$_2$Me | Me |
| Br | 4-F—Ph | H | Cl | CO$_2$Me | Et |
| CF$_3$ | 4-F—Ph | H | Br | CO$_2$Me | Et |
| OCF$_3$ | 4-F—Ph | H | CF$_3$ | CO$_2$Me | Et |
| Cl | 4-F—Ph | Me | OCF$_3$ | CO$_2$Me | Et |
| Br | 4-F—Ph | Me | Cl | CO$_2$Me | COMe |
| CF$_3$ | 4-F—Ph | Me | Br | CO$_2$Me | COMe |
| OCF$_3$ | 4-F—Ph | Me | CF$_3$ | CO$_2$Me | COMe |
| Cl | 4-F—Ph | Et | OCF$_3$ | CO$_2$Me | COMe |
| Br | 4-F—Ph | Et | Cl | CO$_2$Me | CO$_2$Me |
| CF$_3$ | 4-F—Ph | Et | Br | CO$_2$Me | CO$_2$Me |
| OCF$_3$ | 4-F—Ph | Et | CF$_3$ | CO$_2$Me | CO$_2$Me |
| Cl | 4-F—Ph | COMe | OCF$_3$ | CO$_2$Me | CO$_2$Me |
| Br | 4-F—Ph | COMe | Cl | n-Pr | H |
| CF$_3$ | 4-F—Ph | COMe | Br | n-Pr | H |
| OCF$_3$ | 4-F—Ph | COMe | CF$_3$ | n-Pr | H |
| Cl | 4-F—Ph | CO$_2$Me | OCF$_3$ | n-Pr | H |
| Br | 4-F—Ph | CO$_2$Me | Cl | n-Pr | Me |
| CF$_3$ | 4-F—Ph | CO$_2$Me | Br | n-Pr | Me |
| OCF$_3$ | 4-F—Ph | CO$_2$Me | CF$_3$ | n-Pr | Me |
| Cl | CO$_2$Me | H | OCF$_3$ | n-Pr | Me |
| Br | CO$_2$Me | H | Cl | n-Pr | Et |
| CF$_3$ | CO$_2$Me | H | Br | n-Pr | Et |
| OCF$_3$ | CO$_2$Me | H | CF$_3$ | n-Pr | Et |
| Cl | CO$_2$Me | Me | OCF$_3$ | n-Pr | Et |
| Br | CO$_2$Me | Me | OCF$_2$H | 4-Cl—Ph | Et |
| CF$_3$ | CO$_2$Me | Me | OCF$_2$H | 4-Cl—Ph | n-Pr |
| OCF$_2$H | Ph | CO(n-Pr) | OCF$_2$H | 4-Cl—Ph | COMe |
| OCF$_2$H | Ph | CO(i-Pr) | OCF$_2$H | 4-Cl—Ph | CO$_2$Me |
| OCF$_2$H | Ph | CO(t-Bu) | OCF$_2$H | 4-Cl—Ph | COEt |
| OCF$_2$H | 4-Cl—Ph | H | OCF$_2$H | 4-Cl—Ph | CO$_2$Et |
| OCF$_2$H | 4-Cl—Ph | Me | OCF$_2$H | 4-Cl—Ph | CO(n-Pr) |
| Cl | n-Pr | COMe | Cl | CHCH$_2$ | CO$_2$Me |
| Br | n-Pr | COMe | Br | CHCH$_2$ | CO$_2$Me |
| CF$_3$ | n-Pr | COMe | CF$_3$ | CHCH$_2$ | CO$_2$Me |
| OCF$_3$ | n-Pr | COMe | OCF$_3$ | CHCH$_2$ | CO$_2$Me |
| Cl | n-Pr | CO$_2$Me | Cl | C(CH$_3$)CH$_2$ | H |
| Br | n-Pr | CO$_2$Me | Br | C(CH$_3$)CH$_2$ | H |
| CF$_3$ | n-Pr | CO$_2$Me | CF$_3$ | C(CH$_3$)CH$_2$ | H |
| OCF$_3$ | n-Pr | CO$_2$Me | OCF$_3$ | C(CH$_3$)CH$_2$ | H |
| Cl | CHCH$_2$ | H | Cl | C(CH$_3$)CH$_2$ | Me |

TABLE 12-continued

| R¹ | R³ | Y | R¹ | R³ | Y |
|---|---|---|---|---|---|
| Br | CHCH₂ | H | Br | C(CH₃)CH₂ | Me |
| CF₃ | CHCH₂ | H | CF₃ | C(CH₃)CH₂ | Me |
| OCF₃ | CHCH₂ | H | OCF₃ | C(CH₃)CH₂ | Me |
| Cl | CHCH₂ | Me | Cl | C(CH₃)CH₂ | Et |
| Br | CHCH₂ | Me | Br | C(CH₃)CH₂ | Et |
| CF₃ | CHCH₂ | Me | CF₃ | C(CH₃)CH₂ | Et |
| OCF₃ | CHCH₂ | Me | OCF₃ | C(CH₃)CH₂ | Et |
| Cl | CHCH₂ | Et | Cl | C(CH₃)CH₂ | COMe |
| Br | CHCH₂ | Et | Br | C(CH₃)CH₂ | COMe |
| CF₃ | CHCH₂ | Et | CF₃ | C(CH₃)CH₂ | COMe |
| OCF₃ | CHCH₂ | Et | OCF₃ | C(CH₃)CH₂ | COMe |
| Cl | CHCH₂ | COMe | Cl | C(CH₃)CH₂ | CO₂Me |
| Br | CHCH₂ | COMe | Br | C(CH₃)CH₂ | CO₂Me |
| CF₃ | CHCH₂ | COMe | CF₃ | C(CH₃)CH₂ | CO₂Me |
| OCF₃ | CHCH₂ | COMe | OCF₃ | C(CH₃)CH₂ | CO₂Me |
| OCF₂H | 4-Cl—Ph | CO(i-Pr) | OCF₂H | 4-F—Ph | COEt |
| OCF₂H | 4-Cl—Ph | CO(t-Bu) | OCF₂H | 4-F—Ph | CO₂Et |
| OCF₂H | 4-F—Ph | H | OCF₂H | 4-F—Ph | CO(n-Pr) |
| OCF₂H | 4-F—Ph | Me | OCF₂H | 4-F—Ph | CO(i-Pr) |
| OCF₂H | 4-F—Ph | Et | OCF₂H | 4-F—Ph | CO(t-Bu) |
| OCF₂H | 4-F—Ph | n-Pr | OCF₂H | CO₂Me | H |
| OCF₂H | 4-F—Ph | COMe | OCF₂H | CO₂Me | Me |
| OCF₂H | 4-F—Ph | CO₂Me | OCF₂H | CO₂Me | Et |
| CF₃ | Ph | COEt | CF₃ | 4-F—Ph | COEt |
| CF₃ | Ph | CO₂Et | CF₃ | 4-F—Ph | CO₂Et |
| CF₃ | Ph | CO(n-Pr) | CF₃ | 4-F—Ph | CO (n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | CO₂Me | COEt |
| CF₃ | 4-Cl—Ph | CO₂Et | CF₃ | CO₂Me | CO₂Et |
| CF₃ | 4-Cl—Ph | CO(n-Pr) | CF₃ | CO₂Me | CO(n-Pr) |
| CF₃ | 4-Cl—Ph | CO(i-Pr) | CF₃ | CO₂Me | CO(i-Pr) |
| CF₃ | 4-Cl—Ph | CO(t-Bu) | CF₃ | CO₂Me | CO(t-Bu) |
| CF₃ | 4-Cl—Ph | n-Pr | CF₃ | CO₂Me | n-Pr |
| OCF₃ | 4-Cl—Ph | COEt | OCF₃ | CO₂Me | COEt |
| OCF₃ | 4-Cl—Ph | CO₂Et | OCF₃ | CO₂Me | CO₂Et |
| OCF₃ | 4-Cl—Ph | CO(n-Pr) | OCF₃ | CO₂Me | CO(n-Pr) |
| OCF₃ | 4-Cl—Ph | CO(i-Pr) | OCF₃ | CO₂Me | CO(i-Pr) |
| OCF₃ | 4-Cl—Ph | CO(t-Bu) | OCF₃ | CO₂Me | CO(t-Bu) |
| OCF₃ | 4-Cl—Ph | n-Pr | OCF₃ | CO₂Me | n-Pr |
| OCF₂H | CO₂Me | n-Pr | OCF₂H | n-Pr | H |
| OCF₂H | CO₂Me | COMe | OCF₂H | n-Pr | Me |
| OCF₂H | CO₂Me | CO₂Me | OCF₂H | n-Pr | Et |
| OCF₂H | CO₂Me | COEt | OCF₂H | n-Pr | n-Pr |
| OCF₂H | CO₂Me | CO₂Et | OCF₂H | n-Pr | COMe |
| OCF₂H | CO₂Me | CO(n-Pr) | OCF₂H | n-Pr | CO₂Me |
| OCF₂H | CO₂Me | CO(i-Pr) | OCF₂H | n-Pr | COMe |
| OCF₂H | CO₂Me | CO(t-Bu) | OCF₂H | n-Pr | CO₂Et |
| CF₃ | n-Pr | COEt | CF₃ | C(CH₃)CH₂ | COEt |
| CF₃ | n-Pr | CO₂Et | CF₃ | C(CH₃)CH₂ | CO₂Et |
| CF₃ | n-Pr | CO(n-Pr) | CF₃ | C(CH₃)CH₂ | CO(n-Pr) |
| CF₃ | n-Pr | CO(i-Pr) | CF₃ | C(CH₃)CH₂ | CO(i-Pr) |
| CF₃ | n-Pr | CO(t-Bu) | CF₃ | C(CH₃)CH₂ | CO(t-Bu) |
| CF₃ | n-Pr | n-Pr | CF₃ | C(CH₃)CH₂ | n-Pr |
| OCF₃ | n-Pr | COEt | OCF₃ | C(CH₃)CH₂ | COEt |
| OCF₃ | n-Pr | CO₂Et | OCF₃ | C(CH₃)CH₂ | CO₂Et |
| OCF₃ | n-Pr | CO(n-Pr) | OCF₃ | C(CH₃)CH₂ | CO(n-Pr) |
| OCF₃ | n-Pr | CO(i-Pr) | OCF₃ | C(CH₃)CH₂ | CO(i-Pr) |

TABLE 12-continued

| R¹ | R³ | Y | R¹ | R³ | Y |
|---|---|---|---|---|---|
| OCF₃ | n-Pr | CO(t-Bu) | OCF₃ | C(CH₃)CH₂ | CO(t-Bu) |
| OCF₃ | n-Pr | n-Pr | OCF₃ | C(CH₃)CH₂ | n-Pr |
| CF₃ | CHCH₂ | COEt | OCF₂H | CHCH₂ | CO₂Me |
| CF₃ | CHCH₂ | CO₂Et | OCF₂H | CHCH₂ | COEt |
| CF₃ | CHCH₂ | CO(n-Pr) | OCF₂H | CHCH₂ | CO₂Et |
| CF₃ | CHCH₂ | CO(i-Pr) | OCF₂H | CHCH₂ | CO(n-Pr) |
| CF₃ | CHCH₂ | CO(t-Bu) | OCF₂H | CHCH₂ | CO(i-Pr) |
| CF₃ | CHCH₂ | n-Pr | OCF₂H | CHCH₂ | CO(t-Bu) |
| OCF₃ | CHCH₂ | COEt | OCF₂H | C(CH₃)CH₂ | H |
| OCF₃ | CHCH₂ | CO₂Et | OCF₂H | C(CH₃)CH₂ | Me |
| OCF₃ | CHCH₂ | CO(n-Pr) | OCF₂H | C(CH₃)CH₂ | Et |
| OCF₃ | CHCH₂ | CO(i-Pr) | OCF₂H | C(CH₃)CH₂ | n-Pr |
| OCF₃ | CHCH₂ | CO(t-Bu) | OCF₂H | C(CH₃)CH₂ | COMe |
| OCF₃ | CHCH₂ | n-Pr | OCF₂H | C(CH₃)CH₂ | CO₂Me |
| OCF₂H | n-Pr | CO(n-Pr) | OCF₂H | C(CH₃)CH₂ | COEt |
| OCF₂H | n-Pr | CO(i-Pr) | OCF₂H | C(CH₃)CH₂ | CO₂Et |
| OCF₂H | n-Pr | CO(t-Bu) | OCF₂H | C(CH₃)CH₂ | CO(n-Pr) |
| OCF₂H | CHCH₂ | H | OCF₂H | C(CH₃)CH₂ | CO(i-Pr) |
| OCF₂H | CHCH₂ | Me | OCF₂H | C(CH₃)CH₂ | CO(t-Bu) |
| OCF₂H | CHCH₂ | Et | | | |
| OCF₂H | CHCH₂ | n-Pr | | | |
| OCF₂H | CHCH₂ | COMe | | | |

TABLE 13

| R¹ | R³ | Y | R¹ | R³ | Y |
|---|---|---|---|---|---|
| Cl | Ph | H | Cl | 4-Cl—Ph | H |
| Br | Ph | H | Br | 4-Cl—Ph | H |
| CF₃ | Ph | H | CF₃ | 4-Cl—Ph | H |
| OCF₃ | Ph | H | OCF₃ | 4-Cl—Ph | H |
| Cl | Ph | Me | Cl | 4-Cl—Ph | Me |
| Br | Ph | Me | Br | 4-Cl—Ph | Me |
| CF₃ | Ph | Me | CF₃ | 4-Cl—Ph | Me |
| OCF₃ | Ph | Me | OCF₃ | 4-Cl—Ph | Me |
| Cl | Ph | Et | Cl | 4-Cl—Ph | Et |
| Br | Ph | Et | Br | 4-Cl—Ph | Et |
| CF₃ | Ph | Et | CF₃ | 4-Cl—Ph | Et |
| OCF₃ | Ph | Et | OCF₃ | 4-Cl—Ph | Et |
| Cl | Ph | COMe | Cl | 4-Cl—Ph | COMe |
| Br | Ph | COMe | Br | 4-Cl—Ph | COMe |
| CF₃ | Ph | COMe | CF₃ | 4-Cl—Ph | COMe |
| OCF₃ | Ph | COMe | OCF₃ | 4-Cl—Ph | COMe |
| Cl | Ph | CO₂Me | Cl | 4-Cl—Ph | CO₂Me |
| Br | Ph | CO₂Me | Br | 4-Cl—Ph | CO₂Me |
| CF₃ | Ph | CO₂Me | CF₃ | 4-Cl—Ph | CO₂Me |
| OCF₃ | Ph | CO₂Me | OCF₃ | 4-Cl—Ph | CO₂Me |
| OCF₂H | Ph | H | OCF₂H | Ph | COMe |
| OCF₂H | Ph | Me | OCF₂H | Ph | CO₂Me |
| OCF₂H | Ph | Et | OCF₂H | Ph | COEt |
| OCF₂H | Ph | n-Pr | OCF₂H | Ph | CO₂Et |

TABLE 13-continued

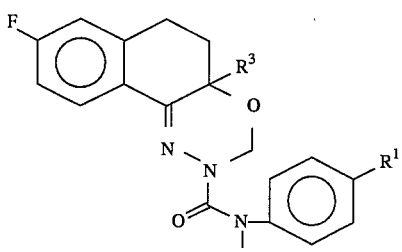

| R¹ | R³ | Y | R¹ | R³ | Y |
|---|---|---|---|---|---|
| Cl | 4-F—Ph | H | OCF₃ | CO₂Me | Me |
| Br | 4-F—Ph | H | Cl | CO₂Me | Et |
| CF₃ | 4-F—Ph | H | Br | CO₂Me | Et |
| OCF₃ | 4-F—Ph | H | CF₃ | CO₂Me | Et |
| Cl | 4-F—Ph | Me | OCF₃ | CO₂Me | Et |
| Br | 4-F—Ph | Me | Cl | CO₂Me | COMe |
| CF₃ | 4-F—Ph | Me | Br | CO₂Me | COMe |
| OCF₃ | 4-F—Ph | Me | CF₃ | CO₂Me | COMe |
| Cl | 4-F—Ph | Et | OCF₃ | CO₂Me | COMe |
| Br | 4-F—Ph | Et | Cl | CO₂Me | CO₂Me |
| CF₃ | 4-F—Ph | Et | Br | CO₂Me | CO₂Me |
| OCF₃ | 4-F—Ph | Et | CF₃ | CO₂Me | CO₂Me |
| Cl | 4-F—Ph | COMe | OCF₃ | CO₂Me | CO₂Me |
| Br | 4-F—Ph | COMe | Cl | n-Pr | H |
| CF₃ | 4-F—Ph | COMe | Br | n-Pr | H |
| OCF₃ | 4-F—Ph | COMe | CF₃ | n-Pr | H |
| Cl | 4-F—Ph | CO₂Me | OCF₃ | n-Pr | H |
| Br | 4-F—Ph | CO₂Me | Cl | n-Pr | Me |
| CF₃ | 4-F—Ph | CO₂Me | Br | n-Pr | Me |
| OCF₃ | 4-F—Ph | CO₂Me | CF₃ | n-Pr | Me |
| Cl | CO₂Me | H | OCF₃ | n-Pr | Me |
| Br | CO₂Me | H | Cl | n-Pr | Et |
| CF₃ | CO₂Me | H | Br | n-Pr | Et |
| OCF₃ | CO₂Me | H | CF₃ | n-Pr | Et |
| Cl | CO₂Me | Me | OCF₃ | n-Pr | Et |
| Br | CO₂Me | Me | OCF₂H | 4-Cl—Ph | Et |
| CF₃ | CO₂Me | Me | OCF₂H | 4-Cl—Ph | n-Pr |
| OCF₂H | Ph | CO(n-Pr) | OCF₂H | 4-Cl—Ph | COMe |
| OCF₂H | Ph | CO(i-Pr) | OCF₂H | 4-Cl—Ph | CO₂Me |
| OCF₂H | Ph | CO(t-Bu) | OCF₂H | 4-Cl—Ph | COEt |
| OCF₂H | 4-Cl—Ph | H | OCF₂H | 4-Cl—Ph | CO₂Et |
| OCF₂H | 4-Cl—Ph | Me | OCF₂H | 4-Cl—Ph | CO(n-Pr) |
| Cl | n-Pr | COMe | Cl | CHCH₂ | CO₂Me |
| Br | n-Pr | COMe | Br | CHCH₂ | CO₂Me |
| CF₃ | n-Pr | COMe | CF₃ | CHCH₂ | CO₂Me |
| OCF₃ | n-Pr | COMe | OCF₃ | CHCH₂ | CO₂Me |
| Cl | n-Pr | CO₂Me | Cl | C(CH₃)CH₂ | H |
| Br | n-Pr | CO₂Me | Br | C(CH₃)CH₂ | H |
| CF₃ | n-Pr | CO₂Me | CF₃ | C(CH₃)CH₂ | H |
| OCF₃ | n-Pr | CO₂Me | OCF₃ | C(CH₃)CH₂ | H |
| Cl | CHCH₂ | H | Cl | C(CH₃)CH₂ | Me |
| Br | CHCH₂ | H | Br | C(CH₃)CH₂ | Me |
| CF₃ | CHCH₂ | H | CF₃ | C(CH₃)CH₂ | Me |
| OCF₃ | CHCH₂ | H | OCF₃ | C(CH₃)CH₂ | Me |
| Cl | CHCH₂ | Me | Cl | C(CH₃)CH₂ | Et |
| Br | CHCH₂ | Me | Br | C(CH₃)CH₂ | Et |
| CF₃ | CHCH₂ | Me | CF₃ | C(CH₃)CH₂ | Et |
| OCF₃ | CHCH₂ | Me | OCF₃ | C(CH₃)CH₂ | Et |
| Cl | CHCH₂ | Et | Cl | C(CH₃)CH₂ | COMe |
| Br | CHCH₂ | Et | Br | C(CH₃)CH₂ | COMe |
| CF₃ | CHCH₂ | Et | CF₃ | C(CH₃)CH₂ | COMe |
| OCF₃ | CHCH₂ | Et | OCF₃ | C(CH₃)CH₂ | COMe |
| Cl | CHCH₂ | COMe | Cl | C(CH₃)CH₂ | CO₂Me |
| Br | CHCH₂ | COMe | Br | C(CH₃)CH₂ | CO₂Me |
| CF₃ | CHCH₂ | COMe | CF₃ | C(CH₃)CH₂ | CO₂Me |
| OCF₃ | CHCH₂ | COMe | OCF₃ | C(CH₃)CH₂ | CO₂Me |
| OCF₂H | 4-Cl—Ph | CO(i-Pr) | OCF₂H | 4-F—Ph | COEt |
| OCF₂H | 4-Cl—Ph | CO(t-Bu) | OCF₂H | 4-F—Ph | CO₂Et |
| OCF₂H | 4-F—Ph | H | OCF₂H | 4-F—Ph | CO(n-Pr) |
| OCF₂H | 4-F—Ph | Me | OCF₂H | 4-F—Ph | CO(i-Pr) |
| OCF₂H | 4-F—Ph | Et | OCF₂H | 4-F—Ph | CO(t-Bu) |
| OCF₂H | 4-F—Ph | n-Pr | OCF₂H | CO₂Me | H |
| OCF₂H | 4-F—Ph | COMe | OCF₂H | CO₂Me | Me |
| OCF₂H | 4-F—Ph | CO₂Me | OCF₂H | CO₂Me | Et |
| CF₃ | Ph | COEt | CF₃ | 4-F—Ph | COEt |

TABLE 13-continued

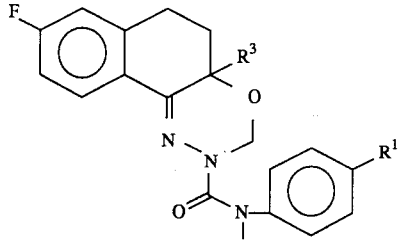

| R¹ | R³ | Y | R¹ | R³ | Y |
|---|---|---|---|---|---|
| CF₃ | Ph | CO₂Et | CF₃ | 4-F—Ph | CO₂Et |
| CF₃ | Ph | CO(n-Pr) | CF₃ | 4-F—Ph | CO(n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | CO₂Me | COEt |
| CF₃ | 4-Cl—Ph | CO₂Et | CF₃ | CO₂Me | CO₂Et |
| CF₃ | 4-Cl—Ph | CO(n-Pr) | CF₃ | CO₂Me | CO(n-Pr) |
| CF₃ | 4-Cl—Ph | CO(i-Pr) | CF₃ | CO₂Me | CO(i-Pr) |
| CF₃ | 4-Cl—Ph | CO(t-Bu) | CF₃ | CO₂Me | CO(t-Bu) |
| CF₃ | 4-Cl—Ph | n-Pr | CF₃ | CO₂Me | n-Pr |
| OCF₃ | 4-Cl—Ph | COEt | OCF₃ | CO₂Me | COEt |
| OCF₃ | 4-Cl—Ph | CO₂Et | OCF₃ | CO₂Me | CO₂Et |
| OCF₃ | 4-Cl—Ph | CO(n-Pr) | OCF₃ | CO₂Me | CO(n-Pr) |
| OCF₃ | 4-Cl—Ph | CO(i-Pr) | OCF₃ | CO₂Me | CO(i-Pr) |
| OCF₃ | 4-Cl—Ph | CO(t-Bu) | OCF₃ | CO₂Me | CO(t-Bu) |
| OCF₃ | 4-Cl—Ph | n-Pr | OCF₃ | CO₂Me | n-Pr |
| OCF₂H | CO₂Me | n-Pr | OCF₂H | n-Pr | H |
| OCF₂H | CO₂Me | COMe | OCF₂H | n-Pr | Me |
| OCF₂H | CO₂Me | CO₂Me | OCF₂H | n-Pr | Et |
| OCF₂H | CO₂Me | COEt | OCF₂H | n-Pr | n-Pr |
| OCF₂H | CO₂Me | CO₂Et | OCF₂H | n-Pr | COMe |
| OCF₂H | CO₂Me | CO(n-Pr) | OCF₂H | n-Pr | CO₂Me |
| OCF₂H | CO₂Me | CO(i-Pr) | OCF₂H | n-Pr | COEt |
| OCF₂H | CO₂Me | CO(t-Bu) | OCF₂H | n-Pr | CO₂Et |
| CF₃ | n-Pr | COEt | CF₃ | C(CH₃)CH₂ | COEt |
| CF₃ | n-Pr | CO₂Et | CF₃ | C(CH₃)CH₂ | CO₂Et |
| CF₃ | n-Pr | CO(n-Pr) | CF₃ | C(CH₃)CH₂ | CO(n-Pr) |
| CF₃ | n-Pr | CO(i-Pr) | CF₃ | C(CH₃)CH₂ | CO(i-Pr) |
| CF₃ | n-Pr | CO(t-Bu) | CF₃ | C(CH₃)CH₂ | CO(t-Bu) |
| CF₃ | n-Pr | n-Pr | CF₃ | C(CH₃)CH₂ | n-Pr |
| OCF₃ | n-Pr | COEt | OCF₃ | C(CH₃)CH₂ | COEt |
| OCF₃ | n-Pr | CO₂Et | OCF₃ | C(CH₃)CH₂ | CO₂Et |
| OCF₃ | n-Pr | CO(n-Pr) | OCF₃ | C(CH₃)CH₂ | CO(n-Pr) |
| OCF₃ | n-Pr | CO(i-Pr) | OCF₃ | C(CH₃)CH₂ | CO(i-Pr) |
| OCF₃ | n-Pr | CO(t-Bu) | OCF₃ | C(CH₃)CH₂ | CO(t-Bu) |
| OCF₃ | n-Pr | n-Pr | OCF₃ | C(CH₃)CH₂ | n-Pr |
| CF₃ | CHCH₂ | COEt | OCF₂H | CHCH₂ | CO₂Me |
| CF₃ | CHCH₂ | CO₂Et | OCF₂H | CHCH₂ | COEt |
| CF₃ | CHCH₂ | CO(n-Pr) | OCF₂H | CHCH₂ | CO₂Et |
| CF₃ | CHCH₂ | CO(i-Pr) | OCF₂H | CHCH₂ | CO(n-Pr) |
| CF₃ | CHCH₂ | CO(t-Bu) | OCF₂H | CHCH₂ | CO(i-Pr) |
| CF₃ | CHCH₂ | n-Pr | OCF₂H | CHCH₂ | CO(t-Bu) |
| OCF₃ | CHCH₂ | COEt | OCF₂H | C(CH₃)CH₂ | H |
| OCF₃ | CHCH₂ | CO₂Et | OCF₂H | C(CH₃)CH₂ | Me |
| OCF₃ | CHCH₂ | CO(n-Pr) | OCF₂H | C(CH₃)CH₂ | Et |
| OCF₃ | CHCH₂ | CO(i-Pr) | OCF₂H | C(CH₃)CH₂ | n-Pr |
| OCF₃ | CHCH₂ | CO(t-Bu) | OCF₂H | C(CH₃)CH₂ | COMe |
| OCF₃ | CHCH₂ | n-Pr | OCF₂H | C(CH₃)CH₂ | CO₂Me |
| OCF₂H | n-Pr | CO(n-Pr) | OCF₂H | C(CH₃)CH₂ | COEt |
| OCF₂H | n-Pr | CO(i-Pr) | OCF₂H | C(CH₃)CH₂ | CO₂Et |
| OCF₂H | n-Pr | CO(t-Bu) | OCF₂H | C(CH₃)CH₂ | CO(n-Pr) |
| OCF₂H | CHCH₂ | H | OCF₂H | C(CH₃)CH₂ | CO(i-Pr) |
| OCF₂H | CHCH₂ | Me | OCF₂H | C(CH₃)CH₂ | CO(t-Bu) |
| OCF₂H | CHCH₂ | Et | | | |
| OCF₂H | CHCH₂ | n-Pr | | | |
| OCF₂H | CHCH₂ | COMe | | | |

TABLE 14

| R¹ | R³ | Y | R¹ | R³ | Y |
|---|---|---|---|---|---|
| $CF_3$ | Ph | H | $CF_3$ | 4-F—Ph | H |
| $CF_3$ | Ph | Me | $CF_3$ | 4-F—Ph | Me |
| $CF_3$ | Ph | Et | $CF_3$ | 4-F—Ph | Et |
| $CF_3$ | Ph | COMe | $CF_3$ | 4-F—Ph | COMe |
| $CF_3$ | Ph | $CO_2Me$ | $CF_3$ | 4-F—Ph | $CO_2Me$ |
| $OCF_3$ | Ph | H | $OCF_3$ | 4-F—Ph | H |
| $OCF_3$ | Ph | Me | $OCF_3$ | 4-F—Ph | Me |
| $OCF_3$ | Ph | Et | $OCF_3$ | 4-F—Ph | Et |
| $OCF_3$ | Ph | COMe | $OCF_3$ | 4-F—Ph | COMe |
| $OCF_3$ | Ph | $CO_2Me$ | $OCF_3$ | 4-F—Ph | $CO_2Me$ |
| $CF_3$ | 4-Cl—Ph | H | $CF_3$ | n-Pr | H |
| $CF_3$ | 4-Cl—Ph | Me | $CF_3$ | n-Pr | Me |
| $CF_3$ | 4-Cl—Ph | Et | $CF_3$ | n-Pr | Et |
| $CF_3$ | 4-Cl—Ph | COMe | $CF_3$ | n-Pr | COMe |
| $CF_3$ | 4-Cl—Ph | $CO_2Me$ | $CF_3$ | n-Pr | $CO_2Me$ |
| $OCF_3$ | 4-Cl—Ph | H | $OCF_3$ | n-Pr | H |
| $OCF_3$ | 4-Cl—Ph | Me | $OCF_3$ | n-Pr | Me |
| $OCF_3$ | 4-Cl—Ph | Et | $OCF_3$ | n-Pr | Et |
| $OCF_3$ | 4-Cl—Ph | COMe | $OCF_3$ | n-Pr | COMe |
| $OCF_3$ | 4-Cl—Ph | $CO_2Me$ | $OCF_3$ | n-Pr | $CO_2Me$ |
| $CF_3$ | Ph | COEt | $CF_3$ | 4-F—Ph | COEt |
| $CF_3$ | Ph | $CO_2Et$ | $CF_3$ | 4-F—Ph | $CO_2Et$ |
| $CF_3$ | Ph | CO(n-Pr) | $CF_3$ | 4-F—Ph | CO(n-Pr) |
| $CF_3$ | Ph | CO(i-Pr) | $CF_3$ | 4-F—Ph | CO(i-Pr) |
| $CF_3$ | Ph- | CO(t-Bu) | $CF_3$ | 4-F—Ph | CO(t-Bu) |
| $CF_3$ | Ph | n-Pr | $CF_3$ | 4-F—Ph | n-Pr |
| $OCF_3$ | Ph | COEt | $OCF_3$ | 4-F—Ph | COEt |
| $OCF_3$ | Ph | $CO_2Et$ | $OCF_3$ | 4-F—Ph | $CO_2Et$ |
| $OCF_3$ | Ph | CO(n-Pr) | $OCF_3$ | 4-F—Ph | CO(n-Pr) |
| $OCF_3$ | Ph | CO(i-Pr) | $OCF_3$ | 4-F—Ph | CO(i-Pr) |
| $OCF_3$ | Ph | CO(t-Bu) | $OCF_3$ | 4-F—Ph | CO(t-Bu) |
| $OCF_3$ | Ph | n-Pr | $OCF_3$ | 4-F—Ph | n-Pr |
| $CF_3$ | 4-Cl—Ph | COEt | $CF_3$ | n-Pr | COEt |
| $CF_3$ | 4-Cl—Ph | $CO_2Et$ | $CF_3$ | n-Pr | $CO_2Et$ |
| $CF_3$ | 4-Cl—Ph | CO(n-Pr) | $CF_3$ | n-Pr | CO(n-Pr) |
| $CF_3$ | 4-Cl—Ph | CO(i-Pr) | $CF_3$ | n-Pr | CO(i-Pr) |
| $CF_3$ | 4-Cl—Ph | CO(t-Bu) | $CF_3$ | n-Pr | CO(t-Bu) |
| $CF_3$ | 4-Cl—Ph | n-Pr | $CF_3$ | n-Pr | n-Pr |
| $OCF_3$ | 4-Cl—Ph | COEt | $OCF_3$ | n-Pr | COEt |
| $OCF_3$ | 4-Cl—Ph | $CO_2Et$ | $OCF_3$ | n-Pr | $CO_2Et$ |
| $OCF_3$ | 4-Cl—Ph | CO(n-Pr) | $OCF_3$ | n-Pr | CO(n-Pr) |
| $OCF_3$ | 4-Cl—Ph | CO(i-Pr) | $OCF_3$ | n-Pr | CO(i-Pr) |
| $OCF_3$ | 4-Cl—Ph | CO(t-Bu) | $OCF_3$ | n-Pr | CO(t-Bu) |
| $OCF_3$ | 4-Cl—Ph | n-Pr | $OCF_3$ | n-Pr | n-Pr |

TABLE 15

| R¹ | R³ | Y | R¹ | R³ | Y |
|---|---|---|---|---|---|
| $CF_3$ | Ph | H | $CF_3$ | 4-F—Ph | H |
| $CF_3$ | Ph | Me | $CF_3$ | 4-F—Ph | Me |
| $CF_3$ | Ph | Et | $CF_3$ | 4-F—Ph | Et |
| $CF_3$ | Ph | COMe | $CF_3$ | 4-F—Ph | COMe |
| $CF_3$ | Ph | $CO_2Me$ | $CF_3$ | 4-F—Ph | $CO_2Me$ |
| $OCF_3$ | Ph | H | $OCF_3$ | 4-F—Ph | H |
| $OCF_3$ | Ph | Me | $OCF_3$ | 4-F—Ph | Me |
| $OCF_3$ | Ph | Et | $OCF_3$ | 4-F—Ph | Et |
| $OCF_3$ | Ph | COMe | $OCF_3$ | 4-F—Ph | COMe |
| $OCF_3$ | Ph | $CO_2Me$ | $OCF_3$ | 4-F—Ph | $CO_2Me$ |
| $CF_3$ | 4-Cl—Ph | H | $CF_3$ | n-Pr | H |
| $CF_3$ | 4-Cl—Ph | Me | $CF_3$ | n-Pr | Me |
| $CF_3$ | 4-Cl—Ph | Et | $CF_3$ | n-Pr | Et |
| $CF_3$ | 4-Cl—Ph | COMe | $CF_3$ | n-Pr | COMe |
| $CF_3$ | 4-Cl—Ph | $CO_2Me$ | $CF_3$ | n-Pr | $CO_2Me$ |
| $OCF_3$ | 4-Cl—Ph | H | $OCF_3$ | n-Pr | H |
| $OCF_3$ | 4-Cl—Ph | Me | $OCF_3$ | n-Pr | Me |
| $OCF_3$ | 4-Cl—Ph | Et | $OCF_3$ | n-Pr | Et |
| $OCF_3$ | 4-Cl—Ph | COMe | $OCF_3$ | n-Pr | COMe |
| $OCF_3$ | 4-Cl—Ph | $CO_2Me$ | $OCF_3$ | n-Pr | $CO_2Me$ |
| $CF_3$ | Ph | COEt | $CF_3$ | 4-F—Ph | COEt |
| $CF_3$ | Ph | $CO_2Et$ | $CF_3$ | 4-F—Ph | $CO_2Et$ |
| $CF_3$ | Ph | CO(n-Pr) | $CF_3$ | 4-F—Ph | CO(n-Pr) |
| $CF_3$ | Ph | CO(i-Pr) | $CF_3$ | 4-F—Ph | CO(i-Pr) |
| $CF_3$ | Ph | CO(t-Bu) | $CF_3$ | 4-F—Ph | CO(t-Bu) |
| $CF_3$ | Ph | n-Pr | $CF_3$ | 4-F—Ph | n-Pr |
| $OCF_3$ | Ph | COEt | $OCF_3$ | 4-F—Ph | COEt |
| $OCF_3$ | Ph | $CO_2Et$ | $OCF_3$ | 4-F—Ph | $CO_2Et$ |
| $OCF_3$ | Ph | CO(n-Pr) | $OCF_3$ | 4-F—Ph | CO(n-Pr) |
| $OCF_3$ | Ph | CO(i-Pr) | $OCF_3$ | 4-F—Ph | CO(i-Pr) |
| $OCF_3$ | Ph | CO(t-Bu) | $OCF_3$ | 4-F—Ph | CO(t-Bu) |
| $OCF_3$ | Ph | n-Pr | $OCF_3$ | 4-F—Ph | n-Pr |
| $CF_3$ | 4-Cl—Ph | COEt | $CF_3$ | n-Pr | COEt |
| $CF_3$ | 4-Cl—Ph | $CO_2Et$ | $CF_3$ | n-Pr | $CO_2Et$ |
| $CF_3$ | 4-Cl—Ph | CO(n-Pr) | $CF_3$ | n-Pr | CO(n-Pr) |
| $CF_3$ | 4-Cl—Ph | CO(i-Pr) | $CF_3$ | n-Pr | CO(i-Pr) |
| $CF_3$ | 4-Cl—Ph | CO(t-Bu) | $CF_3$ | n-Pr | CO(t-Bu) |
| $CF_3$ | 4-Cl—Ph | n-Pr | $CF_3$ | n-Pr | n-Pr |
| $OCF_3$ | 4-Cl—Ph | COEt | $OCF_3$ | n-Pr | COEt |
| $OCF_3$ | 4-Cl—Ph | $CO_2Et$ | $OCF_3$ | n-Pr | $CO_2Et$ |
| $OCF_3$ | 4-Cl—Ph | CO(n-Pr) | $OCF_3$ | n-Pr | CO(n-Pr) |
| $OCF_3$ | 4-Cl—Ph | CO(i-Pr) | $OCF_3$ | n-Pr | CO(i-Pr) |
| $OCF_3$ | 4-Cl—Ph | CO(t-Bu) | $OCF_3$ | n-Pr | CO(t-Bu) |
| $OCF_3$ | 4-Cl—Ph | n-Pr | $OCF_3$ | n-Pr | n-Pr |

TABLE 16

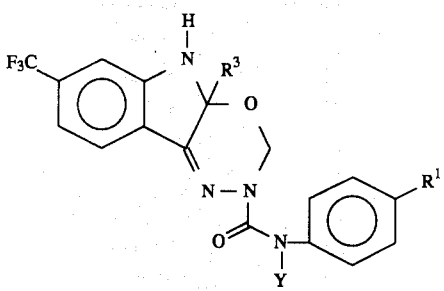

| R¹ | R³ | Y | R¹ | R³ | Y |
|---|---|---|---|---|---|
| CF₃ | Ph | H | CF₃ | 4-F—Ph | H |
| CF₃ | Ph | Me | CF₃ | 4-F—Ph | Me |
| CF₃ | Ph | Et | CF₃ | 4-F—Ph | Et |
| CF₃ | Ph | COMe | CF₃ | 4-F—Ph | COMe |
| CF₃ | Ph | CO₂Me | CF₃ | 4-F—Ph | CO₂Me |
| OCF₃ | Ph | H | OCF₃ | 4-F—Ph | H |
| OCF₃ | Ph | Me | OCF₃ | 4-F—Ph | Me |
| OCF₃ | Ph | Et | OCF₃ | 4-F—Ph | Et |
| OCF₃ | Ph | COMe | OCF₃ | 4-F—Ph | COMe |
| OCF₃ | Ph | CO₂Me | OCF₃ | 4-F—Ph | CO₂Me |
| CF₃ | 4-Cl—Ph | H | CF₃ | n-Pr | H |
| CF₃ | 4-Cl—Ph | Me | CF₃ | n-Pr | Me |
| CF₃ | 4-Cl—Ph | Et | CF₃ | n-Pr | Et |
| CF₃ | 4-Cl—Ph | COMe | CF₃ | n-Pr | COMe |
| CF₃ | 4-Cl—Ph | CO₂Me | CF₃ | n-Pr | CO₂Me |
| OCF₃ | 4-Cl—Ph | H | OCF₃ | n-Pr | H |
| OCF₃ | 4-Cl—Ph | Me | OCF₃ | n-Pr | Me |
| OCF₃ | 4-Cl—Ph | Et | OCF₃ | n-Pr | Et |
| OCF₃ | 4-Cl—Ph | COMe | OCF₃ | n-Pr | COMe |
| OCF₃ | 4-Cl—Ph | CO₂Me | OCF₃ | n-Pr | CO₂Me |
| CF₃ | Ph | COEt | CF₃ | 4-F—Ph | COEt |
| CF₃ | Ph | CO₂Et | CF₃ | 4-F—Ph | CO₂Et |
| CF₃ | Ph | CO(n-Pr) | CF₃ | 4-F—Ph | CO(n-Pr) |
| CF₃ | Ph | CO(i-Pr) | CF₃ | 4-F—Ph | CO(i-Pr) |
| CF₃ | Ph | CO(t-Bu) | CF₃ | 4-F—Ph | CO(t-Bu) |
| CF₃ | Ph | n-Pr | CF₃ | 4-F—Ph | n-Pr |
| OCF₃ | Ph | COEt | OCF₃ | 4-F—Ph | COEt |
| OCF₃ | Ph | CO₂Et | OCF₃ | 4-F—Ph | CO₂Et |
| OCF₃ | Ph | CO(n-Pr) | OCF₃ | 4-F—Ph | CO(n-Pr) |
| OCF₃ | Ph | CO(i-Pr) | OCF₃ | 4-F—Ph | CO(i-Pr) |
| OCF₃ | Ph | CO(t-Bu) | OCF₃ | 4-F—Ph | CO(t-Bu) |
| OCF₃ | Ph | n-Pr | OCF₃ | 4-F—Ph | n-Pr |
| CF₃ | 4-Cl—Ph | COEt | CF₃ | n-Pr | COEt |
| CF₃ | 4-Cl—Ph | CO₂Et | CF₃ | n-Pr | CO₂Et |
| CF₃ | 4-Cl—Ph | CO(n-Pr) | CF₃ | n-Pr | CO(n-Pr) |
| CF₃ | 4-Cl—Ph | CO(i-Pr) | CF₃ | n-Pr | CO(i-Pr) |
| CF₃ | 4-Cl—Ph | CO(t-Bu) | CF₃ | n-Pr | CO(t-Bu) |
| CF₃ | 4-Cl—Ph | n-Pr | CF₃ | n-Pr | n-Pr |
| OCF₃ | 4-Cl—Ph | COEt | OCF₃ | n-Pr | COEt |
| OCF₃ | 4-Cl—Ph | CO₂Et | OCF₃ | n-Pr | CO₂Et |
| OCF₃ | 4-Cl—Ph | CO(n-Pr) | OCF₃ | n-Pr | CO(n-Pr) |
| OCF₃ | 4-Cl—Ph | CO(i-Pr) | OCF₃ | n-Pr | CO(i-Pr) |
| OCF₃ | 4-Cl—Ph | CO(t-Bu) | OCF₃ | n-Pr | CO(t-Bu) |
| OCF₃ | 4-Cl—Ph | n-Pr | OCF₃ | n-Pr | n-Pr |

TABLE 17

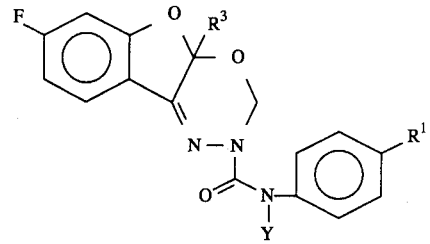

| R¹ | R³ | Y | R¹ | R³ | Y |
|---|---|---|---|---|---|
| CF₃ | Et | H | CF₃ | 4-Cl—Ph | H |
| CF₃ | Et | Me | CF₃ | 4-Cl—Ph | Me |
| CF₃ | Et | Et | CF₃ | 4-Cl—Ph | Et |
| CF₃ | Et | COMe | CF₃ | 4-Cl—Ph | COMe |
| CF₃ | Et | CO₂Me | CF₃ | 4-Cl—Ph | CO₂Me |
| OCF₃ | Et | H | OCF₃ | 4-Cl—Ph | H |
| OCF₃ | Et | Me | OCF₃ | 4-Cl—Ph | Me |
| OCF₃ | Et | Et | OCF₃ | 4-Cl—Ph | Et |
| OCF₃ | Et | COMe | OCF₃ | 4-Cl—Ph | COMe |
| OCF₃ | Et | CO₂Me | OCF₃ | 4-Cl—Ph | CO₂Me |
| CF₃ | n-Pr | H | CF₃ | 4-F—Ph | H |
| CF₃ | n-Pr | Me | CF₃ | 4-F—Ph | Me |
| CF₃ | n-Pr | Et | CF₃ | 4-F—Ph | Et |
| CF₃ | n-Pr | COMe | CF₃ | 4-F—Ph | COMe |
| CF₃ | n-Pr | CO₂Me | CF₃ | 4-F—Ph | CO₂Me |
| OCF₃ | n-Pr | H | OCF₃ | 4-F—Ph | H |
| OCF₃ | n-Pr | Me | OCF₃ | 4-F—Ph | Me |
| OCF₃ | n-Pr | Et | OCF₃ | 4-F—Ph | Et |
| OCF₃ | n-Pr | COMe | OCF₃ | 4-F—Ph | COMe |
| OCF₃ | n-Pr | CO₂Me | OCF₃ | 4-F—Ph | CO₂Me |
| OCF₂H | Et | H | OCF₂H | Et | COMe |
| OCF₂H | Et | Me | OCF₂H | Et | CO₂Me |
| OCF₂H | Et | Et | OCF₂H | Et | COEt |
| OCF₂H | Et | n-Pr | OCF₂H | Et | CO₂Et |
| CF₃ | Et | COEt | CF₃ | 4-Cl—Ph | COEt |
| CF₃ | Et | CO₂Et | CF₃ | 4-Cl—Ph | CO₂Et |
| CF₃ | Et | CO(n-Pr) | CF₃ | 4-Cl—Ph | CO(n-Pr) |
| CF₃ | Et | CO(i-Pr) | CF₃ | 4-Cl—Ph | CO(i-Pr) |
| CF₃ | Et | CO(t-Bu) | CF₃ | 4-Cl—Ph | CO(t-Bu) |
| CF₃ | Et | n-Pr | CF₃ | 4-Cl—Ph | n-Pr |
| OCF₃ | Et | COEt | OCF₃ | 4-Cl—Ph | COEt |
| OCF₃ | Et | CO₂Et | OCF₃ | 4-Cl—Ph | CO₂Et |
| OCF₃ | Et | CO(n-Pr) | OCF₃ | 4-Cl—Ph | CO(n-Pr) |
| OCF₃ | Et | CO(i-Pr) | OCF₃ | 4-Cl—Ph | CO(i-Pr) |
| OCF₃ | Et | CO(t-Bu) | OCF₃ | 4-Cl—Ph | CO(t-Bu) |
| OCF₃ | Et | n-Pr | OCF₃ | 4-Cl—Ph | n-Pr |
| CF₃ | n-Pr | COEt | CF₃ | 4-F—Ph | COEt |
| CF₃ | n-Pr | CO₂Et | CF₃ | 4-F—Ph | CO₂Et |
| CF₃ | n-Pr | CO(n-Pr) | CF₃ | 4-F—Ph | CO(n-Pr) |
| CF₃ | n-Pr | CO(i-Pr) | CF₃ | 4-F—Ph | CO(i-Pr) |
| CF₃ | n-Pr | CO(t-Bu) | CF₃ | 4-F—Ph | CO(t-Bu) |
| CF₃ | n-Pr | n-Pr | CF₃ | 4-F—Ph | n-Pr |
| OCF₃ | n-Pr | COEt | OCF₃ | 4-F—Ph | COEt |
| OCF₃ | n-Pr | CO₂Et | OCF₃ | 4-F—Ph | CO₂Et |
| OCF₃ | n-Pr | CO(n-Pr) | OCF₃ | 4-F—Ph | CO(n-Pr) |
| OCF₃ | n-Pr | CO(i-Pr) | OCF₃ | 4-F—Ph | CO(i-Pr) |
| OCF₃ | n-Pr | CO(t-Bu) | OCF₃ | 4-F—Ph | CO(t-Bu) |
| OCF₃ | n-Pr | n-Pr | OCF₃ | 4-F—Ph | n-Pr |
| OCF₂H | Et | CO(n-Pr) | OCF₂H | n-Pr | CO₂Me |
| OCF₂H | Et | CO(i-Pr) | OCF₂H | n-Pr | COEt |
| OCF₂H | Et | CO(t-Bu) | OCF₂H | n-Pr | CO₂Et |
| OCF₂H | n-Pr | H | OCF₂H | n-Pr | CO(n-Pr) |
| OCF₂H | n-Pr | Me | OCF₂H | n-Pr | CO(i-Pr) |
| OCF₂H | n-Pr | Et | OCF₂H | n-Pr | CO(t-Bu) |
| OCF₂H | n-Pr | n-Pr | OCF₂H | 4-Cl—Ph | H |
| OCF₂H | n-Pr | COMe | OCF₂H | 4-Cl—Ph | Me |
| CF₃ | CO₂Me | H | CF₃ | Ph | H |
| CF₃ | CO₂Me | Me | CF₃ | Ph | Me |
| CF₃ | CO₂Me | Et | CF₃ | Ph | Et |
| CF₃ | CO₂Me | COMe | CF₃ | Ph | COMe |
| CF₃ | CO₂Me | CO₂Me | CF₃ | Ph | CO₂Me |
| OCF₃ | CO₂Me | H | OCF₃ | Ph | H |
| OCF₃ | CO₂Me | Me | OCF₃ | Ph | Me |
| OCF₃ | CO₂Me | Et | OCF₃ | Ph | Et |
| OCF₃ | CO₂Me | COMe | OCF₃ | Ph | COMe |

TABLE 17-continued

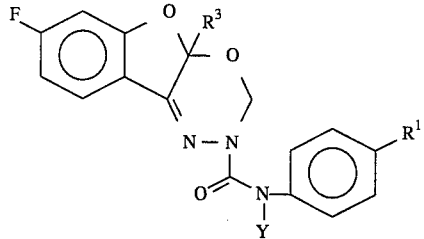

| R¹ | R³ | Y | R¹ | R³ | Y |
|---|---|---|---|---|---|
| OCF₃ | CO₂Me | CO₂Me | OCF₃ | Ph | CO₂Me |
| CF₃ | Me | H | CF₃ | CO₂Et | H |
| CF₃ | Me | Me | CF₃ | CO₂Et | Me |
| CF₃ | Me | Et | CF₃ | CO₂Et | Et |
| CF₃ | Me | COMe | CF₃ | CO₂Et | COMe |
| CF₃ | Me | CO₂Me | CF₃ | CO₂Et | CO₂Me |
| OCF₃ | Me | H | OCF₃ | CO₂Et | H |
| OCF₃ | Me | Me | OCF₃ | CO₂Et | Me |
| OCF₃ | Me | Et | OCF₃ | CO₂Et | Et |
| OCF₃ | Me | COMe | OCF₃ | CO₂Et | COMe |
| OCF₃ | Me | CO₂Me | OCF₃ | CO₂Et | CO₂Me |
| OCF₂H | 4-Cl—Ph | Et | OCF₂H | 4-F—Ph | Et |
| OCF₂H | 4-Cl—Ph | n-Pr | OCF₂H | 4-F—Ph | n-Pr |
| OCF₂H | 4-Cl—Ph | COMe | OCF₂H | 4-F—Ph | COMe |
| OCF₂H | 4-Cl—Ph | CO₂Me | OCF₂H | 4-F—Ph | CO₂Me |
| OCF₂H | 4-Cl—Ph | COEt | OCF₂H | 4-F—Ph | COEt |
| OCF₂H | 4-Cl—Ph | CO₂Et | OCF₂H | 4-F—Ph | CO₂Et |
| OCF₂H | 4-Cl—Ph | CO(n-Pr) | OCF₂H | 4-F—Ph | CO(n-Pr) |
| OCF₂H | 4-Cl—Ph | CO(i-Pr) | OCF₂H | 4-F—Ph | CO(i-Pr) |
| OCF₂H | 4-Cl—Ph | CO(t-Bu) | OCF₂H | 4-F—Ph | CO(t-Bu) |
| OCF₂H | 4-F—Ph | H | OCF₂H | CO₂Me | H |
| OCF₂H | 4-F—Ph | Me | OCF₂H | CO₂Me | Me |
| CF₃ | CO₂Me | COEt | CF₃ | Ph | COEt |
| CF₃ | CO₂Me | CO₂Et | CF₃ | Ph | CO₂Et |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | n-Pr | CF₃ | Ph | n-Pr |
| OCF₃ | CO₂Me | COEt | OCF₃ | Ph | COEt |
| OCF₃ | CO₂Me | CO₂Et | OCF₃ | Ph | CO₂Et |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | n-Pr | OCF₃ | Ph | n-Pr |
| CF₃ | Me | COEt | CF₃ | CO₂Et | COEt |
| CF₃ | Me | CO₂Et | CF₃ | CO₂Et | CO₂Et |
| CF₃ | Me | CO(n-Pr) | CF₃ | CO₂Et | CO(n-Pr) |
| CF₃ | Me | CO(i-Pr) | CF₃ | CO₂Et | CO(i-Pr) |
| CF₃ | Me | CO(t-Bu) | CF₃ | CO₂Et | CO(t-Bu) |
| CF₃ | Me | n-Pr | CF₃ | CO₂Et | n-Pr |
| OCF₃ | Me | COEt | OCF₃ | CO₂Et | COEt |
| OCF₃ | Me | CO₂Et | OCF₃ | CO₂Et | CO₂Et |
| OCF₃ | Me | CO(n-Pr) | OCF₃ | CO₂Et | CO(n-Pr) |
| OCF₃ | Me | CO(i-Pr) | OCF₃ | CO₂Et | CO(i-Pr) |
| OCF₃ | Me | CO(t-Bu) | OCF₃ | CO₂Et | CO(t-Bu) |
| OCF₃ | Me | n-Pr | OCF₃ | CO₂Et | n-Pr |
| OCF₂H | CO₂Me | Et | OCF₂H | CO₂Me | CO(t-Bu) |
| OCF₂H | CO₂Me | n-Pr | | | |
| OCF₂H | CO₂Me | COMe | | | |
| OCF₂H | CO₂Me | CO₂Me | | | |
| OCF₂H | CO₂Me | COEt | | | |
| OCF₂H | CO₂Me | CO₂Et | | | |
| OCF₂H | CO₂Me | CO(n-Pr) | | | |
| OCF₂H | CO₂Me | CO(i-Pr) | | | |

TABLE 18

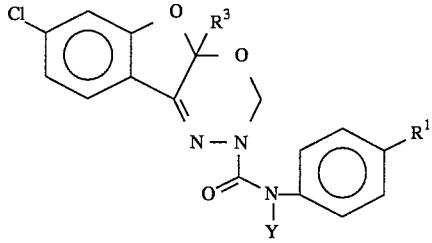

| R¹ | R³ | Y | R¹ | R³ | Y |
|---|---|---|---|---|---|
| CF₃ | Et | H | CF₃ | 4-Cl—Ph | H |
| CF₃ | Et | Me | CF₃ | 4-Cl—Ph | Me |
| CF₃ | Et | Et | CF₃ | 4-Cl—Ph | Et |
| CF₃ | Et | COMe | CF₃ | 4-Cl—Ph | COMe |
| CF₃ | Et | CO₂Me | CF₃ | 4-Cl—Ph | CO₂Me |
| OCF₃ | Et | H | OCF₃ | 4-Cl—Ph | H |
| OCF₃ | Et | Me | OCF₃ | 4-Cl—Ph | Me |
| OCF₃ | Et | Et | OCF₃ | 4-Cl—Ph | Et |
| OCF₃ | Et | COMe | OCF₃ | 4-Cl—Ph | COMe |
| OCF₃ | Et | CO₂Me | OCF₃ | 4-Cl—Ph | CO₂Me |
| CF₃ | n-Pr | H | CF₃ | 4-F—Ph | H |
| CF₃ | n-Pr | Me | CF₃ | 4-F—Ph | Me |
| CF₃ | n-Pr | Et | CF₃ | 4-F—Ph | Et |
| CF₃ | n-Pr | COMe | CF₃ | 4-F—Ph | COMe |
| CF₃ | n-Pr | CO₂Me | CF₃ | 4-F—Ph | CO₂Me |
| OCF₃ | n-Pr | H | OCF₃ | 4-F—Ph | H |
| OCF₃ | n-Pr | Me | OCF₃ | 4-F—Ph | Me |
| OCF₃ | n-Pr | Et | OCF₃ | 4-F—Ph | Et |
| OCF₃ | n-Pr | COMe | OCF₃ | 4-F—Ph | COMe |
| OCF₃ | n-Pr | CO₂Me | OCF₃ | 4-F—Ph | CO₂Me |
| OCF₂H | Et | H | OCF₂H | Et | COMe |
| OCF₂H | Et | Me | OCF₂H | Et | CO₂Me |
| OCF₂H | Et | Et | OCF₂H | Et | COEt |
| OCF₂H | Et | n-Pr | OCF₂H | Et | CO₂Et |
| CF₃ | Et | COEt | CF₃ | 4-Cl—Ph | COEt |
| CF₃ | Et | CO₂Et | CF₃ | 4-Cl—Ph | CO₂Et |
| CF₃ | Et | CO(n-Pr) | CF₃ | 4-Cl—Ph | CO(n-Pr) |
| CF₃ | Et | CO(i-Pr) | CF₃ | 4-Cl—Ph | CO(i-Pr) |
| CF₃ | Et | CO(t-Bu) | CF₃ | 4-Cl—Ph | CO(t-Bu) |
| CF₃ | Et | n-Pr | CF₃ | 4-Cl—Ph | n-Pr |
| OCF₃ | Et | COEt | OCF₃ | 4-Cl—Ph | COEt |
| OCF₃ | Et | CO₂Et | OCF₃ | 4-Cl—Ph | CO₂Et |
| OCF₃ | Et | CO(n-Pr) | OCF₃ | 4-Cl—Ph | CO(n-Pr) |
| OCF₃ | Et | CO(i-Pr) | OCF₃ | 4-Cl—Ph | CO(i-Pr) |
| OCF₃ | Et | CO(t-Bu) | OCF₃ | 4-Cl—Ph | CO(t-Bu) |
| OCF₃ | Et | n-Pr | OCF₃ | 4-Cl—Ph | n-Pr |
| CF₃ | n-Pr | COEt | CF₃ | 4-F—Ph | COEt |
| CF₃ | n-Pr | CO₂Et | CF₃ | 4-F—Ph | CO₂Et |
| CF₃ | n-Pr | CO(n-Pr) | CF₃ | 4-F—Ph | CO(n-Pr) |
| CF₃ | n-Pr | CO(i-Pr) | CF₃ | 4-F—Ph | CO(i-Pr) |
| CF₃ | n-Pr | CO(t-Bu) | CF₃ | 4-F—Ph | CO(t-Bu) |
| CF₃ | n-Pr | n-Pr | CF₃ | 4-F—Ph | n-Pr |
| OCF₃ | n-Pr | COEt | OCF₃ | 4-F—Ph | COEt |
| OCF₃ | n-Pr | CO₂Et | OCF₃ | 4-F—Ph | CO₂Et |
| OCF₃ | n-Pr | CO(n-Pr) | OCF₃ | 4-F—Ph | CO(n-Pr) |
| OCF₃ | n-Pr | CO(i-Pr) | OCF₃ | 4-F—Ph | CO(i-Pr) |
| OCF₃ | n-Pr | CO(t-Bu) | OCF₃ | 4-F—Ph | CO(t-Bu) |
| OCF₃ | n-Pr | n-Pr | OCF₃ | 4-F—Ph | n-Pr |
| OCF₂H | Et | CO(n-Pr) | OCF₂H | n-Pr | CO₂Me |
| OCF₂H | Et | CO(i-Pr) | OCF₂H | n-Pr | COEt |
| OCF₂H | Et | CO(t-Bu) | OCF₂H | n-Pr | CO₂Et |
| OCF₂H | n-Pr | H | OCF₂H | n-Pr | CO(n-Pr) |
| OCF₂H | n-Pr | Me | OCF₂H | n-Pr | CO(i-Pr) |
| OCF₂H | n-Pr | Et | OCF₂H | n-Pr | CO(t-Bu) |
| OCF₂H | n-Pr | n-Pr | OCF₂H | 4-Cl—Ph | H |
| OCF₂H | n-Pr | COMe | OCF₂H | 4-Cl—Ph | Me |
| CF₃ | CO₂Me | H | CF₃ | Ph | H |
| CF₃ | CO₂Me | Me | CF₃ | Ph | Me |
| CF₃ | CO₂Me | Et | CF₃ | Ph | Et |
| CF₃ | CO₂Me | COMe | CF₃ | Ph | COMe |
| CF₃ | CO₂Me | CO₂Me | CF₃ | Ph | CO₂Me |
| OCF₃ | CO₂Me | H | OCF₃ | Ph | H |
| OCF₃ | CO₂Me | Me | OCF₃ | Ph | Me |
| OCF₃ | CO₂Me | Et | OCF₃ | Ph | Et |
| OCF₃ | CO₂Me | COMe | OCF₃ | Ph | COMe |

TABLE 18-continued

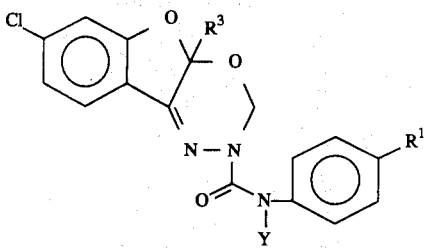

| R¹ | R³ | Y | R¹ | R³ | Y |
|---|---|---|---|---|---|
| OCF₃ | CO₂Me | CO₂Me | OCF₃ | Ph | CO₂Me |
| CF₃ | Me | H | CF₃ | CO₂Et | H |
| CF₃ | Me | Me | CF₃ | CO₂Et | Me |
| CF₃ | Me | Et | CF₃ | CO₂Et | Et |
| CF₃ | Me | COMe | CF₃ | CO₂Et | COMe |
| CF₃ | Me | CO₂Me | CF₃ | CO₂Et | CO₂Me |
| OCF₃ | Me | H | OCF₃ | CO₂Et | H |
| OCF₃ | Me | Me | OCF₃ | CO₂Et | Me |
| OCF₃ | Me | Et | OCF₃ | CO₂Et | Et |
| OCF₃ | Me | COMe | OCF₃ | CO₂Et | COMe |
| OCF₃ | Me | CO₂Me | OCF₃ | CO₂Et | CO₂Me |
| OCF₂H | 4-Cl—Ph | Et | OCF₂H | 4-F—Ph | Et |
| OCF₂H | 4-Cl—Ph | n-Pr | OCF₂H | 4-F—Ph | n-Pr |
| OCF₂H | 4-Cl—Ph | COMe | OCF₂H | 4-F—Ph | COMe |
| OCF₂H | 4-Cl—Ph | CO₂Me | OCF₂H | 4-F—Ph | CO₂Me |
| OCF₂H | 4-Cl—Ph | COEt | OCF₂H | 4-F—Ph | COEt |
| OCF₂H | 4-Cl—Ph | CO₂Et | OCF₂H | 4-F—Ph | CO₂Et |
| OCF₂H | 4-Cl—Ph | CO(n-Pr) | OCF₂H | 4-F—Ph | CO(n-Pr) |
| OCF₂H | 4-Cl—Ph | CO(i-Pr) | OCF₂H | 4-F—Ph | CO(i-Pr) |
| OCF₂H | 4-Cl—Ph | CO(t-Bu) | OCF₂H | 4-F—Ph | CO(t-Bu) |
| OCF₂H | 4-F—Ph | H | OCF₂H | CO₂Me | H |
| OCF₂H | 4-F—Ph | Me | OCF₂H | CO₂Me | Me |
| CF₃ | CO₂Me | COEt | CF₃ | Ph | COEt |
| CF₃ | CO₂Me | CO₂Et | CF₃ | Ph | CO₂Et |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | n-Pr | CF₃ | Ph | n-Pr |
| OCF₃ | CO₂Me | COEt | OCF₃ | Ph | COEt |
| OCF₃ | CO₂Me | CO₂Et | OCF₃ | Ph | CO₂Et |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |
| OCF₃ | CO₂Me | n-Pr | OCF₃ | Ph | n-Pr |
| CF₃ | Me | COEt | CF₃ | CO₂Et | COEt |
| CF₃ | Me | CO₂Et | CF₃ | CO₂Et | CO₂Et |
| CF₃ | Me | CO(n-Pr) | CF₃ | CO₂Et | CO(n-Pr) |
| CF₃ | Me | CO(i-Pr) | CF₃ | CO₂Et | CO(i-Pr) |
| CF₃ | Me | CO(t-Bu) | CF₃ | CO₂Et | CO(t-Bu) |
| CF₃ | Me | n-Pr | CF₃ | CO₂Et | n-Pr |
| OCF₃ | Me | COEt | OCF₃ | CO₂Et | COEt |
| OCF₃ | Me | CO₂Et | OCF₃ | CO₂Et | CO₂Et |
| OCF₃ | Me | CO(n-Pr) | OCF₃ | CO₂Et | CO(n-Pr) |
| OCF₃ | Me | CO(i-Pr) | OCF₃ | CO₂Et | CO(i-Pr) |
| OCF₃ | Me | CO(t-Bu) | OCF₃ | CO₂Et | CO(t-Bu) |
| OCF₃ | Me | n-Pr | OCF₃ | CO₂Et | n-Pr |
| OCF₂H | CO₂Me | Et | OCF₂H | CO₂Me | CO(t-Bu) |
| OCF₂H | CO₂Me | n-Pr | | | |
| OCF₂H | CO₂Me | COMe | | | |
| OCF₂H | CO₂Me | CO₂Me | | | |
| OCF₂H | CO₂Me | COEt | | | |
| OCF₂H | CO₂Me | CO₂Et | | | |
| OCF₂H | CO₂Me | CO(n-Pr) | | | |
| OCF₂H | CO₂Me | CO(i-Pr) | | | |

TABLE 19

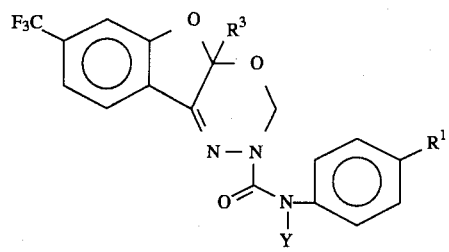

| R¹ | R³ | Y | R¹ | R³ | Y |
|---|---|---|---|---|---|
| CF₃ | Et | H | CF₃ | 4-Cl—Ph | H |
| CF₃ | Et | Me | CF₃ | 4-Cl—Ph | Me |
| CF₃ | Et | Et | CF₃ | 4-Cl—Ph | Et |
| CF₃ | Et | COMe | CF₃ | 4-Cl—Ph | COMe |
| CF₃ | Et | CO₂Me | CF₃ | 4-Cl—Ph | CO₂Me |
| OCF₃ | Et | H | OCF₃ | 4-Cl—Ph | H |
| OCF₃ | Et | Me | OCF₃ | 4-Cl—Ph | Me |
| OCF₃ | Et | Et | OCF₃ | 4-Cl—Ph | Et |
| OCF₃ | Et | COMe | OCF₃ | 4-Cl—Ph | COMe |
| OCF₃ | Et | CO₂Me | OCF₃ | 4-Cl—Ph | CO₂Me |
| CF₃ | n-Pr | R | CF₃ | 4-F—Ph | H |
| CF₃ | n-Pr | Me | CF₃ | 4-F—Ph | Me |
| CF₃ | n-Pr | Et | CF₃ | 4-F—Ph | Et |
| CF₃ | n-Pr | COMe | CF₃ | 4-F—Ph | COMe |
| CF₃ | n-Pr | CO₂Me | CF₃ | 4-F—Ph | CO₂Me |
| OCF₃ | n-Pr | H | OCF₃ | 4-F—Ph | H |
| OCF₃ | n-Pr | Me | OCF₃ | 4-F—Ph | Me |
| OCF₃ | n-Pr | Et | OCF₃ | 4-F—Ph | Et |
| OCF₃ | n-Pr | COMe | OCF₃ | 4-F—Ph | COMe |
| OCF₃ | n-Pr | CO₂Me | OCF₃ | 4-F—Ph | CO₂Me |
| OCF₂H | Et | H | OCF₂H | Et | COMe |
| OCF₂H | Et | Me | OCF₂H | Et | CO₂Me |
| OCF₂H | Et | Et | OCF₂H | Et | COEt |
| OCF₂H | Et | n-Pr | OCF₂H | Et | CO₂Et |
| CF₃ | Et | COEt | CF₃ | 4-Cl—Ph | COEt |
| CF₃ | Et | CO₂Et | CF₃ | 4-Cl—Ph | CO₂Et |
| CF₃ | Et | CO(n-Pr) | CF₃ | 4-Cl—Ph | CO(n-Pr) |
| CF₃ | Et | CO(i-Pr) | CF₃ | 4-Cl—Ph | CO(i-Pr) |
| CF₃ | Et | CO(t-Bu) | CF₃ | 4-Cl—Ph | CO(t-Bu) |
| CF₃ | Et | n-Pr | CF₃ | 4-Cl—Ph | n-Pr |
| OCF₃ | Et | COEt | OCF₃ | 4-Cl—Ph | COEt |
| OCF₃ | Et | CO₂Et | OCF₃ | 4-Cl—Ph | CO₂Et |
| OCF₃ | Et | CO(n-Pr) | OCF₃ | 4-Cl—Ph | CO(n-Pr) |
| OCF₃ | Et | CO(i-Pr) | OCF₃ | 4-Cl—Ph | CO(i-Pr) |
| OCF₃ | Et | CO(t-Bu) | OCF₃ | 4-Cl—Ph | CO(t-Eu) |
| OCF₃ | Et | n-Pr | OCF₃ | 4-Cl—Ph | n-Pr |
| CF₃ | n-Pr | COEt | CF₃ | 4-F—Ph | COEt |
| CF₃ | n-Pr | CO₂Et | CF₃ | 4-F—Ph | CO₂Et |
| CF₃ | n-Pr | CO(n-Pr) | CF₃ | 4-F—Ph | CO(n-Pr) |
| CF₃ | n-Pr | CO(i-Pr) | CF₃ | 4-F—Ph | CO(i-Pr) |
| CF₃ | n-Pr | CO(t-Bu) | CF₃ | 4-F—Ph | CO(t-Bu) |
| CF₃ | n-Pr | n-Pr | CF₃ | 4-F—Ph | n-Pr |
| OCF₃ | n-Pr | COEt | OCF₃ | 4-F—Ph | COEt |
| OCF₃ | n-Pr | CO₂Et | OCF₃ | 4-F—Ph | CO₂Et |
| OCF₃ | n-Pr | CO(n-Pr) | OCF₃ | 4-F—Ph | CO(n-Pr) |
| OCF₃ | n-Pr | CO(i-Pr) | OCF₃ | 4-F—Ph | CO(i-Pr) |
| OCF₃ | n-Pr | CO(t-Bu) | OCF₃ | 4-F—Ph | CO(t-Bu) |
| OCF₃ | n-Pr | n-Pr | OCF₃ | 4-F—Ph | n-Pr |
| OCF₂H | Et | CO(n-Pr) | OCF₂H | n-Pr | CO₂Me |
| OCF₂H | Et | CO(i-Pr) | OCF₂H | n-Pr | COEt |
| OCF₂H | Et | CO(t-Bu) | OCF₂H | n-Pr | CO₂Et |
| OCF₂H | n-Pr | H | OCF₂H | n-Pr | CO(n-Pr) |
| OCF₂H | n-Pr | Me | OCF₂H | n-Pr | CO(i-Pr) |
| OCF₂H | n-Pr | Et | OCF₂H | n-Pr | CO(t-Bu) |
| OCF₂H | n-Pr | n-Pr | OCF₂H | 4-Cl—Ph | H |
| OCF₂H | n-Pr | COMe | OCF₂H | 4-Cl—Ph | Me |
| CF₃ | CO₂Me | H | CF₃ | Ph | H |
| CF₃ | CO₂Me | Me | CF₃ | Ph | Me |
| CF₃ | CO₂Me | Et | CF₃ | Ph | Et |
| CF₃ | CO₂Me | COMe | CF₃ | Ph | COMe |
| CF₃ | CO₂Me | CO₂Me | CF₃ | Ph | CO₂Me |
| OCF₃ | CO₂Me | H | OCF₃ | Ph | H |
| OCF₃ | CO₂Me | Me | OCF₃ | Ph | Me |
| OCF₃ | CO₂Me | Et | OCF₃ | Ph | Et |
| OCF₃ | CO₂Me | COMe | OCF₃ | Ph | COMe |

TABLE 19-continued

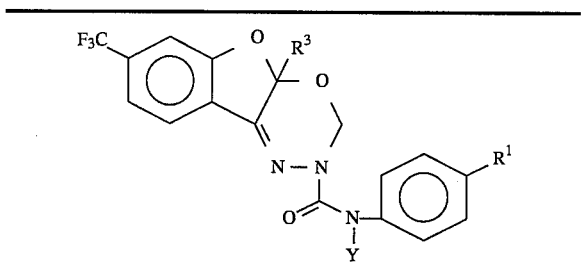

| R¹ | R³ | Y | R¹ | R³ | Y |
|---|---|---|---|---|---|
| OCF₃ | CO₂Me | CO₂Me | OCF₃ | Ph | CO₂Me |
| CF₃ | Me | H | CF₃ | CO₂Et | H |
| CF₃ | Me | Me | CF₃ | CO₂Et | Me |
| CF₃ | Me | Et | CF₃ | CO₂Et | Et |
| CF₃ | Me | COMe | CF₃ | CO₂Et | COMe |
| CF₃ | Me | CO₂Me | CF₃ | CO₂Et | CO₂Me |
| OCF₃ | Me | H | OCF₃ | CO₂Et | H |
| OCF₃ | Me | Me | OCF₃ | CO₂Et | Me |
| OCF₃ | Me | Et | OCF₃ | CO₂Et | Et |
| OCF₃ | Me | COMe | OCF₃ | CO₂Et | COMe |
| OCF₃ | Me | CO₂Me | OCF₃ | CO₂Et | CO₂Me |
| OCF₂H | 4-Cl—Ph | Et | OCF₂H | 4-F—Ph | Et |
| OCF₂H | 4-Cl—Ph | n-Pr | OCF₂H | 4-F—Ph | n-Pr |
| OCF₂H | 4-Cl—Ph | COMe | OCF₂H | 4-F—Ph | COMe |
| OCF₂H | 4-Cl—Ph | CO₂Me | OCF₂H | 4-F—Ph | CO₂Me |
| OCF₂H | 4-Cl—Ph | COEt | OCF₂H | 4-F—Ph | COEt |
| OCF₂H | 4-Cl—Ph | CO₂Et | OCF₂H | 4-F—Ph | CO₂Et |
| OCF₂H | 4-Cl—Ph | CO(n-Pr) | OCF₂H | 4-F—Ph | CO(n-Pr) |
| OCF₂H | 4-Cl—Ph | CO(i-Pr) | OCF₂H | 4-F—Ph | CO(i-Pr) |
| OCF₂H | 4-Cl—Ph | CO(t-Bu) | OCF₂H | 4-F—Ph | CO(t-Bu) |
| OCF₂H | 4-F—Ph | H | OCF₂H | CO₂Me | H |
| OCF₂H | 4-F—Ph | Me | OCF₂H | CO₂Me | Me |
| CF₃ | CO₂Me | H | CF₃ | Ph | H |
| CF₃ | CO₂Me | Me | CF₃ | Ph | Me |
| CF₃ | CO₂Me | Et | CF₃ | Ph | Et |
| CF₃ | CO₂Me | COMe | CF₃ | Ph | COMe |
| CF₃ | CO₂Me | CO₂Me | CF₃ | Ph | CO₂Me |
| OCF₃ | CO₂Me | H | OCF₃ | Ph | H |
| OCF₃ | CO₂Me | Me | OCF₃ | Ph | Me |
| OCF₃ | CO₂Me | Et | OCF₃ | Ph | Et |
| OCF₃ | CO₂Me | COMe | OCF₃ | Ph | COMe |
| OCF₃ | CO₂Me | CO₂Me | OCF₃ | Ph | CO₂Me |
| CF₃ | Me | H | CF₃ | CO₂Et | H |
| CF₃ | Me | Me | CF₃ | CO₂Et | Me |
| CF₃ | Me | Et | CF₃ | CO₂Et | Et |
| CF₃ | Me | COMe | CF₃ | CO₂Et | COMe |
| CF₃ | Me | CO₂Me | CF₃ | CO₂Et | CO₂Me |
| OCF₃ | Me | H | OCF₃ | CO₂Et | H |
| OCF₃ | Me | Me | OCF₃ | CO₂Et | Me |
| OCF₃ | Me | Et | OCF₃ | CO₂Et | Et |
| OCF₃ | Me | COMe | OCF₃ | CO₂Et | COMe |
| OCF₃ | Me | CO₂Me | OCF₃ | CO₂Et | CO₂Me |
| OCF₂H | 4-Cl—Ph | Et | OCF₂H | 4-F—Ph | Et |
| OCF₂H | 4-Cl—Ph | n-Pr | COF₂H | 4-F—Ph | n-Pr |
| OCF₂H | 4-Cl—Ph | COMe | OCF₂H | 4-F—Ph | COMe |
| OCF₂H | 4-Cl—Ph | CO₂Me | OCF₂H | 4-F—Ph | CO₂Me |
| OCF₂H | 4-Cl—Ph | COEt | OCF₂H | 4-F—Ph | COEt |
| OCF₂H | 4-Cl—Ph | CO₂Et | OCF₂H | 4-F—Ph | CO₂Et |
| OCF₂H | 4-Cl—Ph | CO(n-Pr) | OCF₂H | 4-F—Ph | CO(n-Pr) |
| OCF₂H | 4-Cl—Ph | CO(i-Pr) | OCF₂H | 4-F—Ph | CO(i-Pr) |
| OCF₂H | 4-Cl—Ph | CO(t-Bu) | OCF₂H | 4-F—Ph | CO(t-Bu) |
| OCF₂H | 4-F—Ph | H | OCF₂H | CO₂Me | H |
| OCF₂H | 4-F—Ph | Me | OCF₂H | CO₂Me | Me |
| CF₃ | CO₂Me | COEt | CF₃ | Ph | COEt |
| CF₃ | CO₂Me | CO₂Et | CF₃ | Ph | CO₂Et |
| CF₃ | CO₂Me | CO(n-Pr) | CF₃ | Ph | CO(n-Pr) |
| CF₃ | CO₂Me | CO(i-Pr) | CF₃ | Ph | CO(i-Pr) |
| CF₃ | CO₂Me | CO(t-Bu) | CF₃ | Ph | CO(t-Bu) |
| CF₃ | CO₂Me | n-Pr | CF₃ | Ph | n-Pr |
| OCF₃ | CO₂Me | COEt | OCF₃ | Ph | COEt |
| OCF₃ | CO₂Me | CO₂Et | OCF₃ | Ph | CO₂Et |
| OCF₃ | CO₂Me | CO(n-Pr) | OCF₃ | Ph | CO(n-Pr) |
| OCF₃ | CO₂Me | CO(i-Pr) | OCF₃ | Ph | CO(i-Pr) |
| OCF₃ | CO₂Me | CO(t-Bu) | OCF₃ | Ph | CO(t-Bu) |

TABLE 19-continued

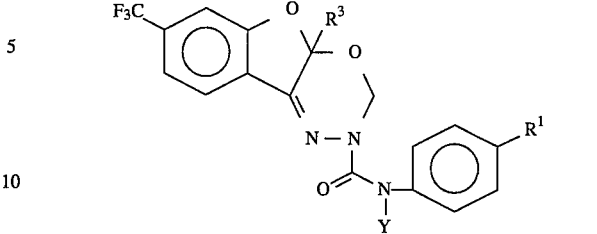

| R¹ | R³ | Y | R¹ | R³ | Y |
|---|---|---|---|---|---|
| OCF₃ | CO₂Me | n-Pr | OCF₃ | Ph | n-Pr |
| CF₃ | Me | COEt | CF₃ | CO₂Et | COEt |
| CF₃ | Me | CO₂Et | CF₃ | CO₂Et | CO₂Et |
| CF₃ | Me | CO(n-Pr) | CF₃ | CO₂Et | CO(n-Pr) |
| CF₃ | Me | CO(i-Pr) | CF₃ | CO₂Et | CO(i-Pr) |
| CF₃ | Me | CO(t-Bu) | CF₃ | CO₂Et | CO(t-Bu) |
| CF₃ | Me | n-Pr | CF₃ | CO₂Et | n-Pr |
| OCF₃ | Me | COEt | OCF₃ | CO₂Et | COEt |
| OCF₃ | Me | CO₂Et | OCF₃ | CO₂Et | CO₂Et |
| OCF₃ | Me | CO(n-Pr) | OCF₃ | CO₂Et | CO(n-Pr) |
| OCF₃ | Me | CO(i-Pr) | OCF₃ | CO₂Et | CO(i-Pr) |
| OCF₃ | Me | CO(t-Bu) | OCF₃ | CO₂Et | CO(t-Bu) |
| OCF₃ | Me | n-Pr | OCF₃ | CO₂Et | n-Pr |
| OCF₂H | CO₂Me | Et | OCF₂H | CO₂Me | CO(t-Bu) |
| OCF₂H | CO₂Me | n-Pr | | | |
| OCF₂H | CO₂Me | COMe | | | |
| OCF₂H | CO₂Me | CO₂Me | | | |
| OCF₂H | CO₂Me | COEt | | | |
| OCF₂H | CO₂Me | CO₂Et | | | |
| OCF₂H | CO₂Me | CO(n-Pr) | | | |
| OCF₂H | CO₂Me | CO(i-Pr) | | | |

TABLE 20

![structure]

| R¹ | R² | R³ | R¹ | R² | R³ |
|---|---|---|---|---|---|
| CF₃ | 6-Cl | Me | CF₃ | 7-Cl | Me |
| CF₃ | 6-Cl | Et | CF₃ | 7-Cl | Et |
| CF₃ | 6-Cl | n-Pr | CF₃ | 7-Cl | n-Pr |
| CF₃ | 6-Cl | CO₂Me | CF₃ | 7-Cl | CO₂Me |
| CF₃ | 6-Cl | 4-F-Ph | CF₃ | 7-Cl | 4-F-Ph |
| OCF₃ | 6-Cl | Me | OCF₃ | 7-Cl | Me |
| OCF₃ | 6-Cl | Et | OCF₃ | 7-Cl | Et |
| OCF₃ | 6-Cl | n-Pr | OCF₃ | 7-Cl | n-Pr |
| OCF₃ | 6-Cl | CO₂Me | OCF₃ | 7-Cl | CO₂Me |
| OCF₃ | 6-Cl | 4-F-Ph | OCF₃ | 7-Cl | 4-F-Ph |
| CF₃ | 6-F | Me | CF₃ | 7-F | Me |
| CF₃ | 6-F | Et | CF₃ | 7-F | Et |
| CF₃ | 6-F | n-Pr | CF₃ | 7-F | n-Pr |
| CF₃ | 6-F | CO₂Me | CF₃ | 7-F | CO₂Me |
| CF₃ | 6-F | 4-F-Ph | CF₃ | 7-F | 4-F-Ph |
| OCF₃ | 6-F | Me | OCF₃ | 7-F | Me |
| OCF₃ | 6-F | Et | OCF₃ | 7-F | Et |
| OCF₃ | 6-F | n-Pr | OCF₃ | 7-F | n-Pr |
| OCF₃ | 6-F | CO₂Me | OCF₃ | 7-F | CO₂Me |
| OCF₃ | 6-F | 4-F-Ph | OCF₃ | 7-F | 4-F-Ph |

TABLE 21

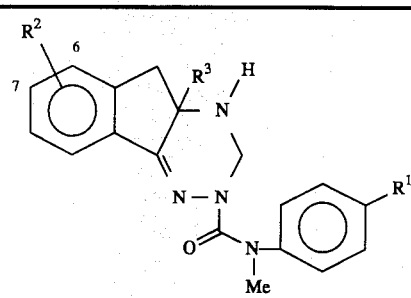

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 22

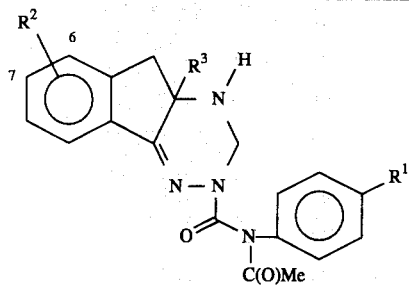

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 23

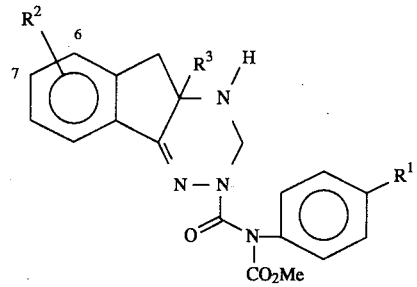

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 24

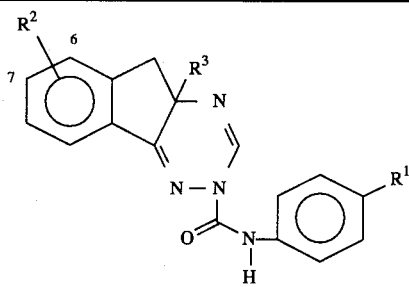

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-r | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 25

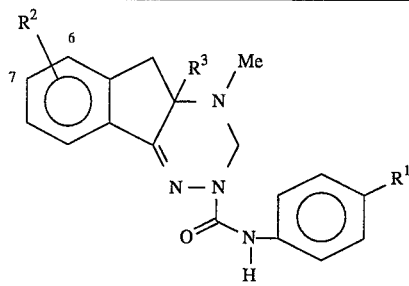

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 26

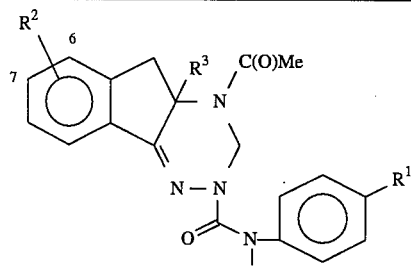

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF+3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 27

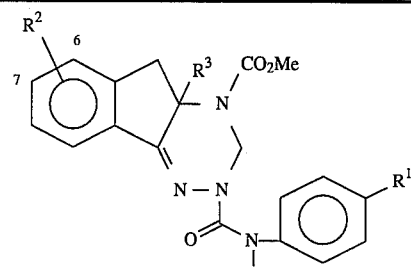

| R¹ | R² | R³ | R¹ | R² | R³ |
|---|---|---|---|---|---|
| $CF_3$ | 6-Cl | Me | $CF_3$ | 7-Cl | Me |
| $CF_3$ | 6-Cl | Et | $CF_3$ | 7-Cl | Et |
| $CF_3$ | 6-Cl | n-Pr | $CF_3$ | 7-Cl | n-Pr |
| $CF_3$ | 6-Cl | $CO_2Me$ | $CF_3$ | 7-Cl | $CO_2Me$ |
| $CF_3$ | 6-Cl | 4-F-Ph | $CF_3$ | 7-Cl | 4-F-Ph |
| $OCF_3$ | 6-Cl | Me | $OCF_3$ | 7-Cl | Me |
| $OCF_3$ | 6-Cl | Et | $OCF_3$ | 7-Cl | Et |
| $OCF_3$ | 6-Cl | n-Pr | $OCF_3$ | 7-Cl | n-Pr |
| $OCF_3$ | 6-Cl | $CO_2Me$ | $OCF_3$ | 7-Cl | $CO_2Me$ |
| $OCF_3$ | 6-Cl | 4-F-Ph | $OCF_3$ | 7-Cl | 4-F-Ph |
| $CF_3$ | 6-F | Me | $CF_3$ | 7-F | Me |
| $CF_3$ | 6-F | Et | $CF_3$ | 7-F | Et |
| $CF_3$ | 6-F | n-Pr | $CF_3$ | 7-F | n-Pr |
| $CF_3$ | 6-F | $CO_2Me$ | $CF_3$ | 7-F | $CO_2Me$ |
| $CF_3$ | 6-F | 4-F-Ph | $CF_3$ | 7-F | 4-F-Ph |
| $OCF_3$ | 6-F | Me | $OCF_3$ | 7-F | Me |
| $OCF_3$ | 6-F | Et | $OCF_3$ | 7-F | Et |
| $OCF_3$ | 6-F | n-Pr | $OCF_3$ | 7-F | n-Pr |
| $OCF_3$ | 6-F | $CO_2Me$ | $OCF_3$ | 7-F | $CO_2Me$ |
| $OCF_3$ | 6-F | 4-F-Ph | $OCF_3$ | 7-F | 4-F-Ph |

TABLE 28

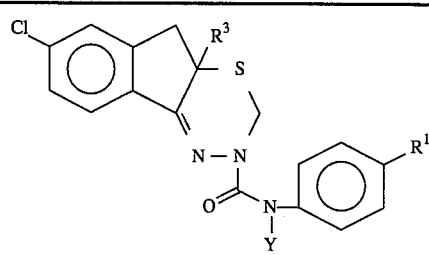

| R¹ | R³ | Y | R¹ | R³ | Y |
|---|---|---|---|---|---|
| $CF_3$ | Et | H | $CF_3$ | $CO_2Me$ | H |
| $CF_3$ | Et | Me | $CF_3$ | $CO_2Me$ | Me |
| $CF_3$ | Et | Et | $CF_3$ | $CO_2Me$ | Et |
| $CF_3$ | Et | COMe | $CF_3$ | $CO_2Me$ | COMe |
| $CF_3$ | Et | $CO_2Me$ | $CF_3$ | $CO_2Me$ | $CO_2Me$ |
| $OCF_3$ | Et | H | $OCF_3$ | $CO_2Me$ | H |
| $OCF_3$ | Et | Me | $OCF_3$ | $CO_2Me$ | Me |
| $OCF_3$ | Et | Et | $OCF_3$ | $CO_2Me$ | Et |
| $OCF_3$ | Et | COMe | $OCF_3$ | $CO_2Me$ | COMe |
| $OCF_3$ | Et | $CO_2Me$ | $OCF_3$ | $CO_2Me$ | $CO_2Me$ |
| $CF_3$ | n-Pr | H | $CF_3$ | 4-F-Ph | H |
| $CF_3$ | n-Pr | Me | $CF_3$ | 4-F-Ph | Me |
| $CF_3$ | n-Pr | Et | $CF_3$ | 4-F-Ph | Et |
| $CF_3$ | n-Pr | COMe | $CF_3$ | 4-F-Ph | COMe |
| $CF_3$ | n-Pr | $CO_2Me$ | $CF_3$ | 4-F-Ph | $CO_2Me$ |
| $OCF_3$ | n-Pr | H | $OCF_3$ | 4-F-Ph | H |
| $OCF_3$ | n-Pr | Me | $OCF_3$ | 4-F-Ph | Me |
| $OCF_3$ | n-Pr | Et | $OCF_3$ | 4-F-Ph | Et |
| $OCF_3$ | n-Pr | COMe | $OCF_3$ | 4-F-Ph | COMe |
| $OCF_3$ | n-Pr | $CO_2Me$ | $OCF_3$ | 4-F-Ph | $CO_2Me$ |
| $CF_3$ | Et | COEt | $CF_3$ | $CO_2Me$ | COEt |
| $CF_3$ | Et | $CO_2Et$ | $CF_3$ | $CO_2Me$ | $CO_2Et$ |
| $CF_3$ | Et | CO(n-Pr) | $CF_3$ | $CO_2Me$ | CO(n-Pr) |
| $CF_3$ | Et | CO(i-Pr) | $CF_3$ | $CO_2Me$ | CO(i-Pr) |
| $CF_3$ | Et | CO(t-Bu) | $CF_3$ | $CO_2Me$ | CO(t-Bu) |

TABLE 28-continued

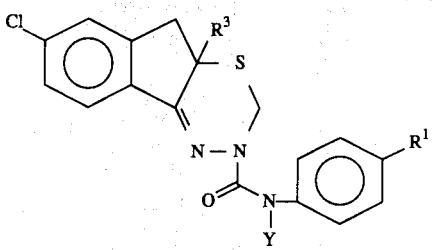

| R¹ | R³ | Y | R¹ | R³ | Y |
|---|---|---|---|---|---|
| CF₃ | Et | n-Pr | CF₃ | CO₂Me | n-Pr |
| OCF₃ | Et | COEt | OCF₃ | CO₂Me | COEt |
| OCF₃ | Et | CO₂Et | OCF₃ | CO₂Me | CO₂Et |
| OCF₃ | Et | CO(n-Pr) | OCF₃ | CO₂Me | CO(n-Pr) |
| OCF₃ | Et | CO(i-Pr) | OCF₃ | CO₂Me | CO(i-Pr) |
| OCF₃ | Et | CO(t-Bu) | OCF₃ | CO₂Me | CO(t-Bu) |
| OCF₃ | Et | n-Pr | OCF₃ | CO₂Me | n-Pr |
| CF₃ | n-Pr | COEt | CF₃ | 4-F-Ph | COEt |
| CF₃ | n-Pr | CO₂Et | CF₃ | 4-F-Ph | CO₂Et |
| CF₃ | n-Pr | CO(n-Pr) | CF₃ | 4-F-Ph | CO(n-Pr) |
| CF₃ | n-Pr | CO(i-Pr) | CF₃ | 4-F-Ph | CO(i-Pr) |
| CF₃ | n-Pr | CO(t-Bu) | CF₃ | 4-F-Ph | CO(t-Bu) |
| CF₃ | n-Pr | n-Pr | CF₃ | 4-F-Ph | n-Pr |
| OCF₃ | n-Pr | COEt | OCF₃ | 4-F-Ph | COEt |
| OCF₃ | n-Pr | CO₂Et | OCF₃ | 4-F-Ph | CO₂Et |
| OCF₃ | n-Pr | CO(n-Pr) | OCF₃ | 4-F-Ph | CO(n-Pr) |
| OCF₃ | n-Pr | CO(i-Pr) | OCF₃ | 4-F-Ph | CO(i-Pr) |
| OCF₃ | n-Pr | CO(t-Bu) | OCF₃ | 4-F-Ph | CO(t-Bu) |
| OCF₃ | n-Pr | n-Pr | OCF₃ | 4-F-Ph | n-Pr |

TABLE 29

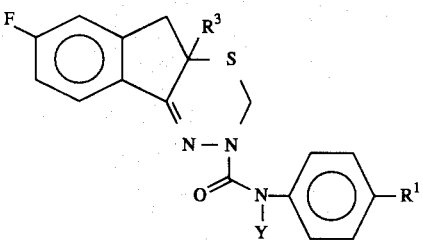

| R¹ | R³ | Y | R¹ | R³ | Y |
|---|---|---|---|---|---|
| CF₃ | Et | H | CF₃ | CO₂Me | H |
| CF₃ | Et | Me | CF₃ | CO₂Me | Me |
| CF₃ | Et | Et | CF₃ | CO₂Me | Et |
| CF₃ | Et | COMe | CF₃ | CO₂Me | COMe |
| CF₃ | Et | CO₂Me | CF₃ | CO₂Me | CO₂Me |
| OCF₃ | Et | H | OCF₃ | CO₂Me | H |
| OCF₃ | Et | Me | OCF₃ | CO₂Me | Me |
| OCF₃ | Et | Et | OCF₃ | CO₂Me | Et |
| OCF₃ | Et | COMe | OCF₃ | CO₂Me | COMe |
| OCF₃ | Et | CO₂Me | OCF₃ | CO₂Me | CO₂Me |
| CF₃ | n-Pr | H | CF₃ | 4-F-Ph | H |
| CF₃ | n-Pr | Me | CF₃ | 4-F-Ph | Me |
| CF₃ | n-Pr | Et | CF₃ | 4-F-Ph | Et |
| CF₃ | n-Pr | COMe | CF₃ | 4-F-Ph | COMe |
| CF₃ | n-Pr | CO₂Me | CF₃ | 4-F-Ph | CO₂Me |
| OCF₃ | n-Pr | H | OCF₃ | 4-F-Ph | H |
| OCF₃ | n-Pr | Me | OCF₃ | 4-F-Ph | Me |
| OCF₃ | n-Pr | Et | OCF₃ | 4-F-Ph | Et |
| OCF₃ | n-Pr | COMe | OCF₃ | 4-F-Ph | COMe |
| OCF₃ | n-Pr | CO₂Me | OCF₃ | 4-F-Ph | CO₂Me |
| CF₃ | Et | COEt | CF₃ | CO₂Me | COEt |
| CF₃ | Et | CO₂Et | CF₃ | CO₂Me | CO₂Et |
| CF₃ | Et | CO(n-Pr) | CF₃ | CO₂Me | CO(n-Pr) |
| CF₃ | Et | CO(i-Pr) | CF₃ | CO₂Me | CO(i-Pr) |
| CF₃ | Et | CO(t-Bu) | CF₃ | CO₂Me | CO(t-Bu) |
| CF₃ | Et | n-Pr | CF₃ | CO₂Me | n-Pr |
| OCF₃ | Et | COEt | OCF₃ | CO₂Me | COEt |

TABLE 29-continued

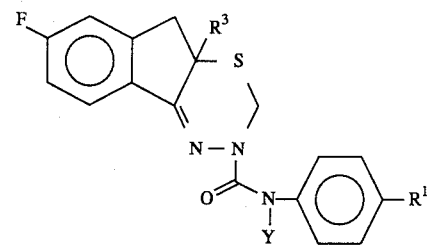

| R¹ | R³ | Y | R¹ | R³ | Y |
|---|---|---|---|---|---|
| OCF₃ | Et | CO₂Et | OCF₃ | CO₂Me | CO₂Et |
| OCF₃ | Et | CO(n-Pr) | OCF₃ | CO₂Me | CO(n-Pr) |
| OCF₃ | Et | CO(i-Pr) | OCF₃ | CO₂Me | CO(i-Pr) |
| OCF₃ | Et | CO(t-Bu) | OCF₃ | CO₂Me | CO(t-Bu) |
| OCF₃ | Et | n-Pr | OCF₃ | CO₂Me | n-Pr |
| CF₃ | n-Pr | COEt | CF₃ | 4-F-Ph | COEt |
| CF₃ | n-Pr | CO₂Et | CF₃ | 4-F-Ph | CO₂Et |
| CF₃ | n-Pr | CO(n-Pr) | CF₃ | 4-F-Ph | CO(n-Pr) |
| CF₃ | n-Pr | CO(i-Pr) | CF₃ | 4-F-Ph | CO(i-Pr) |
| CF₃ | n-Pr | CO(t-Bu) | CF₃ | 4-F-Ph | CO(t-Bu) |
| CF₃ | n-Pr | n-Pr | CF₃ | 4-F-Ph | n-Pr |
| OCF₃ | n-Pr | COEt | OCF₃ | 4-F-Ph | COEt |
| OCF₃ | n-Pr | CO₂Et | OCF₃ | 4-F-Ph | CO₂Et |
| OCF₃ | n-Pr | CO(n-Pr) | OCF₃ | 4-F-Ph | CO(n-Pr) |
| OCF₃ | n-Pr | CO(i-Pr) | OCF₃ | 4-F-Ph | CO(i-Pr) |
| OCF₃ | n-Pr | CO(t-Bu) | OCF₃ | 4-F-Ph | CO(t-Bu) |
| OCF₃ | n-Pr | n-Pr | OCF₃ | 4-F-Ph | n-Pr |

TABLE 30

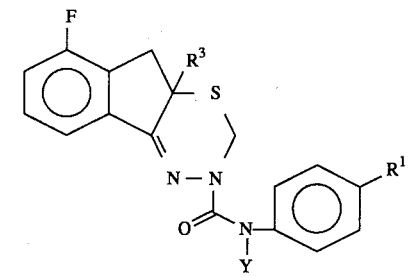

| R¹ | R³ | Y | R¹ | R³ | Y |
|---|---|---|---|---|---|
| CF₃ | Et | H | CF₃ | CO₂Me | H |
| CF₃ | Et | Me | CF₃ | CO₂Me | Me |
| CF₃ | Et | Et | CF₃ | CO₂Me | Et |
| CF₃ | Et | COMe | CF₃ | CO₂Me | COMe |
| CF₃ | Et | CO₂Me | CF₃ | CO₂Me | CO₂Me |
| OCF₃ | Et | H | OCF₃ | CO₂Me | H |
| OCF₃ | Et | Me | OCF₃ | CO₂Me | Me |
| OCF₃ | Et | Et | OCF₃ | CO₂Me | Et |
| OCF₃ | Et | COMe | OCF₃ | CO₂Me | COMe |
| OCF₃ | Et | CO₂Me | OCF₃ | CO₂Me | CO₂Me |
| CF₃ | n-Pr | H | CF₃ | 4-F-Ph | H |
| CF₃ | n-Pr | Me | CF₃ | 4-F-Ph | Me |
| CF₃ | n-Pr | Et | CF₃ | 4-F-Ph | Et |
| CF₃ | n-Pr | COMe | CF₃ | 4-F-Ph | COMe |
| CF₃ | n-Pr | CO₂Me | CF₃ | 4-F-Ph | CO₂Me |
| OCF₃ | n-Pr | H | OCF₃ | 4-F-Ph | H |
| OCF₃ | n-Pr | Me | OCF₃ | 4-F-Ph | Me |
| OCF₃ | n-Pr | Et | OCF₃ | 4-F-Ph | Et |
| OCF₃ | n-Pr | COMe | OCF₃ | 4-F-Ph | COMe |
| OCF₃ | n-Pr | CO₂Me | OCF₃ | 4-F-Ph | CO₂Me |
| CF₃ | Et | COEt | CF₃ | CO₂Me | COEt |
| CF₃ | Et | CO₂Et | CF₃ | CO₂Me | CO₂Et |
| CF₃ | Et | CO(n-Pr) | CF₃ | CO₂Me | CO(n-Pr) |
| CF₃ | Et | CO(i-Pr) | CF₃ | CO₂Me | CO(i-Pr) |
| CF₃ | Et | CO(t-Bu) | CF₃ | CO₂Me | CO(t-Bu) |
| CF₃ | Et | n-Pr | CF₃ | CO₂Me | n-Pr |
| OCF₃ | Et | COEt | OCF₃ | CO₂Me | COEt |
| OCF₃ | Et | CO₂Et | OCF₃ | CO₂Me | CO₂Et |

TABLE 30-continued

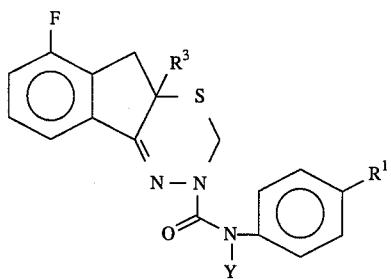

| R¹ | R³ | Y | R¹ | R³ | Y |
|---|---|---|---|---|---|
| OCF₃ | Et | CO(n-Pr) | OCF₃ | CO₂Me | CO(n-Pr) |
| OCF₃ | Et | CO(i-Pr) | OCF₃ | CO₂Me | CO(i-Pr) |
| OCF₃ | Et | CO(t-Bu) | OCF₃ | CO₂Me | CO(t-Bu) |
| OCF₃ | Et | n-Pr | OCF₃ | CO₂Me | n-Pr |
| CF₃ | n-Pr | COEt | CF₃ | 4-F-Ph | COEt |
| CF₃ | n-Pr | CO₂Et | CF₃ | 4-F-Ph | CO₂Et |
| CF₃ | n-Pr | CO(n-Pr) | CF₃ | 4-F-Ph | CO(n-Pr) |
| CF₃ | n-Pr | CO(i-Pr) | CF₃ | 4-F-Ph | CO(i-Pr) |
| CF₃ | n-Pr | CO(t-Bu) | CF₃ | 4-F-Ph | CO(t-Bu) |
| CF₃ | n-Pr | n-Pr | CF₃ | 4-F-Ph | n-Pr |
| OCF₃ | n-Pr | COEt | OCF₃ | 4-F-Ph | COEt |
| OCF₃ | n-Pr | CO₂Et | OCF₃ | 4-F-Ph | CO₂Et |
| OCF₃ | n-Pr | CO(n-Pr) | OCF₃ | 4-F-Ph | CO(n-Pr) |
| OCF₃ | n-Pr | CO(i-Pr) | OCF₃ | 4-F-Ph | CO(i-Pr) |
| OCF₃ | n-Pr | CO(t-Bu) | OCF₃ | 4-F-Ph | CO(t-Bu) |
| OCF₃ | n-Pr | n-Pr | OCF₃ | 4-F-Ph | n-Pr |

TABLE 31

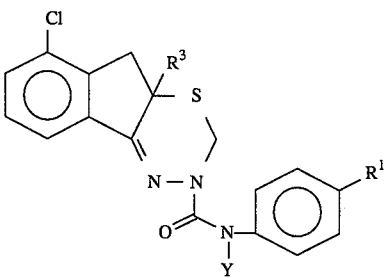

| R¹ | R³ | Y | R¹ | R³ | Y |
|---|---|---|---|---|---|
| CF₃ | Et | H | CF₃ | CO₂Me | H |
| CF₃ | Et | Me | CF₃ | CO₂Me | Me |
| CF₃ | Et | Et | CF₃ | CO₂Me | Et |
| CF₃ | Et | COMe | CF₃ | CO₂Me | COMe |
| CF₃ | Et | CO₂Me | CF₃ | CO₂Me | CO₂Me |
| OCF₃ | Et | H | OCF₃ | CO₂Me | H |
| OCF₃ | Et | Me | OCF₃ | CO₂Me | Me |
| OCF₃ | Et | Et | OCF₃ | CO₂Me | Et |
| OCF₃ | Et | COMe | OCF₃ | CO₂Me | COMe |
| OCF₃ | Et | CO₂Me | OCF₃ | CO₂Me | CO₂Me |
| CF₃ | n-Pr | H | CF₃ | 4-F-Ph | H |
| CF₃ | n-Pr | Me | CF₃ | 4-F-Ph | Me |
| CF₃ | n-Pr | Et | CF₃ | 4-F-Ph | Et |
| CF₃ | n-Pr | COMe | CF₃ | 4-F-Ph | COMe |
| CF₃ | n-Pr | CO₂Me | CF₃ | 4-F-Ph | CO₂Me |
| OCF₃ | n-Pr | H | OCF₃ | 4-F-Ph | H |
| OCF₃ | n-Pr | Me | OCF₃ | 4-F-Ph | Me |
| OCF₃ | n-Pr | Et | OCF₃ | 4-F-Ph | Et |
| OCF₃ | n-Pr | COMe | OCF₃ | 4-F-Ph | COMe |
| OCF₃ | n-Pr | CO₂Me | OCF₃ | 4-F-Ph | CO₂Me |
| CF₃ | Et | COEt | CF₃ | CO₂Me | COEt |
| CF₃ | Et | CO₂Et | CF₃ | CO₂Me | CO₂Et |
| CF₃ | Et | CO(n-Pr) | CF₃ | CO₂Me | CO(n-Pr) |
| CF₃ | Et | CO(i-Pr) | CF₃ | CO₂Me | CO(i-Pr) |
| CF₃ | Et | CO(t-Bu) | CF₃ | CO₂Me | CO(t-Bu) |
| CF₃ | Et | n-Pr | CF₃ | CO₂Me | n-Pr |
| OCF₃ | Et | COEt | OCF₃ | CO₂Me | COEt |

TABLE 31-continued

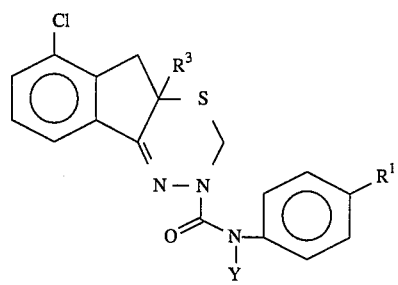

| R¹ | R³ | Y | R¹ | R³ | Y |
|---|---|---|---|---|---|
| OCF₃ | Et | CO₂Et | OCF₃ | CO₂Me | CO₂Et |
| OCF₃ | Et | CO(n-Pr) | OCF₃ | CO₂Me | CO(n-Pr) |
| OCF₃ | Et | CO(i-Pr) | OCF₃ | CO₂Me | CO(i-Pr) |
| OCF₃ | Et | CO(t-Bu) | OCF₃ | CO₂Me | CO(t-Bu) |
| OCF₃ | Et | n-Pr | OCF₃ | CO₂Me | n-Pr |
| CF₃ | n-Pr | COEt | CF₃ | 4-F-Ph | COEt |
| CF₃ | n-Pr | CO₂Et | CF₃ | 4-F-Ph | CO₂Et |
| CF₃ | n-Pr | CO(n-Pr) | CF₃ | 4-F-Ph | CO(n-Pr) |
| CF₃ | n-Pr | CO(i-Pr) | CF₃ | 4-F-Ph | CO(i-Pr) |
| CF₃ | n-Pr | CO(t-Bu) | CF₃ | 4-F-Ph | CO(t-Bu) |
| CF₃ | n-Pr | n-Pr | CF₃ | 4-F-Ph | n-Pr |
| OCF₃ | n-Pr | COEt | OCF₃ | 4-F-Ph | COEt |
| OCF₃ | n-Pr | CO₂Et | OCF₃ | 4-F-Ph | CO₂Et |
| OCF₃ | n-Pr | CO(n-Pr) | OCF₃ | 4-F-Ph | CO(n-Pr) |
| OCF₃ | n-Pr | CO(i-Pr) | OCF₃ | 4-F-Ph | CO(i-Pr) |
| OCF₃ | n-Pr | CO(t-Bu) | OCF₃ | 4-F-Ph | CO(t-Eu) |
| OCF₃ | n-Pr | n-Pr | OCF₃ | 4-F-Ph | n-Pr |

TABLE 32

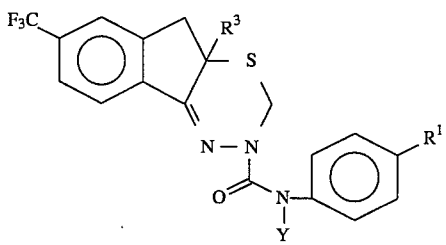

| R¹ | R³ | Y | R¹ | R³ | Y |
|---|---|---|---|---|---|
| CF₃ | Et | H | CF₃ | CO₂Me | H |
| CF₃ | Et | Me | CF₃ | CO₂Me | Me |
| CF₃ | Et | Et | CF₃ | CO₂Me | Et |
| CF₃ | Et | COMe | CF₃ | CO₂Me | COMe |
| CF₃ | Et | CO₂Me | CF₃ | CO₂Me | CO₂Me |
| OCF₃ | Et | H | OCF₃ | CO₂Me | H |
| OCF₃ | Et | Me | OCF₃ | CO₂Me | Me |
| OCF₃ | Et | Et | OCF₃ | CO₂Me | Et |
| OCF₃ | Et | COMe | OCF₃ | CO₂Me | COMe |
| OCF₃ | Et | CO₂Me | OCF₃ | CO₂Me | CO₂Me |
| CF₃ | n-Pr | H | CF₃ | 4-F-Ph | H |
| CF₃ | n-Pr | Me | CF₃ | 4-F-Ph | Me |
| CF₃ | n-Pr | Et | CF₃ | 4-F-Ph | Et |
| CF₃ | n-Pr | COMe | CF₃ | 4-F-Ph | COMe |
| CF₃ | n-Pr | CO₂Me | CF₃ | 4-F-Ph | CO₂Me |
| OCF₃ | n-Pr | H | OCF₃ | 4-F-Ph | H |
| OCF₃ | n-Pr | Me | OCF₃ | 4-F-Ph | Me |
| OCF₃ | n-Pr | Et | OCF₃ | 4-F-Ph | Et |
| OCF₃ | n-Pr | COMe | OCF₃ | 4-F-Ph | COMe |
| OCF₃ | n-Pr | CO₂Me | OCF₃ | 4-F-Ph | CO₂Me |
| CF₃ | Et | COEt | CF₃ | CO₂Me | COEt |
| CF₃ | Et | CO₂Et | CF₃ | CO₂Me | CO₂Et |
| CF₃ | Et | CO(n-Pr) | CF₃ | CO₂Me | CO(n-Pr) |
| CF₃ | Et | CO(i-Pr) | CF₃ | CO₂Me | CO(i-Pr) |
| CF₃ | Et | CO(t-Bu) | CF₃ | CO₂Me | CO(t-Bu) |
| CF₃ | Et | n-Pr | CF₃ | CO₂Me | n-Pr |
| OCF₃ | Et | COEt | OCF₃ | CO₂Me | COEt |

TABLE 32-continued

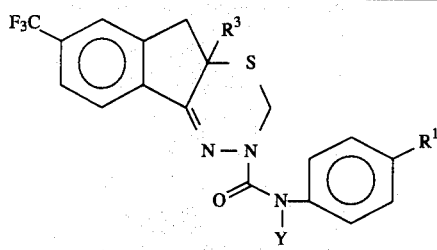

| R¹ | R³ | Y | R¹ | R³ | Y |
|---|---|---|---|---|---|
| OCF₃ | Et | CO₂Et | OCF₃ | CO₂Me | CO₂Et |
| OCF₃ | Et | CO(n-Pr) | OCF₃ | CO₂Me | CO(n-Pr) |
| OCF₃ | Et | CO(i-Pr) | OCF₃ | CO₂Me | CO(i-Pr) |
| OCF₃ | Et | CO(t-Bu) | OCF₃ | CO₂Me | CO(t-Bu) |
| OCF₃ | Et | n-Pr | OCF₃ | CO₂Me | n-Pr |
| CF₃ | n-Pr | COEt | CF₃ | 4-F-Ph | COEt |
| CF₃ | n-Pr | CO₂Et | CF₃ | 4-F-Ph | CO₂Et |
| CF₃ | n-Pr | CO(n-Pr) | CF₃ | 4-F-Ph | CO(n-Pr) |
| CF₃ | n-Pr | CO(i-Pr) | CF₃ | 4-F-Ph | CO(i-Pr) |
| CF₃ | n-Pr | CO(t-Bu) | CF₃ | 4-F-Ph | CO(t-Bu) |
| CF₃ | n-Pr | n-Pr | CF₃ | 4-F-Ph | n-Pr |
| OCF₃ | n-Pr | COEt | OCF₃ | 4-F-Ph | COEt |
| OCF₃ | n-Pr | CO₂Et | OCF₃ | 4-F-Ph | CO₂Et |
| OCF₃ | n-Pr | CO(n-Pr) | OCF₃ | 4-F-Ph | CO(n-Pr) |
| OCF₃ | n-Pr | CO(i-Pr) | OCF₃ | 4-F-Ph | CO(i-Pr) |
| OCF₃ | n-Pr | CO(t-Bu) | OCF₃ | 4-F-Ph | CO(t-Bu) |
| OCF₃ | n-Pr | n-Pr | OCF₃ | 4-F-Ph | n-Pr |

TABLE 33

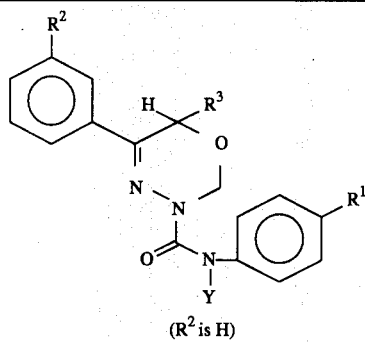

(R² is H)

| R¹ | R³ | Y | R¹ | R³ | Y |
|---|---|---|---|---|---|
| CF₃ | CO₂Me | H | CF₃ | 4-Cl-Ph | H |
| CF₃ | CO₂Me | Me | CF₃ | 4-Cl-Ph | Me |
| CF₃ | CO₂Me | Et | CF₃ | 4-Cl-Ph | Et |
| CF₃ | CO₂Me | COMe | CF₃ | 4-Cl-Ph | COMe |
| CF₃ | CO₂Me | CO₂Me | CF₃ | 4-Cl-Ph | CO₂Me |
| OCF₃ | CO₂Me | H | OCF₃ | 4-Cl-Ph | H |
| OCF₃ | CO₂Me | Me | OCF₃ | 4-Cl-Ph | Me |
| OCF₃ | CO₂Me | Et | OCF₃ | 4-Cl-Ph | Et |
| OCF₃ | CO₂Me | COMe | OCF₃ | 4-Cl-Ph | COMe |
| OCF₃ | CO₂Me | CO₂Me | OCF₃ | 4-Cl-Ph | CO₂Me |
| CF₃ | Ph | H | CF₃ | 4-F-Ph | H |
| CF₃ | Ph | Me | CF₃ | 4-F-Ph | Me |
| CF₃ | Ph | Et | CF₃ | 4-F-Ph | Et |
| CF₃ | Ph | COMe | CF₃ | 4-F-Ph | COMe |
| CF₃ | Ph | CO₂Me | CF₃ | 4-F-Ph | CO₂Me |
| OCF₃ | Ph | H | OCF₃ | 4-F-Ph | H |
| OCF₃ | Ph | Me | OCF₃ | 4-F-Ph | Me |
| OCF₃ | Ph | Et | OCF₃ | 4-F-Ph | Et |
| OCF₃ | Ph | COMe | OCF₃ | 4-F-Ph | COMe |
| OCF₃ | Ph | CO₂Me | OCF₃ | 4-F-Ph | CO₂Me |
| CF₃ | CO₂Me | COEt | CF₃ | 4-Cl-Ph | COEt |
| CF₃ | CO₂Me | CO₂Et | CF₃ | 4-Cl-Ph | CO₂Et |
| CF₃ | CO₂Me | CO(n-Pr) | CF₃ | 4-Cl-Ph | CO(n-Pr) |
| CF₃ | CO₂Me | CO(i-Pr) | CF₃ | 4-Cl-Ph | CO(i-Pr) |
| CF₃ | CO₂Me | CO(t-Bu) | CF₃ | 4-Cl-Ph | CO(t-Bu) |

TABLE 33-continued

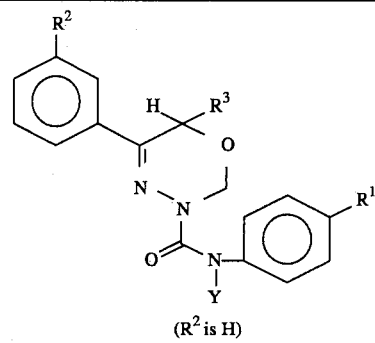

(R² is H)

| R¹ | R³ | Y | R¹ | R³ | Y |
|---|---|---|---|---|---|
| CF₃ | CO₂Me | CO₂(t-Bu) | CF₃ | 4-Cl-Ph | CO₂(t-Bu) |
| OCF₃ | CO₂Me | COEt | OCF₃ | 4-Cl-Ph | COEt |
| OCF₃ | CO₂Me | CO₂Et | OCF₃ | 4-Cl-Ph | CO₂Et |
| OCF₃ | CO₂Me | CO(n-Pr) | OCF₃ | 4-Cl-Ph | CO(n-Pr) |
| OCF₃ | CO₂Me | CO(i-Pr) | OCF₃ | 4-Cl-Ph | CO(i-Pr) |
| OCF₃ | CO₂Me | CO(t-Bu) | OCF₃ | 4-Cl-Ph | CO(t-Bu) |
| OCF₃ | CO₂Me | CO₂(t-Bu) | OCF₃ | 4-Cl-Ph | CO₂(t-BU) |
| CF₃ | Ph | COEt | CF₃ | 4-F-Ph | COEt |
| CF₃ | Ph | CO₂Et | CF₃ | 4-F-Ph | CO₂Et |
| CF₃ | Ph | CO(n-Pr) | CF₃ | 4-F-Ph | CO(n-Pr) |
| CF₃ | Ph | CO(i-Pr) | CF₃ | 4-F-Ph | CO(i-Pr) |
| CF₃ | Ph | CO(t-Bu) | CF₃ | 4-F-Ph | CO(t-Bu) |
| CF₃ | Ph | CO₂(t-Bu) | CF₃ | 4-F-Ph | CO₂(t-Bu) |
| OCF₃ | Ph | COEt | OCF₃ | 4-F-Ph | COEt |
| OCF₃ | Ph | CO₂Et | OCF₃ | 4-F-Ph | CO₂Et |
| OCF₃ | Ph | CO(n-Pr) | OCF₃ | 4-F-Ph | CO(n-Pr) |
| OCF₃ | Ph | CO(i-Pr) | OCF₃ | 4-F-Ph | CO(i-Pr) |
| OCF₃ | Ph | CO(t-Bu) | OCF₃ | 4-F-Ph | CO(t-Bu) |
| OCF₃ | Ph | CO₂(t-Bu) | OCF₃ | 4-F-Ph | CO₂(t-Bu) |
| CF₃ | CO₂Me | n-Pr | CF₃ | 4-Cl-Ph | n-Pr |
| CF₃ | CO₂Me | i-Bu | CF₃ | 4-Cl-Ph | i-Bu |
| OCF₃ | CO₂Me | n-Pr | OCF₃ | 4-Cl-Ph | n-Pr |
| OCF₃ | CO₂Me | i-Bu | OCF₃ | 4-Cl-Ph | i-Eu |
| OCF₃ | Ph | n-Pr | CF₃ | 4-F-Ph | n-Pr |
| OCF₃ | Ph | i-Bu | CF₃ | 4-F-Ph | i-Bu |
| CF₃ | Ph | n-Pr | OCF₃ | 4-F-Ph | n-Pr |
| CF₃ | Ph | i-Bu | OCF₃ | 4-F-Ph | i-Bu |

TABLE 34

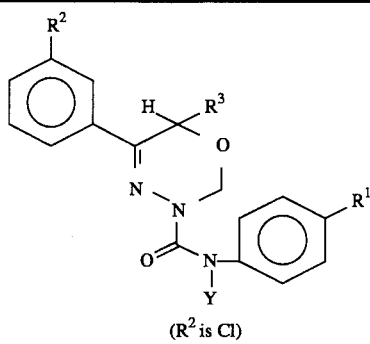

(R² is Cl)

| R¹ | R³ | Y | R¹ | R³ | Y |
|---|---|---|---|---|---|
| CF₃ | CO₂Me | H | CF₃ | 4-Cl-Ph | H |
| CF₃ | CO₂Me | Me | CF₃ | 4-Cl-Ph | Me |
| CF₃ | CO₂Me | Et | CF₃ | 4-Cl-Ph | Et |
| CF₃ | CO₂Me | COMe | CF₃ | 4-Cl-Ph | COMe |
| CF₃ | CO₂Me | CO₂Me | CF₃ | 4-Cl-Ph | CO₂Me |
| OCF₃ | CO₂Me | H | OCF₃ | 4-Cl-Ph | H |
| OCF₃ | CO₂Me | Me | OCF₃ | 4-Cl-Ph | Me |
| OCF₃ | CO₂Me | Et | OCF₃ | 4-Cl-Ph | Et |
| OCF₃ | CO₂Me | COMe | OCF₃ | 4-Cl-Ph | COMe |
| OCF₃ | CO₂Me | CO₂Me | OCF₃ | 4-Cl-Ph | CO₂Me |
| CF₃ | Ph | H | CF₃ | 4-F-Ph | H |

TABLE 34-continued

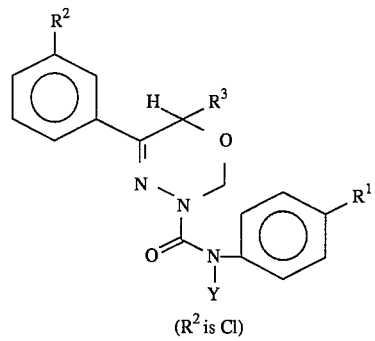

($R^2$ is Cl)

| $R^1$ | $R^3$ | Y | $R^1$ | $R^3$ | Y |
|---|---|---|---|---|---|
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $CF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 35

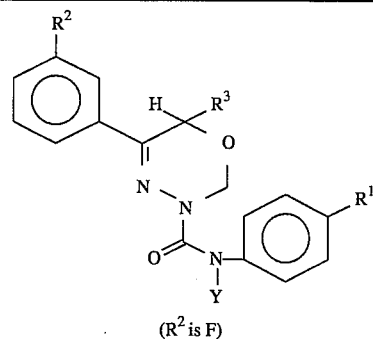

($R^2$ is F)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 36

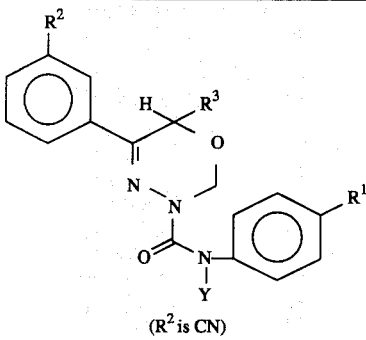

($R^2$ is CN)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| CF$_3$ | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Bu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 37

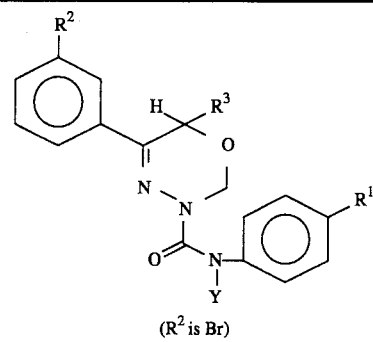

($R^2$ is Br)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| CF$_3$ | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Bu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 38

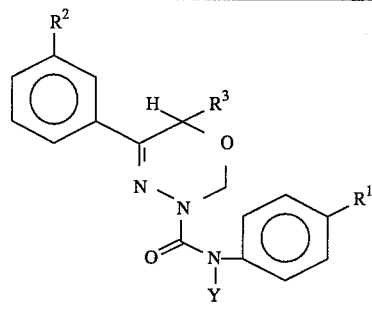

($R^2$ is $CF_3$)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $OCF_3$ | 4-F-Ph | n-Pr |
| $OCF_3$ | Ph | i-Bu | $OCF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 39

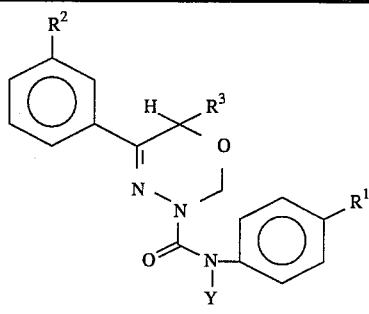

($R^2$ is $OCF_2H$)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 40

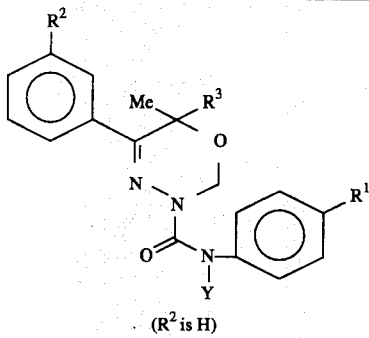

($R^2$ is H)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | OCF | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph. | n-Pr |
| $CF_3$ | Ph | i-Bu | $OCF_3$ | 4-F-Ph | i-Bu |

TABLE 41

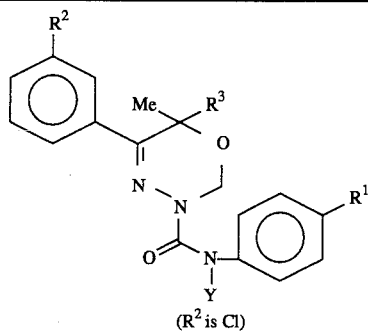

($R^2$ is Cl)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COET | $CF_3$ | 4-Cl-Ph | COET |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Eu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $CCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 42

(Structure with $R^2$ is F)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| CF$_3$ | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Bu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 43

(Structure with $R^2$ is CN)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| CF$_3$ | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Bu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 44

($R^2$ is Br)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| CF$_3$ | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Bu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 45

($R^2$ is CF$_3$)

| $R^1$ | $R^3$ | Y | $R^1$ | $R^3$ | Y |
|---|---|---|---|---|---|
| CF$_3$ | CO$_2$Me | H | CF$_3$ | 4-Cl-Ph | H |
| CF$_3$ | CO$_2$Me | Me | CF$_3$ | 4-Cl-Ph | Me |
| CF$_3$ | CO$_2$Me | Et | CF$_3$ | 4-Cl-Ph | Et |
| CF$_3$ | CO$_2$Me | COMe | CF$_3$ | 4-Cl-Ph | COMe |
| CF$_3$ | CO$_2$Me | CO$_2$Me | CF$_3$ | 4-Cl-Ph | CO$_2$Me |
| OCF$_3$ | CO$_2$Me | H | OCF$_3$ | 4-Cl-Ph | H |
| OCF$_3$ | CO$_2$Me | Me | OCF$_3$ | 4-Cl-Ph | Me |
| OCF$_3$ | CO$_2$Me | Et | OCF$_3$ | 4-Cl-Ph | Et |
| OCF$_3$ | CO$_2$Me | COMe | OCF$_3$ | 4-Cl-Ph | COMe |
| OCF$_3$ | CO$_2$Me | CO$_2$Me | OCF$_3$ | 4-Cl-Ph | CO$_2$Me |
| CF$_3$ | Ph | H | CF$_3$ | 4-F-Ph | H |
| CF$_3$ | Ph | Me | CF$_3$ | 4-F-Ph | Me |
| CF$_3$ | Ph | Et | CF$_3$ | 4-F-Ph | Et |
| CF$_3$ | Ph | COMe | CF$_3$ | 4-F-Ph | COMe |
| CF$_3$ | Ph | CO$_2$Me | CF$_3$ | 4-F-Ph | CO$_2$Me |
| OCF$_3$ | Ph | H | OCF$_3$ | 4-F-Ph | H |
| OCF$_3$ | Ph | Me | OCF$_3$ | 4-F-Ph | Me |
| OCF$_3$ | Ph | Et | OCF$_3$ | 4-F-Ph | Et |
| OCF$_3$ | Ph | COMe | OCF$_3$ | 4-F-Ph | COMe |
| OCF$_3$ | Ph | CO$_2$Me | OCF$_3$ | 4-F-Ph | CO$_2$Me |
| CF$_3$ | CO$_2$Me | COEt | CF$_3$ | 4-Cl-Ph | COEt |
| CF$_3$ | CO$_2$Me | CO$_2$Et | CF$_3$ | 4-Cl-Ph | CO$_2$Et |
| CF$_3$ | CO$_2$Me | CO(n-Pr) | CF$_3$ | 4-Cl-Ph | CO(n-Pr) |
| CF$_3$ | CO$_2$Me | CO(i-Pr) | CF$_3$ | 4-Cl-Ph | CO(i-Pr) |
| CF$_3$ | CO$_2$Me | CO(t-Bu) | CF$_3$ | 4-Cl-Ph | CO(t-Bu) |
| CF$_3$ | CO$_2$Me | CO$_2$(t-Bu) | CF$_3$ | 4-Cl-Ph | CO$_2$(t-Bu) |
| OCF$_3$ | CO$_2$Me | COEt | OCF$_3$ | 4-Cl-Ph | COEt |
| OCF$_3$ | CO$_2$Me | CO$_2$Et | OCF$_3$ | 4-Cl-Ph | CO$_2$Et |
| OCF$_3$ | CO$_2$Me | CO(n-Pr) | OCF$_3$ | 4-Cl-Ph | CO(n-Pr) |
| OCF$_3$ | CO$_2$Me | CO(i-Pr) | OCF$_3$ | 4-Cl-Ph | CO(i-Pr) |
| OCF$_3$ | CO$_2$Me | CO(t-Bu) | OCF$_3$ | 4-Cl-Ph | CO(t-Bu) |
| OCF$_3$ | CO$_2$Me | CO$_2$(t-Bu) | OCF$_3$ | 4-Cl-Ph | CO$_2$(t-Bu) |
| CF$_3$ | Ph | COEt | CF$_3$ | 4-F-Ph | COEt |
| CF$_3$ | Ph | CO$_2$Et | CF$_3$ | 4-F-Ph | CO$_2$Et |
| Cr3 | Ph | CO(n-Pr) | CF$_3$ | 4-F-Ph | CO(n-Pr) |
| CF$_3$ | Ph | CO(i-Pr) | CF$_3$ | 4-F-Ph | CO(i-Pr) |
| CF$_3$ | Ph | CO(t-Bu) | CF$_3$ | 4-F-Ph | CO(t-Bu) |
| CF$_3$ | Ph | CO$_2$(t-Bu) | CF$_3$ | 4-F-Ph | CO$_2$(t-Bu) |
| OCF$_3$ | Ph | COEt | OCF$_3$ | 4-F-Ph | COEt |
| OCF$_3$ | Ph | CO$_2$Et | OCF$_3$ | 4-F-Ph | CO$_2$Et |
| OCF$_3$ | Ph | CO(n-Pr) | OCF$_3$ | 4-F-Ph | CO(n-Pr) |
| OCF$_3$ | Ph | CO(i-Pr) | OCF$_3$ | 4-F-Ph | CO(i-Pr) |
| OCF$_3$ | Ph | CO(t-Bu) | OCF$_3$ | 4-F-Ph | CO(t-Bu) |
| OCF$_3$ | Ph | CO$_2$(t-Bu) | OCF$_3$ | 4-F-Ph | CO$_2$(t-Eu) |
| CF$_3$ | CO$_2$Me | n-Pr | CF$_3$ | 4-Cl-Ph | n-Pr |
| CF$_3$ | CO$_2$Me | i-Bu | CF$_3$ | 4-Cl-Ph | i-Bu |
| OCF$_3$ | CO$_2$Me | n-Pr | OCF$_3$ | 4-Cl-Ph | n-Pr |
| OCF$_3$ | CO$_2$Me | i-Bu | OCF$_3$ | 4-Cl-Ph | i-Bu |
| OCF$_3$ | Ph | n-Pr | CF$_3$ | 4-F-Ph | n-Pr |
| OCF$_3$ | Ph | i-Bu | CF$_3$ | 4-F-Ph | i-Bu |
| CF$_3$ | Ph | n-Pr | OCF$_3$ | 4-F-Ph | n-Pr |
| CF$_3$ | Ph | i-Bu | OCF$_3$ | 4-F-Ph | i-Bu |

TABLE 46

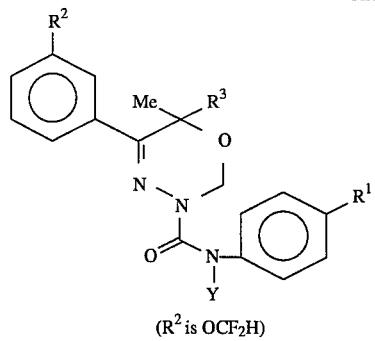

($R^2$ is $OCF_2H$)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | OCF3 | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2$(t-Bu) | $CF_3$ | 4-Cl-Ph | $CO_2$(t-Bu) |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2$(t-Bu) | $OCF_3$ | 4-Cl-Ph | $CO_2$(t-Bu) |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2$(t-Bu) | $CF_3$ | 4-F-Ph | $CO_2$(t-Bu) |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2$(t-Bu) | $OCF_3$ | 4-F-Ph | $CO_2$(t-Bu) |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 47

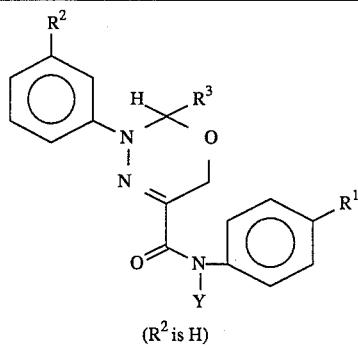

($R^2$ is H)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2$(t-Bu) | $CF_3$ | 4-Cl-Ph | $CO_2$(t-Bu) |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO (i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2$(t-Bu) | $OCF_3$ | 4-Cl-Ph | $CO_2$(t-Bu) |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2$(t-Bu) | $CF_3$ | 4-F-Ph | $CO_2$(t-Bu) |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2$(t-Bu) | $OCF_3$ | 4-F-Ph | $CO_2$(t-Bu) |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 48

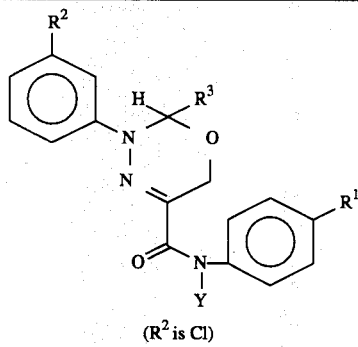

($R^2$ is Cl)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Eu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-BU)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 49

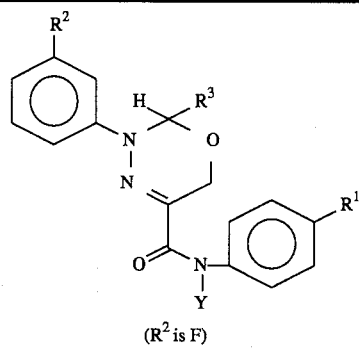

($R^2$ is F)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 50

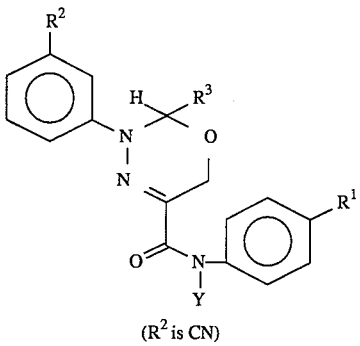

($R^2$ is CN)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2$(t-Bu) | $CF_3$ | 4-Cl-Ph | $CO_2$(t-Bu) |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2$(t-Bu) | $OCF_3$ | 4-Cl-Ph | $CO_2$(t-Bu) |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2$(t-Bu) | $CF_3$ | 4-F-Ph | $CO_2$(t-Bu) |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2$(t-Bu) | $OCF_3$ | 4-F-Ph | $CO_2$(t-Bu) |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 51

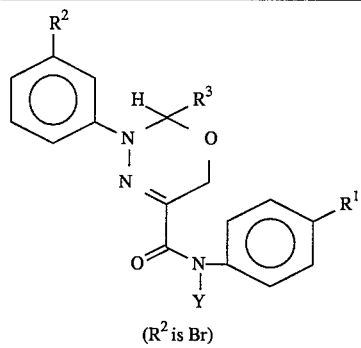

($R^2$ is Br)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2He$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2$(t-Bu) | $CF_3$ | 4-Cl-Ph | $CO_2$(t-Bu) |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2$(t-Bu) | $OCF_3$ | 4-Cl-Ph | $CO_2$(t-Bu) |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2$(t-Bu) | $CF_3$ | 4-F-Ph | $CO_2$(t-Bu) |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2$(t-Bu) | $OCF_3$ | 4-F-Ph | $CO_2$(t-Bu) |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 52

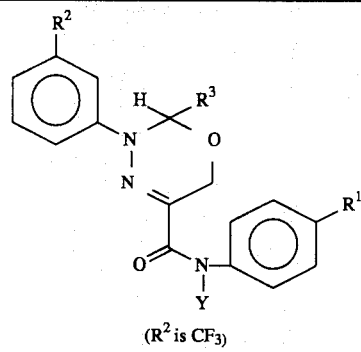

($R^2$ is $CF_3$)

| $R^1$ | $R^3$ | Y | $R^1$ | $R^3$ | Y |
|---|---|---|---|---|---|
| $CF_3$ | $CO_2Me$ | H | $CF_3$ | 4-Cl-Ph | H |
| $CF_3$ | $CO_2Me$ | Me | $CF_3$ | 4-Cl-Ph | Me |
| $CF_3$ | $CO_2Me$ | Et | $CF_3$ | 4-Cl-Ph | Et |
| $CF_3$ | $CO_2Me$ | COMe | $CF_3$ | 4-Cl-Ph | COMe |
| $CF_3$ | $CO_2Me$ | $CO_2Me$ | $CF_3$ | 4-Cl-Ph | $CO_2Me$ |
| $OCF_3$ | $CO_2Me$ | H | $OCF_3$ | 4-Cl-Ph | H |
| $OCF_3$ | $CO_2Me$ | Me | $OCF_3$ | 4-Cl-Ph | Me |
| $OCF_3$ | $CO_2Me$ | Et | $OCF_3$ | 4-Cl-Ph | Et |
| $OCF_3$ | $CO_2Me$ | COMe | $OCF_3$ | 4-Cl-Ph | COMe |
| $OCF_3$ | $CO_2Me$ | $CO_2Me$ | $OCF_3$ | 4-Cl-Ph | $CO_2Me$ |
| $CF_3$ | Ph | H | $CF_3$ | 4-F-Ph | H |
| $CF_3$ | Ph | Me | $CF_3$ | 4-F-Ph | Me |
| $CF_3$ | Ph | Et | $CF_3$ | 4-F-Ph | Et |
| $CF_3$ | Ph | COMe | $CF_3$ | 4-F-Ph | COMe |
| $CF_3$ | Ph | $CO_2Me$ | $CF_3$ | 4-F-Ph | $CO_2Me$ |
| $OCF_3$ | Ph | H | $OCF_3$ | 4-F-Ph | H |
| $OCF_3$ | Ph | Me | $OCF_3$ | 4-F-Ph | Me |
| $OCF_3$ | Ph | Et | $OCF_3$ | 4-F-Ph | Et |
| $OCF_3$ | Ph | COMe | $OCF_3$ | 4-F-Ph | COMe |
| $OCF_3$ | Ph | $CO_2Me$ | $OCF_3$ | 4-F-Ph | $CO_2Me$ |
| $CF_3$ | $CO_2Me$ | COEt | $CF_3$ | 4-Cl-Ph | COEt |
| $CF_3$ | $CO_2Me$ | $CO_2Et$ | $CF_3$ | 4-Cl-Ph | $CO_2Et$ |
| $CF_3$ | $CO_2Me$ | CO(n-Pr) | $CF_3$ | 4-Cl-Ph | CO(n-Pr) |
| $CF_3$ | $CO_2Me$ | CO(i-Pr) | $CF_3$ | 4-Cl-Ph | CO(i-Pr) |
| $CF_3$ | $CO_2Me$ | CO(t-Bu) | $CF_3$ | 4-Cl-Ph | CO(t-Bu) |
| $CF_3$ | $CO_2Me$ | $CO_2(t-Bu)$ | $CF_3$ | 4-Cl-Ph | $CO_2(t-Bu)$ |
| $OCF_3$ | $CO_2Me$ | COEt | $OCF_3$ | 4-Cl-Ph | COEt |
| $OCF_3$ | $CO_2Me$ | $CO_2Et$ | $OCF_3$ | 4-Cl-Ph | $CO_2Et$ |
| $OCF_3$ | $CO_2Me$ | CO(n-Pr) | $OCF_3$ | 4-Cl-Ph | CO(n-Pr) |
| $OCF_3$ | $CO_2Me$ | CO(i-Pr) | $OCF_3$ | 4-Cl-Ph | CO(i-Pr) |
| $OCF_3$ | $CO_2Me$ | CO(t-Bu) | $OCF_3$ | 4-Cl-Ph | CO(t-Bu) |
| $OCF_3$ | $CO_2Me$ | $CO_2(t-Bu)$ | $OCF_3$ | 4-Cl-Ph | $CO_2(t-Bu)$ |
| $CF_3$ | Ph | COEt | $CF_3$ | 4-F-Ph | COEt |
| $CF_3$ | Ph | $CO_2Et$ | $CF_3$ | 4-F-Ph | $CO_2Et$ |
| $CF_3$ | Ph | CO(n-Pr) | $CF_3$ | 4-F-Ph | CO(n-Pr) |
| $CF_3$ | Ph | CO(i-Pr) | $CF_3$ | 4-F-Ph | CO(i-Pr) |
| $CF_3$ | Ph | CO(t-Bu) | $CF_3$ | 4-F-Ph | CO(t-Bu) |
| $CF_3$ | Ph | $CO_2(t-Bu)$ | $CF_3$ | 4-F-Ph | $CO_2(t-Bu)$ |
| $OCF_3$ | Ph | COEt | $OCF_3$ | 4-F-Ph | COEt |
| $OCF_3$ | Ph | $CO_2Et$ | $OCF_3$ | 4-F-Ph | $CO_2Et$ |
| $OCF_3$ | Ph | CO(n-Pr) | $OCF_3$ | 4-F-Ph | CO(n-Pr) |
| $OCF_3$ | Ph | CO(i-Pr) | $OCF_3$ | 4-F-Ph | CO(i-Pr) |
| $OCF_3$ | Ph | CO(t-Bu) | $OCF_3$ | 4-F-Ph | CO(t-Bu) |
| $OCF_3$ | Ph | $CO_2(t-Bu)$ | $OCF_3$ | 4-F-Ph | $CO_2(t-Bu)$ |
| $CF_3$ | $CO_2Me$ | n-Pr | $CF_3$ | 4-Cl-Ph | n-Pr |
| $CF_3$ | $CO_2Me$ | i-Bu | $CF_3$ | 4-Cl-Ph | i-Bu |
| $OCF_3$ | $CO_2Me$ | n-Pr | $OCF_3$ | 4-Cl-Ph | n-Pr |
| $OCF_3$ | $CO_2Me$ | i-Bu | $OCF_3$ | 4-Cl-Ph | i-Bu |
| $OCF_3$ | Ph | n-Pr | $CF_3$ | 4-F-Ph | n-Pr |
| $OCF_3$ | Ph | i-Bu | $CF_3$ | 4-F-Ph | i-Bu |
| $CF_3$ | Ph | n-Pr | $OCF_3$ | 4-F-Ph | n-Pr |
| $CF_3$ | Ph | i-Bu | $OCF_3$ | 4-F-Ph | i-Bu |

TABLE 53

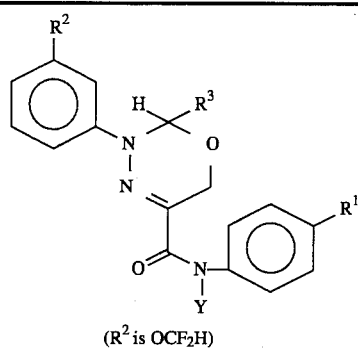

($R^2$ is $OCF_2H$)

| $R^1$ | $R^3$ | Y | $R^1$ | $R^3$ | Y |
|---|---|---|---|---|---|
| $CF_3$ | $CO_2Me$ | H | $CF_3$ | 4-Cl—Ph | H |
| $CF_3$ | $CO_2Me$ | Me | $CF_3$ | 4-Cl—Ph | Me |
| $CF_3$ | $CO_2Me$ | Et | $CF_3$ | 4-Cl—Ph | Et |
| $CF_3$ | $CO_2Me$ | COMe | $CF_3$ | 4-Cl—Ph | COMe |
| $CF_3$ | $CO_2Me$ | $CO_2Me$ | $CF_3$ | 4-Cl—Ph | $CO_2Me$ |
| $OCF_3$ | $CO_2Me$ | H | $OCF_3$ | 4-Cl—Ph | H |
| $OCF_3$ | $CO_2Me$ | Me | $OCF_3$ | 4-Cl—Ph | Me |
| $OCF_3$ | $CO_2Me$ | Et | $OCF_3$ | 4-Cl—Ph | Et |
| $OCF_3$ | $CO_2Me$ | COMe | $OCF_3$ | 4-Cl—Ph | COMe |
| $OCF_3$ | $CO_2Me$ | $CO_2Me$ | $OCF_3$ | 4-Cl—Ph | $CO_2Me$ |
| $CF_3$ | Ph | H | $CF_3$ | 4-F—Ph | H |
| $CF_3$ | Ph | Me | $Clr3$ | 4-F—Ph | Me |
| $CF_3$ | Ph | Et | $CF_3$ | 4-F—Ph | Et |
| $CF_3$ | Ph | COMe | $CF_3$ | 4-F—Ph | COMe |
| $CF_3$ | Ph | $CO_2Me$ | $CF_3$ | 4-F—Ph | $CO_2Me$ |
| $OCF_3$ | Ph | H | $OCF_3$ | 4-F—Ph | H |
| $OCF_3$ | Ph | Me | $OCF_3$ | 4-F—Ph | Me |
| $OCF_3$ | Ph | Et | $OCF_3$ | 4-F—Ph | Et |
| $OCF_3$ | Ph | COMe | $OCF_3$ | 4-F—Ph | COMe |
| $OCF_3$ | Ph | $CO_2Me$ | $OCF_3$ | 4-F—Ph | $CO_2Me$ |
| $CF_3$ | $CO_2Me$ | COEt | $CF_3$ | 4-Cl—Ph | COEt |
| $CF_3$ | $CO_2Me$ | $CO_2Et$ | $CF_3$ | 4-Cl—Ph | $CO_2Et$ |
| $CF_3$ | $CO_2Me$ | CO(n-Pr) | $CF_3$ | 4-Cl—Ph | CO(n-Pr) |
| $CF_3$ | $CO_2Me$ | CO(i-Pr) | $CF_3$ | 4-Cl—Ph | CO(i-Pr) |
| $CF_3$ | $CO_2Me$ | CO(t-Bu) | $CF_3$ | 4-Cl—Ph | CO(t-Bu) |
| $CF_3$ | $CO_2Me$ | $CO_2(t-Bu)$ | $CF_3$ | 4-Cl—Ph | $CO_2(t-Bu)$ |
| $OCF_3$ | $CO_2Me$ | COEt | $OCF_3$ | 4-Cl—Ph | COEt |
| $OCF_3$ | $CO_2Me$ | $CO_2Et$ | $OCF_3$ | 4-Cl—Ph | $CO_2Et$ |
| $OCF_3$ | $CO_2Me$ | CO(n-Pr) | $OCF_3$ | 4-Cl—Ph | CO(n-Pr) |
| $OCF_3$ | $CO_2Me$ | CO(i-Pr) | $OCF_3$ | 4-Cl—Ph | CO(i-Pr) |
| $OCF_3$ | $CO_2Me$ | CO(t-Bu) | $OCF_3$ | 4-Cl—Ph | CO(t-Bu) |
| $OCF_3$ | $CO_2Me$ | $CO_2(t-Bu)$ | $OCF_3$ | 4-Cl—Ph | $CO_2(t-Bu)$ |
| $CF_3$ | Ph | COEt | $CF_3$ | 4-F—Ph | COEt |
| $CF_3$ | Ph | $CO_2Et$ | $CF_3$ | 4-F—Ph | $CO_2Et$ |
| $CF_3$ | Ph | CO(n-Pr) | $CF_3$ | 4-F—Ph | CO(n-Pr) |
| $CF_3$ | Ph | CO(i-Pr) | $CF_3$ | 4-F—Ph | CO(i-Pr) |
| $CF_3$ | Ph | CO(t-Bu) | $CF_3$ | 4-F—Ph | CO(t-Bu) |
| $CF_3$ | Ph | $CO_2(t-Bu)$ | $CF_3$ | 4-F—Ph | $CO_2(t-Bu)$ |
| $OCF_3$ | Ph | COEt | $OCF_3$ | 4-F—Ph | COEt |
| $OCF_3$ | Ph | $CO_2Et$ | $OCF_3$ | 4-F—Ph | $CO_2Et$ |
| $OCF_3$ | Ph | CO(n-Pr) | $OCF_3$ | 4-F—Ph | CO(n-Pr) |
| $OCF_3$ | Ph | CO(i-Pr) | $OCF_3$ | 4-F—Ph | CO(i-Pr) |
| $OCF_3$ | Ph | CO(t-Bu) | $OCF_3$ | 4-F—Ph | CO(t-Bu) |
| $OCF_3$ | Ph | $CO_2(t-Bu)$ | $OCF_3$ | 4-F—Ph | $CO_2(t-Bu)$ |
| $CF_3$ | $CO_2Me$ | n-Pr | $CF_3$ | 4-Cl—Ph | n-Pr |
| $CF_3$ | $CO_2Me$ | i-Bu | $CF_3$ | 4-Cl—Ph | i-Bu |
| $OCF_3$ | $CO_2Me$ | n-Pr | $OCF_3$ | 4-Cl—Ph | n-Pr |
| $OCF_3$ | $CO_2Me$ | i-Bu | $OCF_3$ | 4-Cl—Ph | i-Bu |
| $OCF_3$ | Ph | n-Pr | $CF_3$ | 4-F—Ph | n-Pr |
| $OCF_3$ | Ph | i-Bu | $CF_3$ | 4-F—Ph | i-Bu |
| $CF_3$ | Ph | n-Pr | $OCF_3$ | 4-F—Ph | n-Pr |
| $CF_3$ | Ph | i-Bu | $OCF_3$ | 4-F—Ph | i-Bu |

TABLE 54

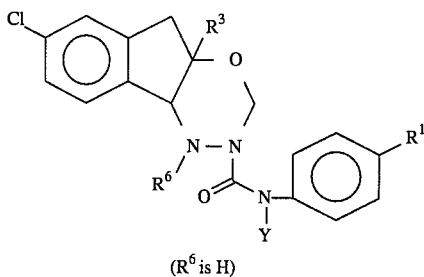

(R⁶ is H)

| R¹ | R³ | Y | R¹ | R³ | Y |
|---|---|---|---|---|---|
| CF₃ | 4-F—Ph | H | CF₃ | i-Pr | H |
| CF₃ | 4-F—Ph | Me | CF₃ | i-Pr | Me |
| CF₃ | 4-F—Ph | Et | CF₃ | i-Pr | Et |
| CF₃ | 4-F—Ph | COMe | CF₃ | i-Pr | COMe |
| CF₃ | 4-F—Ph | CO₂Me | CF₃ | i-Pr | CO₂Me |
| OCF₃ | 4-F—Ph | H | OCF₃ | i-Pr | H |
| OCF₃ | 4-F—Ph | Me | OCF₃ | i-Pr | Me |
| OCF₃ | 4-F—Ph | Et | OCF₃ | i-Pr | Et |
| OCF₃ | 4-F—Ph | COMe | OCF₃ | i-Pr | COMe |
| OCF₃ | 4-F—Ph | CO₂Me | OCF₃ | i-Pr | CO₂Me |
| CF₃ | n-Pr | H | CF₃ | CO₂Me | H |
| CF₃ | n-Pr | Me | CF₃ | CO₂Me | Me |
| CF₃ | n-Pr | Et | CF₃ | CO₂Me | Et |
| CF₃ | n-Pr | COMe | CF₃ | CO₂Me | COMe |
| CF₃ | n-Pr | CO₂Me | CF₃ | CO₂Me | CO₂Me |
| OCF₃ | n-Pr | H | OCF₃ | CO₂Me | H |
| OCF | n-Pr | Me | OCF₃ | CO₂Me | Me |
| OCF₃ | n-Pr | Et | OCF₃ | CO₂Me | Et |
| OCF₃ | n-Pr | COMe | OCF₃ | CO₂Me | COMe |
| OCF₃ | n-Pr | CO₂Me | OCF₃ | CO₂Me | CO₂Me |

TABLE 55

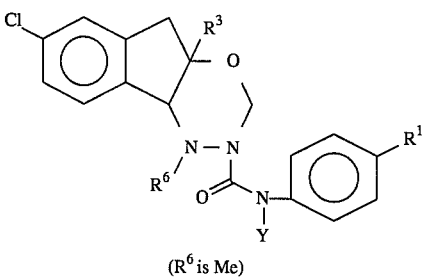

(R⁶ is Me)

| R¹ | R³ | Y | R¹ | R³ | Y |
|---|---|---|---|---|---|
| CF₃ | 4-F—Ph | H | CF₃ | i-Pr | H |
| CF₃ | 4-F—Ph | Me | CF₃ | i-Pr | Me |
| CF₃ | 4-F—Ph | Et | CF₃ | i-Pr | Et |
| CF₃ | 4-F—Ph | COMe | CF₃ | i-Pr | COMe |
| CF₃ | 4-F—Ph | CO₂Me | CF₃ | i-Pr | CO₂Me |
| OCF₃ | 4-F—Ph | H | OCF₃ | i-Pr | H |
| OCF₃ | 4-F—Ph | Me | OCF₃ | i-Pr | Me |
| OCF₃ | 4-F—Ph | Et | OCF₃ | i-Pr | Et |
| OCF₃ | 4-F—Ph | COMe | OCF₃ | i-Pr | COMe |
| OCF₃ | 4-F—Ph | CO₂Me | OCF₃ | i-Pr | CO₂Me |
| CF₃ | n-Pr | H | CF₃ | CO₂Me | H |
| CF₃ | n-Pr | Me | CF₃ | CO₂Me | Me |
| CF₃ | n-Pr | Et | CF₃ | CO₂Me | Et |
| CF₃ | n-Pr | COMe | CF₃ | CO₂Me | COMe |
| CF₃ | n-Pr | CO₂Me | CF₃ | CO₂Me | CO₂Me |
| OCF₃ | n-Pr | H | OCF₃ | CO₂Me | H |
| OCF₃ | n-Pr | Me | OCF₃ | CO₂Me | Me |
| OCF₃ | n-Pr | Et | OCF₃ | CO₂Me | Et |
| OCF₃ | n-Pr | COMe | OCF₃ | CO₂Me | COMe |
| OCF₃ | n-Pr | CO₂Me | OCF₃ | CO₂Me | CO₂Me |

TABLE 56

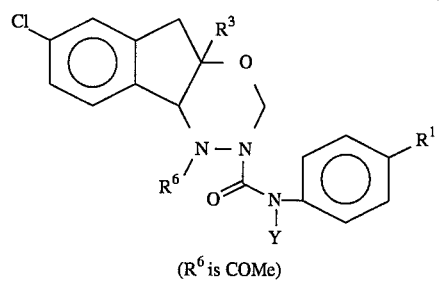

(R⁶ is COMe)

| R¹ | R³ | Y | R¹ | R³ | Y |
|---|---|---|---|---|---|
| CF₃ | 4-F—Ph | H | CF₃ | i-Pr | H |
| CF₃ | 4-F—Ph | Me | CF₃ | i-Pr | Me |
| CF₃ | 4-F—Ph | Et | CF₃ | i-Pr | Et |
| CF₃ | 4-F—Ph | COMe | CF₃ | i-Pr | COMe |
| CF₃ | 4-F—Ph | CO₂Me | CF₃ | i-Pr | CO₂Me |
| OCF₃ | 4-F—Ph | H | OCF₃ | i-Pr | H |
| OCF₃ | 4-F—Ph | Me | OCF₃ | i-Pr | Me |
| OCF₃ | 4-F—Ph | Et | OCF₃ | i-Pr | Et |
| OCF₃ | 4-F—Ph | COMe | OCF₃ | i-Pr | COMe |
| OCF₃ | 4-F—Ph | CO₂Me | OCF₃ | i-Pr | CO₂Me |
| CF₃ | n-Pr | H | CF₃ | CO₂Me | H |
| CF₃ | n-Pr | Me | CF₃ | CO₂Me | Me |
| CF₃ | n-Pr | Et | CF₃ | CO₂Me | Et |
| CF₃ | n-Pr | COMe | CF₃ | CO₂Me | COMe |
| CF₃ | n-Pr | CO₂Me | CF₃ | CO₂Me | CO₂Me |
| OCF₃ | n-Pr | H | OCF₃ | CO₂Me | H |
| OCF₃ | n-Pr | Me | OCF₃ | CO₂Me | Me |
| OCF₃ | n-Pr | Et | OCF₃ | CO₂Me | Et |
| OCF₃ | n-Pr | COMe | OCF₃ | CO₂Me | COMe |
| OCF₃ | n-Pr | CO₂Me | OCF₃ | CO₂Me | CO₂Me |

TABLE 57

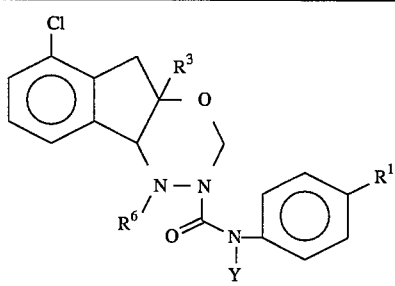

(R⁶ is H)

| R¹ | R³ | Y | R¹ | R³ | Y |
|---|---|---|---|---|---|
| CF₃ | 4-F—Ph | H | CF₃ | i-Pr | H |
| CF₃ | 4-F—Ph | Me | CF₃ | i-Pr | Me |
| CF₃ | 4-F—Ph | Et | CF₃ | i-Pr | Et |
| CF₃ | 4-F—Ph | COMe | CF₃ | i-Pr | COMe |
| CF₃ | 4-F—Ph | CO₂Me | CF₃ | i-Pr | CO₂Me |
| OCF₃ | 4-F—Ph | H | OCF₃ | i-Pr | H |
| OCF₃ | 4-F—Ph | Me | OCF₃ | i-Pr | Me |
| OCF₃ | 4-F—Ph | Et | OCF₃ | i-Pr | Et |
| OCF₃ | 4-F—Ph | COMe | OCF₃ | i-Pr | COMe |
| OCF₃ | 4-F—Ph | CO₂Me | OCF₃ | i-Pr | CO₂Me |
| CF₃ | n-Pr | H | CF₃ | CO₂Me | H |
| CF₃ | n-Pr | Me | CF₃ | CO₂Me | Me |
| CF₃ | n-Pr | Et | CF₃ | CO₂Me | Et |
| CF₃ | n-Pr | COMe | CF₃ | CO₂Me | COMe |
| CF₃ | n-Pr | CO₂Me | CF₃ | CO₂Me | CO₂Me |
| OCF₃ | n-Pr | H | OCF₃ | CO₂Me | H |
| OCF₃ | n-Pr | Me | OCF₃ | CO₂Me | Me |
| OCF₃ | n-Pr | Et | OCF₃ | CO₂Me | Et |
| OCF₃ | n-Pr | COMe | OCF₃ | CO₂Me | COMe |
| OCF₃ | n-Pr | CO₂Me | OCF₃ | CO₂Me | CO₂Me |

TABLE 58

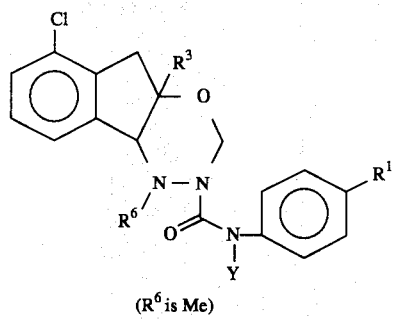

($R^6$ is Me)

| $R^1$ | $R^3$ | Y | $R^1$ | $R^3$ | Y |
|---|---|---|---|---|---|
| $CF_3$ | 4-F—Ph | H | $CF_3$ | i-Pr | H |
| $CF_3$ | 4-F—Ph | Me | $CF_3$ | i-Pr | Me |
| $CF_3$ | 4-F—Ph | Et | $CF_3$ | i-Pr | Et |
| $CF_3$ | 4-F—Ph | COMe | $CF_3$ | i-Pr | COMe |
| $CF_3$ | 4-F—Ph | $CO_2Me$ | $CF_3$ | i-Pr | $CO_2Me$ |
| $OCF_3$ | 4-F—Ph | H | $OCF_3$ | i-Pr | H |
| $OCF_3$ | 4-F—Ph | Me | $OCF_3$ | i-Pr | Me |
| $OCF_3$ | 4-F—Ph | Et | $OCF_3$ | i-Pr | Et |
| $OCF_3$ | 4-F—Ph | COMe | $OCF_3$ | i-Pr | COMe |
| $OCF_3$ | 4-F—Ph | $CO_2Me$ | $OCF_3$ | i-Pr | $CO_2Me$ |
| $CF_3$ | n-Pr | H | $CF_3$ | $CO_2Me$ | H |
| $CF_3$ | n-Pr | Me | $CF_3$ | $CO_2Me$ | Me |
| $CF_3$ | n-Pr | Et | $CF_3$ | $CO_2Me$ | Et |
| $CF_3$ | n-Pr | COMe | $CF_3$ | $CO_2Me$ | COMe |
| $CF_3$ | n-Pr | $CO_2Me$ | $CF_3$ | $CO_2Me$ | $CO_2Me$ |
| $OCF_3$ | n-Pr | H | $OCF_3$ | $CO_2Me$ | H |
| $OCF_3$ | n-Pr | Me | $OCF_3$ | $CO_2Me$ | Me |
| $OCF_3$ | n-Pr | Et | $OCF_3$ | $CO_2Me$ | Et |
| $OCF_3$ | n-Pr | COMe | $OCF_3$ | $CO_2Me$ | COMe |
| $OCF_3$ | n-Pr | $CO_2Me$ | $OCF_3$ | $CO_2Me$ | $CO_2Me$ |

TABLE 59

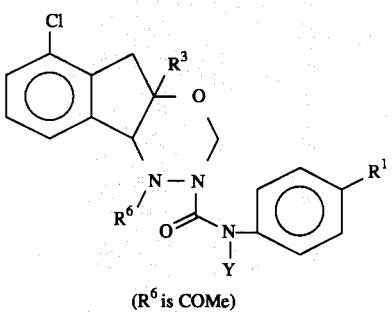

($R^6$ is COMe)

| $R^1$ | $R^3$ | Y | $R^1$ | $R^3$ | Y |
|---|---|---|---|---|---|
| $CF_3$ | 4-F—Ph | H | $CF_3$ | i-Pr | H |
| $CF_3$ | 4-F—Ph | Me | $CF_3$ | i-Pr | Me |
| $CF_3$ | 4-F—Ph | Et | $CF_3$ | i-Pr | Et |
| $CF_3$ | 4-F—Ph | COMe | $CF_3$ | i-Pr | COMe |
| $CF_3$ | 4-F—Ph | $CO_2Me$ | $CF_3$ | i-Pr | $CO_2Me$ |
| $OCF_3$ | 4-F—Ph | H | $OCF_3$ | i-Pr | H |
| $OCF_3$ | 4-F—Ph | Me | $OCF_3$ | i-Pr | Me |
| $OCF_3$ | 4-F—Ph | Et | $OCF_3$ | i-Pr | Et |
| $OCF_3$ | 4-F—Ph | COMe | $OCF_3$ | i-pr | COMe |
| $OCF_3$ | 4-F—Ph | $CO_2Me$ | $OCF_3$ | i-Pr | $CO_2Me$ |
| $CF_3$ | n-Pr | H | $CF_3$ | $CO_2Me$ | H |
| $CF_3$ | n-Pr | Me | $CF_3$ | $CO_2Me$ | Me |
| $CF_3$ | n-Pr | Et | $CF_3$ | $CO_2Me$ | Et |
| $CF_3$ | n-Pr | COMe | $CF_3$ | $CO_2Me$ | COMe |
| $CF_3$ | n-Pr | $CO_2Me$ | $CF_3$ | $CO_2Me$ | $CO_2Me$ |
| $OCF_3$ | n-Pr | H | $OCF_3$ | $CO_2Me$ | H |
| $OCF_3$ | n-Pr | Me | $OCF_3$ | $CO_2Me$ | Me |
| $OCF_3$ | n-Pr | Et | $OCF_3$ | $CO_2Me$ | Et |
| $OCF_3$ | n-Pr | COMe | $OCF_3$ | $CO_2Me$ | COMe |

TABLE 59-continued

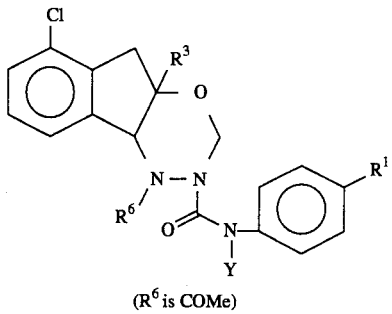

($R^6$ is COMe)

| $R^1$ | $R^3$ | Y | $R^1$ | $R^3$ | Y |
|---|---|---|---|---|---|
| $OCF_3$ | n-Pr | $CO_2Me$ | $OCF_3$ | $CO_2Me$ | $CO_2Me$ |

TABLE 60

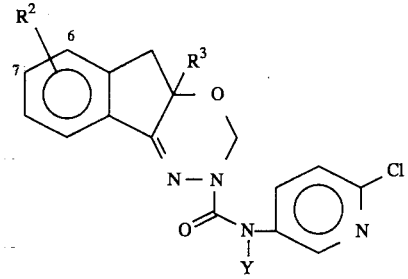

| $R^2$ | $R^3$ | Y | $R^2$ | $R^3$ | Y |
|---|---|---|---|---|---|
| 6-Cl | $CO_2Me$ | H | 7-F | $CO_2Me$ | H |
| 6-Cl | $CO_2Me$ | Me | 7-F | $CO_2Me$ | Me |
| 6-Cl | $CO_2Me$ | Et | 7-F | $CO_2Me$ | Et |
| 6-Cl | $CO_2Me$ | COMe | 7-F | $CO_2Me$ | COMe |
| 6-Cl | $CO_2Me$ | $CO_2Me$ | 7-F | $CO_2Me$ | $CO_2Me$ |
| 6-Cl | $CO_2Me$ | COEt | 7-F | $CO_2Me$ | COEt |
| 6-Cl | $CO_2Me$ | $CO_2Et$ | 7-F | $CO_2Me$ | $CO_2Et$ |
| 7-Cl | $CO_2Me$ | H | 6-Cl | 4-Cl—Ph | H |
| 7-Cl | $CO_2Me$ | Me | 6-Cl | 4-Cl—Ph | Me |
| 7-Cl | $CO_2Me$ | Et | 6-Cl | 4-Cl—Ph | Et |
| 7-Cl | $CO_2Me$ | COMe | 6-Cl | 4-Cl—Ph | COMe |
| 7-Cl | $CO_2Me$ | $CO_2Me$ | 6-Cl | 4-Cl—Ph | $CO_2Me$ |
| 7-Cl | $CO_2Me$ | COEt | 6-Cl | 4-Cl—Ph | COEt |
| 7-Cl | $CO_2Me$ | $CO_2Et$ | 6-Cl | 4-Cl—Ph | $CO_2Et$ |
| 6-F | $CO_2Me$ | H | 7-Cl | 4-Cl—Ph | H |
| 6-F | $CO_2Me$ | Me | 7-Cl | 4-Cl—Ph | Me |
| 6-F | $CO_2Me$ | Et | 7-Cl | 4-Cl—Ph | Et |
| 6-F | $CO_2Me$ | COMe | 7-Cl | 4-Cl—Ph | COMe |
| 6-F | $CO_2Me$ | $CO_2Me$ | 7-Cl | 4-Cl—Ph | $CO_2Me$ |
| 6-F | $CO_2Me$ | COEt | 7-Cl | 4-Cl—Ph | COEt |
| 6-F | $CO_2Me$ | $CO_2Et$ | 7-Cl | 4-Cl—Ph | $CO_2Et$ |
| 6-F | 4-Cl—Ph | H | 6-F | 4-F—Ph | H |
| 6-F | 4-Cl—Ph | Me | 6-F | 4-F—Ph | Me |
| 6-F | 4-Cl—Ph | Et | 6-F | 4-F—Ph | Et |
| 6-F | 4-Cl—Ph | COMe | 6-F | 4-F—Ph | COMe |
| 6-F | 4-Cl—Ph | $CO_2Me$ | 6-F | 4-F—Ph | $CO_2Me$ |
| 6-F | 4-Cl—Ph | COEt | 6-F | 4-F—Ph | COEt |
| 6-F | 4-Cl—Ph | $CO_2Et$ | 6-F | 4-F—Ph | $CO_2Et$ |
| 7-F | 4-Cl—Ph | H | 7-F | 4-F—Ph | H |
| 7-F | 4-Cl—Ph | Me | 7-F | 4-F—Ph | Me |
| 7-F | 4-Cl—Ph | Et | 7-F | 4-F—Ph | Et |
| 7-F | 4-Cl—Ph | COMe | 7-F | 4-F—Ph | COMe |
| 7-F | 4-Cl—Ph | $CO_2Me$ | 7-F | 4-F—Ph | $CO_2Me$ |
| 7-F | 4-Cl—Ph | COEt | 7-T | 4-F—Ph | COEt |
| 7-F | 4-Cl—Ph | $CO_2Et$ | 7-F | 4-F—Ph | $CO_2Et$ |
| 6-Cl | 4-F—Ph | H | 7-Cl | 4-F—Ph | H |
| 6-Cl | 4-F—Ph | Me | 7-Cl | 4-F—Ph | Me |
| 6-Cl | 4-F—Ph | Et | 7-Cl | 4-F—Ph | Et |
| 6-Cl | 4-F—Ph | COMe | 7-Cl | 4-F—Ph | COMe |
| 6-Cl | 4-F—Ph | $CO_2Me$ | 7-Cl | 4-F—Ph | $CO_2Me$ |
| 6-Cl | 4-F—Ph | COEt | 7-Cl | 4-F—Ph | COEt |

TABLE 60-continued

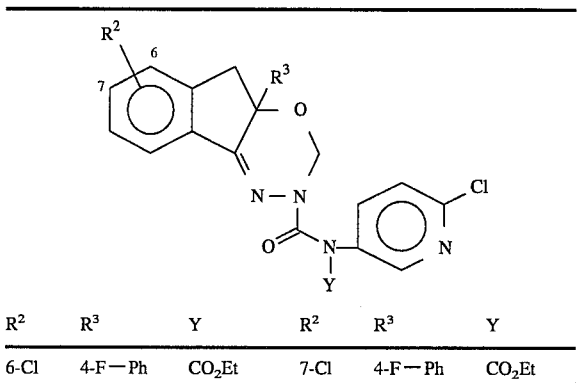

| $R^2$ | $R^3$ | Y | $R^2$ | $R^3$ | Y |
|---|---|---|---|---|---|
| 6-Cl | 4-F—Ph | $CO_2Et$ | 7-Cl | 4-F—Ph | $CO_2Et$ |

TABLE 61

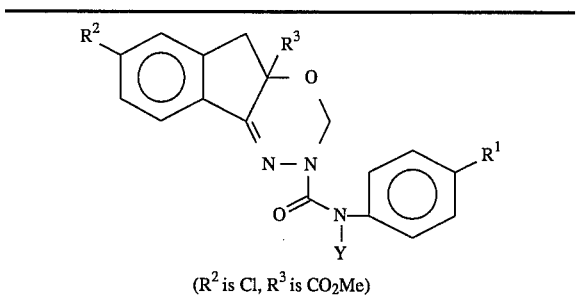

($R^2$ is Cl, $R^3$ is $CO_2Me$)

| $R^1$ | Y | $R^1$ | Y |
|---|---|---|---|
| $CF_3$ | $CH_2SiMe_3$ | $CF_3$ | CO(n-Bu) |
| $CF_3$ | $CH_2CF_3$ | $CF_3$ | $CO_2$(n-Bu) |
| $CF_3$ | $CH_2CCH$ | $CF_3$ | CO(i-Bu) |
| $CF_3$ | $CH_2CO_2Me$ | $CF_3$ | $CO_2$(i-Bu) |
| $CF_3$ | $CH_2CN$ | $CF_3$ | CO(4-Cl—Ph) |
| $CF_3$ | i-Pr | $CF_3$ | $CO_2Ph$ |
| $CF_3$ | Ph | $CF_3$ | $CH_2CO_2Et$ |
| $CF_3$ | 4-Cl—Ph | $CF_3$ | $CH_2CH_2CN$ |
| $CF_3$ | 4-OMe—Ph | $CF_3$ | $CH_2CH_2CO_2Me$ |
| $CF_3$ | 4-F—Ph | $CF_3$ | $CH_2CH_2Cl$ |
| $CF_3$ | t-Bu | $OCF_3$ | $CH_2SiMe_3$ |
| $CF_3$ | $CH_2SOCH_3$ | $OCF_3$ | $CH_2CF_3$ |
| $CF_3$ | $CH_2SO_2CH_3$ | $OCF_3$ | $CH_2CCH$ |
| $CF_3$ | $SN$(i-Pr)$CO_2Et$ | $OCF_3$ | $CH_2CO_2Me$ |
| $CF_3$ | $SN$(Me)$CO_2Et$ | $OCF_3$ | $CH_2CN$ |
| $CF_3$ | $SN$(n-Bu)$_2$ | $OCF_3$ | i-Pr |
| $CF_3$ | $SN$(Me)$CO_2$(n-Bu) | $OCF_3$ | Ph |
| $CF_3$ | $SN$(i-Pr)$CO_2$(n-Bu) | $OCF_3$ | 4-Cl—Ph |
| $CF_3$ | $SN$(i-Pr)$CO_2$(n-Pr) | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN$(i-Pr)$CO_2Et$ | Br | 4-Cl—Ph |
| $OCF_3$ | $SN$(Me)$CO_2Et$ | Br | 4-OMe—Ph |
| $OCF_3$ | $SN$(n-Bu)$_2$ | Br | 4-F—Ph |
| $OCF_3$ | $SN$(Me)$CO_2$(n-Bu) | Br | t-Bu |
| $OCF_3$ | $SN$(i-Pr)$CO_2$(n-Bu) | Br | $CH_2SOCH_3$ |
| $OCF_3$ | $SN$(i-Pr)$CO_2$(n-Pr) | Br | $CH_2SO_2CH_3$ |
| $OCF_3$ | CO(n-Bu) | Br | $SN$(i-Pr)$CO_2Et$ |
| $OCF_3$ | $CO_2$(n-Bu) | Br | $SN$(Me)$CO_2Et$ |
| $OCF_3$ | CO(i-Bu) | Br | $SN$(n-Bu)$_2$ |
| $OCF_3$ | $CO_2$(i-Bu) | Br | $SN$(Me)$CO_2$(n-Bu) |
| $OCF_3$ | CO(4-Cl—Ph) | Br | $SN$(i-Pr)$CO_2$(n-Bu) |
| $OCF_3$ | $CO_2Ph$ | Br | $SN$(i-Pr)$CO_2$(n-Pr) |
| $OCF_3$ | $CH_2CO_2Et$ | Br | CO(n-Bu) |
| $OCF_3$ | $CH_2CH_2CN$ | Br | $CO_2$(n-Bu) |
| $OCF_3$ | $CH_2CH_2CO_2Me$ | Br | CO(i-Bu) |
| $OCF_3$ | $CH_2CH_2Cl$ | Br | $CO_2$(i-Bu) |
| $OCF_3$ | $CH_2Ph$ | Br | CO(4-Cl—Ph) |

TABLE 61-continued

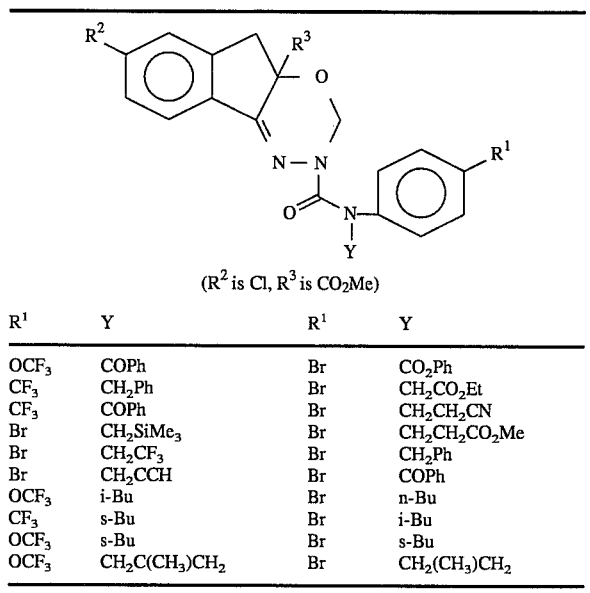

($R^2$ is Cl, $R^3$ is $CO_2Me$)

| $R^1$ | Y | $R^1$ | Y |
|---|---|---|---|
| $OCF_3$ | COPh | Br | $CO_2Ph$ |
| $CF_3$ | $CH_2Ph$ | Br | $CH_2CO_2Et$ |
| $CF_3$ | COPh | Br | $CH_2CH_2CN$ |
| Br | $CH_2SiMe_3$ | Br | $CH_2CH_2CO_2Me$ |
| Br | $CH_2CF_3$ | Br | $CH_2Ph$ |
| Br | $CH_2CCH$ | Br | COPh |
| $OCF_3$ | i-Bu | Br | n-Bu |
| $CF_3$ | s-Bu | Br | i-Bu |
| $OCF_3$ | s-Bu | Br | s-Bu |
| $OCF_3$ | $CH_2C(CH_3)CH_2$ | Br | $CH_2(CH_3)CH_2$ |

TABLE 62

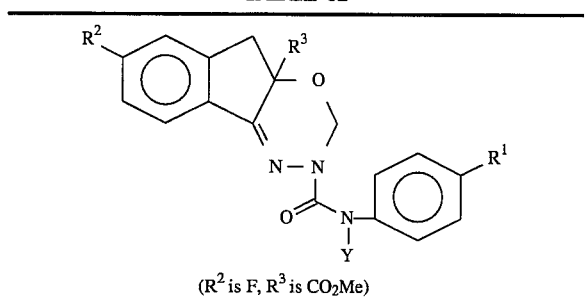

($R^2$ is F, $R^3$ is $CO_2Me$)

| $R^1$ | Y | $R^1$ | Y |
|---|---|---|---|
| $CF_3$ | $CH_2SiMe_3$ | $CF_3$ | CO(n-Bu) |
| $CF_3$ | $CH_2CF_3$ | $CF_3$ | $CO_2$(n-Bu) |
| $CF_3$ | $CH_2CCH$ | $CF_3$ | CO(i-Bu) |
| $CF_3$ | $CH_2CO_2Me$ | $CF_3$ | $CO_2$(i-Bu) |
| $CF_3$ | $CH_2CN$ | $CF_3$ | CO(4-Cl—Ph) |
| $CF_3$ | i-Pr | $CF_3$ | $CO_2Ph$ |
| $CF_3$ | Ph | $CF_3$ | $CH_2CO_2Et$ |
| $CF_3$ | 4-Cl—Ph | $CF_3$ | $CH_2CH_2CN$ |
| $CF_3$ | 4-OMe—Ph | $CF_3$ | $CH_2CH_2CO_2Me$ |
| $CF_3$ | 4-F—Ph | $CF_3$ | $CH_2CH_2Cl$ |
| $CF_3$ | t-Bu | $OCF_3$ | $CH_2SiMe_3$ |
| $CF_3$ | $CH_2SOCH_3$ | $OCF_3$ | $CH_2CF_3$ |
| $CF_3$ | $CH_2SO_2CH_3$ | $OCF_3$ | $CH_2CCH$ |
| $CF_3$ | $SN$(i-Pr) $CO_2Et$ | $OCF_3$ | $CH_2CO_2Me$ |
| $CF_3$ | $SN$(Me)$CO_2Et$ | $OCF_3$ | $CH_2CN$ |
| $CF_3$ | $SN$(n-Bu)$_2$ | $OCF_3$ | i-Pr |
| $CF_3$ | $SN$(Me)$CO_2$(n-Bu) | $OCF_3$ | Ph |
| $CF_3$ | $SN$(i-Pr)$CO_2$(n-Bu) | $OCF_3$ | 4-Cl—Ph |
| CFS | $SN$(i-Pr)$CO_2$(n-Pr) | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN$(i-Pr)$CO_2Et$ | Br | 4-Cl—Ph |
| $OCF_3$ | $SN$(Me)$CO_2Et$ | Br | 4-OMe—Ph |
| $OCF_3$ | $SN$(n-Bu)$_2$ | Br | 4-F—Ph |
| $OCF_3$ | $SN$(Me)$CO_2$(n-Bu) | Br | t-Bu |
| $OCF_3$ | $SN$(i-Pr)$CO_2$(n-Bu) | Br | $CH_2SOCH_3$ |
| $OCF_3$ | $SN$(i-Pr)$CO_2$(n-Pr) | Br | $CH_2SO_2CH_3$ |
| $OCF_3$ | CO(n-Bu) | Br | $SN$(i-Pr)$CO_2Et$ |
| $OCF_3$ | $CO_2$(n-Bu) | Br | $SN$(Me)$CO_2Et$ |

TABLE 62-continued

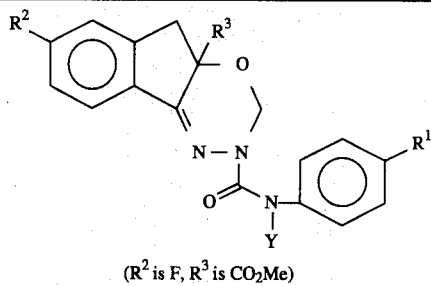

($R^2$ is F, $R^3$ is $CO_2Me$)

| $R^1$ | Y | $R^1$ | Y |
|---|---|---|---|
| OCF₃ | CO(i-Bu) | Br | SN(n-Bu)₂ |
| OCF₃ | CO₂(i-Bu) | Br | SN(Me)CO₂(n-Bu) |
| OCF₃ | CO(4-Cl—Ph) | Br | SN(i-Pr)CO₂(n-Bu) |
| OCF₃ | CO₂Ph | Br | SN(i-Pr)CO₂(n-Pr) |
| OCF₃ | CH₂CO₂Et | Br | CO(n-Bu) |
| OCF₃ | CH₂CH₂CN | Br | CO₂(n-Bu) |
| OCF₃ | CH₂CH₂CO₂Me | Br | CO(i-Bu) |
| OCF₃ | CH₂CH₂Cl | Br | CO₂(i-Bu) |
| OCF₃ | CH₂Ph | Br | CO(4-Cl—Ph) |
| OCF₃ | COPh | Br | CO₂Ph |
| CF₃ | CH₂Ph | Br | CH₂CO₂Et |
| CF₃ | COPh | Br | CH₂CH₂CN |
| Br | CH₂SiMe₃ | Br | CH₂CH₂CO₂Me |
| Br | CH₂CF₃ | Br | CH₂Ph |
| Br | CH₂CCH | Br | COPh |
| OCF₃ | i-Bu | Br | n-Bu |
| CF₃ | s-Bu | Br | i-Bu |
| OCF₃ | s-Bu | Br | s-Bu |
| OCF₃ | CH₂C(CH₃)CH₂ | Br | CH₂(CH₃)CH₂ |

TABLE 63

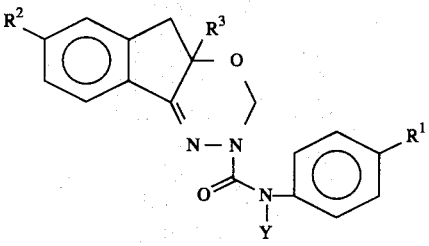

($R^2$ is OCH₂CF₃, $R^3$ is $CO_2Me$)

| $R^1$ | Y | $R^1$ | Y |
|---|---|---|---|
| CF₃ | CH₂SiMe₃ | CF₃ | CO(n-Bu) |
| CF₃ | CH₂CF₃ | CF₃ | CO₂(n-Bu) |
| CF₃ | CH₂CCH | CF₃ | CO(i-Bu) |
| CF₃ | CH₂CO₂Me | CF₃ | CO₂(i-Bu) |
| CF₃ | CH₂CN | CF₃ | CO(4-Cl—Ph) |
| CF₃ | i-Pr | CF₃ | CO₂Ph |
| CF₃ | Ph | CF₃ | CH₂CO₂Et |
| CF₃ | 4-Cl—Ph | CF₃ | CH₂CH₂CN |
| CF₃ | 4-OMe—Ph | CF₃ | CH₂CH₂CO₂Me |
| CF₃ | 4-F—Ph | CF₃ | CH₂CH₂Cl |
| CF₃ | t-Bu | OCF₃ | CH₂SiMe₃ |
| CF₃ | CH₂SOCH₃ | OCF₃ | CH₂CF₃ |
| CF₃ | CH₂SO₂CH₃ | OCF₃ | CH₂CCH |
| CF₃ | SN(i-Pr)CO₂Et | OCF₃ | CH₂CO₂Me |
| CF₃ | SN(Me)CO₂Et | OCF₃ | CH₂CN |
| CF₃ | SN(n-Bu)₂ | OCF₃ | i-Pr |
| CF₃ | SN(Me)CO₂(n-Bu) | OCF₃ | Ph |
| CF₃ | SN(i-Pr)CO₂(n-Bu) | OCF₃ | 4-Cl—Ph |
| CF₃ | SN(i-Pr)CO₂(n-Pr) | OCF₃ | 4-OMe—Ph |
| CF₃ | n-Bu | CF₃ | CH₂C(CH₃)CH₂ |
| CF₃ | i-Bu | OCF₃ | n-Bu |
| OCF₃ | 4-F—Ph | Br | CH₂CO₂Me |
| OCF₃ | t-Bu | Br | CH₂CN |
| OCF₃ | CH₂SOCH₃ | Br | i-Pr |

TABLE 63-continued

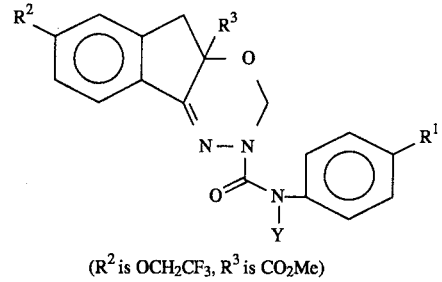

($R^2$ is OCH₂CF₃, $R^3$ is $CO_2Me$)

| $R^1$ | Y | $R^1$ | Y |
|---|---|---|---|
| OCF₃ | CH₂SO₂CH₃ | Br | Ph |
| OCF₃ | SN(i-Pr)CO₂Et | Br | 4-Cl—Ph |
| OCF₃ | SN(Me)CO₂Et | Br | 4-OMe—Ph |
| OCF₃ | SN(n-Bu)₂ | Br | 4-F—Ph |
| OCF₃ | SN(Me)CO₂(n-Bu) | Br | t-Bu |
| OCF₃ | SN(i-Pr)CO₂(n-Bu) | Br | CH₂SOCH₃ |
| OCF₃ | SN(i-Pr)CO₂(n-Pr) | Br | CH₂SO₂CH₃ |
| OCF₃ | CO(n-Bu) | Br | SN(i-Pr)CO₂Et |
| OCF₃ | CO₂(n-Bu) | Br | SN(Me)CO₂Et |
| OCF₃ | CO(i-Bu) | Br | SN(n-Bu)₂ |
| OCF₃ | CO₂(i-Bu) | Br | SN(Me)CO₂(n-Bu) |
| OCF₃ | CO(4-Cl—Ph) | Br | SN(i-Pr)CO₂(n-Bu) |
| OCF₃ | CO₂Ph | Br | SN(i-Pr)CO₂(n-Pr) |
| OCF₃ | CH₂CO₂Et | Br | CO(n-Bu) |
| OCF₃ | CH₂CH₂CN | Br | CO₂(n-Bu) |
| OCF₃ | CH₂CH₂CO₂Me | Br | CO(i-Bu) |
| OCF₃ | CH₂CH₂Cl | Br | CO₂(i-Bu) |
| OCF₃ | CH₂Ph | Br | CO(4-Cl—Ph) |
| OCF₃ | COPh | Br | CO₂Ph |
| CF₃ | CH₂Ph | Br | CH₂CO₂Et |
| CF₃ | COPh | Br | CH₂CH₂CN |
| Br | CH₂SiMe₃ | Br | CH₂CH₂CO₂Me |
| Br | CH₂CF₃ | Br | CH₂Ph |
| Br | CH₂CCH | Br | COPh |
| OCF₃ | i-Bu | Br | n-Bu |
| CF₃ | s-Bu | Br | i-Bu |
| OCF₃ | s-Bu | Br | s-Bu |
| OCF₃ | CH₂C(CH₃)CH₂ | Br | CH₂(CH₃)CH₂ |

TABLE 64

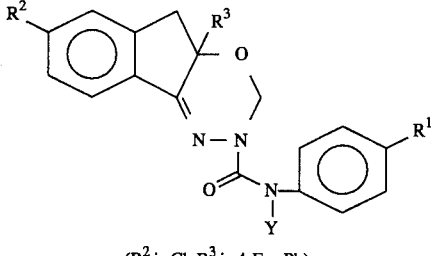

($R^2$ is Cl, $R^3$ is 4-F—Ph)

| $R^1$ | Y | $R^1$ | Y |
|---|---|---|---|
| CF₃ | CH₂SiMe₃ | CF₃ | CO(n-Bu) |
| CF₃ | CH₂CF₃ | CF₃ | CO₂(n-Bu) |
| CF₃ | CH₂CCH | CF₃ | CO(i-Bu) |
| CF₃ | CH₂CO₂Me | CF₃ | CO₂(i-Bu) |
| CF₃ | CH₂CN | CF₃ | CO(4-Cl—Ph) |
| CF₃ | i-Pr | CF₃ | CO₂Ph |
| CF₃ | Ph | CF₃ | CH₂CO₂Et |
| CF₃ | 4-Cl—Ph | CF₃ | CH₂CH₂CN |
| CF₃ | 4-OMe—Ph | CF₃ | CH₂CH₂CO₂Me |
| CF₃ | 4-F—Ph | CF₃ | CH₂CH₂Cl |
| CF₃ | t-Bu | OCF₃ | CH₂SiMe₃ |
| CF₃ | CH₂SOCH₃ | OCF₃ | CH₂CF₃ |
| CF₃ | CH₂SO₂CH₃ | OCF₃ | CH₂CCH |
| CF₃ | SN(i-Pr)CO₂Et | OCF₃ | CH₂CO₂Me |
| CF₃ | SN(Me)CO₂Et | OCF₃ | CH₂CN |

TABLE 64-continued

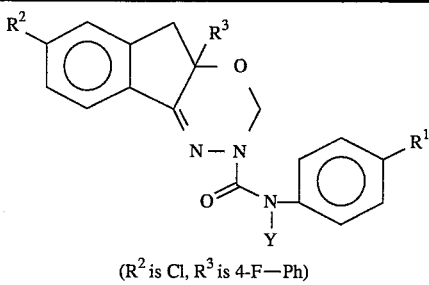

($R^2$ is Cl, $R^3$ is 4-F—Ph)

| $R^1$ | Y | $R^1$ | Y |
|---|---|---|---|
| $CF_3$ | $SN(n-Bu)_2$ | $OCF_3$ | i-Pr |
| $CF_3$ | $SN(Me)CO_2(n-Bu)$ | $OCF_3$ | Ph |
| $CF_3$ | $SN(i-Pr)CO_2(n-Bu)$ | $OCF_3$ | 4-Cl—Ph |
| $CF_3$ | $SN(i-Pr)CO_2(n-Pr)$ | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN(i-Pr)CO_2Et$ | Br | 4-Cl—Ph |
| $OCF_3$ | $SN(Me)CO_2Et$ | Br | 4-OMe—Ph |
| $OCF_3$ | $SN(n-Bu)_2$ | Br | 4-F—Ph |
| $OCF_3$ | $SN(Me)CO_2(n-Bu)$ | Br | t-Bu |
| $OCF_3$ | $SN(i-Pr)CO_2(n-Bu)$ | Br | $CH_2SOCH_3$ |
| $OCF_3$ | $SN(i-Pr)CO_2(n-Pr)$ | Br | $CH_2SO_2CH_3$ |
| $OCF_3$ | CO(n-Bu) | Br | $SN(i-Pr)CO_2Et$ |
| $OCF_3$ | $CO_2(n-Bu)$ | Br | $SN(Me)CO_2Et$ |
| $OCF_3$ | CO(i-Bu) | Br | $SN(n-Bu)_2$ |
| $OCF_3$ | $CO_2(i-Bu)$ | Br | $SN(Me)CO_2(n-Bu)$ |
| $OCF_3$ | CO(4-Cl—Ph) | Br | $SN(i-Pr)CO_2(n-Bu)$ |
| $OCF_3$ | $CO_2Ph$ | Br | $SN(i-Pr)CO_2(n-Pr)$ |
| $OCF_3$ | $CH_2CO_2Et$ | Br | CO(n-Bu) |
| $OCF_3$ | $CH_2CH_2CN$ | Br | $CO_2(n-Bu)$ |
| $OCF_3$ | $CH_2CH_2CO_2Me$ | Br | CO(i-Bu) |
| $OCF_3$ | $CH_2CH_2Cl$ | Br | $CO_2(i-Bu)$ |
| $OCF_3$ | $CH_2Ph$ | Br | CO(4-Cl—Ph) |
| $OCF_3$ | COPh | Br | $CO_2Ph$ |
| $CF_3$ | $CH_2Ph$ | Br | $CH_2CO_2Et$ |
| $CF_3$ | COPh | Br | $CH_2CH_2CN$ |
| Br | $CH_2SiMe_3$ | Br | $CH_2CH_2CO_2Me$ |
| Br | $CH_2CF_3$ | Br | $CH_2Ph$ |
| Br | $CH_2CCH$ | Br | COPh |
| $OCF_3$ | i-Bu | Br | n-Bu |
| $CF_3$ | s-Bu | Br | i-Bu |
| $OCF_3$ | s-Bu | Br | s-Bu |
| $OCF_3$ | $CH_2C(CH_3)CH_2$ | Br | $CH_2(CH_3)CH_2$ |

TABLE 65

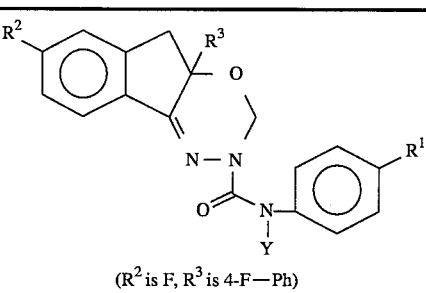

($R^2$ is F, $R^3$ is 4-F—Ph)

| $R^1$ | Y | $R^1$ | Y |
|---|---|---|---|
| $CF_3$ | $CH_2SiMe_3$ | $CF_3$ | CO(n-Bu) |
| $CF_3$ | $CH_2CF_3$ | $CF_3$ | $CO_2(n-Bu)$ |

TABLE 65-continued

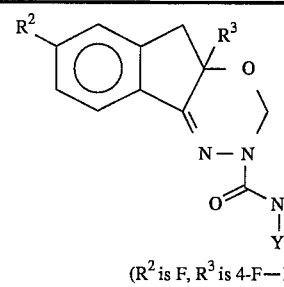

($R^2$ is F, $R^3$ is 4-F—Ph)

| $R^1$ | Y | $R^1$ | Y |
|---|---|---|---|
| $CF_3$ | $CH_2CCH$ | $CF_3$ | CO(i-Bu) |
| $CF_3$ | $CH_2CO_2Me$ | $CF_3$ | $CO_2(i-Bu)$ |
| $CF_3$ | $CH_2CN$ | $CF_3$ | CO(4-Cl—Ph) |
| $CF_3$ | i-Pr | $CF_3$ | $CO_2Ph$ |
| $CF_3$ | Ph | $CF_3$ | $CH_2CO_2Et$ |
| $CF_3$ | 4-Cl—Ph | $CF_3$ | $CH_2CH_2CN$ |
| $CF_3$ | 4-OMe—Ph | $CF_3$ | $CH_2CH_2CO_2Me$ |
| $CF_3$ | 4-F—Ph | $CF_3$ | $CH_2CH_2Cl$ |
| $CF_3$ | t-Bu | $OCF_3$ | $CH_2SiMe_3$ |
| $CF_3$ | $CH_2SOCH_3$ | $OCF_3$ | $CH_2CF_3$ |
| $CF_3$ | $CH_2SO_2CH_3$ | $OCF_3$ | $CH_2CCH$ |
| $CF_3$ | $SN(i-Pr)CO_2Et$ | $OCF_3$ | $CH_2CO_2Me$ |
| $CF_3$ | $SN(Me)CO_2Et$ | $OCF_3$ | $CH_2CN$ |
| $CF_3$ | $SN(n-Bu)_2$ | $OCF_3$ | i-Pr |
| $CF_3$ | $SN(Me)CO_2(n-Bu)$ | $OCF_3$ | Ph |
| $CF_3$ | $SN(i-Pr)CO_2(n-Bu)$ | $OCF_3$ | 4-Cl—Ph |
| $CF_3$ | $SN(i-Pr)CO_2(n-Pr)$ | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN(i-Pr)CO_2Et$ | Br | 4-Cl—Ph |
| $OCF_3$ | $SN(Me)CO_2Et$ | Br | 4-OMe—Ph |
| $OCF_3$ | $SN(n-Bu)_2$ | Br | 4-F—Ph |
| $OCF_3$ | $SN(Me)CO_2(n-Bu)$ | Br | t-Bu |
| $OCF_3$ | $SN(i-Pr)CO_2(n-Bu)$ | Br | $CH_2SOCH_3$ |
| $OCF_3$ | $SN(i-Pr)CO_2(n-Pr)$ | Br | $CH_2SO_2CH_3$ |
| $OCF_3$ | CO(n-Bu) | Br | $SN(i-Pr)CO_2Et$ |
| $OCF_3$ | $CO_2(n-Bu)$ | Br | $SN(Me)CO_2Et$ |
| $OCF_3$ | CO(i-Bu) | Br | $SN(n-Bu)_2$ |
| $OCF_3$ | $CO_2(i-Bu)$ | Br | $SN(Me)CO_2(n-Bu)$ |
| $OCF_3$ | CO(4-Cl—Ph) | Br | $SN(i-Pr)CO_2(n-Bu)$ |
| $OCF_3$ | $CO_2Ph$ | Br | $SN(i-Pr)CO_2(n-Pr)$ |
| $OCF_3$ | $CH_2CO_2Et$ | Br | CO(n-Bu) |
| $OCF_3$ | $CH_2CH_2CN$ | Br | $CO_2(n-Bu)$ |
| $OCF_3$ | $CH_2CH_2CO_2Me$ | Br | CO(i-Bu) |
| $OCF_3$ | $CH_2CH_2Cl$ | Br | $CO_2(i-Bu)$ |
| $OCF_3$ | $CH_2Ph$ | Br | CO(4-Cl—Ph) |
| $OCF_3$ | COPh | Br | $CO_2Ph$ |
| $CF_3$ | $CH_2Ph$ | Br | $CH_2CO_2Et$ |
| $CF_3$ | COPh | Br | $CH_2CH_2CN$ |
| Br | $CH_2SiMe_3$ | Br | $CH_2CH_2CO_2Me$ |
| Br | $CH_2CF_3$ | Br | $CH_2Ph$ |
| Br | $CH_2CCH$ | Br | COPh |
| $OCF_3$ | i-Bu | Br | n-Bu |
| $CF_3$ | s-Bu | Br | i-Bu |
| $OCF_3$ | s-Bu | Br | s-Bu |
| $OCF_3$ | $CH_2C(CH_3)CH_2$ | Br | $CH_2(CH_3)CH_2$ |

TABLE 66

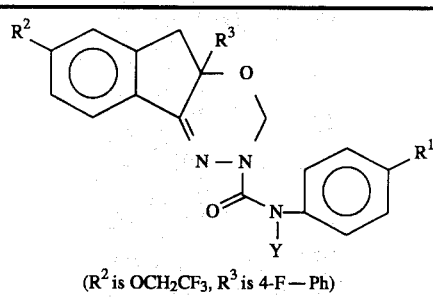

($R^2$ is $OCH_2CF_3$, $R^3$ is 4-F—Ph)

| $R^1$ | Y | $R^1$ | Y |
|---|---|---|---|
| $CF_3$ | $CH_2SMe_3$ | $CF_3$ | CO(n-Bu) |
| $CF_3$ | $CH_2CF_3$ | $CF_3$ | $CO_2$(n-Bu) |
| $CF_3$ | $CH_2CCH$ | $CF_3$ | CO(i-Bu) |
| $CF_3$ | $CH_2CO_2Me$ | $CF_3$ | $CO_2$(i-Bu) |
| $CF_3$ | $CH_2CN$ | $CF_3$ | CO(4-Cl—Ph) |
| $CF_3$ | i-Pr | $CF_3$ | $CO_2Ph$ |
| $CF_3$ | Ph | $CF_3$ | $CH_2CO_2Et$ |
| $CF_3$ | 4-Cl—Ph | $CF_3$ | $CH_2CH_2CN$ |
| $CF_3$ | 4-OMe—Ph | $CF_3$ | $CH_2CH_2CO_2Me$ |
| $CF_3$ | 4-F—Ph | $CF_3$ | $CH_2CH_2Cl$ |
| $CF_3$ | t-Bu | $OCF_3$ | $CH_2SiMe_3$ |
| $CF_3$ | $CH_2SOCH_3$ | $OCF_3$ | $CH_2CF_3$ |
| $CF_3$ | $CH_2SO_2CH_3$ | $OCF_3$ | $CH_2CCH$ |
| $CF_3$ | $SN(i-Pr)CO_2Et$ | $OCF_3$ | $CH_2CO_2Me$ |
| $CF_3$ | $SN(Me)CO_2Et$ | $OCF_3$ | $CH_2CN$ |
| $CF_3$ | $SN(n-Bu)_2$ | $OCF_3$ | i-Pr |
| $CF_3$ | $SN(Me)CO_2$(n-Bu) | $OCF_3$ | Ph |
| $CF_3$ | $SN(i-Pr)CO_2$(n-Bu) | $OCF_3$ | 4-Cl—Ph |
| $CF_3$ | $SN(i-Pr)CO_2$(n-Pr) | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN(i-Pr)CO_2Et$ | Br | 4-Cl—Ph |
| $OCF_3$ | $SN(Me)CO_2Et$ | Br | 4-OMe—Ph |
| $OCF_3$ | $SN(n-Bu)_2$ | Br | 4-F—Ph |
| $OCF_3$ | $SN(Me)CO_2$(n-Bu) | Br | t-Bu |
| $OCF_3$ | $SN(i-Pr)CO_2$(n-Bu) | Br | $CH_2SOCH_3$ |
| $OCF_3$ | $SN(i-Pr)CO_2$(n-Pr) | Br | $CH_2SO_2CH_3$ |
| $OCF_3$ | CO(n-Bu) | Br | $SN(i-Pr)CO_2Et$ |
| $OCF_3$ | $CO_2$(n-Bu) | Br | $SN(Me)CO_2Et$ |
| $OCF_3$ | CO(i-Bu) | Br | $SN(n-Bu)_2$ |
| $OCF_3$ | $CO_2$(i-Bu) | Br | $SN(Me)CO_2$(n-Bu) |
| $OCF_3$ | CO(4-Cl—Ph) | Br | $SN(i-Pr)CO_2$(n-Bu) |
| $OCF_3$ | $CO_2Ph$ | Br | $SN(i-Pr)CO_2$(n-Pr) |
| $OCF_3$ | $CH_2CO_2Et$ | Br | CO(n-Bu) |
| $OCF_3$ | $CH_2CH_2CN$ | Br | $CO_2$(n-Bu) |
| $OCF_3$ | $CH_2CH_2CO_2Me$ | Br | CO(i-Bu) |
| $OCF_3$ | $CH_2CH_2Cl$ | Br | $CO_2$(i-Bu) |
| $OCF_3$ | $CH_2Ph$ | Br | CO(4-Cl—Ph) |
| $OCF_3$ | COPh | Br | $CO_2Ph$ |
| $CF_3$ | $CH_2Ph$ | Br | $CH_2CO_2Et$ |
| $CF_3$ | COPh | Br | $CH_2CH_2CN$ |
| Br | $CH_2SiMe_3$ | Br | $CH_2CH_2CO_2Me$ |
| Br | $CH_2CF_3$ | Br | $CH_2Ph$ |
| Br | $CH_2CCH$ | Br | COPh |
| $OCF_3$ | i-Bu | Br | n-Bu |
| $CF_3$ | s-Bu | Br | i-Bu |
| $OCF_3$ | s-Bu | Br | s-Bu |
| $OCF_3$ | $CH_2C(CH_3)CH_2$ | Br | $CH_2(CH_3)CH_2$ |

TABLE 67

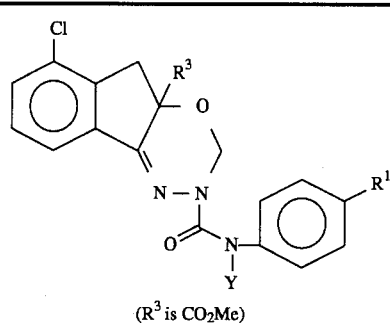

($R^3$ is $CO_2Me$)

| $R^1$ | Y | $R^1$ | Y |
|---|---|---|---|
| $CF_3$ | $CH_2SiMe_3$ | $CF_3$ | CO(n-Bu) |
| $CF_3$ | $CH_2CF_3$ | $CF_3$ | $CO_2$(n-Bu) |
| $CF_3$ | $CH_2CCH$ | $CF_3$ | CO(i-Bu) |
| $CF_3$ | $CH_2CO_2Me$ | $CF_3$ | $CO_2$(i-Bu) |
| $CF_3$ | $CH_2CN$ | $CF_3$ | CO(4-Cl—Ph) |
| $CF_3$ | i-Pr | $CF_3$ | $CO_2Ph$ |
| $CF_3$ | Ph | $CF_3$ | $CH_2CO_2Et$ |
| $CF_3$ | 4-Cl—Ph | $CF_3$ | $CH_2CH_2CN$ |
| $CF_3$ | 4-OMe—Ph | $CF_3$ | $CH_2CH_2CO_2Me$ |
| $CF_3$ | 4-F—Ph | $CF_3$ | $CH_2CH_2Cl$ |
| $CF_3$ | t-Bu | $OCF_3$ | $CH_2SiMe_3$ |
| $CF_3$ | $CH_2SOCH_3$ | $OCF_3$ | $CH_2CF_3$ |
| $CF_3$ | $CH_2SO_2CH_3$ | $OCF_3$ | $CH_2CCH$ |
| $CF_3$ | $SN(i-Pr)CO_2Et$ | $OCF_3$ | $CH_2CO_2Me$ |
| $CF_3$ | $SN(Me)CO_2Et$ | $OCF_3$ | $CH_2CN$ |
| $CF_3$ | $SN(n-Bu)_2$ | $OCF_3$ | i-Pr |
| $CF_3$ | $SN(Me)CO_2$(n-Bu) | $OCF_3$ | Ph |
| $CF_3$ | $SN(i-Pr)CO_2$(n-Bu) | $OCF_3$ | 4-Cl—Ph |
| $CF_3$ | $SN(i-Pr)CO_2$(n-Pr) | $OCF_3$ | 4-OMe—Ph |
| $CF_3$ | n-Bu | $CF_3$ | $CH_2C(CH_3)CH_2$ |
| $CF_3$ | i-Bu | $OCF_3$ | n-Bu |
| $OCF_3$ | 4-F—Ph | Br | $CH_2CO_2Me$ |
| $OCF_3$ | t-Bu | Br | $CH_2CN$ |
| $OCF_3$ | $CH_2SOCH_3$ | Br | i-Pr |
| $OCF_3$ | $CH_2SO_2CH_3$ | Br | Ph |
| $OCF_3$ | $SN(i-Pr)CO_2Et$ | Br | 4-Cl—Ph |
| $OCF_3$ | $SN(Me)CO_2Et$ | Br | 4-OMe—Ph |
| $OCF_3$ | $SN(n-Bu)_2$ | Br | 4-F—Ph |
| $OCF_3$ | $SN(Me)CO_2$(n-Bu) | Br | t-Bu |
| $OCF_3$ | $SN(i-Pr)CO_2$(n-Bu) | Br | $CH_2SOCH_3$ |
| $OCF_3$ | $SN(i-Pr)CO_2$(n-Pr) | Br | $CH_2SO_2CH_3$ |
| $OCF_3$ | CO(n-Bu) | Br | $SN(i-Pr)CO_2Et$ |
| $OCF_3$ | $CO_2$(n-Bu) | Br | $SN(Me)CO_2Et$ |
| $OCF_3$ | CO(i-Bu) | Br | $SN(n-Bu)_2$ |
| $OCF_3$ | $CO_2$(i-Bu) | Br | $SN(Me)CO_2$(n-Bu) |
| $OCF_3$ | CO(4-Cl—Ph) | Br | $SN(i-Pr)CO_2$(n-Bu) |
| $OCF_3$ | $CO_2Ph$ | Br | $SN(i-Pr)CO_2$(n-Pr) |
| $OCF_3$ | $CH_2CO_2Et$ | Br | CO(n-Bu) |
| $OCF_3$ | $CH_2CH_2CN$ | Br | $CO_2$(n-Bu) |
| $OCF_3$ | $CH_2CH_2CO_2Me$ | Br | CO(i-Bu) |
| $OCF_3$ | $CH_2CH_2Cl$ | Br | $CO_2$(i-Bu) |
| $OCF_3$ | $CH_2Ph$ | Br | CO(4-Cl—Ph) |
| $OCF_3$ | COPh | Br | $CO_2Ph$ |
| $CF_3$ | $CH_2Ph$ | Br | $CH_2CO_2Et$ |
| $CF_3$ | COPh | Br | $CH_2CH_2CN$ |
| Br | $CH_2SiMe_3$ | Br | $CH_2CH_2CO_2Me$ |
| Br | $CH_2CF_3$ | Br | $CH_2Ph$ |
| Br | $CH_2CCH$ | Br | COPh |
| $OCF_3$ | i-Bu | Br | n-Bu |
| $CF_3$ | s-Bu | Br | i-Bu |
| $OCF_3$ | s-Bu | Br | s-Bu |
| $OCF_3$ | $CH_2C(CH_3)CH_2$ | Br | $CH_2(CH_3)CH_2$ |

TABLE 68

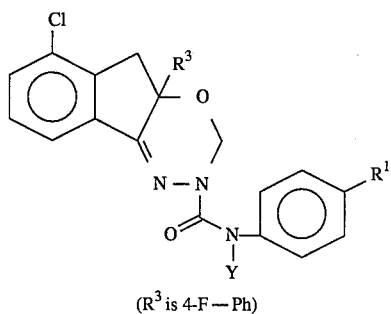

(R³ is 4-F—Ph)

| R¹ | Y | R¹ | Y |
|---|---|---|---|
| CF₃ | CH₂SiMe₃ | CF₃ | CO(n-Bu) |
| CF₃ | CH₂CF₃ | CF₃ | CO₂(n-Bu) |
| CF₃ | CH₂CCH | CF₃ | CO(i-Bu) |
| CF₃ | CH₂CO₂Me | CF₃ | CO₂(i-Bu) |
| CF₃ | CH₂CN | CF₃ | CO(4-Cl—Ph) |
| CF₃ | i-Pr | CF₃ | CO₂Ph |
| CF₃ | Ph | CF₃ | CH₂CO₂Et |
| CF₃ | 4-Cl—Ph | CF₃ | CH₂CH₂CN |
| CF₃ | 4-OMe—Ph | CF₃ | CH₂CH₂CO₂Me |
| CF₃ | 4-F—Ph | CF₃ | CH₂CH₂Cl |
| CF₃ | t-Bu | OCF₃ | CH₂SiMe₃ |
| CF₃ | CH₂SOCH₃ | OCF₃ | CH₂CF₃ |
| CF₃ | CH₂SO₂CH₃ | OCF₃ | CH₂CCH |
| CF₃ | SN(i-Pr)CO₂Et | OCF₃ | CH₂CO₂Me |
| CF₃ | SN(Me)CO₂Et | OCF₃ | CH₂CN |
| CF₃ | SN(n-Bu)₂ | OCF₃ | i-Pr |
| CF₃ | SN(Me)CO₂(n-Bu) | OCF₃ | Ph |
| CF₃ | SN(i-Pr)CO₂(n-Bu) | OCF₃ | 4-Cl—Ph |
| CF₃ | SN(i-Pr)CO₂(n-Pr) | OCF₃ | 4-OMe—Ph |
| CF₃ | n-Bu | CF₃ | CH₂C(CH₃)CH₂ |
| CF₃ | i-Bu | OCF₃ | n-Bu |
| OCF₃ | 4-F—Ph | Br | CH₂CO₂Me |
| OCF₃ | t-Bu | Br | CH₂CN |
| OCF₃ | CH₂SOCH₃ | Br | i-Pr |
| OCF₃ | CH₂SO₂CH₃ | Br | Ph |
| OCF₃ | SN(i-Pr)CO₂Et | Br | 4-Cl—Ph |
| OCF₃ | SN(Me)CO₂Et | Br | 4-OMe—Ph |
| OCF₃ | SN(n-Bu)₂ | Br | 4-F—Ph |
| OCF₃ | SN(Me)CO₂(n-Bu) | Br | t-Bu |
| OCF₃ | SN(i-Pr)CO₂(n-Bu) | Br | CH₂SOCH₃ |
| OCF₃ | SN(i-Pr)CO₂(n-Pr) | Br | CH₂SO₂CH₃ |
| OCF₃ | CO(n-Bu) | Br | SN(i-Pr)CO₂Et |
| OCF₃ | CO₂(n-Bu) | Br | SN(Me)CO₂Et |
| OCF₃ | CO(i-Bu) | Br | SN(n-Bu)₂ |
| OCF₃ | CO₂(i-Bu) | Br | SN(Me)CO₂(n-Bu) |
| OCF₃ | CO(4-Cl—Ph) | Br | SN(i-Pr)CO₂(n-Bu) |
| OCF₃ | CO₂Ph | Br | SN(i-Pr)CO₂(n-Pr) |
| OCF₃ | CH₂CO₂Et | Er | CO(n-Bu) |
| OCF₃ | CH₂CH₂CN | Br | CO₂(n-Bu) |
| OCF₃ | CH₂CH₂CO₂Me | Br | CO(i-Bu) |
| OCF₃ | CH₂CH₂Cl | Br | CO₂(i-Bu) |
| OCF₃ | CH₂Ph | Br | CO(4-Cl—Ph) |
| OCF₃ | COPh | Br | CO₂Ph |
| CF₃ | CH₂Ph | Br | CH₂CO₂Et |
| CF₃ | COPh | Br | CH₂CH₂CN |
| Br | CH₂SiMe₃ | Br | CH₂CH₂CO₂Me |
| Br | CH₂CF₃ | Br | CH₂Ph |
| Br | CH₂CCH | Br | COPh |
| OCF₃ | i-Bu | Br | n-Bu |
| CF₃ | s-Bu | Br | i-Bu |
| OCF₃ | s-Bu | Br | s-Bu |
| OCF₃ | CH₂C(CH₃)CH₂ | Br | CH₂(CH₃)CH₂ |

TABLE 69

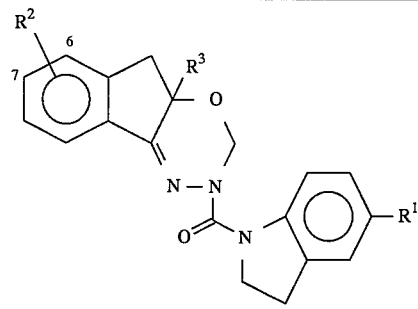

| R¹ | R² | R³ | R¹ | R² | R³ |
|---|---|---|---|---|---|
| Cl | 7-Cl | Me | Cl | 7-CF₃ | Ph |
| Cl | 7-Cl | Et | Cl | 7-CF₃ | 4-Cl—Ph |
| Cl | 7-Cl | n-Pr | Cl | 7-CF₃ | 4-F—Ph |
| Cl | 7-Cl | i-Pr | Cl | 7-OCH₂CF₃ | Me |
| Cl | 7-Cl | CO₂Me | Cl | 7-OCH₂CF₃ | Et |
| Cl | 7-Cl | CO₂Et | Cl | 7-OCH₂CF₃ | n-Pr |
| Cl | 7-Cl | Ph | Cl | 7-OCH₂CF₃ | CO₂Me |
| Cl | 7-Cl | 4-Cl—Ph | Cl | 7-OCH₂CF₃ | CO₂Et |
| Cl | 7-Cl | 4-F—Ph | Cl | 7-OCH₂CF₃ | Ph |
| Cl | 7-F | Me | Cl | 7-OCH₂CF₃ | 4-Cl—Ph |
| Cl | 7-F | Et | Cl | 7-OCH₂CF₃ | 4-F—Ph |
| Cl | 7-F | n-Pr | Cl | 6-Cl | Me |
| Cl | 7-F | i-Pr | Cl | 6-Cl | Et |
| Cl | 7-F | CO₂Me | Cl | 6-Cl | n-Pr |
| Cl | 7-F | CO₂Et | Cl | 6-Cl | CO₂Me |
| Cl | 7-F | Ph | Cl | 6-Cl | CO₂Et |
| Cl | 7-F | 4-Cl—Ph | Cl | 6-Cl | Ph |
| Cl | 7-F | 4-F—Ph | Cl | 6-Cl | 4-Cl—Ph |
| Cl | 7-CF₃ | Me | Cl | 6-Cl | 4-F—Ph |
| Cl | 7-CF₃ | Et | Br | 7-Cl | Me |
| Cl | 7-CF₃ | n-Pr | Br | 7-Cl | Et |
| Cl | 7-CF₃ | i-Pr | Br | 7-Cl | n-Pr |
| Cl | 7-CF₃ | CO₂Me | Br | 7-Cl | i-Pr |
| Cl | 7-CF₃ | CO₂Et | Br | 7-Cl | CO₂Me |
| Br | 7-Cl | CO₂Et | Br | 7-OCH₂CF₃ | Ph |
| Br | 7-Cl | Ph | Br | 7-OCH₂CF₃ | 4-Cl—Ph |
| Br | 7-Cl | 4-Cl—Ph | Br | 7-OCH₂CF₃ | 4-F—Ph |
| Br | 7-Cl | 4-F—Ph | Br | 6-Cl | Me |
| Br | 7-F | Me | Br | 6-Cl | Et |
| Br | 7-F | Et | Br | 6-Cl | n-Pr |
| Br | 7-F | n-Pr | Br | 6-Cl | i-Pr |
| Br | 7-F | i-Pr | Br | 6-Cl | CO₂Me |
| Br | 7-F | CO₂Me | Br | 6-Cl | CO₂Et |
| Br | 7-F | CO₂Et | Br | 6-Cl | Ph |
| Br | 7-F | Ph | Br | 6-Cl | 4-Cl—Ph |
| Er | 7-F | 4-Cl—Ph | Br | 6-Cl | 4-F—Ph |
| Br | 7-F | 4-F—Ph | CF₃ | 7-Cl | Me |
| Br | 7-CF₃ | Me | CF₃ | 7-Cl | Et |
| Br | 7-CF₃ | Et | CF₃ | 7-Cl | n-Pr |
| Br | 7-CF₃ | n-Pr | CF₃ | 7-Cl | i-Pr |
| Br | 7-CF₃ | i-Pr | CF₃ | 7-Cl | CO₂Me |
| Br | 7-CF₃ | CO₂Me | CF₃ | 7-Cl | CO₂Et |
| Br | 7-CF₃ | CO₂Et | CF₃ | 7-Cl | Ph |
| Br | 7-CF₃ | Ph | CF₃ | 7-Cl | 4-Cl—Ph |
| Br | 7-CF₃ | 4-Cl—Ph | CF₃ | 7-Cl | 4-F—Ph |
| Br | 7-CF₃ | 4-F—Ph | CF₃ | 7-F | Me |
| Br | 7-OCH₂CF₃ | Me | CF₃ | 7-F | Et |
| Br | 7-OCH₂CF₃ | Et | CF₃ | 7-F | n-Pr |
| Br | 7-OCH₂CF₃ | n-Pr | CF₃ | 7-F | i-Pr |
| Br | 7-OCH₂CF₃ | i-Pr | CF₃ | 7-F | CO₂Me |
| Br | 7-OCH₂CF₃ | CO₂Me | CF₃ | 7-F | CO₂Et |
| Br | 7-OCH₂CF₃ | CO₂Et | CF₃ | 7-F | Ph |
| CF₃ | 7-F | 4-F—Ph | CF₃ | 7-F | 4-Cl—Ph |
| CF₃ | 7-CF₃ | Me | OCF₃ | 7-Cl | Me |
| CF₃ | 7-CF₃ | Et | OCF₃ | 7-Cl | Et |
| CF₃ | 7-CF₃ | n-Pr | OCF₃ | 7-Cl | n-Pr |
| CF₃ | 7-CF₃ | i-Pr | OCF₃ | 7-Cl | i-Pr |

TABLE 69-continued

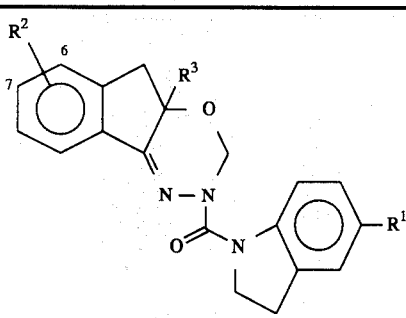

| R¹ | R² | R³ | R¹ | R² | R³ |
|---|---|---|---|---|---|
| CF₃ | 7-CF₃ | CO₂Me | OCF₃ | 7-Cl | CO₂Me |
| CF₃ | 7-CF₃ | CO₂Et | OCF₃ | 7-Cl | CO₂Et |
| CF₃ | 7-CF₃ | Ph | OCF₃ | 7-Cl | Ph |
| CF₃ | 7-CF₃ | 4-Cl—Ph | OCF₃ | 7-Cl | 4-Cl—Ph |
| CF₃ | 7-CF₃ | 4-F—Ph | OCF₃ | 7-Cl | 4-F—Ph |
| CF₃ | 7-OCH₂CF₃ | Me | OCF₃ | 7-F | Me |
| CF₃ | 7-OCH₂CF₃ | Et | OCF₃ | 7-F | Et |
| CF₃ | 7-OCH₂CF₃ | n-Pr | OCF₃ | 7-F | n-Pr |
| CF₃ | 7-OCH₂CF₃ | i-Pr | OCF₃ | 7-F | i-Pr |
| CF₃ | 7-OCH₂CF₃ | CO₂Me | OCF₃ | 7-F | CO₂Me |
| CF₃ | 7-OCH₂CF₃ | CO₂Et | OCF₃ | 7-F | CO₂Et |
| CF₃ | 7-OCH₂CF₃ | Ph | OCF₃ | 7-F | Ph |
| CF₃ | 7-OCH₂CF₃ | 4-Cl—Ph | OCF₃ | 7-F | 4-Cl—Ph |
| CF₃ | 7-OCH₂CF₃ | 4-F—Ph | OCF₃ | 7-F | 4-F—Ph |
| CF₃ | 6-Cl | Me | OCF₃ | 7-CF₃ | Me |
| CF₃ | 6-Cl | Et | OCF₃ | 7-CF₃ | Et |
| CF₃ | 6-Cl | n-Pr | OCF₃ | 7-CF₃ | n-Pr |
| CF₃ | 6-Cl | i-Pr | OCF₃ | 7-CF₃ | i-Pr |
| CF₃ | 6-Cl | CO₂Me | OCF₃ | 7-CF₃ | CO₂Me |
| CF₃ | 6-Cl | CO₂Et | OCF₃ | 7-CF₃ | CO₂Et |
| CF₃ | 6-Cl | Ph | OCF₃ | 7-CF₃ | Ph |
| CF₃ | 6-Cl | 4-Cl—Ph | OCF₃ | 7-CF₃ | 4-Cl—Ph |

TABLE 69-continued

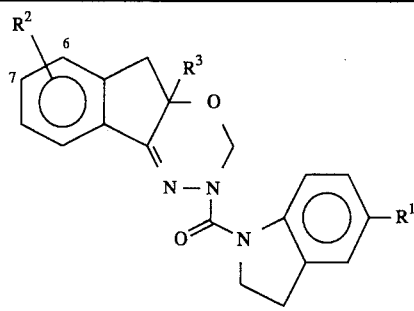

| R¹ | R² | R³ | R¹ | R² | R³ |
|---|---|---|---|---|---|
| CF₃ | 6-Cl | 4-F—Ph | OCF₃ | 7-CF₃ | 4-F—Ph |
| OCF₃ | 7-OCH₂CF₃ | Et | OCF₃ | 7-OCH₂CF₃ | Me |
| OCF₃ | 7-OCH₂CF₃ | n-Pr | | | |
| OCF₃ | 7-OCH₂CF₃ | i-Pr | | | |
| OCF₃ | 7-OCH₂CF₃ | CO₂Me | | | |
| OCF₃ | 7-OCH₂CF₃ | CO₂Et | | | |
| OCF₃ | 7-OCH₂CF₃ | Ph | | | |
| OCF₃ | 7-OCH₂CF₃ | 4-Cl—Ph | | | |
| OCF₃ | 7-OCH₂CF₃ | 4-F—Ph | | | |
| OCF₃ | 6-Cl | Me | | | |
| OCF₃ | 6-Cl | Et | | | |
| OCF₃ | 6-Cl | n-Pr | | | |
| OCF₃ | 6-Cl | i-Pr | | | |
| OCF₃ | 6-Cl | CO₂Me | | | |
| OCF₃ | 6-Cl | CO₂Et | | | |
| OCF₃ | 6-Cl | Ph | | | |
| OCF₃ | 6-Cl | 4-Cl—Ph | | | |
| OCF₃ | 6-Cl | 4-F—Ph | | | |
| Cl | 7-OCH₂CF₃ | i-Pr | | | |
| Cl | 6-Cl | i-Pr | | | |

TABLE 70

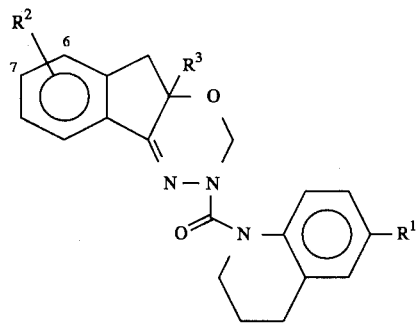

| R¹ | R² | R³ | R¹ | R² | R³ |
|---|---|---|---|---|---|
| Cl | 7-Cl | Me | Cl | 7-CF₃ | Ph |
| Cl | 7-Cl | Et | Cl | 7-CF₃ | 4-Cl—Ph |
| Cl | 7-Cl | n-Pr | Cl | 7-CF₃ | 4-F—Ph |
| Cl | 7-Cl | i-Pr | Cl | 7-OCH₂CF₃ | Me |
| Cl | 7-Cl | CO₂Me | Cl | 7-OCH₂CF₃ | Et |
| Cl | 7-Cl | CO₂Et | Cl | 7-OCH₂CF₃ | n-Pr |
| Cl | 7-Cl | Ph | Cl | 7-OCH₂CF₃ | CO₂Me |
| Cl | 7-Cl | 4-Cl—Ph | Cl | 7-OCH₂CF₃ | CO₂Et |
| Cl | 7-Cl | 4-F—Ph | Cl | 7-OCH₂CF₃ | Ph |

TABLE 70-continued

| R¹ | R² | R³ | R¹ | R² | R³ |
|---|---|---|---|---|---|
| Cl | 7-F | Me | Cl | 7-OCH$_2$CF$_3$ | 4-Cl—Ph |
| Cl | 7-F | Et | Cl | 7-OCH$_2$CF$_3$ | 4-F—Ph |
| Cl | 7-F | n-Pr | Cl | 6-Cl | Me |
| Cl | 7-F | i-Pr | Cl | 6-Cl | Et |
| Cl | 7-F | CO$_2$Me | Cl | 6-Cl | n-Pr |
| Cl | 7-F | CO$_2$Et | Cl | 6-Cl | CO$_2$Me |
| Cl | 7-F | Ph | Cl | 6-Cl | CO$_2$Et |
| Cl | 7-F | 4-Cl—Ph | Cl | 6-Cl | Ph |
| Cl | 7-F | 4-F—Ph | Cl | 6-Cl | 4-Cl—Ph |
| Cl | 7-CF$_3$ | Me | Cl | 6-Cl | 4-F—Ph |
| Cl | 7-CF$_3$ | Et | Br | 7-Cl | Me |
| Cl | 7-CF$_3$ | n-Pr | Br | 7-Cl | Et |
| Cl | 7-CF$_3$ | i-Pr | Br | 7-Cl | n-Pr |
| Cl | 7-CF$_3$ | CO$_2$Me | Br | 7-Cl | i-Pr |
| Cl | 7-CF$_3$ | CO$_2$Et | Br | 7-Cl | CO$_2$Me |
| Br | 7-Cl | CO$_2$Et | Br | 7-OCH$_2$CF$_3$ | Ph |
| Br | 7-Cl | Ph | Br | 7-OCH$_2$CF$_3$ | 4-Cl—Ph |
| Br | 7-Cl | 4-Cl—Ph | Br | 7-OCH$_2$CF$_3$ | 4-F—Ph |
| Br | 7-Cl | 4-F—Ph | Br | 6-Cl | Me |
| Br | 7-F | Me | Br | 6-Cl | Et |
| Br | 7-F | Et | Br | 6-Cl | n-Pr |
| Br | 7-F | n-Pr | Br | 6-Cl | i-Pr |
| Br | 7-F | i-Pr | Br | 6-Cl | CO$_2$Me |
| Br | 7-F | CO$_2$Me | Br | 6-Cl | CO$_2$Et |
| Br | 7-F | CO$_2$Et | Br | 6-Cl | Ph |
| Br | 7-F | Ph | Br | 6-Cl | 4-Cl—Ph |
| Br | 7-F | 4-Cl—Ph | Br | 6-Cl | 4-F—Ph |
| Br | 7-F | 4-F—Ph | CF$_3$ | 7-Cl | Me |
| Br | 7-CF$_3$ | Me | CF$_3$ | 7-Cl | Et |
| Br | 7-CF$_3$ | Et | CF$_3$ | 7-Cl | n-Pr |
| Br | 7-CF$_3$ | n-Pr | CF3 | 7-Cl | i-Pr |
| Br | 7-CF$_3$ | i-Pr | CF$_3$ | 7-Cl | CO$_2$Me |
| Br | 7-CF$_3$ | CO$_2$Me | CF$_3$ | 7-Cl | CO$_2$Et |
| Br | 7-CF$_3$ | CO$_2$Et | CF3 | 7-Cl | Ph |
| Br | 7-CF$_3$ | Ph | CF$_3$ | 7-Cl | 4-Cl—Ph |
| Br | 7-CF$_3$ | 4-Cl—Ph | CF$_3$ | 7-Cl | 4-F—Ph |
| Br | 7-CF$_3$ | 4-F—Ph | CF$_3$ | 7-F | Me |
| Br | 7-OCH$_2$CF$_3$ | Me | CF$_3$ | 7-F | Et |
| Br | 7-OCH$_2$CF$_3$ | Et | CF$_3$ | 7-F | n-Pr |
| Br | 7-OCH$_2$CF$_3$ | n-Pr | CF$_3$ | 7-F | i-Pr |
| Br | 7-OCH$_2$CF$_3$ | i-Pr | CF$_3$ | 7-F | CO$_2$Me |
| Br | 7-OCH$_2$CF$_3$ | CO$_2$Me | CF$_3$ | 7-F | CO$_2$Et |
| Br | 7-CF$_3$ | CO$_2$Et | CF$_3$ | 7-F | Ph |
| CF$_3$ | 7-F | 4-F—Ph | CF$_3$ | 7-F | 4-Cl—Ph |
| CF$_3$ | 7-CF$_3$ | Me | OCF$_3$ | 7-Cl | Me |
| CF$_3$ | 7-CF$_3$ | Et | OCF$_3$ | 7-Cl | Et |
| CF$_3$ | 7-CF$_3$ | n-Pr | OCF$_3$ | 7-Cl | n-Pr |
| CF$_3$ | 7-CF$_3$ | i-Pr | OCF$_3$ | 7-Cl | i-Pr |
| CF$_3$ | 7-CF$_3$ | CO$_2$Me | OCF$_3$ | 7-Cl | CO$_2$Me |
| CF$_3$ | 7-CF$_3$ | CO$_2$Et | OCF$_3$ | 7-Cl | CO$_2$Et |
| CF$_3$ | 7-CF$_3$ | Ph | OCF$_3$ | 7-Cl | Ph |
| CF$_3$ | 7-CF$_3$ | 4-Cl—Ph | OCF$_3$ | 7-Cl | 4-Cl—Ph |
| CF$_3$ | 7-CF$_3$ | 4-F—Ph | OCF$_3$ | 7-Cl | 4-F—Ph |
| CF$_3$ | 7-OCH$_2$CF$_3$ | Me | OCF$_3$ | 7-F | Me |
| CF$_3$ | 7-OCH$_2$CF$_3$ | Et | OCF$_3$ | 7-F | Et |
| CF$_3$ | 7-OCH$_2$CF$_3$ | n-Pr | OCF$_3$ | 7-F | n-Pr |
| CF$_3$ | 7-OCH$_2$CF$_3$ | i-Pr | OCF$_3$ | 7-F | i-Pr |
| CF$_3$ | 7-OCH$_2$CF$_3$ | CO$_2$Me | OCF$_3$ | 7-F | CO$_2$Me |
| CF$_3$ | 7-OCH$_2$CF$_3$ | CO$_2$Et | OCF$_3$ | 7-F. | CO$_2$Et |
| CF$_3$ | 7-OCH$_2$CF$_3$ | Ph | OCF$_3$ | 7-F | Ph |
| CF$_3$ | 7-OCH$_2$CF$_3$ | 4-Cl—Ph | OCF$_3$ | 7-F | 4-Cl—Ph |

TABLE 70-continued

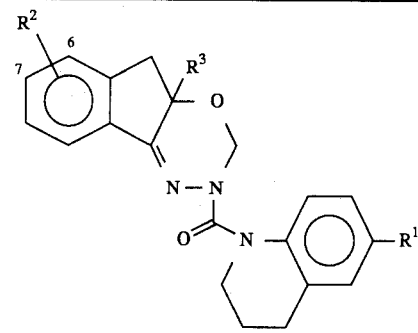

| R¹ | R² | R³ | R¹ | R² | R³ |
|---|---|---|---|---|---|
| CF$_3$ | 7-OCH$_2$CF$_3$ | 4-F—Ph | OCF$_3$ | 7-F | 4-F—Ph |
| CF$_3$ | 6-Cl | Me | OCF$_3$ | 7-CF$_3$ | Me |
| CF$_3$ | 6-Cl | Et | OCF$_3$ | 7-CF$_3$ | Et |
| CF$_3$ | 6-Cl | n-Pr | OCF$_3$ | 7-CF$_3$ | n-Pr |
| CF$_3$ | 6-Cl | i-Pr | OCF$_3$ | 7-CF$_3$ | i-Pr |
| CF$_3$ | 6-Cl | CO$_2$Me | OCF$_3$ | 7-CF$_3$ | CO$_2$Me |
| CF$_3$ | 6-Cl | CO$_2$Et | OCF$_3$ | 7-CF$_3$ | CO$_2$Et |
| CF$_3$ | 6-Cl | Ph | OCF$_3$ | 7-CF$_3$ | Ph |
| CF$_3$ | 6-Cl | 4-Cl—Ph | OCF$_3$ | 7-CF$_3$ | 4-Cl—Ph |
| CF$_3$ | 6-Cl | 4-F—Ph | OCF$_3$ | 7-CF$_3$ | 4-F—Ph |
| OCF$_3$ | 7-OCH$_2$CF$_3$ | Et | OCF$_3$ | 7-OCH$_2$CF$_3$ | Me |
| OCF$_3$ | 7-OCH$_2$CF$_3$ | n-Pr | | | |
| OCF$_3$ | 7-OCH$_2$CH$_3$ | i-Pr | | | |
| OCF$_3$ | 7-OCH$_2$CH$_3$ | CO$_2$Me | | | |
| OCF$_3$ | 7-OCH$_2$CF$_3$ | CO$_2$Et | | | |
| OCF$_3$ | 7-OCH$_2$CF$_3$ | Ph | | | |
| OCF$_3$ | 7-OCH$_2$CF$_3$ | 4-Cl—Ph | | | |
| OCF$_3$ | 7-OCH$_2$CF$_3$ | 4-F—Ph | | | |
| OCF$_3$ | 6-Cl | Me | | | |
| OCF$_3$ | 6-Cl | Et | | | |
| OCF$_3$ | 6-Cl | n-Pr | | | |
| OCF$_3$ | 6-Cl | i-Pr | | | |
| OCF$_3$ | 6-Cl | CO$_2$Me | | | |
| OCF$_3$ | 6-Cl | CO$_2$Et | | | |
| OCF$_3$ | 6-Cl | Ph | | | |
| OCF$_3$ | 6-Cl | 4-Cl—Ph | | | |
| OCF$_3$ | 6-Cl | 4-F—Ph | | | |
| Cl | 7-OCH$_2$CF$_3$ | i-Pr | | | |
| Cl | 6-Cl | i-Pr | | | |

TABLE 71

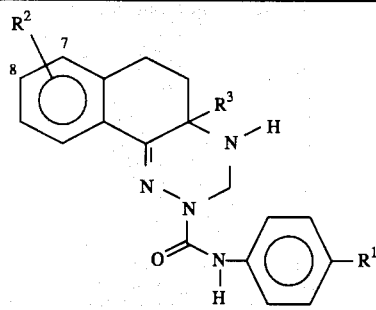

| R¹ | R² | R³ | R¹ | R² | R³ |
|---|---|---|---|---|---|
| CF$_3$ | 7-Cl | Me | CF$_3$ | 8-Cl | Me |
| CF$_3$ | 7-Cl | Et | CF$_3$ | 8-Cl | Et |
| CF$_3$ | 7-Cl | n-Pr | CF$_3$ | 8-Cl | n-Pr |
| CF$_3$ | 7-Cl | CO$_2$Me | CF$_3$ | 8-Cl | CO$_2$Me |
| CF$_3$ | 7-Cl | 4-F—Ph | CF$_3$ | 8-Cl | 4-F—Ph |
| OCF$_3$ | 7-Cl | Me | OCF$_3$ | 8-Cl | Me |
| OCF$_3$ | 7-Cl | Et | OCF$_3$ | 8-Cl | Et |
| OCF$_3$ | 7-Cl | n-Pr | OCF$_3$ | 8-Cl | n-Pr |

TABLE 71-continued

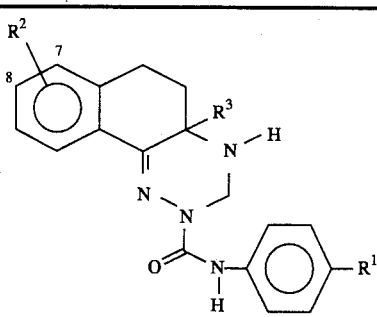

| R¹ | R² | R³ | R¹ | R² | R³ |
|---|---|---|---|---|---|
| OCF$_3$ | 7-Cl | CO$_2$Me | OCF$_3$ | 8-Cl | CO$_2$Me |
| OCF$_3$ | 7-Cl | 4-F—Ph | OCF$_3$ | 8-Cl | 4-F—Ph |
| CF$_3$ | 7-F | Me | CF$_3$ | 8-F | Me |
| CF$_3$ | 7-F | Et | CF$_3$ | 8-F | Et |
| CF$_3$ | 7-F | n-Pr | CF$_3$ | 8-F | n-Pr |
| CF$_3$ | 7-F | CO$_2$Me | CF$_3$ | 8-F | CO$_2$Me |
| CF$_3$ | 7-F | 4-F—Ph | CF$_3$ | 8-F | 4-F—Ph |
| OCF$_3$ | 7-F | Me | OCF$_3$ | 8-F | Me |

TABLE 71-continued

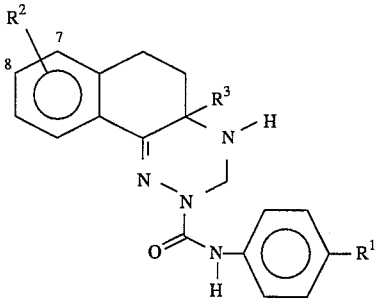

| R¹ | R² | R³ | R¹ | R² | R³ |
|---|---|---|---|---|---|
| OCF₃ | 7-F | Et | OCF₃ | 8-F | Et |
| OCF₃ | 7-F | n-Pr | OCF₃ | 8-F | n-Pr |
| OCF₃ | 7-F | CO₂Me | OCF₃ | 8-F | CO₂Me |
| OCF₃ | 7-F | 4-F—Ph | OCF₃ | 8-F | 4-F—Ph |

TABLE 72

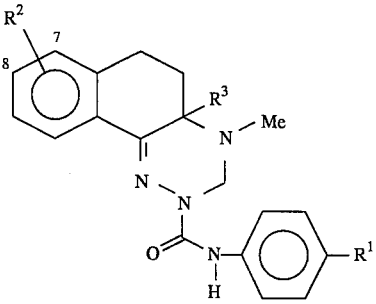

| R¹ | R² | R³ | R¹ | R² | R³ |
|---|---|---|---|---|---|
| CF₃ | 7-Cl | Me | CF₃ | 8-Cl | Me |
| CF₃ | 7-Cl | Et | CF₃ | 8-Cl | Et |
| CF₃ | 7-Cl | n-Pr | CF₃ | 8-Cl | n-Pr |
| CF₃ | 7-Cl | CO₂Me | CF₃ | 8-Cl | CO₂Me |
| CF₃ | 7-Cl | 4-F—Ph | CF₃ | 8-Cl | 4-F—Ph |
| OCF₃ | 7-Cl | Me | OCF₃ | 8-Cl | Me |
| OCF₃ | 7-Cl | Et | OCF₃ | 8-Cl | Et |
| OCF₃ | 7-Cl | n-Pr | OCF₃ | 8-Cl | n-Pr |
| OCF₃ | 7-Cl | CO₂Me | OCF₃ | 8-Cl | CO₂Me |
| OCF₃ | 7-Cl | 4-F—Ph | OCF₃ | 8-Cl | 4-F—Ph |
| CF₃ | 7-F | Me | CF₃ | 8-F | Me |
| CF₃ | 7-F | Et | CF₃ | 8-F | Et |
| CF₃ | 7-F | n-Pr | CF₃ | 8-F | n-Pr |
| CF₃ | 7-F | CO₂Me | CF₃ | 8-F | CO₂Me |
| CF₃ | 7-F | 4-F—Ph | CF₃ | 8-F | 4-F—Ph |
| OCF₃ | 7-F | Me | OCF₃ | 8-F | Me |
| OCF₃ | 7-F | Et | OCF₃ | 8-F | Et |
| OCF₃ | 7-F | n-Pr | OCF₃ | 8-F | n-Pr |
| OCF₃ | 7-F | CO₂Me | OCF₃ | 8-F | CO₂Me |
| OCF₃ | 7-F | 4-F—Ph | OCF₃ | 8-F | 4-F—Ph |

Formulation and Use

The compounds of this invention will generally be used in formulation with an agriculturally suitable carrier comprising a liquid or solid diluent or an organic solvent. Useful formulations of the compounds of Formulas I and II can be prepared in conventional ways. They include dusts, granules, baits, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1% to 20% surfactant(s) and b) about 5% to 99% solid or liquid diluent(s). More specifically, they will contain effective amounts of these ingredients in the following approximate proportions:

|  | Percent By Weight | | |
|---|---|---|---|
|  | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed , Interscience, New York, 1950. Solubility under 0.1% is preferred for suspension concentrates; solution concentrates are preferably stable against phase separation at 0° C. "McCutcheon's Detergents and Emulsifiers Annual" Allured Publ Corp , Ridgewood, N.J., as well as Sisely and Wood, "Encyclopedia of Surface Active Agents" Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques See J. E. Browning, "Agglomeration" *Chemical Engineering*, Dec. 4, 1967, pages 147 and following, and "Perry's Chemical Engineer's Handbook", 4th-Ed., McGraw-Hill, New York, 1963, pages 8 to 59 and following.

EXAMPLE A

| Emulsifiable Concentrate | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 20% |
| blend of oil soluble sulfonates and polyoxyethylene ethers | 10% |

-continued

| Emulsifiable Concentrate | |
|---|---|
| isophorone | 70% |

The ingredients are combined and stirred with gentle warming to speed solution. A fine screen filter is included in packaging operation to insure the absence of any extraneous undissolved material in the product.

EXAMPLE B

| Wettable Powder | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

EXAMPLE C

| Dust | |
|---|---|
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

| Granule | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 10% |
| attapulgite granules (low volatile matter, 0.71/0.30 mm; U.S.S. No. 25–50 sieves) | 90% |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

EXAMPLE E

| Granule | |
|---|---|
| Wettable powder of Example B | 15% |
| gypsum | 69% |

-continued

| Granule | |
|---|---|
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE F

| Solution | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 25% |
| N-methyl-pyrrolidone | 75% |

The ingredients are combined and stirred to produce a solution suitable for direct, low volume application.

EXAMPLE G

| Aqueous Suspension | |
|---|---|
| 7-chloro-4a-(4-chlorophenyl)-4a,5-dihydro-N-[4-(trifluoromethyl)phenyl]indeno-[1,2-e](1,3,4)-oxadiazine-2(3H)-carboxamide | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles substantially all under 5 microns in size.

EXAMPLE H

| Oil Suspension | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 35.0% |
| blend of polyalcohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

EXAMPLE I

| Bait Granules | |
|---|---|
| 7-chloro-4a-(4-chlorophenyl)-4a,5-dihydro-N-[4-(trifluoromethyl)phenyl]indeno-[1,2-e][1,3,4]-oxadiazine-2(3H)-carboxamide | 3.0% |
| blend of polyethoxylated nonyl-phenols and sodium dodecyl-benzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formulas I and II can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with a-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon) octachlorocamphene (toxaphene)
0-ethyl-O-p-nitrophenyl phenylphosphonothioate (EPN)
(S)-α-cyano-m-phenoxybenzyl (1R, 3R)-3-(2,2-dibromovinyl)-2,2-dimethylcyclopropanecarboxylate (deltamethrin)
Methyl-N',N'-dimethyl-N-[(methylcarbamoyl)oxy]-1-thioox amimidate (oxamyl)
cyano (3-phenoxyphenyl)-methyl-4-chloro-a-(1-methylethyl)benzeneacetate (fenvalerate)
(3-phenoxyphenyl)methyl(+)-cis,trans-3-(2,2-dichloroethenyl)-2,2-dimethylcyclopropanecarboxylate (permethrin)
a-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos) phosphorothiolothionic acid,
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotophos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1- [[[bis(4-fluorophenyl)][methyl]silyl]methyl]-1H-1,2,4-triazole Nematicides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid O-ethyl O'-[4-(methylthio)-m-tolyl]diester (fenamiphos)

Bactericides:
tribasic copper sulfate
streptomycin sulfate

Acaricides:
senecioic acid, ester with 2-sec-butyl-4,6-dinitrophenol (binapacryl)
6-methyl-1,3-cithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide Biological
*Bacillus thuringiensis*
Avermectin B.

Utility

Some of the compounds of this invention are characterized by favorable metabolic and/or soil residual patterns and exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests. For example, some of the compounds where Y is alkyl have enhanced field efficacy. The compounds of this invention display activity against economically important agronomic, forestry, greenhouse, ornamental food and fiber product, stored product, domestic structure, and nursery pests, such as:

larvae of the order Lepidoptera including fall and beet armyworm and other *Spodoptera spp.*, tobacco budworm, corn earworm and other *Heliothis spp.*, European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other *Diabrotica spp.*, Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids scales (coccidae and diaspididae), lace bugs (tingidae), stink bugs (pentatomidae), cinch bugs and other seed bugs (lygaeidae), cicadas (cicadidae), spittlebugs (cercopids), squash bugs (coreidae), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda*; tobacco budworm, *Heliothis virescens*; boll weevil, *Anthonomus grandis*; aster leafhopper, *Macrosteles fascifrons*; black bean aphid, (Aphis Fabae); southern corn rootworm, *Diabrotica undecimpunctata*. The pest control protection afforded by the compounds of the present invention is not limited, however, to these species. The compounds of this invention may also be utilized as rodenticides.

Application

Arthropod pests are controlled and protection of agronomic crops, animal and human health is achieved by applying one or more of the Formula I or II compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, foggers, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrates, and synergists such as piperonyl butoxide often enhance the efficacy of the compounds of Formulae I and II.

The rate of application of the Formula I and II compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/square meter but as little as about 0.1 mg/square meter or as much as 150 mg/square meter may be required.

The following Tests demonstrate the control efficacy of compounds of Formulae I and II on specific pests; see Index Tables A, B, C, D, E and F for compound descriptions.

INDEX TABLE A

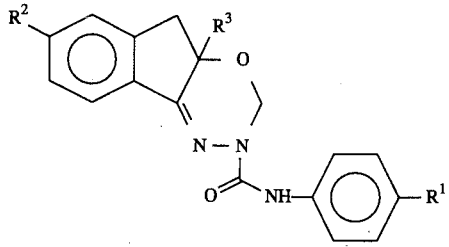

| Cmpd | $R^1$ | $R^2$ | $R^3$ | mp (°C.) |
|------|-------|-------|-------|----------|
| 1 | $CF_3$ | Cl | 4-Cl—Ph | 213–214 |
| 2 | $OCF_3$ | Cl | $CO_2Me$ | 126.5–128 |
| 3 | $CF_3$ | Cl | $CO_2Me$ | 153–155 |
| 4 | Br | Cl | $CO_2Me$ | 168–170 |
| 5 | Cl | Cl | $CO_2Me$ | 159–162 |
| 6 | $OCF_3$ | F | 4-F—Ph | 158–160 |
| 7 | Cl | F | 4-F—Ph | 189–190 |
| 8 | Br | F | 4-F—Ph | 208–209 |
| 9 | $OCF_3$ | Cl | Me | foam* |
| 10 | Br | Cl | Me | 88–90 |
| 11 | $OCF_3$ | Cl | n-Pr | oil* |
| 12 | Br | Cl | n-Pr | oil* |
| 13 | Cl | Cl | n-Pr | oil* |

INDEX TABLE A-continued

[Structure: indane with R², R³ substituents, connected via N-N-C(=O)-NH-phenyl-R¹, with ethoxy group]

| Cmpd | R¹ | R² | R³ | mp (°C.) |
|---|---|---|---|---|
| 14 | OCF₃ | CF₃ | CO₂Me | oil* |
| 15 | Cl | CF₃ | CO₂Me | 176–181 |
| 16 | CF₃ | F | CO₂Me | 216–218 |
| 17 | Br | F | CO₂Me | 186–188 |
| 18 | Cl | F | CO₂Me | 179–180 |
| 19 | OCF₃ | F | CO₂Me | 174–176 |
| 20 | Br | F | Ph | 180–182 |
| 21 | OCF₃ | F | Ph | 154–156 |
| 51 | CF₃ | F | 4-F—Ph | 182–190 |
| 52 | OCF₃ | F | Et | 44–48 |
| 53 | CF₃ | F | Et | 58–60 |
| 54 | OCF₃ | F | Me | 60–61 |
| 55 | CF₃ | F | Me | 61–62 |
| 63 | OCF₃ | Cl | CO₂Et | 122–124 |
| 64 | CF₃ | CF₃ | CO₂Me | 154–156 |
| 81 | Cl | F | Me | oil* |

INDEX TABLE B

[Structure: indane with R², R³ substituents, connected via N-N(Y)-C(=O)-phenyl-R¹, with CH(R⁴)-O group]

| Cmpd | R¹ | R² | R³ | R⁴ | Y | mp (°C.) |
|---|---|---|---|---|---|---|
| 22 | OCF₃ | Cl | CO₂Me | H | Me | 130–131 |
| 23 | OCF₃ | Cl | CO₂Me | Me | H | 162–166 |
| 24 | OCF₃ | Cl | CO₂Me | H | CO₂Me | oil* |
| 25 | OCF₃ | Cl | CO₂Me | H | COMe | oil* |
| 26 | Br | F | 4-F—Ph | H | Me | 161–163 |
| 27 | Br | F | 4-F—Ph | H | CO₂Me | 187–189 |
| 28 | Br | F | 4-F—Ph | H | COMe | 91–93 |
| 29 | Br | F | 4-F—Ph | Me | H | 198(dec) |
| 30 | Br | F | 4-F—Ph | Et | H | 219–221 |
| 31 | OCF₃ | Cl | CO₂Me | Et | H | 151–152 |
| 32 | CF₃ | F | CO₂Me | Me | H | 168–171 |
| 33 | OCF₃ | F | CO₂Me | Me | H | 155–157 |
| 34 | OCF₃ | F | 4-F—Ph | Et | H | 150–152 |
| 35 | OCF₃ | F | 4-F—Ph | Me | H | 149–151 |
| 36 | Br | Cl | CO₂Me | H | Me | 114–116 |
| 37 | CF₃ | Cl | CO₂Me | H | Me | 133–135 |
| 38 | CF₃ | F | CO₂Me | Et | H | 168–170 |
| 39 | CF₃ | Cl | CO₂Me | H | COMe | gum* |
| 40 | Br | Cl | CO₂Me | H | CO₂Me | oil* |
| 41 | OCF₃ | F | CO₂Me | H | Me | 143–145 |
| 42 | CF₃ | F | CO₂Me | H | Me | 198–200 |
| 43 | OCF₃ | Cl | CO₂Et | H | Et | oil* |
| 44 | OCF₃ | Cl | CO₂Me | H | Et | 120.5–122 |
| 45 | CF₃ | Cl | CO₂Et | H | Et | oil* |
| 46 | CF₃ | Cl | CO₂Me | H | Et | oil* |
| 47 | OCF₃ | Cl | CO₂Me | H | CO₂Et | oil* |
| 48 | Br | F | 4-F—Ph | H | CO₂Et | oil* |
| 49 | Br | F | 4-F—Ph | H | Et | 177–178 |
| 50 | Br | F | 4-F—Ph | H | COMe | oil* |
| 65 | OCF₃ | Cl | CO₂Et | H | Me | oil* |

INDEX TABLE B-continued

| Cmpd | R¹ | R² | R³ | R⁴ | Y | mp (°C.) |
|---|---|---|---|---|---|---|
| 66 | OCF₃ | F | 4-F—Ph | H | CO₂Et | 170–173 |
| 67 | OCF₃ | F | 4-F—Ph | H | Et | 164–166 |
| 68 | Br | F | 4-F—Ph | H | CH₂SMe | 158–160 |

INDEX TABLE C

[Structure: tetrahydronaphthalene with R², R³ substituents, connected via N-N-C(=O)-NH-phenyl-R¹]

| Cmpd | R¹ | R² | R³ | mp (°C.) |
|---|---|---|---|---|
| 56 | OCF₃ | F | 4-F—Ph | 180–184 |
| 57 | OCF₃ | Cl | 4-F—Ph | 129–133 |
| 58 | OCF₃ | F | Me | 125–127 |

INDEX TABLE D

[Structure: indane with R², R³ substituents, connected via N-N(Y)-C(=O)-NH-phenyl-R¹, with ethoxy group]

| Cmpd | R¹ | R² | R³ | Y | mp (°C.) |
|---|---|---|---|---|---|
| 58 | OCF₃ | Cl | Me | H | 115–117 |
| 59 | CF₃ | Cl | Me | H | 162–163 |
| 60 | CF₃ | Cl | Et | H | 132–133 |
| 61 | CF₃ | F | Et | H | 123–124 |
| 62 | OCF₃ | F | Et | H | 100–101 |
| 70 | OCF₃ | Cl | CO₂Me | H | 160–161 |
| 71 | CF₃ | Cl | CO₂Me | H | 199–200 |
| 72 | Br | Cl | CO₂Me | H | 230(dec) |
| 73 | Cl | Cl | CO₂Me | H | 221–223 |
| 74 | OCF₃ | F | CO₂Me | H | 163–164 |
| 75 | CF₃ | F | CO₂Me | H | 199–200 |
| 76 | Br | F | CO₂Me | H | 205–207 |
| 77 | Cl | F | CO₂Me | H | 194–196 |
| 78 | OCF₃ | Cl | CO₂Me | Me | 147–148 |
| 79 | CF₃ | Cl | CO₂Me | Me | 148–149 |
| 80 | Br | Cl | CO₂Me | Me | 178–179 |

INDEX TABLE E

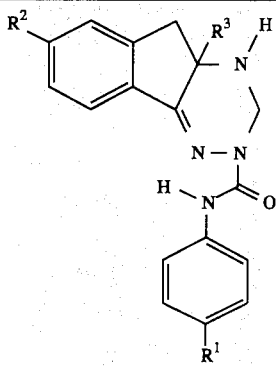

| Cmpd | R¹ | R² | R³ | mp (°C.) |
|---|---|---|---|---|
| 82 | OCF₃ | Cl | CO₂CH₃ | 135–140(d) |

INDEX TABLE F

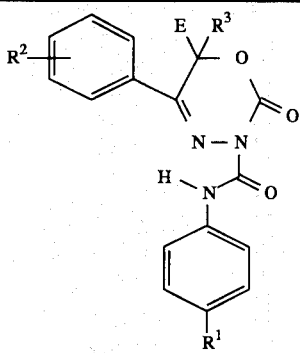

| Cmpd | R¹ | R² | R³ | E | mp (°C.) |
|---|---|---|---|---|---|
| 83 | H | H | Ph | H | oil* |

*See Table G for additional data on selected compounds of Tables A–F.

TABLE G

| CMPD | ¹H NMR Data (200 MHz, CDCl₃ solution) |
|---|---|
| 9 | δ 1.51 (s, 3H), 3.14 (abq, 2H), 5.20 (d, 1H), 5.73 (d, 1H), 7.18 (d, 2H), 7.35 (d, 2H), 7.51–7.61 (m, 3H), 8.40 (s, 1H). |
| 11 | δ 0.92 (t, 3H), 1.22–1.62 (m, 3H), 1.8–2.0 (m, 1H), 3.13 (abq, 2H), 5.19 (d, 1H), 5.56 (d, 1H), 7.18 (d, 2H), 7.33 (d, 2H), 7.51–7.62 (m, 3H), 8.39 (s, 1H). |
| 12 | δ 0.92 (t, 3H), 1.3–1.6 (m, 3H), 1.8–2.0 (m, 1H), 3.12 (abq, 2H), 5.19 (d, 1H), 5.55 (d, 1H), 7.31 (apparent d, 2H), 7.43 (apparent s, 4H), 7.57 (d, 1H), 8.36 (s, 1H). |
| 13 | δ 0.92 (t, 3H), 1.2–1.6 (m, 3H), 1.8–2.0 (m, 1H), 3.15 (abq, 2H), 5.18 (d, 1H), 5.55 (d, 1H), 7.24–7.38 (m, 4H), 7.50 (d, 2H), 7.57 (d, 1H), 8.36 (s, 1H). |
| 14 | δ 3.43 (abq, 2H), 3.74 (s, 3H), 5.07 (d, 1H), 5.97 (d, 1H), 7.21 (d, 2H), 7.5–7.7 (m, 4H), 7.81 (d, 1H), 8.38 (br s, 1H). |
| 24 | δ 3.25 (d, 1H), 3.51 (d, 1H), 3.72 (s, 3H), 3.73 (s, 3H), 5.22 (d, 1H), 5.72 (d, 1H), 7.20–7.42 (m, 6H), 7.53 (d, 1H). |
| 25 | δ 2.23 (s, 3H), 3.21 (d, 1H), 3.47 (d, 1H), 3.66 (s, 3H), 5.22 (d, 1H), 5.65 (d, 1H), 7.18–7.45 (m, 7H). |
| 39 | δ 2.27 (s, 3H), 3.20 (d, 1H), 3.44 (d, 1H), 3.65 (s, 3H), 5.24 (d, 1H), 5.66 (d, 1H), |

TABLE G-continued

| CMPD | ¹H NMR Data (200 MHz, CDCl₃ solution) |
|---|---|
|  | 7.23–7.45 (m, 5H), 7.64 (d, 2H). |
| 40 | δ 3.39 (abq, 2H), 3.71 (s, 3H), 3.72 (s, 3H), 5.21 (d, 1H), 5.69 (d, 1H), 7.18–7.38 (m, 4H), 7.43–7.57 (m, 3H). |
| 43 | δ 1.05–1.20 (m, 5H), 3.23 (abq, 2H), 3.65–3.95 (m, 2H), 4.02–4.2 (m, 2H), 5.17 (d, 1H), 5.44 (d, 1H), 6.93 (d, 1H), 7.14 (apparent s, 5H), 7.19 (apparent s, 1H). |
| 45 | δ 1.08–1.30 (m, 5H), 3.10 (d, 1H), 3.37 (d, 1H), 3.70–3.95 (m, 2H), 4.0–4.2 (m, 2H), 5.17 (d, 1H), 5.47 (d, 1H), 6.72 (d, 1H), 7.19 (distorted t, 4H), 7.54 (d, 2H). |
| 46 | δ 1.22 (t, 3H), 3.09 (d, 1H), 3.38 (d, 1H), 3.67 (s, 3H), 3.72–3.98 (m, 2H), 5.20 (d, 1H), 5.42 (d, 1H), 6.75 (d, 1H), 7.19 (distorted t, 4H), 7.54 (d, 2H). |
| 47 | δ 1.16 (t, 3H), 3.38 (abq, 2H), 3.72 (s, 3H), 4.05–4.25 (m, 2H), 5.20 (d, 1H), 5.76 (d, 1H), 7.10–7.26 (m, 2H), 7.36 (distorted t, 4H), 7.54 (d, 1H). |
| 48 | δ 1.22 (t, 3H), 3.47 (abq, 2H), 4.23 (q, 2H), 4.60 (d, 1H), 5.61 (d, 1H), 6.92–7.10 (m, 4H), 7.12–7.25 (m, 4H), 7.49 (distorted d, 2H), 7.63 (dd, 1H). |
| 50 | δ 2.19 (s, 3H), 3.34 (abq, 2H), 3.66 (s, 3H), 5.22 (d, 1H), 5.64 (d, 1H), 7.18–7.37 (m, 4H), 7.42–7.51 (m, 3H). |
| 65 | δ 1.15 (t, 3H), 3.13 (d, 1H), 3.35 (d, 1H), 3.38 (s, 3H), 4.0–4.2 (m, 2H), 5.19 (d, 1H), 5.44 (d, 1H), 6.83 (d, 1H), 7.15 (apparent s, 5H), 7.19 (br s, 1H). |
| 81 | δ 1.51 (s, 3H), 3.17 (abq, 2H), 5.20 (d, 1H), 5.72 (d, 1H), 7.02–7.17 (m, 2H), 7.43 (s, 4H), 7.62 (dd, 1H), 8.38 (br s, 1H). |
| 83 | δ 6.50 (s, 1H), 7.4–7.8 (m, 14H), 10.6 (bs, 1H). |

TEST A

Fall Armyworm

Test units, each consisting of an 8-ounce (230 mL) plastic cup containing a layer of wheat germ diet, approximately 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed into the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. (207 kPa). The cups were then covered and held at 27° C. and 50% relative humidity for 72 hours, after which time readings were taken. Of the compounds tested, the following resulted in greater than or equal to 80% mortality: 1, 2, 3, 4, 5, 6, 7, 8, 9, 10, 11, 12, 13, 15, 19, 20, 21, 22, 23, 25, 26, 27, 28, 29, 31, 34, 35, 36, 37, 39, 40, 43, 44, 45, 46, 47, 48, 49, 51, 52, 53, 54, 55, 56, 58, 61, 62, 63, 65, 70, 74, 78, 79, 80.

TEST B

Tobacco Budworm

The test procedure of Test I was repeated for efficacy against third-instar larvae of the tobacco budworm (*Heliothis virescens*) except that mortality was assessed at 48 hours. Of the compounds tested, the following resulted in greater than or equal to 80% mortality: 2, 3, 4, 6, 7, 8, 9, 10, 11, 12, 15, 16, 17, 18, 19, 20, 21, 22, 23, 25, 26, 27, 28, 29, 32, 33, 34, 35, 37, 39, 40, 41, 42, 43, 44, 45, 46, 47, 48, 49, 51, 52, 53, 54, 55, 56, 61, 62, 63, 65, 70, 71, 74, 79.

TEST C

Southern Corn Rootworm

Test units, each consisting of an 8-ounce (230 mL) plastic cup containing 1 sprouted corn seed, were prepared. Sets of three test units were sprayed as described in Test A with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested, the following resulted in greater than or equal to 80% mortality: 1, 2, 3, 6, 7, 8, 9, 10, 11, 12, 15, 16, 17, 18, 19, 20, 21, 22, 23, 25, 26, 27, 28, 32, 35, 36, 37, 39, 41, 42, 43, 44, 46, 47, 48, 49, 51, 52, 53, 54, 55, 56, 59, 61, 62, 63, 65, 70, 71, 74, 75, 76, 77, 78, 79, 80.

TEST D

Aster Leafhopper

Test units were prepared from a series of 12-ounce (350 mL) cups, each containing oat (*Avena sativa*) seedlings in a 1-inch (2.54 cm) layer of sterilized soil. The test units were sprayed as described in Test A with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested, the following resulted in greater than or equal to 80% mortality: 2, 3, 4, 5, 6, 7, 8, 9, 10, 11, 12, 13, 15, 16, 17, 18, 19, 21, 22, 25, 26, 27, 28, 35, 36, 37, 39, 40, 41, 43, 44, 45, 46, 47, 48, 49, 51, 52, 53, 54, 55, 56, 63, 65, 70, 71, 74, 76, 77, 78, 79.

TEST E

Boll Weevil

Five adult boll weevils (*Anthonomus grandis grandis*) were placed into each of a series of 9 ounce (260 mL) cups. The test procedure employed was then otherwise the same as in Test A with three cups per treatment. Mortality readings were taken 48 hours after treatment. Of the compounds tested, the following resulted in greater than or equal to 80% mortality: 1, 2, 3, 4, 5, 6, 7, 8, 9, 10, 11, 12, 13, 15, 16, 18, 19, 20, 21, 22, 23, 25, 26, 27, 28, 32, 33, 35, 37, 39, 41, 42, 43, 44, 45, 46, 47, 48, 49, 51, 52, 53, 54, 55, 56, 61, 62, 63, 65, 70, 71, 74, 75, 76, 77, 78, 79, 80.

What is claimed is:

1. A compound of Formula I or II:

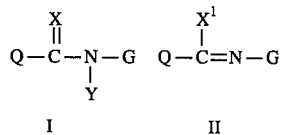

wherein:

Q is selected from the group

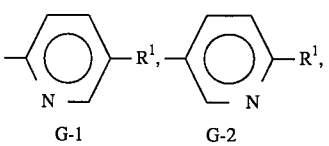

A and E are taken together to form —$CH_2$—, —$CH_2CH_2$—, substituted —$CH_2$—, and substituted —$CH_2CH_2$— the substituents independently selected from 1–2 halogen and 1–2 methyl;

G is selected from the group

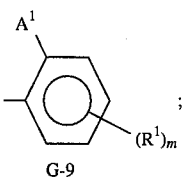

X is selected from the group O, S and N—$X^2$;

$X^1$ is selected from the group Cl, Br, $OR^8$, $SR^8$ and $NR^8R^9$;

$X^2$ is selected from the group $R^8$, OH, $OR^8$, CN, $SO_2R^8$, $SO_2Ph$, $OC(O)NR^9R^{10}$, $OC(O)OR^8$, $NR^9R^{10}$ and phenyl optionally substituted with $R^{11}$;

Y is selected from the group H; $C_1$–$C_6$ alkyl; benzyl; $C_2$–$C_6$ alkoxyalkyl; $C_2$–$C_6$ alkenyl; $C_2$–$C_6$ alkynyl; $C_1$–$C_6$ alkyl optionally substituted by halogen, $C_1$–$C_3$ alkoxy, $C_1$–$C_3$ haloalkoxy, CN, $NO_2$, $S(O)_rR^{32}$, $COR^{32}$, $CO_2R^{32}$, phenyl optionally substituted by halogen, CN, $C_1$–$C_2$ haloalkyl and $C_1$–$C_2$ haloalkoxy; $C_3$–$C_6$ cycloalkyl; $C_3$–$C_6$ cyclohaloalkyl; $C_3$–$C_6$ cycloalkylalkyl; CHO; $C_2$–$C_6$ alkylcarbonyl; $C_2$–$C_6$ alkoxycarbonyl; $C_2$–$C_6$ haloalkylcarbonyl; $COR^{36}$; $CO_2R^{36}$; $C_1$–$C_6$ alkylthio; $C_1$–$C_6$ haloalkylthio; phenylthio; $R^{12}OC(O)N(R^{13})S$— and $R^{14}$ $(R^{15})NS$—;

$A^1$ is H;

$A^1$ and Y can be taken together to form —$(CH_2)_t$—;

Z is C;

$Z^1$ is O;

$R^1$ and $R^2$ are independently selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, halogen, CN, $N_3$, SCN, $NO_2$, $OR^{17}$, $SR^{17}$, $S(O)R^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, $NR^{18}C(O)R^{17}$, $OC(O)NHR^{17}$, $NR^{18}C(O)NHR^{17}$, $NR^{18}SO_2R^{17}$, phenyl optionally substituted with 1 to 3 substituents independently selected from W, and benzyl optionally substituted with 1 to 3 substituents independently selected from W; or when m or n is 2, $(R^1)_2$ can be taken together, or $(R^2)_2$ can be taken together as —$OCH_2O$—, —$OCF_2O$—, —$OCH_2CH_2O$—, —$CH_2C(CH_3)_2O$—, —$CF_2CF_2O$ or —$OCF_2CF_2O$— to form a cyclic bridge; provided that when $R^1$ or $R^2$ is $S(O)R^{17}$, $S(O)_2R^{17}$, $OC(O)R^{17}$ or $OS(O)_2R^{17}$ then $R^{17}$ is other than H;

$R^3$ is selected from the group H, halogen, $N(R^{22})R^{23}$, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ alkoxylalkyl, $CO_2R^{17}$, $C(O)R^{17}$, $C(O)NR^{17}R^{18}$, phenyl, phenyl substituted with 1 to 3 substituents independently selected from halogen, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_3$–$C_6$ cycloalkyl, $C_3$–$C_6$ halocycloalkyl, CN, SCN, $NO_2$, $OR^{17}$, $SR^{17}$, $CO_2R^{17}$, $C(O)R^{17}$, $C(O)NR^{17}R^{18}$ and $SO_2NR^{17}R^{18}$ benzyl and benzyl substituted with 1 to 3 substituents independently selected from halogen;

$R^4$ and $R^5$ are independently selected from the group H, $C_1$–$C_4$ alkyl, $COR^{20}$ and $C_2$–$C_4$ alkoxycarbonyl; or $R^4$ and $R^5$ can be taken together to form =O or =S;

$R^6$ is selected from the group H, $C_1$–$C_4$ alkyl, $C_1$–$C_4$ haloalkyl, $C_2$–$C_4$ alkylcarbonyl, $C_2$–$C_4$ haloalkoxycarbonyl, $C_2$–$C_4$ alkoxycarbonyl $C_2$–$C_4$ haloalkoxycarbonyl, $COR^{36}$, $CO_2R^{36}$, $C_2$–$C_5$ alkylaminocarbonyl, $C_3$–$C_6$ cycloalkyl, $C_3$–$C_6$ halocycloalkyl, $C_4$–$C_7$ alkylcycloalkyl, $C_4$–$C_7$ haloalkylcycloalkyl, $C_1$–$C_4$ alkylsulfonyl, $C_1$–$C_4$ haloalkylsulfonyl and $SO_2Ph$ optionally substituted with Cl, Br or $CH_3$;

$R^8$ is selected from the group $C_1$–$C_3$ alkyl, $C_2$–$C_4$ alkenyl, $C_2$–$C_4$ alkynyl, $C_1$–$C_3$ haloalkyl, $C_2$–$C_4$ haloalkenyl, $C_3$–$C_6$ cycloalkyl; $C_1$–$C_3$ alkyl substituted with $OCH_3$, $OCH_2CH_3$, $NO_2$, CN, $CO_2CH_3$, $CO_2CH_2CH_3$, $SCH_3$ or $SCH_2CH_3$ and benzyl optionally substituted with $R^{11}$;

$R^9$ is selected from the group H, $C_1$–$C_4$ alkyl $C_1$–$C_4$ haloalkyl, $C_2$–$C_4$ alkoxycarbonyl, and optionally substituted phenyl and pyridine wherein the substituent(s) are selected from $R^{15}$; or $R^8$ and $R^9$ can be taken together to form —$(CH_2)_4$—, —$(CH_2)_5$— or —$CH_2CH_2OCH_2CH_2$— each of which is optionally and independently substituted with 1 or 2 $CH_3$ groups;

$R^{10}$ is selected from the group H and $C_1$–$C_4$ alkyl; or $R^9$ and $R^{10}$ can be taken together to form —$(CH_2)_4$—, —$(CH_2)_5$— or —$CH_2CH_2OCH_2CH_2$— each of which is optionally and independently substituted with 1 or 2 $CH_3$ groups;

$R^{11}$ is selected from halogen, CN, $C_1$–$C_3$ haloalkyl and $C_1$–$C_3$ haloalkoxy;

$R^{12}$ is $C_1$–$C_6$ alkyl;

$R^{13}$ is $C_1$–$C_4$ alkyl;

$R^{14}$ and $R^{15}$ are independently $C_1$–$C_4$ alkyl; or $R^{14}$ and $R^{15}$ can be taken together as —$CH_2CH_2CH_2CH_2CH_2$— or —$CH_2CH_2OCH_2CH_2$—;

$R^{17}$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$–$C_6$ alkylthioalkyl, $C_1$–$C_6$ nitroalkyl, $C_2$–$C_6$ cyanoalkyl, $C_3$–$C_8$ alkoxycarbonylalkyl, $C_3$–$C_6$ cycloalkyl, $C_3$–$C_6$ halocycloalkyl, and optionally substituted phenyl and benzyl wherein the substituents are 1 to 3 substituents independently selected from W;

$R^{18}$ is selected from the group H and $C_1$–$C_4$ alkyl; or $R^{17}$ and $R^{18}$, when attached to the same atom, can be taken together as —$(CH_2)_4$—, —$(CH_2)_5$—, or —$CH_2CH_2OCH_2CH_2$—;

$R^{20}$ is $C_1$–$C_3$ alkyl;

$R^{22}$ is selected from the group H, $C_2$–$C_7$ alkylcarbonyl, $C_2$–$C_7$ alkoxycarbonyl, optionally substituted $C_1$–$C_4$ alkyl, optionally substituted $C_2$–$C_4$ alkenyl, and optionally substituted $C_2$–$C_4$ alkynyl, the substituents selected from $C_1$–$C_2$ alkoxy, CN, $C(O)R^{30}$ and $C(O)_2R^{27}$;

$R^{23}$ is selected from the group H, $C_1$–$C_3$ alkyl, phenyl, phenyl substituted with W, benzyl and benzyl substituted with W;

$R^{27}$ is selected from the group $C_1$–$C_3$ alkyl, phenyl and phenyl substituted with W;

$R^{30}$ is selected from the group H, $C_1$–$C_3$ alkyl, phenyl and phenyl substituted by W;

$R^{32}$ is selected from the group $C_1$–$C_3$ alkyl;

$R^{36}$ is selected from the group phenyl and phenyl substituted by W;

W is selected from the group halogen, CN, $NO_2$, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $C_1$–$C_2$ haloalkylthio, $C_1$–$C_2$ alkylsulfonyl and $C_1$–$C_2$ haloalkylsulfonyl;

m is 1 to 3;

n is 1 to 3;

r is 0, 1 or 2;

t is 2 or 3; and u is 1 or 2.

2. A compound according to claim 1 wherein:

$R^1$ is selected from the group H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ haloalkynyl, $C_2$–$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, SCN, $NO_2$, $OR^{17}$, $SR^{17}$, $SO_2R^{17}$, $CO_2R^{17}$, $C(O)R^{17}$, phenyl optionally substituted with 1 to 3 substituents independently selected from W, and benzyl optionally substituted with 1 to 3 substituents independently selected from W; with one $R^1$ substituent in the 4-position, or when m is 2 then $(R^1)_2$ can be taken together as —$CH_2C(CH_3)_2O$—, —$OCH_2CH_2O$—, —$OCF_2CF_2O$—, or —$CF_2CF_2O$— to form a 5- or 6-membered fused ring;

$R^2$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, SCN, $NO_2$, $OR^{17}$, $SR^{17}$, $S(O)_2R^{17}$, $OC(O)R^{17}$, $OS(O)_2R^{17}$, $CO_2R^{17}$, $C(O)R^{17}$, $C(O)NR^{17}R^{18}$, $SO_2NR^{17}R^{18}$, $NR^{17}R^{18}$, phenyl optionally substituted with 1 to 3 substituents independently selected from W, and benzyl optionally substituted with 1 to 3 substituents independently selected from W;

$R^3$ is selected from the group H, $C_1$-$C_4$ alkyl, $CO_2R^{17}$, $C(O)R^{17}$, phenyl and phenyl substituted by 1 to 3 substituents independently selected from halogen;

$R^{17}$ is selected from the group $C_1$-$C_4$ alkyl, $C_1$-$C_2$ haloalkyl, $C_3$-$C_4$ alkenyl and propargyl;

$R^{18}$ is selected from the group H and $CH_3$;

$X^1$ is selected from the group Cl, $OR^8$, $SR^8$ and $N(CH_3)_2$;

$X^2$ is selected from the group $R^8$, $OR^8$ and $N(CH_3)_2$;

m is 1 or 2; and n is 1 or 2.

3. A compound according to claim 2 wherein G is selected from the group G-2 and G-9.

4. A compound according to claim 3 wherein A and E are taken together to form —$CH_2$—, or —$CH_2CH_2$—.

5. A compound according to claim 4 wherein Q is Q-1.

6. A compound according to claim 4 wherein Q is Q-2.

7. A compound according to claim 4 wherein Y is $C_1$-$C_6$ alkyl.

8. A compound according to claim 5 wherein Y is $CO_2R^{17}$ and $R^3$ is $CO_2R^{17}$.

9. A compound according to claim 1:
methyl 7-chloro-2,3-dihydro-2-[[4-trifluoromethoxy)phenylamino] carbonyl]indeno[1,2-e]-[1,3,4]oxadiazine-4a(5H)-carboxylate.

10. A compound according to claim 1:
methyl 7-chloro-2,5-dihydro-2-[N-methyl-N-[4-(trifluoromethoxy)phenyl] aminocarbonyl]indeno-[1,2-e][1,3,4]oxadiazine-4a(3H)-carboxylate.

11. A compound according to claim 1:
methyl 7-chloro-2,5-dihydro-2-[[N-methyl-N-[4-trifluoromethyl)phenyl] amino]carbonyl]indeno-[1,2-e][1,3,4]oxadiazine-4a(3H)-carboxylate.

12. A compound according to claim 1:
7-fluoro-4a-(4-fluorophenyl)-4a,5-dihydro-N-[4-(trifluoromethoxy)phenyl] indeno[1,2-e][1,3,4]-oxadiazine-2(3H)-carboxamide.

13. A compound according to claim 1:
7-chloro-4a,5-dihydro-4a-methyl-N-[4-(trifluoro-methoxy)phenyl] indeno[1,2-e][1,3,4]oxadiazine-2(3H)-carboxamide.

14. A compound according to claim 8: methyl 7-chloro-2,5-dihydro-2-[N-(methoxycarbonyl)-N-[ 4-(trifluoromethoxy)phenyl aminocarbonyl]indeno[1,2-e][1,3,4] oxadiazine-4a(3H)-carboxylate.

15. An arthropodicidal composition comprising a compound according to any one of claims 1 to 13 and claim 14 and a carrier therefor.

16. A method for controlling arthropods comprising contacting them or their environment with an arthropodicidally effective amount of a compound according to any one of claims 1 to 13 and claim 14, said arthropods selected from the group household, foliar, and soil-inhabiting agronomic and nonagronomic pests.

* * * * *

UNITED STATES PATENT AND TRADEMARK OFFICE
CERTIFICATE OF CORRECTION

PATENT NO. : 5,462,938
DATED : October 31, 1995
INVENTOR(S) : Annis et al.

It is certified that error appears in the above-identified patent and that said Letters Patent is hereby corrected as shown below:

It is certified that error appears in the above identified patent and that said Letters Patent is hereby corrected as shown below:

Title page, item [75],

Inventor's name change "Gary David Annus" to "Gary David Annis".

Signed and Sealed this

First Day of July, 1997

Attest:

Attesting Officer

BRUCE LEHMAN
Commissioner of Patents and Trademarks

UNITED STATES PATENT AND TRADEMARK OFFICE
CERTIFICATE OF CORRECTION

PATENT NO. : 5,462,938  
DATED : October 31, 1995  
INVENTOR(S) : Annis, et al

Page 1 of 2

It is certified that error appears in the above-indentified patent and that said Letters Patent is hereby corrected as shown below:

In Columns 146, 147 and 150, immediately after "TABLE 9-continued" delete the structure "
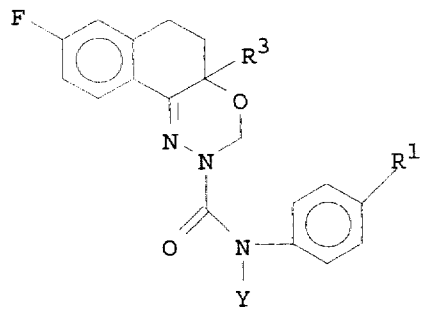
"

and insert therefor

UNITED STATES PATENT AND TRADEMARK OFFICE
CERTIFICATE OF CORRECTION

PATENT NO. : 5,462,938

DATED : October 31, 1995

INVENTOR(S) : Annis, et al

Page 2 of 2

It is certified that error appears in the above-indentified patent and that said Letters Patent is hereby corrected as shown below:

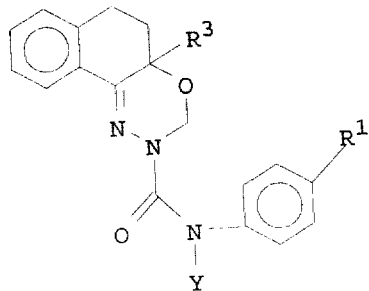

Signed and Sealed this

Twenty-third Day of June, 1998

Attest:

BRUCE LEHMAN

Attesting Officer

Commissioner of Patents and Trademarks